United States Patent
Thelen et al.

(10) Patent No.: US 12,286,649 B2
(45) Date of Patent: Apr. 29, 2025

(54) METHODS OF ALTERING SEED WEIGHT AND SEED OIL CONTENT BY MANIPULATING ALPHA-CARBOXYL-TRANSFERASE (A-CT) ACTIVITY VIA CARBOXYL-TRANSFERASE INTERACTION (CTI) PROTEIN EXPRESSION

(71) Applicant: The Curators of the University of Missouri, Columbia, MO (US)

(72) Inventors: Jay Thelen, Columbia, MO (US); Yajin Ye, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 17/250,117

(22) PCT Filed: May 30, 2019

(86) PCT No.: PCT/US2019/034754
§ 371 (c)(1),
(2) Date: Nov. 30, 2020

(87) PCT Pub. No.: WO2019/232277
PCT Pub. Date: Dec. 5, 2019

(65) Prior Publication Data
US 2021/0230623 A1 Jul. 29, 2021

Related U.S. Application Data

(60) Provisional application No. 62/678,212, filed on May 30, 2018.

(51) Int. Cl.
*C12N 9/10* (2006.01)
*C12N 15/82* (2006.01)

(52) U.S. Cl.
CPC ....... *C12N 9/1018* (2013.01); *C12N 15/8218* (2013.01); *C12N 15/8247* (2013.01); *C12N 15/8213* (2013.01); *C12Y 604/01002* (2013.01)

(58) Field of Classification Search
CPC ................ C12N 15/8247; C12Y 604/01002
See application file for complete search history.

(56) References Cited

U.S. PATENT DOCUMENTS

| | | | | |
|---|---|---|---|---|
| 2007/0214517 A1* | 9/2007 | Alexandrov | ........ | C07K 14/415 536/23.6 |
| 2011/0014706 A2 | 1/2011 | Cao et al. | | |
| 2013/0096032 A1 | 4/2013 | Bush et al. | | |

FOREIGN PATENT DOCUMENTS

| WO | WO 1998005758 | * | 2/1998 | ............... C12N 5/04 |
|---|---|---|---|---|
| WO | 2017039834 A1 | | 3/2017 | |
| WO | WO-2018009626 A2 | * | 1/2018 | ............. C12N 15/52 |
| WO | WO-2019232277 A1 | * | 12/2019 | ......... C12N 15/8213 |

OTHER PUBLICATIONS

Friedberg (Automated protein function prediction—the genomic challenge. Brief. Bioinformatics. 7:225-242, 2006) (Year: 2006).*
Wang et al (From Protein Sequence to Protein Function via Multi-Label Linear Discriminant Analysis. IEEE/ACM Transactions on Computational Biology and Bioinformatics, vol. 14, No. 3, 503-513, 2017) (Year: 2017).*
Ye et al (Docking of acetyl-CoA carboxylase to the plastid envelope membrane attenuates fatty acid production in plants. Nature Communications. 1-14, 2020) (Year: 2020).*
Theologis et al (Sequence and analysis of chromosome 1 of the plant *Arabidopsis thaliana*. Nature. 408, 816-820, 2000) (Year: 2000).*
Chen et al (The transcriptional response of *Arabidopsis* to genotoxic stress—a high-density colony array study (HDCA). Plant. j 35: 771-786, 2003) (Year: 2003).*
International Search Report and Written Opinion in PCT/US2019/034754, mailed Oct. 7, 2019, 9 pages.
Salie et al. "Regulation and structure of the heteromeric acetyl-CoA carboxylase," Biochim Biophys Acta. Apr. 16, 2016 (Apr. 16, 2016), vol. 1861, pp. 1207-1213.
Salie et al. "A Family of Negative Regulators Targets the Committed Step of de Novo Fatty Acid Biosynthesis," Plant Cell. Aug. 24, 2016 .(Aug. 24, 2016), vol. 28, pp. 2312-2325.

* cited by examiner

Primary Examiner — Charles Logsdon
Assistant Examiner — Wayne Zhong
(74) Attorney, Agent, or Firm — Sandberg Phoenix & von Gontard, PC; Tracey S. Truitt

(57) ABSTRACT

A method of altering fatty acid and/or triacylglycerol production in plants and/or algae is provided. The method includes altering activity levels of alpha-carboxyltransferase (α-CT), a catalytic subunit of acetyl-CoA carboxylase (ACCase) by modulating an expression of at least one carboxyltransferase interaction (CTI) gene encoding at least one CTI protein.

16 Claims, 36 Drawing Sheets
Specification includes a Sequence Listing.

```
                        Transit Peptide
CTI1 (SEQ ID NO:2)  -MASLSSTSLSLP--KNSHQLHPSSGFSLNPNARCVSVSFGLNHSNKLHISAPRTKRILT
CTI3 (SEQ ID NO:6)  MASCIATAPLSLSGVSQSHYVK-ANGLSTTKLSSICKTSDLT----IHKKSNRTRK-FS
CTI2 (SEQ ID NO:4)  --MCSSSSCMLLF--SDLLFVLMYNGVLAHRMFNAIRKSSTLT----VQTKSNRSHK-LS
                       .   : . : *       :  :    :   :. : :   : : :      :..:*: :  :

TM
CTI1 (SEQ ID NO:2)  IQSAYRDDDGSGSTGLFVGGFILGGLIVGALGCVYAPQISKAIAGADRKDLMRKLPKFIY
CTI3 (SEQ ID NO:6)  VSAGYRDGSRSGSSGDFIAGFLLGGAVFGAVAYIFAPQIRRSVLNEEDEYGFEKPKQPTY
CTI2 (SEQ ID NO:4)  VSAGYRGGSKGGGSSDFVTGFLLGSAVFGTLAYIFAPQIRRSVL-SENEYGKKPEQPTY
                      ::.**   .:.*::: ***:**.::.::: :.*** *:::**   :::: :* * *.:*
                                              Coiled-Coil
CTI1 (SEQ ID NO:2)  DEEKALEKTRKVLAEKIAQLNSAIDDVSSQLK-------SEDTPNGAALSTDEIEATA
CTI3 (SEQ ID NO:6)  YDE-GLEKTRETLNEKIGQLNSAIDNVSSRLR----GREKINTSSLNVPVETDPEVEATT
CTI2 (SEQ ID NO:4)  YDE-GLEERREILNEKIGQLNSAIDKVSSRLKGGRSGSSKNTSSPSVPVETDAEAEATA
                     ** *:*:*::*.**:.**** :**::     :  ::.:::.: : .*.* **
```

FIG. 6

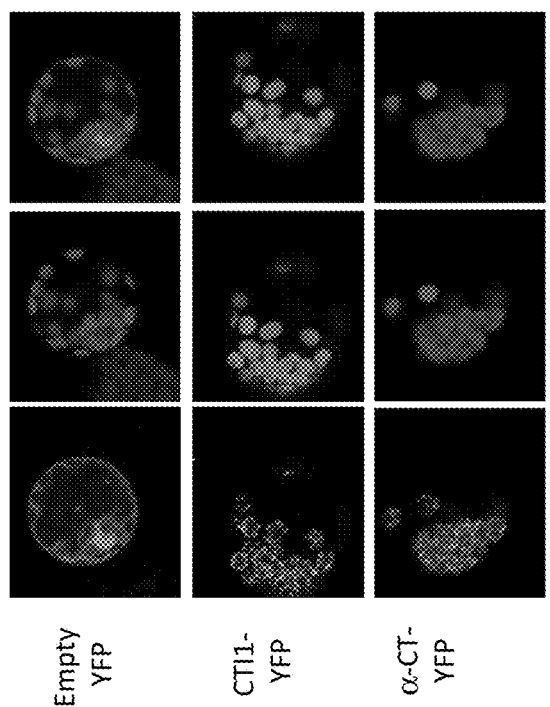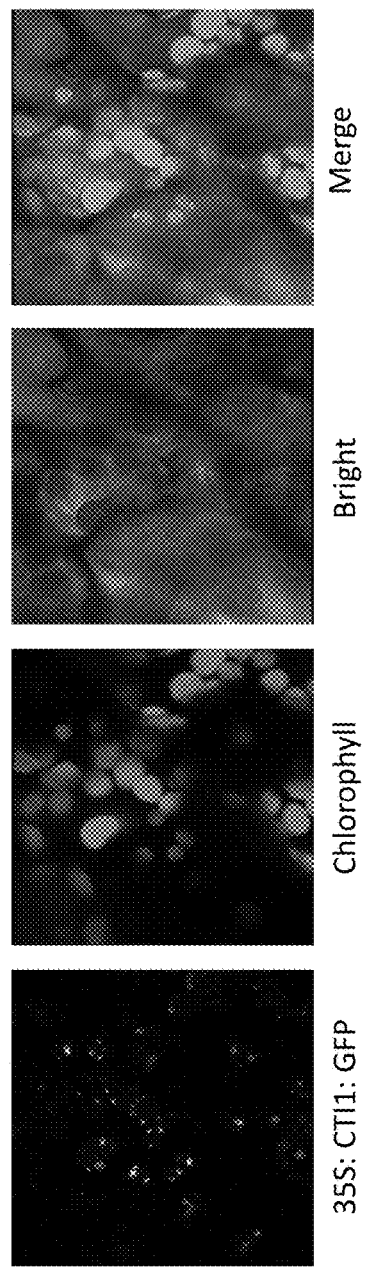

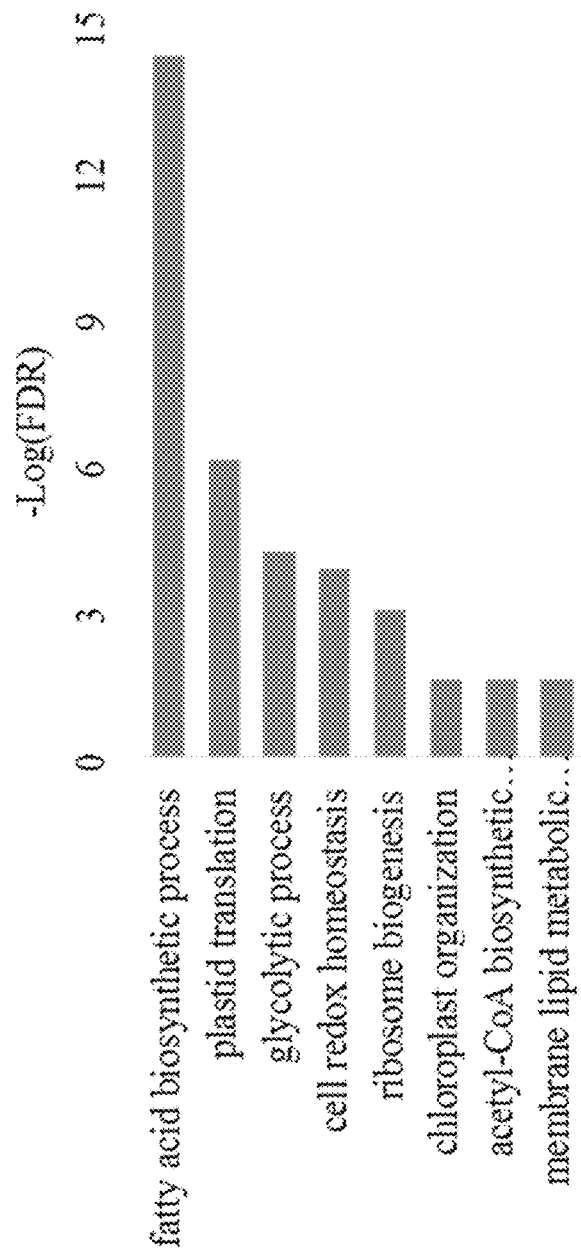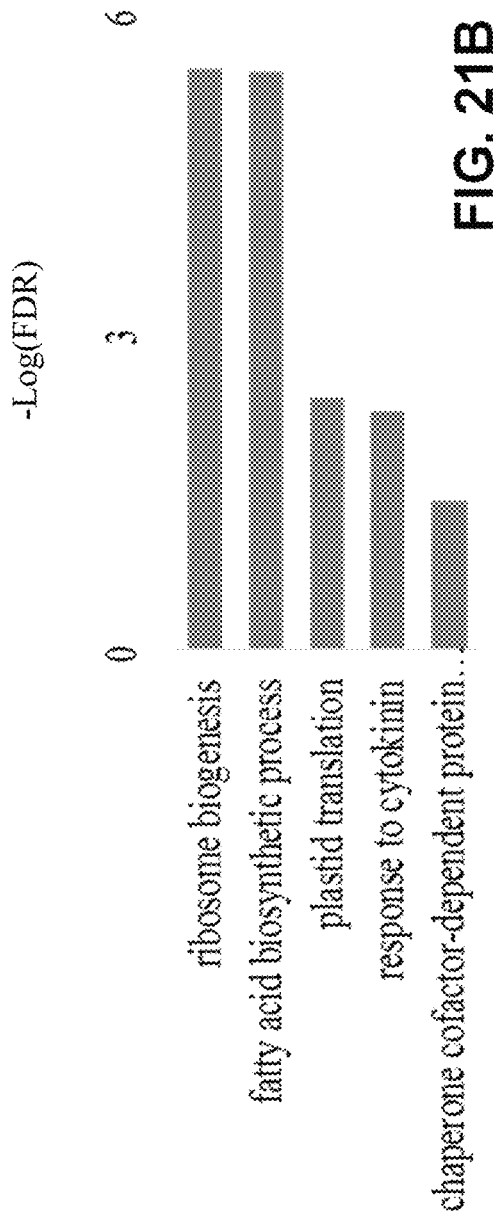
FIG. 21A
FIG. 21B

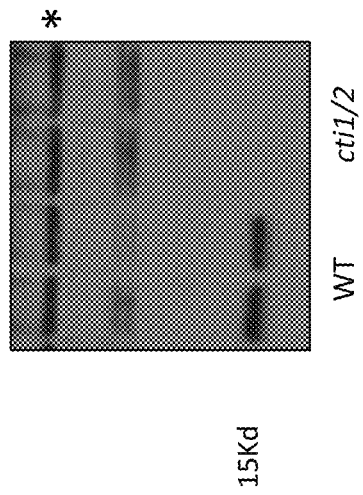

FIG. 26

CTI1
WT  CGGTGCCCTC--GGATGTGTATATGCACCACAGGT
+1C CGGTGCCCTCCGGATGTGTATATGCACCACAGGT
+1G CGGTGCCCTCCGGATGTGTATATGCACCACAGGT

CTI2
WT  AGCAGCCGATGTACTATGACGAAGGCCTAGAGG
-1T AGCAGCCGATG-ACTATGACGAAGGCCTAGAGG

CTI3
WT  TGAAACCATATTCATTCTCGCTCAGCACTGATC
-4  TGAAACCAT----ATTCTCGCTCAGCACTGATC
WT  CGAGTCCGGTTTGATTTCTTGTGAATAGTCAAA
-1T CGAGTCCGGT-TGATTTCTTGTGAATAGTCAAA

FIG. 25

```
Glyma.11g087400.1   ------------------------------------------------------------   0
Glyma.01g157600.1   ------------------------------------------------------------   0
AtCTI1              ------------------------------------------------------------   0
Glyma.06G015800.1   ------------------------------------------------------------   0
Glyma.04g015800.1   MLYLQFFDFCLVGRGRLYKDLCILVSCNFAKLFNITRLLASRLRQKLRLQLDSSIICV     60
Glyma.01g234200     ---------------------------------------------------------MRI    3
Glyma.11g008700.1   ---------------------------------------------------------MRI    3
AtCTI2              ----------------------------------------------------------MR    2
AtCTI3              ---------------------------------------------------------MRS    3

Glyma.11g087400.1   ----------MAILS-SFIAIPKNPKIHFLS---GSS-LIMDKCFLKISSSEHFPGSSLKIK    47
Glyma.01g157600.1   ----------MAILS-SFIITPNPKIHPLS---GSSEHSHDKCFLKISTSGHFIDFSLRRK    48
AtCTI1              ----------MASLSSTSLSLPKS--SEQLRPSSGFSLDPMARCVSVSFGLHSSKLXISAP    50
Glyma.06G015800.1   --MAAVPSIFALIKGALSIHKL--DKSLY----------KIKFYSFSLSLSRLGRMEIS     46
Glyma.04g015800.1   CFYLIEKRLLLQRLLLASSISKV--DESLY----------KIKPTNFSLNLRQSTRQIS    107
Glyma.01g234200     CIAPFS--------VS-GGSHELWL-IKRVG---------PKLIVQRASSIY-I         37
Glyma.11g008700.1   CTAPFS--------VSYGGSHELSS-TKRVG---------PKLSVQRASSIY-I         38
AtCTI2              SLVAAP--------IGFSGDSH--------VQARNFRAIRKSSTLVQIK----S         39
AtCTI3              CIAIAP--------LSLSPVSQSRY-VRANGLSTTKLASICKTSDLTIHKK----S        47

Glyma.11g087400.1   AIRHQPLVIRAGGDGGRPSGGGFVGGFVLGGLIVGALGCLYAPQ----ISRALAGADSK    103
Glyma.01g157600.1   AISHQPLVIRAGGDGGRPGSGSIFVGGFVLGGLIAGALGCLYAPQ----ISRALAGRDSK   104
AtCTI1              RIKGILTIQSRVRDDGGSTGLFVGSFILGGLIVGALGCVYAPQ----ISKALAGADSK    106
Glyma.06G015800.1   LIRRPLTIQRTYSDGGRPSASVFVGGFLLGGLIVGTLGCVYAPQ----ISKAIAGRDRK   101
Glyma.04g015800.1   LIRRPLTIQRTYSDGGRPSKSVFVGSFLLGGLIVGTLGCVYAPQ----ISKALAGADSK   160
Glyma.01g234200     NRHIISSREYRDH-RGGSGDFVASFLLGGRVFGTLAYIFAFQFVRQIRASLLS-EDE     88
Glyma.11g008700.1   NRHIISSQREYRDH-RGGSGDFVASFLLGGRVFGTLAYIFAFQ----IRASLLS-EDE     92
AtCTI2              NRGSKLSVSAGYRGGSKGGSSDPYTGFLLGSAVFGTLAYIFAPQ----IRRSYLS-ENE     93
AtCTI3              NRTRNFSVSAGYRDSGRSGSSGDFIASFLLGGRVFGNVAYIFRFQ----IRASYLNEEDE   103

Glyma.11g087400.1   DLMRKLPKPYDEEKALERTRSVLIEKIAQLNSRIDGVSAQLRPDEDSNEIAINGEEIEA   160
Glyma.01g157600.1   DLMRKLPKPYDEEKALERTRKVLIEKIAQLNSAIDGVSAQLRPDEDSNEIAVSGEEIEI   164
AtCTI1              DLMRKLPKFIYDEEKALEKTRKVLAEKIAQLNSRIDDVSQLRSEDIPNGARLGTDEIEA   166
Glyma.06G015800.1   ELMRKLPKFIYDEEKALEKTRKVLAEKIEQLNRAIDDVSAQLRSEEASNGVRVSGDEIEA   161
Glyma.04g015800.1   ELMRKLPKFIYDEEKALEKTRKVLAEKIEQLNRAIDDVSAQLRSEEASNGVAVSGDEIEA   220
Glyma.01g234200     YGFRKAKSPIYY-DEGLERTRQTLNEKIGQLNSRIDVVSSRLRGSN-------V--PAA   145
Glyma.11g008700.1   YGFRKSKSFIYY-DEGLERTRQTLNEKIGQLNSAIDVVSKLRGSN-------V--PAA   142
AtCTI2              YGFSKPEDPNYY-DEGLEERREILNEKIGQLNSRIDVVSDLRGSRGSSNFSSS-PSV   150
AtCTI3              YGFESPSQFIYY-DEGLERTRETLNEKIGQLNSAIDVVSKLRGRE----KSTSS-LPV   156

Glyma.11g087400.1   SI-----------  165
Glyma.01g157600.1   FISDESEIEVSK   176
AtCTI1              IA-----------  168
Glyma.06G015800.1   AT-----------  163
Glyma.04g015800.1   AT-----------  222
Glyma.01g234200     KIESDPEVEAIH   157
Glyma.11g008700.1   KIESDPEVEAIM   154
AtCTI2              PVEIDAEAEAIA   162
AtCTI3              PVEIDPEVERII   168
```

FIG. 33

>Glyma.06G015800.1

>Glyma.04g015800.1

>Glyma.11g087400.1

>Glyma.01g157600.1

>Glyma.01g234200

>Glyma.11g008700.1

FIG. 40

METHODS OF ALTERING SEED WEIGHT AND SEED OIL CONTENT BY MANIPULATING ALPHA-CARBOXYL-TRANSFERASE (A-CT) ACTIVITY VIA CARBOXYL-TRANSFERASE INTERACTION (CTI) PROTEIN EXPRESSION

CROSS-REFERENCE TO RELATED APPLICATION

This application claims the benefit of U.S. Provisional Application No. 62/678,212 filed May 30, 2018, which is incorporated herein in its entirety.

STATEMENT REGARDING FEDERALLY SPONSORED RESEARCH & DEVELOPMENT

This invention was made with government support under Grant No. IOS-1339385 awarded by National Science Foundation. The government has certain rights in the invention.

INCORPORATION OF SEQUENCE LISTING

A paper copy of the Sequence Listing and a computer readable form of the Sequence Listing containing the file named "31458-39_ST25.txt", which is 122,046 bytes in size (as measured in MICROSOFT WINDOWS® EXPLORER), are herein incorporated by reference. This Sequence Listing consists of SEQ ID NOs:1-92.

BACKGROUND

Vegetable oils are an important renewable source of hydrocarbons for food, energy, and industrial feedstocks. As demand for this commodity increases, discovering ways to enhance oil production in crops will be an agronomic priority. Oil production begins with the de novo fatty acid synthesis (FAS) pathway to generate the acyl chains that are eventually esterified to glycerol to produce triacylglycerol, the major storage lipid in the seed. The committed step of de novo FAS is catalyzed by acetyl-coenzyme A carboxylase (ACCase) which carboxylates acetyl-CoA to form malonyl-CoA in a two-step reaction requiring ATP, bicarbonate, and biotin cofactor. In prokaryotes, and in plastids of most plants, ACCase is a heteromeric complex requiring four distinct subunits: biotin carboxylase (BC), biotin carboxyl carrier protein (BCCP), and α- and β-carboxyl transferases (CT). Graminaceous monocots possess a homomeric form of plastid ACCase where the catalytic components are adjoined in tandem as a single polypeptide. Structural models for the heteromeric ACCase are primarily based on studies in *Escherichia coli*. The *E. coli* ACCase is composed of two subcomplexes: an α/β-CT heterotetramer and a BC/BCCP heterotetramer. The components of the two subcomplexes form stable associations, while the subcomplexes themselves show a relatively weak interaction with one another. This property has contributed to the difficulties in biochemical and structural characterization of heteromeric ACCase from plants. Plastidial ACCase is regulated by light, feedback inhibition, and a 2-oxoglutarate-binding protein PII. It remains unknown if such regulation is mediated by additional proteins, or if other factors are involved, as the plant heteromeric ACCase has never been fully characterized. A comprehensive study of ACCase protein interactions is needed.

Therefore, there is a need to provide a better understanding of protein structure and regulation of ACCase to leverage the potential for manipulating fluxes through this committed and irreversible step for de novo FAS. There is also a need to develop a novel method to efficiently increase ACCase activity to consequently increase fatty acid and, ultimately, triacylglycerol production in plants and algae.

SUMMARY

In one aspect, a method of altering fatty acid and/or triacylglycerol production in plants and/or algae is provided. The method generally includes altering activity levels of alpha-carboxyltransferase (α-CT), a catalytic subunit of acetyl-CoA carboxylase (ACCase).

In another aspect, a method of breeding a plant with increased seed oil content is provided. The method generally includes genetically modifying a first plant line to silence at least one CTI gene encoding at least one CTI protein, crossing the genetically modified first plant line with a second plant line, and obtaining seeds.

In an additional aspect, a method of enhancing an amount of seed oil produced by a seed oil production method is provided. The method generally includes genetically modifying a first plant to silence at least one CTI gene encoding at least one CTI protein and to obtain a first plant line, growing a plurality of seeds from the first plant line to obtain a seed crop, and extracting an enhanced amount of seed oil from the seed crop using the seed oil production method. In this method, the first plant line includes an increased seed oil content.

In another additional method, a method of producing a plant seed with an enhanced fractional protein content is provided. The method includes genetically modifying a first plant to overexpress at least one CTI gene encoding at least one CTI protein and to obtain a first plant line, and growing a plurality of seeds from the first plant line to obtain a seed crop. The seed crop includes the plant seed with the enhanced fractional protein content in comparison to the first plant. In some forms of this method, the first plant line includes a decreased seed oil and/or a decreased fractional protein content.

In another aspect, a modified plant having an altered activity level of alpha-carboxyltransferase (α-CT) in comparison to a wild-type plant of the same species grown under the same conditions is provided. In some forms, the α-CT comprises a catalytic subunit of acetyl-CoA carboxylase (ACCase). In some forms, the modified plant has an altered content of fatty acid and/or triacylglycerol in comparison to a wild-type plant of the same species grown under the same conditions. In some forms, the modified plant is a species selected from the group consisting of *Amborella trichopoda, Arabidopsis lyrata, Arabidopsis alpine, Arabidopsis thaliana, Arachis hypogaea, Auxenochlorella protothecoides, Brassica napus, Brassica rapa, Camelina sativa, Capsella rubella, Cathamus tinctorius, Chlamydomonas reinhardtii, Chlorella variabilis, Cicer arietinum, Citrus clementina, Citrus sinensis, Coccomyxa subellipsoideas C-169, Coffea canephora, Cucumis melo, Cucumis sativus, Cynara cardunculus, Elaeis guineensis, Erythranthe guttata, Eucalyptus grandis, Eutrema salsugineum, Fragaria vesca, Genlisea aurea, Glycine max, Helianthus annuus, Helicosporidium* ATCC50920, *Jatropha curcas, Lotus japonicas, Medicago truncatula, Moms notabilis, Musa acuminate, Nelumbo nucifera, Nicotiana sylvestris, Nicotiana tomentosiformis, Phaseolus vulgaris, Pheonix dactyhfera, Physcomitrella patens, Picea sitchensis, Polytomella parva,*

Populus trichocarpa, Prunus mume, Prunes persica, Pyrus× bretschneideri, Ricinus communis, Selaginella moellendorfli, Sesamum indicum, Solanum lycopersicum, Solanum tuberosum, Theobroma cacao, Thlaspi arvense, Vitis vinifera, and Volvox carteri. In some forms, the activity level of alpha-carboxyltransferase (α-CT) is altered in comparison to a wild type plant of the same species and grown under the same conditions by altering intracellular concentrations of one or more carboxyl transferase interactor (CTI) proteins, wherein the one or more CTI proteins inhibit activity levels of α-CT. In some forms, altering intracellular concentrations of the one or more CTI proteins further comprises altering expression of one or more carboxyl transferase interactor (CTI genes. In some forms, the one or more CTI genes comprise genes and gene orthologs of CTI1, CTI2, and CTI3, or artificial genes containing essential CTI motifs. In some forms, the one or more CTI genes comprise from about 70% to about 100% sequence identity to a nucleotide sequence selected from the group consisting of SEQ ID NOs: 1, 3, 5, and 34-59 or a complement thereof. In some forms, the one or more CTI genes encode a CTI protein with a polypeptide sequence ranging from about 70% to about 100% sequence identity to a polypeptide sequence selected from the group consisting of SEQ ID NOs: 2, 4, 6, 7-33, and 60-92. In some forms, the modified plant has an increased production of fatty acid and/or triacylglycerol. In some forms, the modified plant has an increased activity level of α-CT, and/or a decreased intracellular concentration of the one or more CTI proteins, and/or a decreased expression of the one or more CTI genes. In some forms, expression of the one or more CTI genes is decreased using a gene silencing method selected from the group consisting of antisense, RNAi, CRISPR, TALON, nanobodies, EMS, T-DNA gene knockout, transposon-mediated gene knockout, conventional mutagenesis, and targeted breeding. In some forms, the modified plant further comprises an RNAi cassette. In some forms, the modified plant has a decreased production of fatty acid and/or triacylglycerol. In some forms, the modified plant has a decreased activity level of α-CT, and % or an increased intracellular concentration of the one or more CTI proteins, and/or an increased expression of the one or more CTI genes. In some forms, the modified plant has an insertion of one or more transgenic CTI genes, at least one overexpressed CTI gene, at least one overexpressed transgenic gene, or any combination thereof.

In another aspect, a plant or part thereof is provided. In some forms, the plant is produced by a method described above. In some forms, the plant produces seed comprising increased seed oil content. In some forms, the plant is a species selected from the group consisting of Amborella trichopoda, Arabidopsis lyrata, Arabidopsis alpine, Arabidopsis thaliana, Arachis hypogaea, Auxenochlorella prototothecoides, Brassica napus, Brassica rapa, Camelina sativa, Capsella rubella, Cathamus tinctorius, Chlamydomonas reinhardtii, Chlorella variabilis, Cicer arietinum, Citrus clementina, Citrus sinensis, Coccomyxa subellipsoideas C-169, Coffea canephora, Cucumis melo, Cucumis sativus, Cynara cardunculus, Elaeis guineensis, Erythranthe guttata, Eucalyptus grandis, Eutrema salsugineum, Fragaria vesca, Genlisea aurea, Glycine max, Helianthus annuus, Helicosporidium ATCC50920, Jatropha curcas, Lotus japonicas, Medicago truncatula, Moms notabilis, Musa acuminate, Nelumbo nucifera, Nicotiana sylvestris, Nicotiana tomentosiformis, Phaseolus vulgaris, Pheonix dactyhfera, Physcomitrella patens, Picea sitchensis, Polytomella parva, Populus trichocarpa, Prunus mume, Prunes persica, Pyrus× bretschneideri, Ricinus communis, Selaginella moellendorfli, Sesamum indicum, Solanum lycopersicum, Solanum tuberosum, Theobroma cacao, Thlaspi arvense, Vitis vinfera, and Volvox carteri.

In another aspect, a seed produced by a plant or part thereof as described above is provided. In some forms, the seed comprises increased seed oil content. In some forms, the seed is from a plant species selected from the group consisting of Amborella trichopoda, Arabidopsis lyrata, Arabidopsis alpine, Arabidopsis thaliana, Arachis hypogaea, Auxenochlorella prototothecoides, Brassica napus, Brassica rapa, Camelina sativa, Capsella rubella, Cathamus tinctorius, Chlamydomonas reinhardtii, Chlorella variabilis, Cicer arietinum, Citrus clementina, Citrus sinensis, Coccomyxa subellipsoideas C-169, Coffea canephora, Cucumis melo, Cucumis sativus, Cynara cardunculus, Elaeis guineensis, Erythranthe guttata, Eucalyptus grandis, Eutrema salsugineum, Fragaria vesca, Genlisea aurea, Glycine max, Helianthus annuus, Helicosporidium ATCC50920, Jatropha curcas, Lotus japonicas, Medicago truncatula, Moms notabilis, Musa acuminate, Nelumbo nucifera, Nicotiana sylvestris, Nicotiana tomentosiformis, Phaseolus vulgaris, Pheonix dactyhfera, Physcomitrella patens, Picea sitchensis, Polytomella parva, Populus trichocarpa, Prunus mume, Prunes persica, Pyrus× bretschneideri, Ricinus communis, Selaginella moellendorfli, Sesamum indicum, Solanum lycopersicum, Solanum tuberosum, Theobroma cacao, Thlaspi arvense, Vitis vinifera, and Volvox carteri.

In another aspect, a plant or part thereof produced by a method described above is provided. In some forms, the plant produces seed comprising increased seed oil content. In some forms, the plant is a species selected from the group consisting of Amborella trichopoda, Arabidopsis lyrata, Arabidopsis alpine, Arabidopsis thaliana, Arachis hypogaea, Auxenochlorella prototothecoides, Brassica napus, Brassica rapa, Camelina sativa, Capsella rubella, Cathamus tinctorius, Chlamydomonas reinhardtii, Chlorella variabilis, Cicer arietinum, Citrus clementina, Citrus sinensis, Coccomyxa subellipsoideas C-169, Coffea canephora, Cucumis melo, Cucumis sativus, Cynara cardunculus, Elaeis guineensis, Erythranthe guttata, Eucalyptus grandis, Eutrema salsugineum, Fragaria vesca, Genlisea aurea, Glycine max, Helianthus annuus, Helicosporidium ATCC50920, Jatropha curcas, Lotus japonicas, Medicago truncatula, Moms notabilis, Musa acuminate, Nelumbo nucifera, Nicotiana sylvestris, Nicotiana tomentosiformis, Phaseolus vulgaris, Pheonix dactyhfera, Physcomitrella patens, Picea sitchensis, Polytomella parva, Populus trichocarpa, Prunus mume, Prunes persica, Pyrus× bretschneideri, Ricinus communis, Selaginella moellendorfli, Sesamum indicum, Solanum lycopersicum, Solanum tuberosum, Theobroma cacao, Thlaspi arvense, Vitis vinifera, and Volvox carteri. In some forms, the plant part is selected from the group consisting of a leaf, pollen, an ovule, a fruit, rootstock, a scion, a flower, and a cell.

In another aspect, a seed that produces a plant as described above is provided. In some forms, the seed comprises increased seed oil content.

In another aspect, a tissue culture of regenerable cells of the plant or part thereof as described above is provided.

BRIEF DESCRIPTION OF THE DRAWINGS

The figures described herein below illustrate various aspects of the disclosure.

FIG. 6 summarizes an amino acid sequence alignment of CTI proteins CTI1, CTI2, and CTI3.

FIG. 13 contains a series of images illustrating the localization of *Arabidopsis* CTI and α-CT in *Arabidopsis* protoplasts.

FIG. 14 contains a series of images were taken using 2-week old leaf tissues by confocal microscopy illustrating the subcellular localization of CTI1 in a 35S:CTI1:GFP transgenic plant.

FIG. 21A is a graph summarizing a gene ontology enrichment analysis of co-expressed genes with CTI1; ATTED-II was used for co-expression analysis.

FIG. 21B is a graph summarizing a gene ontology enrichment analysis of co-expressed genes with CTI2; ATTED-II was used for co-expression analysis.

FIG. 25 is a sequence comparison illustrating several CRISPR/Cas9-induced mutation types within the CTI family; the targeted sequences are highlighted in bold, the PAM sequences are underlined, and the mutations are in italics.

FIG. 26 is an image summarizing the results of a Western blot analysis of CTI1 protein expression in CRISPR/Cas9 mutants.

FIG. 33 is an amino acid sequence alignment of various CTI protein homologs from different plant species.

Figure 40:
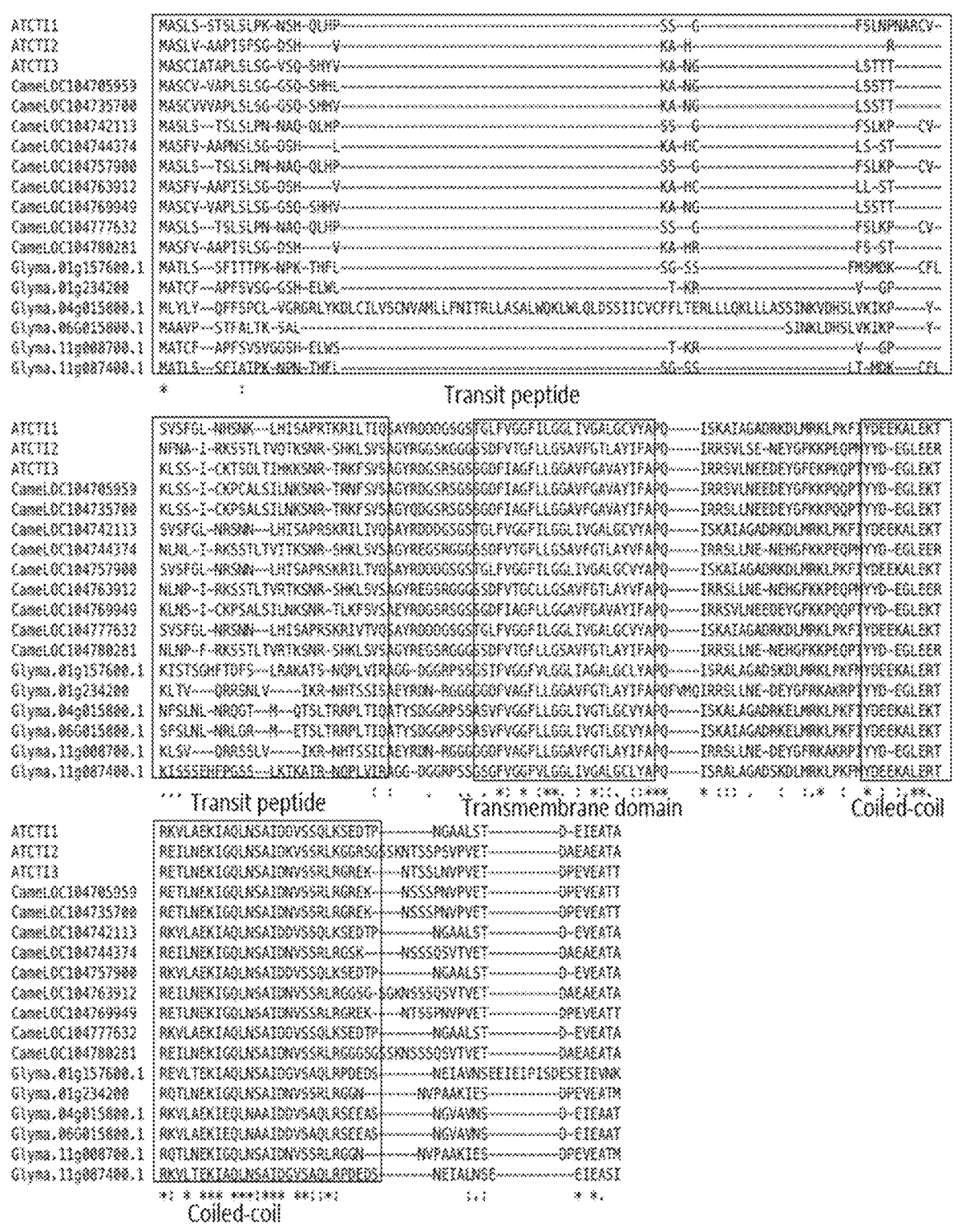

FIG. 40 is an amino acid sequence comparison of CTI proteins and orthologs from various plant species. The tree includes all non-redundant orthologs recovered via PSI-BLAST from the NCBI RefSeq database using *Arabidopsis* CTIs as queries, supplemented with orthologous proteins retrieved via BLAST from in-house Trinity assemblies and from third-party assemblies of various gymnosperms and basal angiosperms. Sequences were initially aligned in MUSCLE (v3.8.425) and the alignment was then refined with MAFFT (v1.3.7), followed by manual removal of redundant and spurious sequences and sequence regions. The final tree was constructed with FastTree (v1.0) using default parameters. Geneious Prime 2018 was used for sequence management and for non-PSI BLAST searches.

DETAILED DESCRIPTION OF THE DISCLOSURE

The present disclosure is directed to methods of modulating fatty acid, and ultimately triacylglycerol, production, as well as protein production, in plants and algae. In various aspects, the disclosed methods comprise altering the activity levels of the committed step for de novo fatty acid biosynthesis, catalyzed by acetyl-CoA carboxylases (ACCase). In various aspects, the disclosed method modulates fatty acid and triacylglycerol production in plants and algae by modulating the expression levels of carboxyltransferase interactor (CTI) proteins that interact with acetyl-CoA carboxylase (ACCase) by down-regulating or up-regulating CTI genes. In particular, the present disclosure is directed to methods of increasing seed oil content by decreasing the expression levels of one or more CTI proteins that inhibit activity of a catalytic subunit of ACCase, alpha-carboxyltransferase (α-CT) by down-regulating one or more CTI genes.

Seed oil biosynthesis is a complex network involving multiple metabolic pathways, and it begins with de novo fatty acid synthesis in the plastid organelle. The first committed step of de novo fatty acid biosynthesis is the carboxylation of acetyl-CoA to form malonyl-CoA, catalyzed by acetyl-CoA carboxylase (ACCase). In most plants, this enzyme is a multisubunit complex comprised of four different catalytic subunits: BCCP, BC, alpha-carboxyltransferase (α-CT), and beta-carboxyltransferase (β-CT). Alpha-carboxyltransferase (α-CT), one of the largest subunits to this complex, contains a large (>30 kDa) non-catalytic domain of unknown function, shown illustrated in FIG. 1. This non-catalytic domain is strongly predicted to have a coiled coil structure, which is typically involved in protein-protein interactions.

Figure 38B:
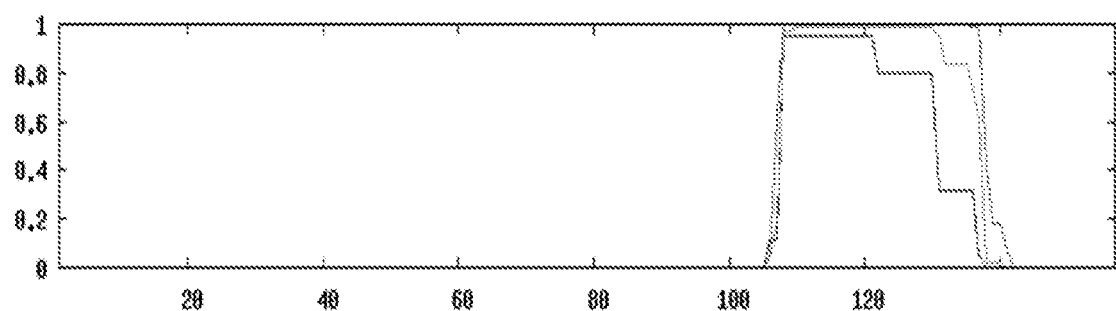
FIG. 38B is a graph summarizing the predicted coiled-coil domain distribution of Glyma.01g234200.
Figure 1:
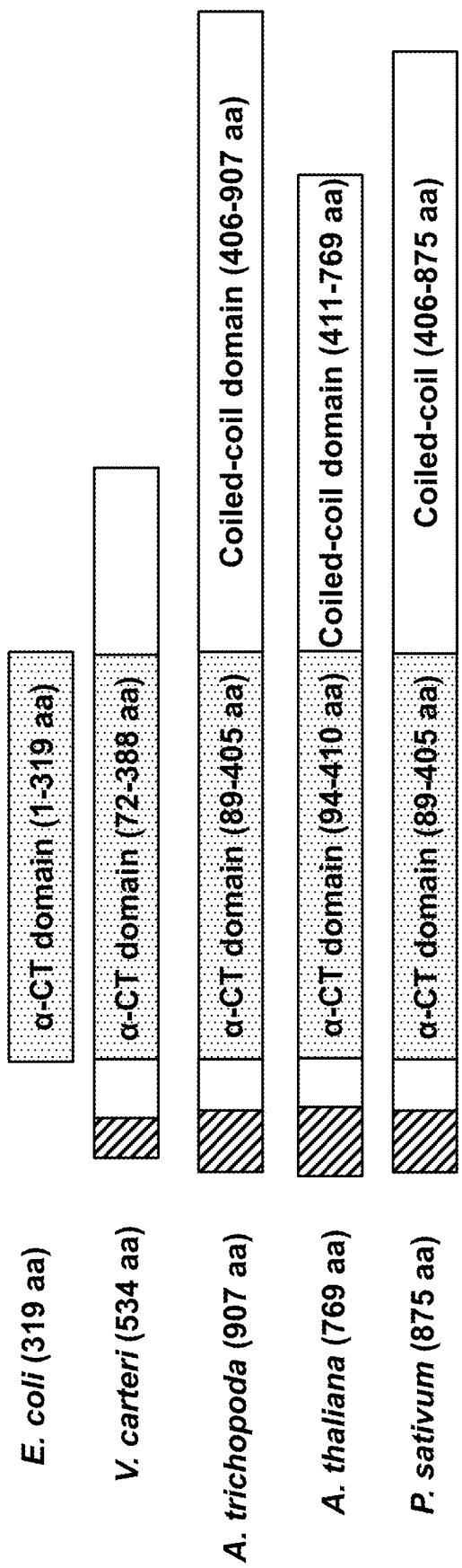
FIG. 1 is a diagrammatic depiction of α-CT protein organization in different plant species.

As illustrated in FIG. 1, the coiled-coil domain of α-CT in higher plants is not present in prokaryotes and green algae. The cross-hatched boxes shown illustrated in FIG. 1 indicate transit peptides as predicted by ChloroP; the stippled boxes indicate α-carboxyltransferase domains for each species, including *E. coli* (*Escherichia coli*), *V. carteri* (*Volvox carteri*), *A. trichopoda* (*Amborella trichopoda*), *A. thaliana* (*Arabidopsis thaliana*), and *P. sativum* (*Pisum sativum*).

The carboxyltransferase interactor (CTI) proteins are a family of three proteins in *Arabidopsis thaliana* of unknown function: CTI1 (also referred to herein as AT1G42960), CTI2 (also referred to herein as AT3G02900) and CTI3 (also referred to herein as AT5G42960). CTI1 was identified as described in detail below using protein-protein interaction assays that included alpha-carboxyltransferase (α-CT) as a capture protein. CTI2 and CTI3 are two homologs of CTI1 in *Arabidopsis*. CTI1, CTI2, and CTI3 are known to localize in the chloroplast inner envelope membrane when transiently expressed in protoplasts and tobacco leaves, and CTI1 is known to co-localize with α-CT in the chloroplast inner membrane.

Figure 22:
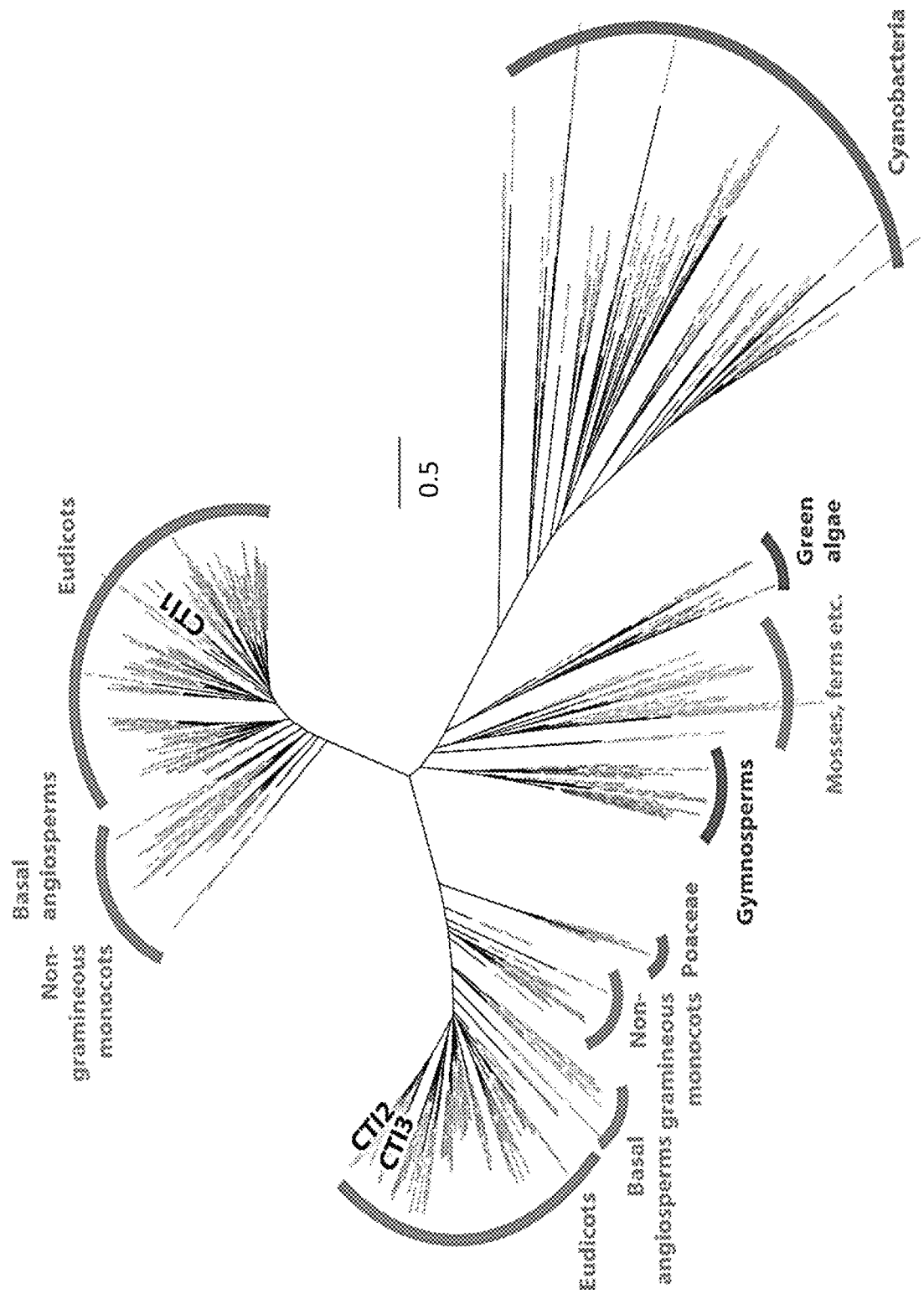
FIG. 22 is an image summarizing the results of a phylogenetic analysis of the CTI protein family.

Based on phylogenetic analysis, illustrated in FIG. 22, the CTI family appears to be of cyanobacterial origin, with the C-terminal domain remaining highly conserved between plants and cyanobacteria (data not shown). While green algae, bryophytes, and gymnosperms generally possess a single CTI, an apparent duplication event in an ancestral angiosperm gave rise to two divergent angiosperm CTI families, one of which includes *Arabidopsis* CTI1, and the other which includes the closely-related *Arabidopsis* CTI2 and 3. The first subfamily is present only in non-gramineous monocots, being apparently absent from those grasses which possess only the homomeric form of ACCase, while the second subfamily is present in some gramineous monocots (though is notably absent from maize).

Figure 5:
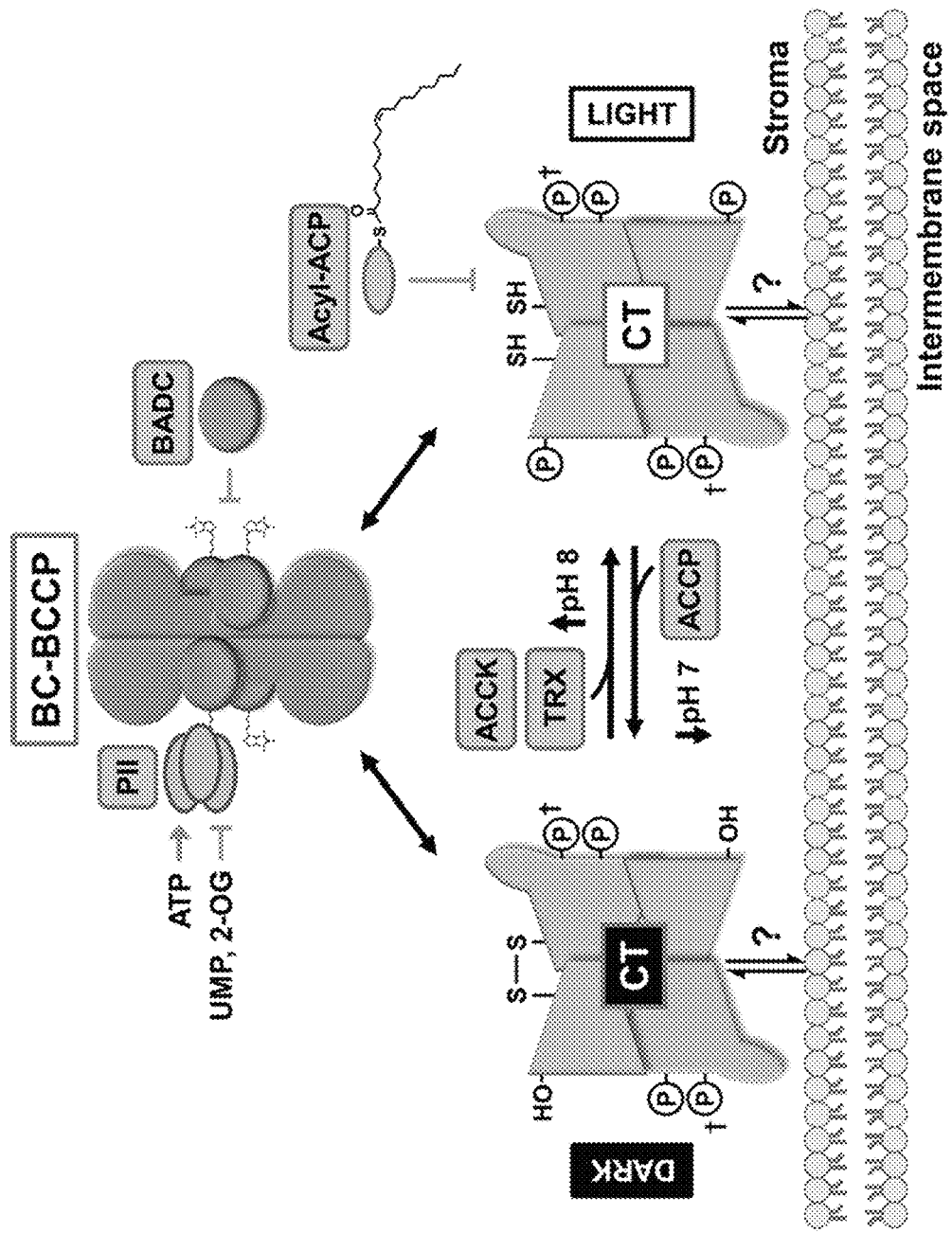
FIG. 5 is a schematic diagram showing components of an ACCase within a chloroplast of a plant.

In various aspects, CTI protein expression has an inhibiting effect on ACCase activity, which in turn affects oil production in plants and algae. The activity of ACCase in catalyzing the committed step of de novo fatty acid synthesis and regulation of flux through this central metabolic pathway is known in the art. In dicot and non-graminaceous monocot plants and algae, plastid ACCase is a heteromeric complex comprised of four catalytic subunits: biotin carboxylase (BC), biotin carboxyl carrier protein (BCCP), α-carboxyltransferase (α-CT) and β-carboxyltransferase (O-CT). The catalytic subunits of a plastid ACCase in one aspect are illustrated schematically in FIG. 5.

Plant ACCase catalyzes the committed step of the de novo fatty acid biosynthesis pathway by converting acetyl-CoA to malonyl-CoA. The observed size of the plant heteromeric ACCase complex is larger than the calculated mass of its known subunits. As illustrated in FIG. 1, the α-CT and β-CT subunits contain large domains of 200 to 300 residues that are not required for catalytic activity, are not present in prokaryotic homologs, and are thought to have no known function. The α-CT and β-CT subunits of the plant ACCase complex associate with the plastid inner envelope through an unknown mechanism. The plant ACCase complex is recalcitrant to conventional purification schemes and hence the structure and composition of the full ACCase assembly is unknown.

As described in detail below, a yeast two-hybrid (Y2H) screen that included the 30 kDa non-catalytic domain of α-CT as bait was used to identify the CTI1 protein, provided herein as SEQ ID NO:2. All three CTI protein isoforms, CTI1, CTI2, and CTI3 (provided herein as SEQ ID NOS:2, 4, and 6, respectively) were observed to interact with α-CT in paired Y2H and BiFC assays, as described in detail below. Further, T-DNA knockdown mutants of CTI2 and CTI3 were characterized as producing seeds with higher seed weight and higher seed oil content as compared to wild type as described in detail below. Overexpression of CTI1 by 35S promoter in wild type plants resulted in a phenotype characterized by curly leaves and tiny plants.

In various aspects, the CTI gene family of inner envelope membrane proteins provides a molecular basis for the previously-observed, tight association of carboxyltransferase with the membrane system of fatty acid synthesis. Without being limited to any particular theory, because most of the fatty acids produced in the plastid by fatty acid synthesis are exported to the cytosol, it is thought that the CTI envelope proteins harmonize the demand of fatty acids in the cytosol with the supply of fatty acids produced in the plastid.

Down-regulating CTI genes (i.e., silencing the expression of CTI proteins) promotes the formation of active ACCase complexes, which in turn increases ACCase activity levels and thus oil production in plants and/or algae. Down-regulating one or more CTI genes may be achieved via various biotechnology or selective breeding approaches as described herein and/or known in the art.

The present disclosure further provides a method of marker-assisted selection as a screening tool for plant and/or algae species that potentially contain higher oil content. The CTI genes are traits that can be monitored to select for specific organisms that may have the potential to produce more triacylglycerol. The expression level of CTI genes may provide a marker used to assist in such selection, wherein organisms with naturally reduced expression of CTI genes may be selected.

Plant oils are an important renewable source of hydrocarbons for food, energy, and industrial feedstocks. Acyl chains stored as triacylglycerol are produced by the de novo fatty acid synthesis (FAS) pathway. The committed step of de novo FAS is catalyzed by the heteromeric acetyl-coenzyme A carboxylase (hetACCase) which carboxylates acetyl-CoA to form malonyl-CoA in a two-step reaction requiring ATP, bicarbonate, and biotin cofactor. In prokaryotes, and in plastids of dicots and non-graminaceous monocots, hetACCase is a heteromeric complex requiring four distinct subunits: biotin carboxylase (BC), biotin carboxyl carrier protein (BCCP), and α- and β-carboxyltransferase (CT). Graminaceous monocots possess a homomeric form of plastid ACCase wherein the catalytic components are fused in tandem as a single polypeptide. Structural models for hetACCase are based on studies of the *Escherichia coli* homolog. The *E. coli* hetACCase is composed of two enzymatic subcomplexes: an α/β-CT heterotetramer and a BC/BCCP heterooctamer. The components of each subcomplex form stable associations while the two subcomplexes themselves show a relatively weak interaction with one another. This property has contributed to the difficulties in biochemical and structural characterization of hetACCase from plants.

Non-limiting examples of plants suitable for modification according to the disclosed methods include: *Amborella trichopoda, Arabidopsis lyrata, Arabidopsis alpine, Arabidopsis thaliana, Arachis hypogaea, Auxenochlorella protothecoides, Brassica napus, Brassica rapa, Camelina sativa, Capsella rubella, Cathamus tinctorius, Chlamydomonas reinhardtii, Chlorella variabilis, Cicer arietinum, Citrus clementina, Citrus sinensis, Coccomyxa subellipsoideas* C-169, *Coffea canephora, Cucumis melo, Cucumis sativus, Cynara cardunculus, Elaeis guineensis, Erythranthe guttata, Eucalyptus grandis, Eutrema salsugineum, Fragaria vesca, Genlisea aurea, Glycine max, Helianthus annuus, Helicosporidium* ATCC50920, *Jatropha curcas, Lotus japonicas, Medicago truncatula, Moms notabilis, Musa acuminate, Nelumbo nucifera, Nicotiana sylvestris, Nicotiana tomentosiformis, Phaseolus vulgaris, Pheonix dactyhfera, Physcomitrella patens, Picea sitchensis, Polytomella parva, Populus trichocarpa, Prunus mume, Prunes persica, Pyrus×bretschneideri, Ricinus communis, Selaginella moellendorfli, Sesamum indicum, Solanum lycopersicum, Solanum tuberosum, Theobroma cacao, Thlaspi arvense, Vitis vinifera,* and *Volvox carteri.*

Non-limiting examples of crop plants suitable for modification according to the disclosed methods include: soybean, canola, rapeseed, *Brassica rapa, Brassica carinata, Brassica juncea,* sunflower, safflower, and oil palm, In some examples the plant is an oilseed crop plant selected from the group consisting of Camelina, penny cress, canola or rapeseed (*Brassica* sp, *Brassica rapa, Brassica carinata, Brassica juncea*), crambe, soybean, sunflower, safflower, oil palm, flax, hemp and cotton.

In various aspects, the method of modulating fatty acid production in plants and algae may include modulating expression levels of various homologs and orthologs of the CTI proteins in other plant species, such as those listed in Table 1, Table 2, and Table 3 below:

TABLE 1

| CTI PROTEIN HOMOLOGS | | |
| --- | --- | --- |
| PROTEIN NAME | SPECIES | DESCRIPTION |
| Aqcoe6G168900 | *A. coerulea* | PTHR34048:SF1 - CHLOROPLAST INNER MEMBRANE LOCALIZED PROTEIN |
| Aco011862 | *A. comosus* | hypothetical protein |
| Aco011922 | *A. comosus* | hypothetical protein |
| Araha.45747s0001 | *A. halleri* | PTHR34048:SF1 - CHLOROPLAST INNER MEMBRANE LOCALIZED PROTEIN |
| AHYPO_020602 | *A. hypochondriacus* | PTHR34048:SF1 - CHLOROPLAST INNER MEMBRANE LOCALIZED PROTEIN |
| AH023756 | *A. hypochondriacus* early-release | PTHR34048:SF1 - CHLOROPLAST INNER MEMBRANE LOCALIZED PROTEIN |
| ALIG51420 | *A. lyrata* | PTHR34048:SF1 - CHLOROPLAST INNER MEMBRANE LOCALIZED PROTEIN |
| Anaoc.0001s1111 | *A. occidentale* early-release | PTHR34048:SF1 - CHLOROPLAST INNER MEMBRANE LOCALIZED PROTEIN |
| Anaoc.0009s0186 | *A. occidentale* early-release | PTHR34048:SF1 - CHLOROPLAST INNER MEMBRANE LOCALIZED PROTEIN |
| evm.TU.AsparagusV1_01.1029 | *A. officinalis* early-release | PTHR34048:SF1 - CHLOROPLAST INNER MEMBRANE LOCALIZED PROTEIN |

TABLE 1-continued

CTI PROTEIN HOMOLOGS

| PROTEIN NAME | SPECIES | DESCRIPTION |
|---|---|---|
| evm.TU.AsparagusV1_07.2326 | *A. officinalis* early-release | PTHR34048:SF1 - CHLOROPLAST INNER MEMBRANE LOCALIZED PROTEIN |
| evm_27.TU.AmTr_v1.0_scaffold00044.100 | *A. trichopoda* | PTHR34048:SF1 - CHLOROPLAST INNER MEMBRANE LOCALIZED PROTEIN |
| Bobra.9_2s0098 | *B. braunii* Showa early-release | |
| Bol033484 | *B. oleracea capitata* | PTHR34048:SF1 - CHLOROPLAST INNER MEMBRANE LOCALIZED PROTEIN |
| Brara.H00538 | *B. rapa* FPsc | PTHR34048:SF1 - CHLOROPLAST INNER MEMBRANE LOCALIZED PROTEIN |
| Bostr.12302s0009 | *B. stricta* | PTHR34048:SF1 - CHLOROPLAST INNER MEMBRANE LOCALIZED PROTEIN |
| evm.TU.Scaffold_214.1022 | *C. arabica* early-release | PTHR34048:SF1 - CHLOROPLAST INNER MEMBRANE LOCALIZED PROTEIN |
| evm.TU.Scaffold_214.1107 | *C. arabica* early-release | PTHR34048:SF1 - CHLOROPLAST INNER MEMBRANE LOCALIZED PROTEIN |
| Ca_04815 | *C. arietinum* early-release | PTHR34048:SF1 - CHLOROPLAST INNER MEMBRANE LOCALIZED PROTEIN |
| Ciclev10002493m.g | *C. clementina* | PTHR34048:SF1 - CHLOROPLAST INNER MEMBRANE LOCALIZED PROTEIN |
| Cagra.0257s0003 | *C. grandiflora* | PTHR34048:SF1 - CHLOROPLAST INNER MEMBRANE LOCALIZED PROTEIN |
| evm.TU.supercontig_6.356 | *C. papaya* | PTHR34048:SF1 - CHLOROPLAST INNER MEMBRANE LOCALIZED PROTEIN |
| AUR62035152 | *C. quinoa* early-release | Protein of unknown function |
| Cre06.g278195 | *C. reinhardtii* | |
| Carubv10010392m.g | *C. rubella* | PTHR34048:SF1 - CHLOROPLAST INNER MEMBRANE LOCALIZED PROTEIN |
| Cucsa.272300 | *C. sativus* | PTHR34048:SF1 - CHLOROPLAST INNER MEMBRANE LOCALIZED PROTEIN |
| orange1.1g030572m.g | *C. sinensis* | PTHR34048:SF1 - CHLOROPLAST INNER MEMBRANE LOCALIZED PROTEIN |
| estExt_Genemark1.C_60275 | *C. subellipsoidea* C-169 | |
| DCAR_009862 | *D. carota* | hypothetical protein |
| Eucgr.F03576 | *E. grandis* | PTHR34048:SF1 - CHLOROPLAST INNER MEMBRANE LOCALIZED PROTEIN |
| Thhalv10005036m.g | *E. salsugineum* | PTHR34048:SF1 - CHLOROPLAST INNER MEMBRANE LOCALIZED PROTEIN |
| gene13024-v1.0-hybrid | *F. vesca* | PTHR34048:SF1 - CHLOROPLAST INNER MEMBRANE LOCALIZED PROTEIN |
| Gohir.A01G102900 | *G. hirsutum* early-release | PTHR34048:SF1 - CHLOROPLAST INNER MEMBRANE LOCALIZED PROTEIN |
| Gohir.A02G085600 | *G. hirsutum* early-release | PTHR34048:SF1 - CHLOROPLAST INNER MEMBRANE LOCALIZED PROTEIN |
| Gohir.D01G088200 | *G. hirsutum* early-release | PTHR34048:SF1 - CHLOROPLAST INNER MEMBRANE LOCALIZED PROTEIN |
| Gohir.D02G101300 | *G. hirsutum* early-release | PTHR34048:SF1 - CHLOROPLAST INNER MEMBRANE LOCALIZED PROTEIN |
| Glyma.04G015800 | *G. max* | PTHR34048:SF1 - CHLOROPLAST INNER MEMBRANE LOCALIZED PROTEIN |

TABLE 1-continued

| CTI PROTEIN HOMOLOGS | | |
|---|---|---|
| PROTEIN NAME | SPECIES | DESCRIPTION |
| Glyma.06G015800 | G. max | PTHR34048:SF1 - CHLOROPLAST INNER MEMBRANE LOCALIZED PROTEIN |
| Gorai.002G113900 | G. raimondii | PTHR34048:SF1 - CHLOROPLAST INNER MEMBRANE LOCALIZED PROTEIN |
| Gorai.005G114700 | G. raimondii | PTHR34048:SF1 - CHLOROPLAST INNER MEMBRANE LOCALIZED PROTEIN |
| HanXRQChr16g0531981 | H. annuus early-release | Uncharacterized protein, conserved in plant genome(s), supported by expression data |
| Kaladp0008s0099 | K. fedtschenkoi | PTHR34048:SF1 - CHLOROPLAST INNER MEMBRANE LOCALIZED PROTEIN |
| Kalax.0128s0039 | K. laxiflora | PTHR34048:SF1 - CHLOROPLAST INNER MEMBRANE LOCALIZED PROTEIN |
| Kalax.0463s0025 | K. laxiflora | PTHR34048:SF1 - CHLOROPLAST INNER MEMBRANE LOCALIZED PROTEIN |
| Lsat_1_v5_gn_3_69860 | L. sativa early-release | |
| Lus10012242.g | L. usitatissimum | PTHR34048:SF1 - CHLOROPLAST INNER MEMBRANE LOCALIZED PROTEIN |
| Lus10016034.g | L. usitatissimum | PTHR34048:SF1 - CHLOROPLAST INNER MEMBRANE LOCALIZED PROTEIN |
| GSMUA_Achr1G17970_001 | M. acuminata | PTHR34048:SF1 - CHLOROPLAST INNER MEMBRANE LOCALIZED PROTEIN |
| GSMUA_Achr7G04040_001 | M. acuminata | PTHR34048:SF1 - CHLOROPLAST INNER MEMBRANE LOCALIZED PROTEIN |
| MDP0000318692 | M. domestica | 1.2.1.13 - Glyceraldehyde-3-phosphate dehydrogenase (NADP(+)) (phosphorylating)/Triosephosphate dehydrogenase (NADP+) |
| Manes.05G125300 | M. esculenta | PTHR34048:SF1 - CHLOROPLAST INNER MEMBRANE LOCALIZED PROTEIN |
| Manes.18G003200 | M. esculenta | PTHR34048:SF1 - CHLOROPLAST INNER MEMBRANE LOCALIZED PROTEIN |
| Migut.N02975 | M. guttatus | PTHR34048:SF1 - CHLOROPLAST INNER MEMBRANE LOCALIZED PROTEIN |
| Medtr3g115930 | M. truncatula | PTHR34048:SF1 - CHLOROPLAST INNER MEMBRANE LOCALIZED PROTEIN |
| Oeu012538.2 | O. europaea early-release | PTHR34048:SF1 - CHLOROPLAST INNER MEMBRANE LOCALIZED PROTEIN |
| Podel.07G072300 | P. deltoides WV94 early-release | |
| Prupe.5G007900 | P. persica | PTHR34048:SF1 - CHLOROPLAST INNER MEMBRANE LOCALIZED PROTEIN |
| Potri.007G064100 | P. trichocarpa | |
| Potri.007G064100 | P. trichocarpa early-release | |
| Phvul.009G006700 | P. vulgaris | PTHR34048:SF1 - CHLOROPLAST INNER MEMBRANE LOCALIZED PROTEIN |
| 30170.t000124 | R. communis | conserved hypothetical protein |
| Sobic.006G197300 | S. bicolor | |
| Solyc04g082640.2 | S. lycopersicum | PTHR34048:SF1 - CHLOROPLAST INNER MEMBRANE LOCALIZED PROTEIN |
| Solyc12g094630.1 | S. lycopersicum | PTHR34048:SF1 - CHLOROPLAST INNER MEMBRANE LOCALIZED PROTEIN |
| Spipo16G0025700 | S. polyrhiza | PTHR34048:SF1 - CHLOROPLAST INNER MEMBRANE LOCALIZED PROTEIN |

TABLE 1-continued

CTI PROTEIN HOMOLOGS

| PROTEIN NAME | SPECIES | DESCRIPTION |
| --- | --- | --- |
| Spipo1G0054000 | *S. polyrhiza* | PTHR34048:SF1 - CHLOROPLAST INNER MEMBRANE LOCALIZED PROTEIN |
| SapurV1A.0085s0280 | *S. purpurea* | transmembrane protein, putative |
| SapurV1A.0266s0200 | *S. purpurea* | transmembrane protein, putative |
| SapurV1A.1516s0010 | *S. purpurea* | transmembrane protein, putative |
| PGSC0003DMG400009993 | *S. tuberosum* | Conserved gene of unknown function |
| PGSC0003DMG400029407 | *S. tuberosum* | Conserved gene of unknown function |
| Thecc1EG034426 | *T. cacao* | Localized to the inner membrane of the chloroplast (65% P) |
| Tp57577_TGAC_v2_gene38097 | *T. pratense* | PTHR34048:SF1 - CHLOROPLAST INNER MEMBRANE LOCALIZED PROTEIN |
| Vocar.0002s0256 | *V. carteri* | |
| Vigun09g262000 | *V. unguiculata* early-release | PTHR34048:SF1 - CHLOROPLAST INNER MEMBRANE LOCALIZED PROTEIN |
| GSVIVG01013404001 | *V. vinifera* | PTHR34048:SF1 - CHLOROPLAST INNER MEMBRANE LOCALIZED PROTEIN |
| Zosma16g00870 | *Z. marina* | Unknown protein |

TABLE 2

CTI PROTEIN/DNA HOMOLOGS AND ORTHOLOGS

| Protein name | Organism | SEQ ID NO: | Sequence |
| --- | --- | --- | --- |
| AT1G42960 Inner membrane localized protein | Arabidopsis thaliana | 1 | ttgtaataaatatttaaataaataattaccactgaatcgaagaagctttgcttagatat catcgaacttgctccaactgctctatctcaggatctctctcagacacagtttcttcc atccatggcgtctctttcttctacctctctctctctcccaagaattctcaccaactcc atccttcatctggtaataacttcttcaatctctccaatcttcgtgctttatagatttcaa tatcctccattttcgagctcatgagattcgtacagtcatgttacgatttctaatttagc atctcacaaaacccaatttaattgtgtattggacgatcttgattcctttatgttgttgg gtcctttcttttacttgtgctgatttgtcaaaacaatgcaaaattagagcttgaagct gttttgttagaaaactgttcaacttgttatgtataagtcactgattgttgtttgttcttgt accttctaggttttttctctgaatccaaatgctcgttgtgtcagtgtttcatttggactg aatcactccaacaaacttcatatttctgctcctagaaccaaaaggatcctaaccatt caatctgcatacaggtatataactttatcttatacaaattattgtttgagatgtcgaaa actgtggttcttgttactccttaatgttttgtgagcatcgtaacatttttagtatactta gttttctattggcaacttatgtttacagagacagtttgcaatgtctaatagcatcaaa acttgcagagatgatgatggttcaggcagcacaggcctattcgtcggagggttta ttttgggcggacttatagtcggtgccctcggatgtgtatatgcaccacaggtagta atctgttacatggtttagtttgatcactcttagagcttgtattcgtttcaatcaagaagt tcttgagtggactcgaggagctctgtaaccttctctgtttcactttgactcatcaatg tgtgatgttacttttgtgaattgtatcagatcagcaaggctatagctggagcagac cgaaaggatctcatgaggaagttgcctaaattcatatatgacgaggaaaaagctt tggaggtaagttattgctaagcctcttgattcatattttatctcacttttttgttgaattta cttatgaacaatgttgtctactgttaatgcagaaaacacgtaaggtactagctgag aaaattgctcagcttaactctgctatcgacgatgtcctctcagctcaaatcagaa gatactccgaatggtgcagctctaagcaccgatgaaatcgaggctacagcctga aatcatctgtttttaggatttgaaattgaatcatgggagattacttactatgatcccaa taattgttttccttctgtgtaatgttgtacaacttttcgtctactatcttcaaatgactg cttctcttccttcttctttttttctcgaaatcgcggtgttgaaggatatatcacagttat gcgaaaccagacgttatgaagactatataatatcctg |
| AT1G42960 Inner membrane localized protein | Arabidopsis thaliana | 2 | MASLSSTSLSLPKNSHQLHPSSGFSLNPNARCVSVS FGLNHSNKLHISAPRTKRILTIQSAYRDDDGSGSTG LFVGGFILGGLIVGALGCVYAPQISKAIAGADRKD LMRKLPKFIYDEEKALEKTRKVLAEKIAQLNSAID DVSSQLKSEDTPNGAALSTDEIEAT |
| AT3G02900 Inner membrane localized protein | Arabidopsis thaliana | 3 | gagtgtattttgggaaataagtaactcttaagggatatgttttagaaaatagataac tcttctggtggacaaatggcgtatgtgttcgtcttcctcttgtatgttactcttctcag atctcttgttcgttttgatgtacaatggcgtccttggtagcagctcctatctcttttctca ggtagtcaatcgctttttctccttctccagttttcagttcattgcttcctctatcttcttcg ttttgaactcaaatttctgagtaacccgagagagaaagattcgccgatttgcatttg cttactcattcaaatttatcctcgtatcttcgattagtattcaaaatttccgttaggtatt taacattttagcgagatcatagtttgttcatagtctgaaactagttcaacatatagca aatcgacgtaaaggaaatacgaaaatccactgatataacggaccaacatatgatt |

TABLE 2-continued

CTI PROTEIN/DNA HOMOLOGS AND ORTHOLOGS

| Protein name | Organism | SEQ ID NO: | Sequence |
|---|---|---|---|
| | | | agagacctgtgtatttgagggtttctccatatctcgttagattactttatatatgaaaa<br>ctcacttgcattttcagagtttactcaaactgaaccaaagcagcttcttgattcaca<br>ccttatggctcaggtgactctcatgtcaaagcacaccgaaacttcaatgcgattc<br>gcaagagctctacattgactgttcaaacaaaatcaaaccgcagtcacaaactctc<br>ggtttctgcaggttaccggtatatttctctctctgtatatatataggccattaaacc<br>tcttctaggttacatttgacagttttactgtgttgattattgcagtggggaagtaag<br>ggtggtggaagtagtgattttgttaccggttttcttctaggaagtgctgtgttcgga<br>actctggcttatatctttgctccacaggtacattcttaaaaaaccatttcattgtttcta<br>taacagaaaactagacatagattatgattttggctttagatcttttaccaactcccttc<br>accttgttatgatttagttgatttcgagctttgtccttcttgaaatcaacaacattaac<br>aacaaactacggttatctattcaattctaacatatcttatgttggcttaaggcatactt<br>agagctgtttattcttggttttatttcttcctctaagatctctgagctttgttcttcctaat<br>gattaagtaattctgagttttgttcttggagggattaaaagattttgagctttgcttttc<br>caaatgattaagtactaattctgacctttgttcttgaggtgattaaatgattctgagct<br>tgttcttgcaaatgaaatcaccaacattaacaatataaattcttaagttgactttgct<br>ttccgagcttgggatgatattctcatgtgatctcttacttccacatgctgtcatgctttt<br>tttattcagatccgaagatcagtgctgagcgagaatgaatatggtttcaagaaacc<br>ggagcagccgatgtactatgacgaaggcctagaggtataaaagaaaaacttag<br>taccgaaattgttaaaaatactaaaactaagacacaaatatgggtttgatgtttata<br>acaggagagaagagagagatattgaatgagaaaatcggccaactcaattccgcca<br>ttgacaaggtttcgtcgcgtctgaaaggaggtcgaagcggtagcagcaagaac<br>acttcttcgccgtctgtcccagttgaaaccgacgcagaagcagaagctactgcat<br>gattgaatgtaatgctctgctccattttaccaattcaaaactgccttccattggttctg<br>tggttttttttgttggaactattcctaggggcttttctgacttttagatattgaaagaaaa<br>agacaatcgtcgtattaactcgtaccgaaccaaaacaaaactatctatactaaga<br>gaacacgatacgaaatcttaatctttcaatattgataatgtcaataagataaatgca<br>aattctaaat |
| AT3G02<br>900<br>Inner<br>membrane<br>localized<br>protein | Arabidopsis<br>thaliana | 4 | MCSSSSCMLLFSDLLFVLMYNGVLAHRNFNAIRKS<br>STLTVQTKSNRSHKLSVSAGYRGGSKGGGSSDFVT<br>GFLLGSAVFGTLAYIFAPQIRRSVLSENEYGFKKPE<br>QPMYYDEGLEERREILNEKIGQLNSAIDKVSSRLK<br>GGRSGSSKNTSSPSVPVETDAEAEATA |
| AT5G16<br>660.1<br>Inner<br>membrane<br>localized<br>protein | Arabidopsis<br>thaliana | 5 | ATTTCATCTGTCTCCACTTCTCTATAGTTGATTAC<br>AATCTGGTTAACATGTGATATTATTTGAAGAAAT<br>TTGTTCATCCAAGTAGTAATCAACTATTTGTAGT<br>CATTTGGTAAAAGATCAATTGGAGCTGTGTCGT<br>ACTCTGTCGTCCGGTCGGTAACTGAGCAAATAA<br>TAAGAACGAGGGTAGAATAGTAAATTTATATAT<br>AGTTTTCCCAAGCAAGGAGAAGAAGATATACAT<br>AGTATATCCAAAAAAAAAAAACATGTCTACATA<br>TTCTTCTTCTAGCTCAGATCTCTCTTTTGTTCGTC<br>TTCAGTTCCAATGGCGTCGTGTATTGCTACTGCT<br>CCTCTTTCTCTATCTGGTAATCGATCCTCCTTTTA<br>GCTTCACCTCGATCCTTAATTTCTCTACCTACTA<br>AGCTCCTTTTTGTTTCCTCCTGAATTTTCAAATTG<br>CTCCGTCTTTACTAGAATTTCATCGTCGAAGTTT<br>CAGATTGATTGAATTTCATTTGATTTTGTACAAT<br>TCGGTAGCGTTTTAATCAGTATGGAGACACTTGT<br>TAATTTGATCGTTGCATCGTTCCTCTATAAATTA<br>GGCTTATTTTCTAGCTTAGGTAAAATAAAATTGA<br>GATCAAAATCAATTCCTTATTTGCGAAGAATTAT<br>AGATAGCTATAGAGTAAGCAACTGAACAAACTC<br>TAGCTGCTATTGAGCTCTACTTTGTGATTTGTAA<br>GAAATTTCAAGAGAGATTCATATTAGCAAGCTT<br>CTTGAATCTGTGGTTTTACAGGCGTGTCTCAATC<br>TCATTATGTGAAAGCTAATGGATTGTCTACAACA<br>ACAAAACTCAGTTCTATTTGTAAAACCTCTGATT<br>TGACTATTCACAAGAAATCAAACCGGACTCGCA<br>AGTTTTCTGTTTCTGCAGGGTATCGGTATGTATG<br>TATGCATTTCGTTCGCTATAGCGTTCTCTCTTCTA<br>TTGAATTGACTTAAAATTGTTGAAACTTAATTCA<br>GAGATGGAAGTAGAAGCGGAAGCAGTGGTGATT<br>TCATTGCTGGTTTTCTTCTAGGAGGTGCTGTCTTT<br>GGCGCTGTTGCTTATATCTTTGCTCCACAGGTAA<br>TGATGATGTTACTCTTTAGAAACCTAAATGGGA<br>ATTAGACATTATCTCATGGTTTTGG<br>TTTATGTTACTGACTGTTTTGATCTAGTCTTTTGA<br>AATGATGAGTAGACTGTGCTTTTGTTCCCTACTT<br>ATGCACATTCCACTGCCTAAAACAGACAGTATC<br>TTTGTTGTTCTCATTACTGCTTCGTTGGTTCTATT<br>TTGATTGGTTCTTGGAGCTTTGGATGATATAACT |

TABLE 2-continued

CTI PROTEIN/DNA HOMOLOGS AND ORTHOLOGS

| Protein name | Organism | SEQ ID NO: | Sequence |
|---|---|---|---|
| | | | GTTTATCTTTCTCATGCAATCTAAAAAGCTGATG GTTATGATTATTCTTGTGTTGTGGTGATTTAGAT CCGAAGATCGGTTCTAAATGAAGAAGACGAGTA CGGTTTTGAGAAGCCGAAACAGCCAACGTACTA CGATGAAGGTTTAGAGAAAACAAGAGAGACACT GAATGAGAAAATAGGACAACTTAATTCAGCGAT AGACAATGTCTCTTCGCGTTTACGAGGTCGAGA AAAGAACACTTCTTCCCTAAATGTACCGGTCGA AACTGACCCAGAGGTTGAAGCTACGACTTGAAG GAAGAAACAAACAGCTTTCTTCTTCTGTGTTTCA TTTGTAAACTAGAGTTAAAAAACCATTACTTATA TGTTTGATTTGGTTCTTTTCTTTCTGGTTTGCCTT TGTGCTCAGTCCTTAGTAGAAAGAACTCTTGCAA AGTGAAATGTATACGTCTTTTGGTTTTAGTGTGA ATTTGGTTCAATTTAATTCGAAAAAATCTTTGTT CTCTTAGTAATATATTG |
| AT5G16 660.1 Inner membrane localized protein | Arabidopsis thaliana | 6 | MASCIATAPLSLSGVSQSHYVKANGLSTTTKLSSIC KTSDLTIHKKSNRTRKFSVSAGYRDGSRSGSSGDFI AGFLLGGAVFGAVAYIFAPQIRRSVLNEEDEYGFE KPKQPTYYDEGLEKTRETLNEKIGQLNSAIDNVSS RLRGREKNTSSLNVPVETDPEVEATT |
| CsCTI1-1 XP_010 478984.1 | Camelina sativa | 7 | MASLSTSLSLPNNAQQLHPSSGFSLKPCVSVSFGLN RSNNLHISAPRSKRILTVQSAYRDDDGSGSTGLFV GGFILGGLIVGALGCVYAPQISKAIAGADRKDLMR KLPKFIYDEEKALEKTRKVLAEKIAQLNSAIDDVSS QLKSEDTPNGAALSTDEVEATA |
| CsCTI1-2 XP_010 461388.1 | Camelina sativa | 8 | MASLSTSLSLPNNAQQLHPSSGFSLKPCVSVSFGLN RSNNLHISAPRSKRILIVQSAYRDDDGSGSTGLFVG GFILGGLIVGALGCVYAPQISKAIAGADRKDLMRK LPKFIYDEEKALEKTRKVLAEKIAQLNSAIDDVSSQ LKSEDTPNGAALSTDEVEATA |
| CsCTI1-3 XP_010 500214.1 | Camelina sativa | 9 | MASLSTSLSLPNNAQQLHPSSGFSLKPCVSVSFGLN RSNNLHISAPRSKRIVTVQSAYRDDDGSGSTGLFV GGFILGGLIVGALGCVYAPQISKAIAGADRKDLMR KLPKFIYDEEKALEKTRKVLAEKIAQLNSAIDDVSS QLKSEDTPNGAALSTDEVEATA |
| CsCTI2-1 XP_010 463722.1 | Camelina sativa | 10 | MASFVAAPNSLSGDSHLKAHCLSSTNLNLIRKSST LTVITKSNRSHKLSVSAGYREGSRGGGSSDFVTGF LLGSAVFGTLAYVFAPQIRRSLLNENEHGFKKPEQ PMYYDEGLEERREILNEKIGQLNSAIDNVSSRLRGS KNSSSQSVTVETDAEAEATA |
| CsCTI2-2 XP_010 485620.1 | Camelina sativa | 11 | MASFVAAPISLSGDSHVKAHCLLSTNLNPIRKSSTL TVRTKSNRSHKLSVSAGYREGSRGGGSSDFVTGCL LGSAVFGTLAYVFAPQIRRSLLNENEHGFKKPEQP MYYDEGLEERREILNEKIGQLNSAIDNVSSRLRGG SGSGKNSSSQSVTVETDAEAEATA |
| LOC110 915823 | Helianthus annuus | 93 | MVAESPIYVNYQFYPSSPTLLCYILHCLAVCFLTHF TLDLSLQSLLMATTTIISPASISVRTSLKGHDSLSGN SSFYGKTALTLQKKSNQQRALKKLATCAQYNDRS GGGGGDFVAGFLLGGALCGTLAYIFAPQIRRSLLN EDEYGFRRAKRPIYYDEGLEKTRQTLNAKISQLNS AIDNVSSRLRGGNNMPPVPVETDPEEATM |
| CsCTI2-3 XP_010 503115.1 | Camelina sativa | 13 | MASFVAAPISLSGDSHVKAHRFSSTNLNPFRKSSTL TVRTKSNRSHKLSVSAGYREGSRGGGSSDFVTGFL LGSAVFGTLAYIFAPQIRRSLLNENEHGFKKPEQPI YYDEGLEERREILNEKIGQLNSAIDNVSSRLRGGGS GSSKNSSSQSVTVETDAEAEATA |
| CsCTI3-1 XP_010 453829.1 | Camelina sativa | 14 | MASCVVAPLSLSGGSQSHHVKANGLSSTTKLSSI CKPSALSILNKSNRTRKFSVSAGYQDGSRSGSSGDF IAGFLLGGAVFGAVAYIFAPQIRRSLLNEEDEYGFK KPQQPTYYDEGLEKTRETLNEKIGQLNSAIDNVSS RLRGREKNSSSPNVPVETDPEVEATT |

TABLE 2-continued

CTI PROTEIN/DNA HOMOLOGS AND ORTHOLOGS

| Protein name | Organism | SEQ ID NO: | Sequence |
|---|---|---|---|
| CsCTI3-2 XP_010 420368.1 | *Camelina sativa* | 15 | MASCVVAPLSLSGGSQSHHLKANGLSSTTKLSSIC KPCALSILNKSNRTRNFSVSAGYRDGSRSGSSGDFI AGFLLGGAVFGAVAYIFAPQIRRSVLNEEDEYGFK KPQQPTYYDEGLEKTRETLNEKIGQLNSAIDNVSS RLRGREKNSSSPNVPVETDPEVEATT |
| CsCTI3-3 XP_010 492580.1 | *Camelina sativa* | 16 | MASCVVAPLSLSGGSQSHHVKANGLSSTTKLNSIC KPSALSILNKSNRTLKFSVSAEYRDGSRSGSSGDFI AGFLLGGAVFGAVAYIFAPQIRRSVLNEEDEYGFK KPQQPTYYDEGLEKTRETLNEKIGQLNSAIDNVSS RLRGREKNTSSPNVPVETDPEVEATT |
| Bna-CTI1-1 BnaA08 g04600 D | *Brassica napus* | 17 | MAALSTSLSLSRNTQQLHPSSGFSLKPIGRRANVSF GLNPSKKIQLSAPSGKRILTIQSAYRDDDSSGSTGL FVGGFILGGLIVGALGCVYAPQISKAIAGADRKLM RKLPKFIYDEEKALEKTRKVLADKIAQLNSAIDD VSSQLKSEDTPNGAALSTDEVEATA |
| Bna-CTI1-2 BnaC08 g46940 D | *Brassica napus* | 18 | MAALSTSLSLSRNTQQLHPSSGFSLKPIARRANVSF GLNPSKKIQLSAPRGKRILTIPSAYRDDDSSGSTGLF VGGFILGGLIVGALGCVYAPQISKAIAGADRKDLM RKLPKFIYDEEKALEKTRKVLADKIAQLNSAIDDV SSQLKSEDTPNGAALSTDEVEATA |
| Bna-CTI3-1 BnaA10 g17830 D | *Brassica napus* | 19 | MASSCVANLSLSGVSQSHYVKANGLSTAKLNSICK TSALSIQKRSNRSRKFSVSAEYGSRRGSGGGDFVA GFLLGGALFGAAAYIFAPQIRRSIMSEEDEYGFKKP DQPSYYDEGLEKTRETLNEKIGQLNSAIDNVSSRL RGRAKKTSSPVETDPEVEATT |
| Bna-CTI3-2 BnaA03 g06140 D | *Brassica napus* | 20 | MASCVAHLSLSSGSQSHLVKANGLSTTKLSSICKT SALTVQKKSSQGRKFSVSARYGDEGSRRASGGGD FIAGFLLGGAVFGAVAYIFAPQIRRSIMSEEDEYGF KKPQQPTYYDEGLEKTRETLNKKIEQLNSAIDNVS SRLRGREKNTSSPNVPVETDPEVEATT |
| Bna-CTI3-3 BnaC09 g41220 D | *Brassica napus* | 21 | MASCVAHLSLSGVSQSHYVKANGLSTTSKLNSIC KTSALSIQKRSNRSRKFSVSAEYGSRRGGGDFVAG FLLGGALFGAAAYIFAPQIRRSIMSEEDEYGFKKPE QPSYYDEGLEKTRETLNEKIGQLNSAIDNVSSRLR GREKKTSSPVQTDPEVEATT |
| Bna-CTI3-4 BnaC03 g07880 D | *Brassica napus* | 22 | MASCVAHLSLSVLVSGGKGGSQSHHVKANGLSAK KLSSICKTSVLTVQKKSSRSGKFSVSARDEGSKRGS GGGGDFIAGFLLGGAVFGAVAYIFAPQIRRIIMSEE DEYGFNKPQQPTYYDEGLEKTRETLNKKIEQLNSA IDNVSSRLRGREKNTSSPNVPVETDPEVEATT |
| ZS11-CTI1-1 BnA08g 0321320.1 | *Brassica napus* | 23 | MAALSTSLSLSRNTQQLHPSSGFSLKPIGRRANVSF GLNPSKQIQLSAPRGKRILTIQSAYRDDDSSGSTGL FVGGFILGGLIVGALGCVYAPQISKAIAGADRKDL MRKLPKFIYDEEKALEKTRKVLADKIAQLNSAIDD VSSQLKSEDTPNGAALSTDEVEATA |
| ZS11-CTI1-2 BnC08g 0883900.1 | *Brassica napus* | 24 | MAALSTSLSLSRNTQQLHPSSGFSLKPIARRANVSF GLNPSKKIQLSAPRGKRILTIQSAYRDDDSSGSTGLF VGGFILGGLIVGALGCVYAPQISKAIAGADRKDL MRKLPKFIYDEEKALEKTRKVLADKIAQLNSAIDD VSSQLKSEDTPNGAALSTDEVEATA |
| ZS11-CTI3-1 BnA10g 0411990.1 | *Brassica napus* | 25 | MASSCVANLSLSGVSQSHYVKANGLSTAKLNSICK TSALSIQKRSNRSRKFSVSAEYGSRRGSGGGDFVA GFLLGGALFGAAAYIFAPQIRRSIMSEEDEYGFKKP DQPSYYDEGLEKTRETLNEKIGQLNSAIDNVSSRL RGRAKKTSSPVETDPEVEATT |
| ZS11-CTI3-2 BnA06g 0238460.1 | *Brassica napus* | 26 | MASCVAHLPLSSGSQSRHVKANGLSTTKLSSICKT SALTVQKKSSRSRKFSVSARYGDEGSRRASGGGG GDFIAGFLLGGAVFGAVAYIFAPQIRRSIMSEEDEY GFKKPQQPTYYDEGLEKTRETLNKKIEQLNSAIDN VSSRLRGRENNTSSPNVPVETGPEVEATT |

TABLE 2-continued

CTI PROTEIN/DNA HOMOLOGS AND ORTHOLOGS

| Protein name | Organism | SEQ ID NO: | Sequence |
|---|---|---|---|
| ZS11-CTI3-3 BnUnng 1011960.1 | Brassica napus | 27 | MASSCVAHLSLSGVSQSHYVKANGLSTTSKLNSIC KTSALSIQKRSNRSRKFSVSAEYGSRRGGGDFVAG FLLGGALFGAAAYIFAPQIRRSIMSEEDEYGFKKPE QPSYYDEGLEKTRETLNEKIGQLNSAIDNVSSRLR GREKKTSSPVQTDPEVEATT |
| ZS11-CTI3-4 BnC03g 0543330.1 | Brassica napus | 28 | MASCVAHLSLSVLVSGGKGGSQSHHVKANGLSAK KLSSICKTSVLTVQKKSSRSGKFSVSARYGDEGSK RGSGGGGDFIAGFLLGGAVFGAVAYIFAPQIRRIIM SEEDEYGFNKPQQPTYYDEGLEKTRETLNKKIEQL NSAIDNVSSRLRGREKNTSSPNVPVETDPEVEATT |
| DH12075-CTI1-1 | Brassica napus | 29 | MAALSTSLSLSRNTQQLHPSSGFSLKPIGRRANVSF GLNPSKKIQLSAPSGKRILTIQSAYRDDDSSGSTGL FVGGFILGGLIVGALGCVYAPQISKAIAGADRKDF MRKLPKFIYDEEKALEKTRKVLADKIAQLNSAIDD VSSQLKSEDTPNGAALSTDEVEATA |
| DH12075-CTI1-2 | Brassica napus | 30 | MAALSTSLSLSRNTQQLHPSSGFSLKPIARRANVSF GLNPSKKIQLSAPRGKRILTIQSAYRDDDSSGSTGL FVGGFILGGLIVGALGCVYAPQISKAIAGADRKDL MRKLPKFIYDEEKALEKTRKVLADKIAQLNSAIDD VSSQLKSEDTPNGAALSTDEVEATA |
| DH12075-CTI3-1 | Brassica napus | 31 | MASSCVANLSLSGVSQSHYVKANGLSTAKLNSICK TSALSIQKRSNRSRKFSVSAEYGSRRGSGGGDFVA GFLLGGALFGAAAYIFAPQIRRSIMSEEDEYGFKKP DQPSYYDEGLEKTRETLNEKIGQLNSAIDNVSSRL RGRAKKTSSPVETDPEVEATT |
| DH12075-CTI3-2 | Brassica napus | 32 | MASCVAHLPLSSGSQSRHVKANGLSTTKLSSICKT SALTVQKKSSQGRKFSVSARYGDEGSRRGSGGGD FIAGFLLGGAVFGAVAYIFAPQIRRSIMSEEDEYGF KKPQQPTYYDEGLEKTRETLNKKIEQLNSAIDNVS SRLRGREKNTSSPNVPVETDPEVEATT |
| DH12075-CTI3-3 | Brassica napus | 33 | MASSCVAHLSLSGVSQSHYVKANGLSTTSKLNSIC KTSALSIQKRSNRSRKFSVSAEYGCGGGGDFVAG FLLGGALFGAAAYIFAPQIRRSIMSEEDEYGFKKPE QPSYYDEGLEKTRETLNEKIGQLNSAIDNVSSRLR GREKKTSSPVQTDPEVEATT |
| CsCTI1-1 XP_010 478984.1 | Camelina sativa | 34 | ATGGCGTCTCTTTCTACCTCTCTCTCTCTCCCAA TAACGCTCAACAACTCCATCCTTCATCCGGCTTT TCCCTGAAGCCATGTGTCAGTGTTTCTTTTGGAC TGAATCGCTCCAACAACCTTCATATTTCTGCTCC TAGAAGCAAAAGGATCCTCACCGTTCAATCAGC ATACAGAGATGATGACGGTTCAGGCAGCACAGG CTTATTTGTCGGAGGGTTTATTCTGGGCGGACTC ATAGTTGGTGCTCTCGGATGTGTATACGCACCAC AGATCAGCAAGGCAATTGCTGGAGCAGACCGAA AGGATCTCATGAGGAAATTGCCGAAATTCATAT ATGATGAGGAAAAAGCTTTGGAGAAAACTCGGA AGGTACTGGCTGAAAAAATTGCTCAGCTTAACT CTGCTATCGACGATGTGTCCTCTCAGCTCAAATC AGAAGATACCCCGAATGGTGCAGCTCTAAGCAC CGATGAAGTCGAGGCTACAGCCTAA |
| CsCTI1-2 XP_010 461388.1 | Camelina sativa | 35 | ATGGCGTCTCTTTCTACCTCGCTCTCTCTCCCCA ATAACGCTCAACAACTCCATCCTTCATCTGGCTT TTCCCTGAAGCCATGTGTCAGTGTTTCTTTTGGA CTGAATCGCTCCAACAACCTTCATATTTCTGCTC CTAGAAGCAAAAGGATCCTCATCGTTCAATCAG CATACAGAGATGATGACGGTTCAGGCAGCACAG GCTTATTTGTCGGAGGGTTTATTTTGGGCGGACT CATAGTTGGTGCTCTCGGATGTGTATACGCACCA CAGATCAGCAAGGCTATAGCTGGAGCAGACCGA AAGGATCTCATGAGGAAATTGCCGAAATTCATA TATGACGAGGAAAAAGCTTTGGAGAAAACACGG AAGGTGCTGGCTGAAAAAATTGCTCAGCTCAAC TCTGCTATCGACGATGTGTCCTCTCAGCTCAAAT CAGAAGATACCCCGAATGGTGCAGCTCTAAGCA CCGATGAAGTCGAGGCTACAGCCTGA |

TABLE 2-continued

CTI PROTEIN/DNA HOMOLOGS AND ORTHOLOGS

| Protein name | Organism | SEQ ID NO: | Sequence |
|---|---|---|---|
| CsCTI1-3 XP_010 500214.1 | Camelina sativa | 36 | ATGGCGTCTCTTTCTACCTCTCTCTCTCCCAA TAACGCTCAACAACTCCATCCTTCATCCGGCTTT TCCCTGAAGCCATGTGTCAGTGTTTCTTTTGGAC TGAATCGATCCAACAACCTTCATATTTCTGCTCC TAGAAGCAAAAGGATCGTCACCGTTCAATCAGC ATACAGAGATGATGACGGTTCAGGCAGCACAGG CTTATTTGTCGGAGGGTTTATTCTGGGCGGACTC ATAGTTGGTGCCCTCGGATGTGTATACGCACCAC AGATCAGCAAGGCTATAGCTGGAGCAGACCGAA AGGATCTCATGAGGAAATTGCCGAAATTCATAT ATGACGAGGAAAAGCTTTGGAGAAAACACGG AAGGTGCTGGCTGAAAAAATTGCTCAGCTCAAC TCTGCTATCGACGACGTGTCCTCTCAGCTCAAAT CAGAAGATACCCCGAATGGTGCAGCTCTAAGCA CCGATGAAGTCGAGGCTACAGCCTGA |
| CsCTI2-1 XP_010 463722.1 | Camelina sativa | 37 | ATGGCGTCCTTCGTAGCAGCTCCTAACTCTCTCT CAGGTGACTCTCATCTCAAAGCACACTGTTTGTC GTCTACAAACCTCAATCTGATTCGCAAGAGCTCT ACATTAACTGTTATAACAAAATCGAATCGCAGT CACAAACTCTCGGTTTCTGCAGGTTACCGTGAAG GAAGCAGGGGCGGTGGAAGTAGTGATTTTGTTA CGGGTTTTCTTCTAGGAAGTGCTGTGTTTGGTAC TTTGGCTTATGTCTTTGCTCCACAGATCCGAAGA TCGTTGCTGAACGAAAATGAACATGGTTTCAAG AAACCAGAGCAGCCAATGTACTACGATGAAGGC CTAGAGGAGAAGAGAGATATTGAATGAGAA AATAGGCCAACTGAATTCAGCCATAGACAATGT TTCGTCGCGTCTGAGAGGAAGCAAGAACAGTTC TTCGCAGTCTGTCACAGTTGAAACCGACGCAGA AGCAGAAGCTACTGCATGA |
| CsCTI2-2 XP_010 485620.1 | Camelina sativa | 38 | ATGGCGTCCTTCGTAGCAGCTCCTATCTCTCTCT CAGGTGACTCTCATGTCAAAGCACACTGTTTGTT GTCTACAAACCTTAATCCGATTCGCAAGAGCTCT ACATTGACTGTTAGAACAAAATCGAACCGCAGT CACAAACTCTCGGTTTCTGCAGGCTACCGTGAA GGAAGCAGGGGCGGTGGAAGTAGTGATTTTGTT ACGGGTTGTCTTCTAGGAAGTGCTGTGTTTGGTA CTTTGGCTTATGTCTTTGCTCCACAGATCCGAAG ATCGTTGCTGAACGAAAATGAACATGGTTTCAA GAAACCAGAGCAGCCGATGTACTACGATGAAGG CCTAGAGGAGAAGAGAAATATTGAATGAGA AAATCGGCCAACTGAATTCAGCCATAGACAATG TTTCATCGCGTCTGAGAGGTGGAAGCGGAAGCG GCAAGAACAGTTCTTCGCAGTCTGTCACCGTTGA AACCGACGCAGAAGCAGAAGCTACTGCATGA |
| CsCTI2-3 XP_010 503115.1 | Camelina sativa | 39 | ATGGCGTCCTTCGTAGCAGCTCCTATCTCTCTCT CAGGTGACTCTCATGTCAAAGCACACCGTTTCTC GTCTACAAACCTCAATCCGTTTCGCAAGAGCTCT ACATTGACTGTTAGAACAAAATCGAATCGCAGT CACAAACTCTCGGTTTCTGCAGGTTACCGTGAAG GAAGCAGGGGCGGTGGAAGTAGTGATTTTGTTA CGGGTTTTCTTCTAGGAAGTGCTGTGTTTGGTAC TTTGGCCTATATCTTTGCTCCGCAGATCCGAAGA TCGTTGCTGAACGAAAATGAACATGGTTTCAAG AAACCAGAGCAGCCGATATACTACGATGAAGGC CTAGAGGAGAAGAGAGATATTGAATGAGAA AATCGGCCAATTGAATTCAGCCATAGACAATGT TTCATCGCGTCTGAGAGGAGGTGGAAGCGGTAG CAGCAAGAACAGTTCTTCGCAGTCTGTCACCGTT GAAACCGACGCAGAAGCAGAAGCTACTGCATGA |
| CsCTI3-1 XP_010 453829.1 | Camelina sativa | 40 | ATGGCGTCATGTGTTGTTGTTGCTCCTCTATCTCT CTCTGGTGGCTCTCAATCTCATCATGTGAAAGCT AATGGATTGTCGTCTACCACAAAGCTCAGTTCTA TTTGTAAACCTTCTGCATTGTCAATCCTGAATAA ATCAAACCGGACTCGCAAGTTTTCTGTTTCTGCT GGGTACCAAGATGGAGTAGGAGTGGAAGCAG TGGTGACTTCATAGCTGGTTTTCTTCTAGGAGGT GCTGTGTTTGGCGCTGTTGCATATATCTTTGCTC CACAGATCCGGAGATCGCTACTGAATGAAGAAG ATGAGTATGGTTTCAAGAAGCCGCAACAGCCAA |

TABLE 2-continued

CTI PROTEIN/DNA HOMOLOGS AND ORTHOLOGS

| Protein name | Organism | SEQ ID NO: | Sequence |
|---|---|---|---|
| | | | CGTACTACGATGAAGGTTTAGAGAAAACAAGAG AGACATTGAATGAGAAAATCGGACAGCTTAATT CCGCGATTGACAATGTTTCTTCGCGTTTAAGAGG TCGAGAAAAGAACAGTTCTTCCCCCAATGTACC GGTCGAAACTGACCCCGAAGTTGAAGCTACAAC TTGA |
| CsCTI3-2 XP_010 420368.1 | Camelina sativa | 41 | ATGGCGTCATGTGTTGTTGCTCCTCTTTCTCTCTC TGGTGGGTCTCAATCTCATCATTTGAAAGCTAAT GGATTGTCGTCTACCACGAAGCTCAGTTCTATTT GTAAACCTTGTGCATTGTCAATCCTGAATAAATC AAACCGGACTCGCAATTTTTCTGTTTCTGCTGGG TACCGAGATGGGAGTAGGAGTGGAAGCAGTGGT GACTTCATAGCTGGTTTTCTTCTAGGAGGTGCTG TGTTTGGCGCTGTTGCTTATATCTTTGCTCCACA GATCCGGAGATCGGTACTGAATGAAGAAGATGA GTATGGTTTCAAGAAGCCGCAACAGCCAACGTA CTACGATGAAGGTTTAGAGAAAACAAGAGAGAC ATTGAATGAGAAAATCGGACAGCTTAATTCCGC GATTGACAATGTTTCTTCGCGTTTAAGAGGTCGA GAAAAGAACAGTTCTTCCCCCAATGTACCGGTC GAAACTGACCCTGAAGTTGAAGCTACAACTTGA |
| CsCTI3-3 XP_010 492580.1 | Camelina sativa | 42 | ATGGCGTCGTGTGTTGTTGCTCCTCTTTCTCTCTC TGGTGGGTCTCAATCTCATCATGTGAAGGCTAAT GGATTGTCTTCTACCACAAAGCTCAATTCTATCT GTAAACCTTCTGCATTGTCAATCCTGAATAAATC AAACCGGACTCTCAAGTTTTCTGTTTCTGCTGAG TACCGAGATGGGAGTAGGAGTGGAAGCAGTGGT GATTTCATAGCTGGTTTTCTTCTAGGAGGTGCTG TGTTTGGCGCTGTTGCTTATATCTTTGCTCCACA GATCCGGAGATCGGTACTGAATGAAGAAGATGA GTATGGTTTCAAGAAGCCGCAACAGCCAACGTA TTACGATGAAGGTTTAGAGAAAACAAGAGAGAC ATTGAATGAGAAAATAGGACAGCTTAATTCGGC GATTGACAATGTTTCTTCGCGTTTAAGAGGTCGA GAAAAGAACACTTCTTCCCCCAATGTACCGGTC GAAACTGACCCCGAAGTTGAAGCTACAACTTGA |
| Bna-CTI1-1 BnaA08 g04600 D | Brassica napus | 43 | ATGGCGGCTCTTTCGACATCTCTCTCTCTTTCCA GGAATACTCAGCAACTCCATCCTTCATCTGGCTT TTCTCTGAAGCCAATTGGTCGTCGTGCCAACGTT TCTTTCGGGCTGAATCCCTCTAAAAAGATCCAGC TTTCTGCTCCTAGTGGCAAAAGGATCCTAACCAT CCAATCAGCATACAGAGATGATGACAGTTCAGG CAGCACTGGCCTGTTTGTGGGAGGGTTCATTTTG GGCGGGCTCATAGTCGGTGCTCTTGGATGTGTGT ATGCACCACAGATCAGCAAGGCTATAGCTGGAG CAGACCGAAAGGATTTCATGAGGAAATTGCCTA AGTTCATATATGATGAGGAAAAAGCTTTGGAGA AAACTCGCAAGGTATTGCTGACAAAATTGCTC AGCTCAACTCTGCTATCGACGATGTGTCCTCTCA GCTAAAATCAGAAGACACCCCTAATGGTGCAGC TCTAAGCACCGATGAAGTCGAGGCTACAGCCTG A |
| Bna-CTI1-2 BnaC08 g46940 D | Brassica napus | 44 | ATGGCGGCTCTTTCGACATCTCTCTCTCTTTCCA GGAATACTCAGCAACTCCATCCTTCATCTGGCTT TTCTCTGAAGCCAATTGCTCGTCGTGCCAACGTT TCTTTCGGGCTGAATCCCTCTAAAAAGATCCAGC TTTCTGCTCCTAGAGGCAAAAGGATCCTAACCAT CCCATCAGCATACAGAGATGATGACAGTTCAGG CAGCACTGGCCTGTTTGTGGGAGGGTTCATTTTG GGCGGGCTCATAGTCGGTGCTCTTGGATGTGTGT ATGCACCACAGATCAGCAAGGCTATAGCTGGAG CAGACCGAAAGGATCTCATGAGGAAATTGCCTA AGTTCATATATGATGAGGAAAAAGCTTTGGAGA AAACTCGCAAGGTATTGCTGACAAAATTGCTC AGCTCAACTCTGCTATCGACGATGTGTCCTCTCA GCTAAAATCAGAAGACACCCCTAATGGTGCAGC TCTAAGCACCGATGAAGTTGAGGCTACAGCCTG A |

TABLE 2-continued

CTI PROTEIN/DNA HOMOLOGS AND ORTHOLOGS

| Protein name | Organism | SEQ ID NO: | Sequence |
|---|---|---|---|
| Bna-CTI3-1 BnaA10 g17830 D | Brassica napus | 45 | ATGGCGTCCTCCTGTGTTGCTAATCTTTCTCTGTC<br>AGGTGTGTCTCAATCTCATTATGTCAAGGCAAAT<br>GGGTTGTCTACCGCAAAGCTCAATTCGATTTGTA<br>AAACCTCTGCATTGAGTATCCAGAAGAGATCAA<br>ACCGGAGTCGCAAGTTTTCAGTTTCTGCAGAGTA<br>TGGGAGTAGGAGAGGAAGTGGTGGTGGTGATTT<br>CGTTGCTGGTTTTCTTCTTGGTGGTGCTTTGTTCG<br>GCGCTGCCGCTTACATCTTTGCTCCACAGATACG<br>AAGATCGATAATGAGTGAAGAAGATGAGTATGG<br>TTTCAAGAAGCCAGATCAACCAAGTTACTACGA<br>TGAAGGTTTAGAGAAAACAAGGGAGACCTTGAA<br>CGAGAAAATCGGACAGCTTAACTCAGCTATTGA<br>CAATGTCTCTTCGCGTTTAAGAGGTCGAGCAAA<br>GAAGACTTCTTCCCCGGTCGAAACTGATCCAGA<br>AGTTGAAGCTACTACTTGA |
| Bna-CTI3-2 BnaA03 g06140 D | Brassica napus | 46 | ATGGCGTCCTGTGTTGCTCATCTTCCACTCTCAA<br>GTGGGTCTCAGTCTCATCTTGTGAAAGCAAATG<br>GATTGTCCACCACAAAGCTCAGTTCCATTTGTAA<br>AACTTCTGCATTGACTGTTCAGAAGAAATCAAG<br>CCAGGGTCGCAAGTTTTCGGTTTCTGCACGGTAT<br>GGAGGGTCGAAGGGAGTAGGAGAGCAAGTGGTGG<br>TGGTGATTTCATAGCTGGTTTTCTTCTAGGAGGT<br>GCTGTCTTTGGCGCTGTTGCCTATATCTTTGCTCC<br>ACAGATCAGAAGATCGATAATGAGTGAAGAAG<br>ATGAGTATGGTTTCAAGAAGCCACAGCAACCAA<br>CGTACTACGATGAAGGTTTGGAGAAAACAAGAG<br>AGACACTGAACAAGAAAATCGAACAACTTAACT<br>CAGCAATCGACAATGTTTCTTCCCGGTTAAGAG<br>GTCGAGAAAAGAACACTTCTTCTCCCAATGTAC<br>CGGTGGAAACTGACCCAGAAGTTGAAGCTACGA<br>CTTGA |
| Bna-CTI3-3 BnaC09 g41220 D | Brassica napus | 47 | ATGGCGTCCTCCTGTGTTGCTCATCTTTCTCTCTC<br>AGGTGTGTCTCAATCTCATTATGTCAAGGCAAAT<br>GGGTTGTCTACCACCTCAAAGCTCAATTCGATTT<br>GTAAAACCTCTGCATTGAGTATCCAGAAGAGAT<br>CAAACCGGAGTCGCAAGTTTTCAGTTTCTGCAG<br>AGTATGGGAGTAGGAGAGGTGGTGGTGATTTCG<br>TAGCTGGTTTTCTTCTTGGTGGTGCTTTGTTTGGC<br>GCTGCTGCCTACATCTTTGCTCCACAGATCAGAA<br>GATCTATAATGAGTGAAGAAGATGAGTATGGAT<br>TCAAGAAGCCAGAACAACCAAGTTACTACGATG<br>AAGGTTTAGAGAAAACAAGGGAGACCTTGAACG<br>AGAAAATCGGACAGCTTAACTCAGCTATTGACA<br>ATGTCTCTTCGCGTTTAAGAGGTCGAGAGAAGA<br>AGACTTCTTCCCCTGTCCAAACTGACCCGGAAGT<br>TGAAGCTACTACTTGA |
| Bna-CTI3-4 BnaC03 g07880 D | Brassica napus | 48 | ATGGCGTCCTGTGTTGCTCATCTTTCTCTCTCAGT<br>TCTTGTATCTGGTGGCAAAGGTGGGTCTCAATCT<br>CATCATGTGAAAGCAAATGGATTGTCTGCCAAA<br>AAGCTCAGTTCCATTTGTAAAACTTCTGTATTGA<br>CTGTTCAGAAGAAATCAAGCCGGAGTGGCAAGT<br>TTTCGGTTTCTGCACGAGACGAAGGGAGTAAGA<br>GAGGAAGTGGTGGTGGTGGTGATTTCATAGCTG<br>GTTTTCTTCTAGGAGGTGCTGTCTTTGGCGCTGT<br>TGCCTATATCTTTGCTCCACAGATCAGAAGAATT<br>ATTATGAGTGAAGAAGATGAGTATGGTTTCAAT<br>AAGCCACAACAACCAACGTACTACGATGAAGGT<br>TTGGAGAAAACAAGAGAGACGCTGAACAAGAA<br>AATCGAACAACTTAACTCAGCAATCGACAATGT<br>TTCTTCCCGGTTAAGAGGTCGAGAAAAGAACAC<br>ATCTTCTCCCAATGTACCGGTGGAAACTGACCCA<br>GAAGTTGAAGCTACGACTTAA |
| ZS11-CTI1-1 BnA08g 0321320.1 | Brassica napus | 49 | ATGGCGGCTCTTTCGACATCTCTCTCTCTTTCCA<br>GGAATACTCAGCAACTCCATCCTTCATCTGGCTT<br>TTCTCTGAAGCCAATTGGTCGTCGTGCCAACGTT<br>TCTTTCGGGCTGAATCCCTCTAAACAGATCCAGC<br>TTTTCTGCTCCTAGAGGCAAAGGATCCTAACCAT<br>CCAATCAGCATACAGAGATGATGACAGTTCAGG<br>CAGCACTGGCCTGTTTGTGGGAGGGTTCATTTTG<br>GGCGGGCTCATAGTCGGTGCTCTTGGATGTGTGT |

TABLE 2-continued

CTI PROTEIN/DNA HOMOLOGS AND ORTHOLOGS

| Protein name | Organism | SEQ ID NO: | Sequence |
|---|---|---|---|
| | | | ATGCACCACAGATCAGCAAGGCTATAGCTGGAG<br>CAGACCGAAAGGATCTCATGAGGAAATTGCCTA<br>AGTTCATATATGATGAGGAAAAAGCTTTGGAGA<br>AAACTCGCAAGGTATTGGCTGACAAAATTGCTC<br>AGCTCAACTCTGCTATCGACGATGTGTCCTCTCA<br>GCTAAAATCAGAAGACACCCCTAATGGTGCAGC<br>TCTAAGCACCGATGAAGTCGAGGCTACAGCCTG<br>A |
| ZS11-<br>CTI1-2<br>BnC08g<br>0883900.1 | Brassica<br>napus | 50 | ATGGCGGCTCTTTCGACATCTCTCTCTCTTTCCA<br>GGAATACTCAGCAACTCCATCCTTCATCTGGCTT<br>TTCTCTGAAGCCAATTGCTCGTCGTGCCAACGTT<br>TCTTTCGGGCTGAATCCCTCTAAAAAGATCCAGC<br>TTTCTGCTCCTAGAGGCAAAAGGATCCTAACCAT<br>CCAATCAGCATACAGAGATGATGACAGTTCAGG<br>CAGCACTGGCCTGTTTGTGGGGGGGTTCATTTTG<br>GGCGGGCTCATAGTCGGTGCTCTTGGATGTGTGT<br>ATGCACCACAGATCAGCAAGGCTATAGCTGGAG<br>CAGACCGAAAGGATCTCATGAGGAAATTGCCTA<br>AGTTCATATATGATGAGGAAAAAGCTTTGGAGA<br>AAACTCGCAAGGTATTGGCTGACAAAATTGCTC<br>AGCTCAACTCTGCTATCGACGATGTGTCCTCTCA<br>GCTAAAATCAGAAGACACCCCTAATGGTGCAGC<br>TCTAAGCACCGATGAAGTTGAGGCTACAGCCTG<br>A |
| ZS11-<br>CTI3-1<br>BnA10g<br>0411990.1 | Brassica<br>napus | 51 | ATGGCGTCCTCCTGTGTTGCTAATCTTTCTCTGTC<br>AGGTGTGTCTCAATCTCATTATGTCAAGGCAAAT<br>GGGTTGTCTACCGCAAAGCTCAATTCGATTTGTA<br>AAACCTCTGCATTGAGTATCCAGAAGAGATCAA<br>ACCGGAGTCGCAAGTTTTCAGTTTCTGCAGAGTA<br>TGGGAGTAGGAGAGGAAGTGGTGGTGGTGATTT<br>CGTTGCTGGTTTTCTTCTTGGTGGTGCTTTGTTCG<br>GCGCTGCCGCTTACATCTTTGCTCCACAGATACG<br>AAGATCGATAATGAGTGAAGAAGATGAGTATGG<br>TTTCAAGAAGCCAGATCAACCAAGTTACTACGA<br>TGAAGGTTTAGAGAAAACAAGGGAGACCTTGAA<br>CGAGAAAATCGGACAGCTTAACTCAGCTATTGA<br>CAATGTCTCTTCGCGTTTAAGAGGTCGAGCAAA<br>GAAGACTTCTTCCCCGGTCGAAACTGATCCAGA<br>AGTTGAAGCTACTACTTGA |
| ZS11-<br>CTI3-2<br>BnA06g<br>0238460.1 | Brassica<br>napus | 52 | ATGGCGTCCTGTGTTGCTCATCTTCCACTCTCAA<br>GTGGGTCTCAGTCTCGTCATGTAAAAGCAAATG<br>GATTGTCCACCACAAAGCTCAGTTCCATTTGTAA<br>AACTTCTGCATTGACTGTTCAGAAGAAATCAAG<br>CCGGAGTCGTAAGTTTTCGGTTTCTGCACGGTAT<br>GGAGACGAAGGGAGTAGGAGAGCAAGTGGTGG<br>TGGTGGTGATTTCATAGCTGGTTTTCTTCTA<br>GGAGGTGCTGTGTTTGGCGCTGTCGCCTATATCT<br>TTGCTCCACAGATCAGAAGATCGATAATGAGTG<br>AAGAAGATGAGTATGGTTTCAAGAAGCCACAGC<br>AACCAACGTACTACGATGAAGGTTTGGAGAAGA<br>CAAGAGAGACGCTGAATAAGAAATCGAACAA<br>CTTAACTCAGCAATCGACAATGTTTCATCGCGGT<br>TAAGAGGTCGAGAAAATAACACTTCTTCTCCCA<br>ATGTACCAGTGGAAACTGGCCCAGAAGTTGAAG<br>CTACGACTTAA |
| ZS11-<br>CTI3-3<br>BnUnng<br>1011960.1 | Brassica<br>napus | 53 | ATGGCGTCCTCCTGTGTTGCTCATCTTTCTCTCTC<br>AGGTGTGTCTCAATCTCATTATGTCAAGGCAAAT<br>GGGTTGTCTACCACCTCAAAGCTCAATTCGATTT<br>GTAAAACCTCTGCATTGAGTATCCAGAAGAGAT<br>CAAACCGGAGTCGCAAGTTTTCAGTTTCTGCAG<br>AGTATGGGAGTAGGAGAGGTGGTGGTGATTTCG<br>TAGCTGGTTTTCTTCTTGGTGGTGCTTTGTTGGC<br>GCTGCTGCCTACATCTTTGCTCCACAGATCAGAA<br>GATCTATAATGAGTGAAGAAGATGAGTATGGAT<br>TCAAGAAGCCAGAACAACCAAGTTACTACGATG<br>AAGGTTTAGAGAAAACAAGGGAGACCTTGAACG<br>AGAAAATCGGACAGCTTAACTCAGCTATTGACA<br>ATGTCTCTTCGCGTTTAAGAGGTCGAGAGAAGA<br>AGACTTCTTCCCCTGTCCAAACTGACCCGGAAGT<br>TGAAGCTACTACTTGA |

TABLE 2-continued

CTI PROTEIN/DNA HOMOLOGS AND ORTHOLOGS

| Protein name | Organism | SEQ ID NO: | Sequence |
|---|---|---|---|
| ZS11-CTI3-4 BnC03g 0543330.1 | Brassica napus | 54 | ATGGCGTCCTGTGTTGCTCATCTTTCTCTCTCAGT TCTTGTATCTGGTGGCAAAGGTGGGTCTCAATCT CATCATGTGAAAGCAAATGGATTGTCTGCCAAA AAGCTCAGTTCCATTTGTAAAACTTCTGTATTGA CTGTTCAGAAGAAATCAAGCCGGAGTGGCAAGT TTTCGGTTTCTGCACGGTATGGAGACGAAGGGA GTAAGAGAGGAAGTGGTGGTGGTGGTGATTTCA TAGCTGGTTTTCTTCTAGGAGGTGCTGTCTTTGG CGCTGTTGCCTATATCTTTGCTCCACAGATCAGA AGAATTATTATGAGTGAAGAAGATGAGTATGGT TTCAATAAGCCACAACAACCAACGTACTACGAT GAAGGTTTGGAGAAAACAAGAGAGACGCTGAA CAAGAAAATCGAACAACTTAACTCAGCAATCGA CAATGTTTCTTCCCGGTTAAGAGGTCGAGAAAA GAACACATCTTCTCCCAATGTACCGGTGGAAAC TGACCCAGAAGTTGAAGCTACGACTTAA |
| DH1207 5-CTI1-1 | Brassica napus | 55 | ATGGCGGCTCTTTCGACATCTCTCTCTCTTTCCA GGAATACTCAGCAACTCCATCCTTCATCTGGCTT TTCTCTGAAGCCAATTGGTCGTCGTGCCAACGTT TCTTTCGGGCTAATCCCTCTAAAAAGATCCAGC TTTCTGCTCCTAGTGGCAAAAGGATCCTAACCAT CCAATCAGCATACAGAGATGATGACAGTTCAGG CAGCACTGGCCTGTTTGTGGGAGGGTTCATTTTG GGCGGGCTCATAGTCGGTGCTCTTGGATGTGTGT ATGCACCACAGATCAGCAAGGCTATAGCTGGAG CAGACCGAAAGGATTTCATGAGGAAATTGCCTA AGTTCATATATGATGAGGAAAAAGCTTTGGAGA AAACTCGCAAGGTATTGGCTGACAAAATTGCTC AGCTCAACTCTGCTATCGACGATGTGTCCTCTCA GCTAAAAATCAGAAGACACCCCTAATGGTGCAGC TCTAAGCACCGATGAAGTCGAGGCTACAGCCTG A |
| DH1207 5-CTI1-2 | Brassica napus | 56 | ATGGCGGCTCTTTCGACATCTCTCTCTCTTTCCA GGAATACTCAGCAACTCCATCCTTCATCTGGCTT TTCTCTGAAGCCAATTGCTCGTCGTGCCAACGTT TCTTTCGGGCTAATCCCTCTAAAAAGATCCAGC TTTCTGCTCCTAGAGGCAAAAGGATCCTAACCAT CCAATCAGCATACAGAGATGATGACAGTTCAGG CAGCACTGGCCTGTTTGTGGGGGGGTTCATTTTG GGCGGGCTCATAGTCGGTGCTCTTGGATGTGTGT ATGCACCACAGATCAGCAAGGCTATAGCTGGAG CAGACCGAAAGGATCTCATGAGGAAATTGCCTA AGTTCATATATGATGAGGAAAAAGCTTTGGAGA AAACTCGCAAGGTATTGGCTGACAAAATTGCTC AGCTCAACTCTGCTATCGACGATGTGTCCTCTCA GCTAAAAATCAGAAGACACCCCTAATGGTGCAGC TCTAAGCACCGATGAAGTTGAGGCTACAGCCTG A |
| DH1207 5-CTI3-1 | Brassica napus | 57 | ATGGCGTCCTCCTGTGTTGCTAATCTTTCTCTGTC AGGTGTGTCTCAATCTCATTATGTCAAGGCAAAT GGGTTGTCTACCGCAAAGCTCAATTCGATTTGTA AAACCTCTGCATTGAGTATCCAGAAGAGATCAA ACCGGAGTCGCAAGTTTTCAGTTTCTGCAGAGTA TGGGAGTAGGAGAGGAAGTGGTGGTGGTGATTT CGTTGCTGGTTTTCTTCTTGGTGGTGCTTTGTTCG GCGCTGCCGCTTACATCTTTGCTCCACAGATACG AAGATCGATAATGAGTGAAGAAGATGAGTATGG TTTCAAGAAGCCAGATCAACCAAGTTACTACGA TGAAGGTTTAGAGAAAACAAGGGAGACCTTGAA CGAGAAAATCGGACAGCTTAACTCAGCTATTGA CAATGTCTCTTCGCGTTTAAGAGGTCGAGCAAA GAAGACTTCTTCCCCGGTCGAAACTGATCCAGA AGTTGAAGCTACTACTTGA |
| DH1207 5-CTI3-2 | Brassica napus | 58 | ATGGCGTCCTGTGTTGCTCATCTTCCACTCTCAA GTGGGTCTCAGTCTCGTCATGTAAAAGCAAATG GATTGTCCACCACAAAGCTCAGTTCCATTTGTAA AACTTCTGCATTGACTGTTCAGAAGAAATCAAG CCAGGGTCGCAAGTTTTCGGTTTCTGCACGGTAT GGAGACGAAGGGAGTAGGAGAGGAAGTGGTGG |

TABLE 2-continued

CTI PROTEIN/DNA HOMOLOGS AND ORTHOLOGS

| Protein name | Organism | SEQ ID NO: | Sequence |
|---|---|---|---|
| | | | TGGTGATTTCATAGCTGGTTTTCTTCTAGGAGGT GCTGTCTTTGGCGCTGTTGCCTATATCTTTGCTCC ACAGATCAGAAGATCGATAATGAGTGAAGAAG ATGAGTATGGTTTCAAGAAGCCACAGCAACCAA CGTACTACGATGAAGGTTTGGAGAAAACAAGAG AGACACTGAACAAGAAAATCGAACAACTTAACT CAGCAATCGACAATGTTTCTTCCCGGTTAAGAG GTCGAGAAAAGAACACTTCTTCTCCCAATGTAC CGGTGGAAACTGACCCAGAAGTTGAAGCTACGA CTTGA |
| DH12075-CTI3-3 | Brassica napus | 59 | ATGGCGTCCTCCTGTGTTGCTCATCTTTCTCTC AGGTGTGTCTCAATCTCATTATGTCAAGGCAAAT GGGTTGTCTACCACCTCAAAGCTCAATTCGATTT GTAAAACCTCTGCATTGAGTATCCAGAAGAGAT CAAACCGGAGTCGCAAGTTTTCAGTTTCTGCAG AGTATGGGTGTGGTGGTGGTGGTGATTTCGT AGCTGGTTTTCTTCTTGGTGGTGCTTTGTTTGGC GCTGCTGCCTACATCTTTGCTCCACAGATCAGAA GATCTATAATGAGTGAAGAAGATGAGTATGGAT TCAAGAAGCCAGAACAACCAAGTTACTACGATG AAGGTTTAGAGAAAACAAGGGAGACCTTGAACG AGAAAATCGGACAGCTTAACTCAGCTATTGACA ATGTCTCTTCGCGTTTAAGAGGTCGAGAGAAGA AGACTTCTTCCCCTGTCCAAACTGACCCGGAAGT TGAAGCTACTACTTGA |
| ATCTI1 | Arabidopsis thaliana | 60 | MASLSSTSLSLPKNSHQLHPSSGFSLNPNARCVSVS FGLNHSNKLHISAPRTKRILTIQSAYRDDDGSGSTG LFVGGFILGGLIVGALGCVYAPQISKAIAGADRKD LMRKLPKFIYDEEKALEKTRKVLAEKIAQLNSAID DVSSQLKSEDTPNGAALSTDEIEATA |
| ATCTI2 | Arabidopsis thaliana | 61 | MASLVAAPISFSGDSHVKAHRNFNAIRKSSTLTVQ TKSNRSHKLSVSAGYRGGSKGGGSSDFVTGFLLGS AVFGTLAYIFAPQIRRSVLSENEYGFKKPEQPMYY DEGLEERREILNEKIGQLNSAIDKVSSRLKGGRSGS SKNTSSPSVPVETDAEAEATA |
| ATCTI3 | Arabidopsis thaliana | 62 | MASCIATAPLSLSGVSQSHYVKANGLSTTTKLSSIC KTSDLTIHKKSNRTRKFSVSAGYRDGSRSGSSGDFI AGFLLGGAVFGAVAYIFAPQIRRSVLNEEDEYGFE KPKQPTYYDEGLEKTRETLNEKIGQLNSAIDNVSS RLRGREKNTSSLNVPVETDPEVEATT |
| LOC106405504 | Brassica napus | 63 | MAALSTSLSLSRNTQQLHPSSGFSLKPIARRANVSF GLNPSKKIQLSAPRGKRILTIQSAYRDDDSSGSTGL FVGGFILGGLIVGALGCVYAPQISKAIAGADRKDL MRKLPKFIYDEEKALEKTRKVLADKIAQLNSAIDD VSSQLKSEDTPNGAALSTDEVEATA |
| LOC106361260 | Brassica napus | 64 | MAALSTSLSLSRNTQQLHPSSGFSLKPIGRRANVSF GLNPSKQIQLSAPRGKRILTIQSAYRDDDSSGSTGL FVGGFILGGLIVGALGCVYAPQISKAIAGADRKDL MRKLPKFIYDEEKALEKTRKVLADKIAQLNSAIDD VSSQLKSEDTPNGAALSTDEVEATA |
| LOC106432156 | Brassica napus | 65 | MASSCVAHLSLSGVSQSHYVKANGLSTTSKLNSIC KTSALSIQKRSNRSRKFSVSAEYGSRRGGGDFVAG FLLGGALFGAAAYIFAPQIRRSIMSEEDEYGFKKPE QPSYYDEGLEKTRETLNEKIGQLNSAIDNVSSRLR GREKKTSSPVQTDPEVEATT |
| LOC106441483 | Brassica napus | 66 | MASCVAHLPLSSGSQSRHVKANGLSTTKLSSICKT SALTVQKKSSRSRKFSVSARYGDEGSRRASGGGG GDFIAGFLLGGAVFGAVAYIFAPQIRRSIMSEEDEY GFKKPQQPTYYDEGLEKTRETLNKKIEQLNSAIDN VSSRLRGRENNTSSPNVPVETGPEVEATT |
| LOC111197939 | Brassica napus | 67 | MASCVAHLSLSGGSQSHHVKANGLSAKKLSSICKT SVLTVQKKSSRSGKFSVSARYGDEGSKRGSGGGG DFIAGFLLGGAVFGAVAYIFAPQIRRIIMSEEDEYG FNKPQQPTYYDEGLEKTRETLNKKIEQLNSAIDNV SSRLRGREKNTSSPNVPVETDPEVEATT |

TABLE 2-continued

CTI PROTEIN/DNA HOMOLOGS AND ORTHOLOGS

| Protein name | Organism | SEQ ID NO: | Sequence |
|---|---|---|---|
| LOC104 757900 | Camelina sativa | 68 | MASLSTSLSLPNNAQQLHPSSGFSLKPCVSVSFGLN RSNNLHISAPRSKRILTVQSAYRDDDGSGSTGLFV GGFILGGLIVGALGCVYAPQISKAIAGADRKDLMR KLPKFIYDEEKALEKTRKVLAEKIAQLNSAIDDVSS QLKSEDTPNGAALSTDEVEATA |
| LOC104 777632 | Camelina sativa | 69 | MASLSTSLSLPNNAQQLHPSSGFSLKPCVSVSFGLN RSNNLHISAPRSKRIVTVQSAYRDDDGSGSTGLFV GGFILGGLIVGALGCVYAPQISKAIAGADRKDLMR KLPKFIYDEEKALEKTRKVLAEKIAQLNSAIDDVSS QLKSEDTPNGAALSTDEVEATA |
| LOC104 742113 | Camelina sativa | 70 | MASLSTSLSLPNNAQQLHPSSGFSLKPCVSVSFGLN RSNNLHISAPRSKRILIVQSAYRDDDGSGSTGLFVG GFILGGLIVGALGCVYAPQISKAIAGADRKDLMRK LPKFIYDEEKALEKTRKVLAEKIAQLNSAIDDVSSQ LKSEDTPNGAALSTDEVEATA |
| LOC104 705959 | Camelina sativa | 71 | MASCVVAPLSLSGGSQSHHLKANGLSSTTKLSSIC KPCALSILNKSNRTRNFSVSAGYRDGSRSGSSGDFI AGFLLGGAVFGAVAYIFAPQIRRSVLNEEDEYGFK KPQQPTYYDEGLEKTRETLNEKIGQLNSAIDNVSS RLRGREKNSSSPNVPVETDPEVEATT |
| LOC104 769949 | Camelina sativa | 72 | MASCVVAPLSLSGGSQSHHVKANGLSSTTKLNSIC KPSALSILNKSNRTLKFSVSAEYRDGSRSGSSGDFI AGFLLGGAVFGAVAYIFAPQIRRSVLNEEDEYGFK KPQQPTYYDEGLEKTRETLNEKIGQLNSAIDNVSS RLRGREKNTSSPNVPVETDPEVEATT |
| LOC104 735700 | Camelina sativa | 73 | MASCVVVAPLSLSGGSQSHHVKANGLSSTTKLSSI CKPSALSILNKSNRTRKFSVSAGYQDGSRSGSSGDF IAGFLLGGAVFGAVAYIFAPQIRRSLLNEEDEYGFK KPQQPTYYDEGLEKTRETLNEKIGQLNSAIDNVSS RLRGREKNSSSPNVPVETDPEVEATT |
| LOC104 744374 | Camelina sativa | 74 | MASFVAAPNSLSGDSHLKAHCLSSTNLNLIRKSST LTVITKSNRSHKLSVSAGYREGSRGGGSSDFVTGF LLGSAVFGTLAYVFAPQIRRSLLNENEHGFKKPEQ PMYYDEGLEERREILNEKIGQLNSAIDNVSSRLRGS KNSSSQSVTVETDAEAEATA |
| LOC104 780281 | Camelina sativa | 75 | MASFVAAPISLSGDSHVKAHRFSSTNLNPFRKSSTL TVRTKSNRSHKLSVSAGYREGSRGGGSSDFVTGFL LGSAVFGTLAYIFAPQIRRSLLNENEHGFKKPEQPI YYDEGLEERREILNEKIGQLNSAIDNVSSRLRGGGS GSSKNSSSQSVTVETDAEAEATA |
| LOC104 763912 | Camelina sativa | 76 | MASFVAAPISLSGDSHVKAHCLLSTNLNPIRKSSTL TVRTKSNRSHKLSVSAGYREGSRGGGSSDFVTGCL LGSAVFGTLAYVFAPQIRRSLLNENEHGFKKPEQP MYYDEGLEERREILNEKIGQLNSAIDNVSSRLRGG SGSGKNSSSQSVTVETDAEAEATA |
| LOC112 513715 | Cynara cardunculus | 77 | MTTLANSFVSVPNQRNQLFSGSLMQADQCLGSTN LCIGHSGTTKLKKHRKSLIVRAGTNDDRLGGASLF VGGFVLGGIVVGTLGAIYAPQISKALAGADRKDL MRKLPKFIYDEEKALEKTRKILTDKIAQLNSAIDDV SAQLRADDPPNGSSVTTNGVEASSY |
| LOC112 510155 | Cynara cardunculus | 78 | MIALSNPLVLPTNNPNQSSSGSSMKSLDQSTKLLFG QGHVGNVRLRTSKRMLSVQARYSDNGRSTNGSAF GFGFVLGGLIVGTLGCVYAPQISKALAEADKKELL RKLPTFIYDEEKALEKTRKKLTEKIAQLNDAIDDVS SQLKSEDEESNKNGAVVFEKSQSVA |
| LOC112 505814 | Cynara cardunculus | 79 | MSAISNSSLLLPKNRSDQLSSGSSVKKLDQGFTKLS FGQSRVGNLQLLTSKRTFSIQAGYSDDGRSNSGSA FVGGFVLGGLLVGTLGCIYAPQISKALAGADKKEL LRKLPDFIYDEEKALEKTRQKLAKKIAELNSAIDD VSSQLKSDDDEPVTNNGVVPDESEALA |

TABLE 2-continued

CTI PROTEIN/DNA HOMOLOGS AND ORTHOLOGS

| Protein name | Organism | SEQ ID NO: | Sequence |
|---|---|---|---|
| LOC112 509980 | *Cynara cardunculus* | 80 | MATTGIVAPASISVRTSLKGHDGWSGNSCLYGKTP TLTHQRKSNQQRTQRKLAISAQYNDRSGGGSGDF VAGFFLGGALCGTLAYIFAPQIRRSLLNEDEYGFRR AKRPIYYDEGLEKTRQTLNAKISQLNSAIDNVSSRL RGGNNMPQVPVETDPEEATM |
| LOC827 3643 | *Rizinus communis* | 81 | MTAISNSLALTRNPVGTVQLSAGSLGKSLQNVGPT KLSFSLNSPGKVQLTTSRRSLTVRAASDDGRPSSGS IFVGGFVLGGLIVGALGCVYAPQISKALAGTDRKD LMRKLPKFIYDEEKALEKTRKVLTEKIAQLNSAID DVSAQLRSDDSPNGVAVNDEIEAAI |
| LOC828 1332 | *Rizinus communis* | 82 | MTSLSSPFLPFTTPQTSGSSLKPSNPSISSISPCNLSS KSKRLPSIQARYNVSVSVSGERDLSSSAGIFIGGGFV LGGIAVGALGCIYAPQISKALAGADRKDLMRKLPK FIYDEEKALEKTRKILTEKIAQLNSAIDEVSTQLHP DDTPNGSTVNSDEIEAST |
| LOC828 0517 | *Rizinus communis* | 83 | MAASLAPVSISGGSNLKARELCSSKSLSFGKTSRLA VQRKLNLVGTNCNLSVRANYQDGNRGGGSDFVA GFLLGGAIFGTLAYVFAPQIRRSLLNEDEYGFRKA KRPIYYDEGLEKTRQTLNAKISQLNSAIDNVSSRLR GGNNNPPTVPVETDPEVEATM |
| Glyma.0 6G0158 00.1 | *Glycine max* | 84 | MAAVPSTFALTKSALSINKLDHSLVKIKPYSFSLNL NRLGRMETSLTRRPLTIQATYSDGGRPSSASVFVG GFLLGGLIVGTLGCVYAPQISKAIAGADRKELMRK LPKFIYDEEKALEKTRKVLAEKIEQLNAAIDDVSA QLRSEEASNGVAVNSDEIEAAT |
| Glyma.0 4g01580 0.1 | *Glycine max* | 85 | MLYLYQFFSPCLVGRGRLYKDLCILVSCNVAMLLF NITRLLASALWQKLWLQLDSSIICVCFFLTERLLLQ KLLLASSINKVDHSLVKIKPYNFSLNLNRQGTMQT SLTRRPLTIQATYSDGGRPSSASVFVGGFLLGGLIV GTLGCVYAPQISKALAGADRKELMRKLPKFIYDEE KALEKTRKVLAEKIEQLNAAIDDVSAQLRSEEASN GVAVNSDEIEAAT |
| Glyma. 1 1g08740 0.1 | *Glycine max* | 86 | MATLSSFIATPKNPNTHFLSGSSLTMDKCFLKISSSE HFPGSSLKTKATRNQPLVIRAGGDGGRPSSGSGFV GGFVLGGLIVGALGCLYAPQISRALAGADSKDLM RKLPKFMYDEEKALERTRKVLTEKIAQLNSAIDGV SAQLRPDEDSNEIALNSEEIEASI |
| Glyma.0 1g15760 0.1 | *Glycine max* | 87 | MATLSSFITTPKNPKTHFLSGSSFMSMDKCFLKIST SGHFTDFSLRAKATSNQPLVIRAGGDGGRPSSGSIF VGGFVLGGLIAGALGCYAPQISRALAGADSKDL MRKLPKFMYDEEKALERTREVLTEKIAQLNSAIDG VSAQLRPDEDSNEIAVNSEEIEIPISDESEIEVNK |
| Glyma.0 1g23420 0 | *Glycine max* | 88 | MATCFAPFSVSGGSHELWLTKRVGPKLTVQRRSN LVIKRNHTSSISAEYRDNRGGGGGDFVAGFLLGGA VFGTLAYIFAPQFVMQIRRSLLNEDEYGFRKAKRPI YYDEGLERTRQTLNEKIGQLNSAIDNVSSRLGGN NVPAAKIESDPEVEATM |
| Glyma. 1 1g00870 0.1 | *Glycine max* | 89 | MATCFAPFSVSGGSHELWSTKRVGPKLSVQRRSS LVIKRNHTSSICAEYRDNRGGGGGDFVAGFLLGGA VFGTLAYIFAPQIRRSLLNEDEYGFRKAKRPIYYDE GLERTRQTLNEKIGQLNSAIDNVSSRLGGNNVPA AKIESDPEVEATM |
| LOC110 915560 | *Helianthus annuus* | 90 | MTTLSNSFLSLQTHRNHFFSDQGIGSSNLLIGHSGT LKLTKQKKSLTVRAGANDDRLGGASLFVGGFVLG GIVVGALGAIYAPQISKALAGADRKDLMRRLPKFI YDEEKALEKTRKILTEKIAQLNSAIDDVSAQLRAD DPPNGSSVPTDEVEASY |
| LOC110 940866 | *Helianthus annuus* | 91 | MAALSNSLILSPPPGSSMKSFDQSTKLLFGQSLAGN VQLHTAKRTLSVQAVYSERSSSGSAFVGGFVLGGL IVGTLGCVYAPQISKTLAGADKKELLRKLPAFIYDE EKALERTRKKLTEKIAQLNDAIDDVSSQLKSDDEN SNEGAVVPETSQSVA |

TABLE 2-continued

CTI PROTEIN/DNA HOMOLOGS AND ORTHOLOGS

| Protein name | Organism | SEQ ID NO: | Sequence |
|---|---|---|---|
| LOC110 907976 | *Helianthus annuus* | 92 | MSMLLPNHPLSSSGSSIKKHDQAFTKLSFGQSHIGN VKLVTSKQTLSVKAGYSDDGRSNNGGAFIGGFVL GGLLIGTLGCIYAPQISKALAGTDKKELLKKLPNFI YDEEKALEKTRQKLAQKIAELNSAIDDVSSQLKTD DDANGVVPDETEALA |

TABLE 3

PUTATIVE CTI ORTHOLOGS IN CAMELINA AND CANOLA
(*B. napus*)

| Name | Protein/Gene ID | Species (cultivar) | Description in GenBank | Protein Size (aa) | % Identity score* |
|---|---|---|---|---|---|
| CsCTI1-1 | XP_010478984.1 (SEQ ID NO: 7) | *C. sativa* cv DH55 | uncharacterized protein LOC104757900 | 164 | 90 |
| CsCTI1-2 | XP_010461388.1 (SEQ ID NO: 8) | *C. sativa* cv DH55 | uncharacterized protein LOC104742113 | 164 | 90 |
| CsCTI1-3 | XP_010500214.1 (SEQ ID NO: 9) | *C. sativa* cv DH55 | uncharacterized protein LOC104777632 | 164 | 90 |
| CsCTI2-1 | XP_010463722.1 (SEQ ID NO: 10) | *C. sativa* cv DH55 | uncharacterized protein LOC104744374 | 161 | 75 |
| CsCTI2-2 | XP_010485620.1 (SEQ ID NO: 11) | *C. sativa* cv DH55 | uncharacterized protein LOC104763912 | 165 | 77 |
| CsCTI2-3 | XP_010503115.1 (SEQ ID NO: 13) | *C. sativa* cv DH55 | uncharacterized protein LOC104780281 | 166 | 77 |
| CsCTI3-1 | XP_010453829.1 (SEQ ID NO: 14) | *C. sativa* cv DH55 | uncharacterized protein LOC104735700 | 168 | 90 |
| CsCTI3-2 | XP_010420368.1 (SEQ ID NO: 15) | *C. sativa* cv DH55 | uncharacterized protein LOC104705959 | 167 | 89 |
| CsCTI3-3 | XP_010492580.1 (SEQ ID NO: 16) | *C. sativa* cv DH55 | uncharacterized protein LOC104769949 | 167 | 90 |
| Bna-CTI1-1 | BnaA08g04600D (SEQ ID NO: 17) | *B. napus* cv. Darmor-bzh | N.A. | 167 | 85 |
| Bna-CTI1-2 | BnaC08g46940D (SEQ ID NO: 18) | *B. napus* cv. Darmor-bzh | N.A. | 167 | 86 |
| Bna-CTI3-1 | BnaA10g17830D (SEQ ID NO: 19) | *B. napus* cv. Darmor-bzh | N.A. | 162 | 77 |
| Bna-CTI3-2 | BnaA03g06140D (SEQ ID NO: 20) | *B. napus* cv. Darmor-bzh | N.A. | 167 | 79 |
| Bna-CTI3-3 | BnaC09g41220D (SEQ ID NO: 21) | *B. napus* cv. Darmor-bzh | N.A. | 161 | 77 |
| Bna-CTI3-4 | BnaC03g07880D (SEQ ID NO: 22) | *B. napus* cv. Darmor-bzh | N.A. | 173 | 77 |
| ZS11-CTI1-1 | BnA08g0321320.1 (SEQ ID NO: 23) | *B. napus* cv. ZS11 | uncharacterized protein LOC106361260 | 167 | 86 |
| ZS11-CTI1-2 | BnC08g0883900.1 (SEQ ID NO: 24) | *B. napus* cv. ZS11 | uncharacterized protein LOC106405504 | 167 | 87 |
| ZS11-CTI3-1 | BnA10g0411990.1 (SEQ ID NO: 25) | *B. napus* cv. ZS11 | uncharacterized protein LOC103846311 | 162 | 77 |
| ZS11-CTI3-2 | BnA06g0238460.1 (SEQ ID NO: 26) | *B. napus* cv. ZS11 | uncharacterized protein LOC106441483 | 169 | 79 |
| ZS11-CTI3-3 | BnUnng1011960.1 (SEQ ID NO: 27) | *B. napus* cv. ZS11 | uncharacterized protein LOC106432156 | 161 | 77 |

TABLE 3-continued

PUTATIVE CTI ORTHOLOGS IN CAMELINA AND CANOLA
(*B. napus*)

| Name | Protein/Gene ID | Species (cultivar) | Description in GenBank | Protein Size (aa) | % Identity score* |
|---|---|---|---|---|---|
| ZS11-CTI3-4 | BnC03g0543330.1 (SEQ ID NO: 28) | *B. napus* cv. ZS11 | uncharacterized protein LOC111197939 isoform X1 | 175 | 75 |
| DH12075-CTI1-1 | (SEQ ID NO: 29) | *B. napus* cv. DH12075 | N.A. | 167 | 87 |
| DH12075-CTI1-2 | (SEQ ID NO: 30) | *B. napus* cv. DH12075 | N.A. | 167 | 87 |
| DH12075-CTI3-1 | (SEQ ID NO: 31) | *B. napus* cv. DH12075 | N.A. | 162 | 77 |
| DH12075-CTI3-2 | (SEQ ID NO: 32) | *B. napus* cv. DH12075 | N.A. | 167 | 79 |
| DH12075-CTI3-3 | (SEQ ID NO: 33) | *B. napus* cv. DH12075 | N.A. | 161 | 77 |
| DH12075-CTI3-4 | N.A. | *B. napus* cv. DH12075 | N.A. (frameshift mutation due to indels) | | |

*The protein sequences were compared to the corresponding CTI orthologs in *Arabidopsis* and the sequence identity scores were calculated using Clustal Omega.

In some embodiments, the polynucleotide is downregulated by techniques through use of various new technologies developed and/or used to create new characteristics in plants through genetic variation, the aim being targeted mutagenesis, targeted introduction of new genes, or gene silencing (RdDM). Examples of such new breeding techniques are targeted sequence changes facilitated thru the use of Zinc finger nuclease (ZFN) technology (ZFN-1, ZFN-2 and ZFN-3, see U.S. Pat. No. 9,145,565, incorporated by reference in its entirety), Oligonucleotide directed mutagenesis (ODM), Cisgenesis and intragenesis, RNA-dependent DNA methylation (RdDM, which does not necessarily change nucleotide sequence but can change the biological activity of the sequence), Grafting (on GM rootstock), Reverse breeding, Agro-infiltration (agro-infiltration "sensu stricto", agro-inoculation, floral dip), Transcription Activator-Like Effector Nucleases (TALENs, see U.S. Pat. Nos. 8,586,363 and 9,181,535, incorporated by reference in their entireties), the CRISPR/Cas system (see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641), engineered meganuclease re-engineered homing endonucleases, DNA guided genome editing (Gao et al., Nature Biotechnology (2016), doi: 10.1038/nbt.3547, incorporated by reference in its entirety), and synthetic genomics. A complete description of each of these techniques can be found in the report made by the Joint Research Center (JRC) Institute for Prospective Technological Studies of the European Commission in 2011 and titled "New plant breeding techniques—State-of-the-art and prospects for commercial development".

Modulation of candidate CTI genes are performed through known techniques in the art, such as without limitation, by genetic means, enzymatic techniques, chemicals methods, or combinations thereof. Inactivation may be conducted at the level of DNA, mRNA or protein, and inhibit the expression of one or more candidate CTI genes or the corresponding activity. Preferred inactivation methods affect the expression of the CTI gene and lead to the absence of gene product in the plant cells. It should be noted that the inhibition can be transient or permanent or stable. Inhibition of the protein can be obtained by suppressing or decreasing its activity or by suppressing or decreasing the expression of the corresponding gene. Inhibition can be obtained via mutagenesis of the cti gene. For example, a mutation in the coding sequence can induce, depending upon the nature of the mutation, expression of an inactive protein, or of a reduced-active protein; a mutation at a splicing site can also alter or abolish the protein's function; a mutation in the promoter sequence can induce the absence of expression of said protein, or the decrease of its expression. Mutagenesis can be performed, e.g., by suppressing all or part of the coding sequence or of the promoter, or by inserting an exogenous sequence, e.g., a transposon, into said coding sequence or said promoter. It can also be performed by inducing point mutations, e.g., using ethyl methanesulfonate (EMS) mutagenesis or radiation. The mutated alleles can be detected, e.g., by PCR, by using specific primers of the gene. Rodriguez-Leal et al. describe a promoter editing method that generates a pool of promoter variants that can be screened to evaluate their phenotypic impact (Rodriguez-Leal et al., 2017, Cell, 171, 1-11). This method can be incorporated into the present disclosure to downregulate native promoters of each CTI in the crop of interest.

Various high-throughput mutagenesis and splicing methods are described in the prior art. By way of examples, we may cite "TILLING" (Targeting Induced Local Lesions In Genome)-type methods, described by Till, Comai and Henikoff (2007) (R. K. Varshney and R. Tuberosa (eds.), Genomics-Assisted Crop Improvement: Vol. 1: Genomics Approaches and Platforms, 333-349.) (the teachings and content of which are incorporated by reference herein).

Plants comprising a mutation in the candidate CTI genes that induce inhibition of the protein product are also part of the goal of the present disclosure. This mutation can be, e.g., a deletion of all or part of the coding sequence or of the promoter, or it may be a point mutation of said coding sequence or of said promoter.

Advantageously, inhibition of the CTI protein is obtained by silencing or by knock-out techniques on the CTI gene. Various techniques for silencing genes in plants are known. Antisense inhibition or co suppression, described, e.g., in Hamilton and Baulcombe, 1999, Science, vol 286, pp 950-952, is noteworthy. It is also possible to use ribozymes targeting the mRNA of one or more CTI protein. Preferably, silencing of the CTI gene is induced by RNA interference targeting said gene. An interfering RNA (iRNA) is a small RNA that can silence a target gene in a sequence-specific way. Interfering RNA include, specifically, "small interfering RNA" (siRNA) and micro-RNA (miRNA). The most widely-used constructions lead to the synthesis of a pre-miRNA in which the target sequence is present in sense and antisense orientation and separated by a short spacing region. The sense and antisense sequence can hybridize together leading to the formation of a hairpin structure called the pre miRNA. This hairpin structure is maturated leading to the production of the final miRNA. This miRNA will hybridize to the target mRNA which will be cleaved or degraded, as described in Schwab et al (Schwab et al, 2006 The Plant Cell, Vol. 18, 1121-1133) or in Ossowski et al (Ossowski et al, 2008, The plant Journal 53, 674-690).

Inhibition of the CTI proteins can also be obtained by gene editing of the candidate CTI genes. Various methods can be used for gene editing, by using transcription activator-like effector nucleases (TALENs), clustered Regularly Interspaced Short Palindromic Repeats (CRISPR/Cas9) or zinc-finger nucleases (ZFN) techniques (as described in Belhaj et al, 2013, Plant Methods, vol 9, p 39, Chen et al, 2014 Methods Volume 69, Issue 1, p 2-8). Preferably, the inhibition of a CTI protein is obtained by using Clustered Regularly Interspaced Short Palindromic Repeats (CRISPR/Cas9) or CRISPR/Cpf1. The use of this technology in genome editing is well described in the art, for example in Fauser et al. (Fauser et al, 2014, The Plant Journal, Vol 79, p 348-359), and references cited herein. In short, CRISPR is a microbial nuclease system involved in defense against invading phages and plasmids. CRISPR loci in microbial hosts contain a combination of CRISPR-associated (Cas) genes as well as non-coding RNA elements capable of programming the specificity of the CRISPR-mediated nucleic acid cleavage (sgRNA). At least classes (Class I and II) and six types (Types I-VI) of Cas proteins have been identified across a wide range of bacterial hosts. One key feature of each CRISPR locus is the presence of an array of repetitive sequences (direct repeats) interspaced by short stretches of non-repetitive sequences (spacers). The non-coding CRISPR array is transcribed and cleaved within direct repeats into short crRNAs containing individual spacer sequences, which direct Cas nucleases to the target site (protospacer). The Type II CRISPR/Cas is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA: tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Cas9 is thus the hallmark protein of the Type II CRISPR-Cas system, and a large monomeric DNA nuclease guided to a DNA target sequence adjacent to the PAM (protospacer adjacent motif) sequence motif by a complex of two noncoding RNAs: CRIPSR RNA (crRNA) and trans-activating crRNA (tracrRNA). The Cas9 protein contains two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA. Heterologous expression of Cas9 together with an sgRNA can introduce site-specific double strand breaks (DSBs) into genomic DNA of live cells from various organisms. For applications in eukaryotic organisms, codon optimized versions of Cas9, which is originally from the bacterium *Streptococcus pyogenes*, have been used. The single guide RNA (sgRNA) is the second component of the CRISPR/Cas system that forms a complex with the Cas9 nuclease. sgRNA is a synthetic RNA chimera created by fusing crRNA with tracrRNA. The sgRNA guide sequence located at its 5' end confers DNA target specificity. Therefore, by modifying the guide sequence, it is possible to create sgRNAs with different target specificities. The canonical length of the guide sequence is 20 bp. In plants, sgRNAs have been expressed using plant RNA polymerase III promoters, such as U6 and U3. Cas9 expression plasmids for use in the methods of the disclosure can be constructed as described in the art.

The absence of or loss of function in modified engineered plants or plant cells can be verified based on the phenotypic characteristics of their offspring; homozygous plants or plant cells for a mutation inactivating the CTI gene have a content of gene product rate that is lower than that of the wild plants (not carrying the mutation in the gene) from which they originated. Alternatively, a desirable phenotypic characteristic such as biomass yield, seed yield, or seed oil content is measured and is at least 10% higher, preferably at least 20% higher, at least preferably 30% higher, preferably at least 40% higher, preferably at least 50% higher than that of the control plants from which they originated. More preferably, seed yield or seed oil content is at least 60% higher, at least 70% higher, at least 80% higher, at least 90% higher than that of the control plants from which they originated. More preferably, seed yield or seed oil content is at least 100% higher, at least 150% higher, at least 200% higher than that of the control plants from which they originated.

The expression of the target gene or genes in the crops of interest can be reduced by any method known in the art, including the transgene based expression of anti-sense RNA or interfering RNA (RNAi) e.g., siRNA or miRNA or through genome editing to modify the DNA sequence of the genes disclosed herein directly in the plant cell chromosome.

Genome editing is a preferred method for practicing this disclosure. As used herein the terms "genome editing," "genome edited", and "genome modified" are used interchangeably to describe plants with specific DNA sequence changes in their genomes wherein those DNA sequence changes include changes of specific nucleotides, the deletion of specific nucleotide sequences or the insertion of specific nucleotide sequences.

As used herein "method for genome editing" includes all methods for genome editing technologies to precisely remove genes, gene fragments, to insert new DNA sequences into genes, to alter the DNA sequence of control sequences or protein coding regions to reduce or increase the expression of target genes in plant genomes (Belhaj, K. 2013, Plant Methods, 9, 39; Khandagale & Nadal, 2016, Plant Biotechnol Rep, 10, 327). Preferred methods involve the in vivo site-specific cleavage to achieve double stranded breaks in the genomic DNA of the plant genome at a specific DNA sequence using nuclease enzymes and the host plant DNA repair system. There are multiple methods to achieve double stranded breaks in genomic DNA, and thus achieve genome editing, including the use of zinc finger nucleases (ZFN), transcription activator-like effector nucleases (TALENs), engineered meganucleases, and the CRISPR/Cas system (CRISPR is an acronym for Clustered, regularly interspaced, short, palindromic repeats and Cas an abbreviation for CRISPR-associated protein) (for review see Khandagal & Nadal, Plant Biotechnol Rep, 2016, 10, 327). US Patent Application 2016/0032297 to Dupont describes these methods in detail. In some cases, the sequence specificity for the target gene in the plant genome is dependent on engineering specific nuclease like zinc finger nucleases (ZFN), which include an engineered DNA-binding zinc finger domain linked to a non-specific endonuclease domain such as FokI, or Tal effector nuclease (TALENS) to recognize the target DNA sequence in the plant genome. The CRISPR/Cas genome editing system is a preferred method because of its sequence targeting flexibility. This technology requires a source of the Cas enzyme and a short single guide RNA (sgRNA, ~20 bp), DNA, RNA/DNA hybrid or double stranded DNA guide with sequence homology to the target DNA sequence in the plant genome to direct the Cas enzyme to the desired cut site for cleavage and a recognition sequence for binding the Cas enzyme. As used herein the term Cas nuclease includes any nuclease which site-specifically recognizes CRISPR sequences based on guide RNA or DNA sequences and includes Cas9, Cpf1 and others described below. CRISPR/Cas genome editing, is a preferred way to edit the genomes of complex organisms (Sander & Joung, 2013, Nat Biotech, 2014, 32, 347; Wright et al., 2016, Cell, 164, 29) including plants (Zhang et al., 2016, Journal of Genetics and Genomics, 43, 151; Puchta, H., 2016, Plant J., 87, 5; Khandagale & Nadaf, 2016, PLANT BIOTECHNOL REP, 10, 327). US Patent Application 2016/020822 to Dupont has an extensive description of the materials and methods useful for genome editing in plants using the CRISPR Cas9 system and describes many of the uses of the CRISPR/Cas9 system for genome editing of a range of gene targets in crops.

There are many variations of the CRISPR/Cas system that can be used for this technology including the use of wild-type Cas9 from *Streptococcus pyogenes* (Type II Cas) (Barakate & Stephens, 2016, Frontiers in Plant Science, 7, 765; Bortesi & Fischer, 2015, *Biotechnology Advances* 5, 33, 41; Cong et al., 2013, Science, 339, 819; Rani et al., 2016, Biotechnology Letters, 1-16; Tsai et al., 2015, Nature biotechnology, 33, 187), the use of a Tru-gRNA/Cas9 in which off-target mutations were significantly decreased (Fu et al., 2014, Nature biotechnology, 32, 279; Osakabe et al., 2016, Scientific Reports, 6, 26685; Smith et al., 2016, Genome biology, 17, 1; Zhang et al., 2016, Scientific Reports, 6, 28566), a high specificity Cas9 (mutated *S. pyogenes* Cas9) with little to no off target activity (Kleinstiver et al., 2016, Nature 529, 490; Slaymaker et al., 2016, Science, 351, 84), the Type I and Type III Cas Systems in which multiple Cas proteins need to be expressed to achieve editing (Li et al., 2016, Nucleic acids research, 44:e34; Luo et al., 2015, Nucleic acids research, 43, 674), the Type V Cas system using the Cpf1 enzyme (Kim et al., 2016, Nature biotechnology, 34, 863; Toth et al., 2016, Biology Direct, 11, 46; Zetsche et al., 2015, Cell, 163, 759), DNA-guided editing using the NgAgo Argonaute enzyme from *Natronobacterium gregoryi* that employs guide DNA (Xu et al., 2016, Genome Biology, 17, 186), and the use of a two vector system in which Cas9 and gRNA expression cassettes are carried on separate vectors (Cong et al., 2013, Science, 339, 819). A unique nuclease Cpf1, an alternative to Cas9, has advantages over the Cas9 system in reducing off-target edits which creates unwanted mutations in the host genome. Examples of crop genome editing using the CRISPR/Cpf1 system include rice (Tang et. al., 2017, Nature Plants 3, 1-5; Wu et. al., 2017, Molecular Plant, Mar. 16, 2017) and soybean (Kim et., al., 2017, *Nat Commun.*, 14406).

Methods for constructing the genome modified plant cells and plants include introducing into plant cells a site-specific nuclease to cleave the plant genome at the target site or target sites and the guide sequences. Modification to the DNA sequence at the cleavage site then occur through the plant cells natural DNA repair processes. In a preferred case using the CRISPR system the target site in the plant genome is determined by providing guide RNA sequences.

A "guide polynucleotide" also relates to a polynucleotide sequence that can form a complex with a Cas endonuclease and enables the Cas endonuclease to recognize and optionally cleave a DNA target site. The guide polynucleotide can be a single molecule or a double molecule. The guide polynucleotide sequence can be a RNA sequence, a DNA sequence, or a combination thereof (a RNA-DNA combination sequence).

As used herein "guide RNA" sequences comprise a variable targeting domain, homologous to the target site in the genome and an RNA sequence that interacts with the Cas9 or Cpf1 endonuclease. A guide polynucleotide that solely comprises ribonucleic acids is also referred to as a "guide RNA".

Preferred embodiments include multiplex of gene edits, integrating the one or more exogenous sequences occurrences. The method also provides introducing single-guide RNAs (sgRNAs) into plants. The guide RNAs (sgRNAs) include nucleotide sequences that are complementary to the target chromosomal DNA. The sgRNAs can be, for example, engineered single chain guide RNAs that comprise a crRNA sequence (complementary to the target DNA sequence) and a common tracrRNA sequence, or as crRNA-tracrRNA hybrids. The sgRNAs can be introduced into the cell or the organism as a DNA with an appropriate promoter, as an in vitro transcribed RNA, or as a synthesized RNA. Methods for designing the guide RNAs for any target gene of interest are well known in the art as described for example by Brazelton et al. (Brazelton, V. A. et al., 2015, GM Crops & Food, 6, 266-276) and Zhu (Zhu, L. J. 2015, Frontiers in Biology, 10, 289-296).

I. Nucleic Acids, Polypeptides and Plant Transformation Constructs

Certain embodiments of the current disclosure concern isolated nucleic acid sequences and the corresponding polypeptide sequences for a novel family of CTI proteins, provided herein as SEQ ID NOs: 1-6, in *Arabidopsis thaliana*. Complements to any nucleic acid or protein sequences described herein are also provided.

"Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. "Identity" can be readily calculated by known methods including, but not limited to, those described in Lesk, ed., (1988); Smith, ed., (1993); Griffin, and Griffin, eds., (1994); von Heinje, (1987); Gribskov and Devereux, eds., (1991); and Carillo and Lipman, (1988). Computer programs can be used to determine "identity" between two sequences these programs include but are not limited to, GCG (Devereux, 1984); suite of five BLAST programs, three designed for nucleotide sequences queries (BLASTN, BLASTX, and TBLASTX) and two designed for protein sequence queries (BLASTP and TBLASTN) (Coulson, 1994; Birren, et al., 1997). The BLASTX program is publicly available from NCBI and other sources (BLAST Manual, Altschul, S., et al., NCBI NLM NIH, Bethesda, Md. 20894; Altschul, S., et al., 1990). The well-known Smith Waterman algorithm can also be used to determine identity.

In accordance with the disclosure, a polynucleotide or polypeptide sequence as described herein may exhibit at least from about 70% to about 100% sequence identity to at least one of the sequences set forth herein. For example, in one embodiment, a CTI gene as described herein may comprise, for example, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a sequence selected from SEQ ID NOs: 1, 3, 5, and 34-59, or a complement thereof. In other embodiments, a CTI protein as described herein may comprise for example, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a sequence selected from SEQ ID NO: 2, 4, 6, 7-33, and 60-92, or a complement thereof.

Parameters for polypeptide sequence comparison include the following: Algorithm: Needleman and Wunsch (1970); Comparison matrix: BLOSUM62 from Hentikoff and Hentikoff, (1992); Gap Penalty: 12; and Gap Length Penalty: 4. A program which can be used with these parameters is publicly available as the "gap" program from Genetics Computer Group, Madison Wis. The above parameters along with no penalty for end gap may serve as default parameters for peptide comparisons.

Parameters for nucleic acid sequence comparison include the following: Algorithm: Needleman and Wunsch (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

As used herein, "hybridization," "hybridizes," or "capable of hybridizing" is understood to mean the forming of a double- or triple-stranded molecule or a molecule with partial double- or triple-stranded nature. Such hybridization may take place under relatively high-stringency conditions, including low salt and/or high temperature conditions, such as provided by a wash in about 0.02 M to about 0.15 M NaCl at temperatures of about 50° C. to about 70° C. for 10 min. In one embodiment of the disclosure, the conditions are 0.15 M NaCl and 70° C. Stringent conditions tolerate little mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like. Also included may be a protein or polypeptide, or fragment thereof, such as any of those set forth herein.

The nucleic acids provided herein as SEQ ID NOs: 1, 3, 5, and 34-59 may be from any source, e.g., identified as naturally occurring in a plant, or synthesized, e.g., by mutagenesis of SEQ ID NOs: 1, 3, 5, and 34-59. In an embodiment, the naturally occurring sequence may be from any plant or algal species, such as *Amborella trichopoda, Arabidopsis lyrata, Arabidopsis alpine, Arabidopsis thaliana, Arachis hypogaea, Auxenochlorella protothecoides, Brassica napus, Brassica rapa, Camelina sativa, Capsella rubella, Cathamus tinctorius, Chlamydomonas reinhardtii, Chlorella variabilis, Cicer arietinum, Citrus clementina, Citrus sinensis, Coccomyxa subellipsoideas C-169, Coffea canephora, Cucumis melo, Cucumis sativus, Cynara cardunculus, Elaeis guineensis, Erythranthe guttata, Eucalyptus grandis, Eutrema salsugineum, Fragaria vesca, Genlisea aurea, Glycine max, Helianthus annuus, Helicosporidium* ATCC50920, *Jatropha curcas, Lotus japonicas, Medicago truncatula, Moms notabilis, Musa acuminate, Nelumbo nucifera, Nicotiana sylvestris, Nicotiana tomentosiformis, Phaseolus vulgaris, Pheonix dactyhfera, Physcomitrella patens, Picea sitchensis, Polytomella parva, Populus trichocarpa, Prunus mume, Prunes persica, Pyrus× bretschneideri, Ricinus communis, Selaginella moellendorfli, Sesamum indicum, Solanum lycopersicum, Solanum tuberosum, Theobroma cacao, Thaspi arvense, Vitis vinifera,* and *Volvox carteri.*

Coding sequences may be provided in a recombinant vector operably linked to a heterologous promoter functional in plants, in either sense or antisense orientation. Expression constructs may also be provided comprising these sequences, including antisense oligonucleotides thereof. In other embodiments, plants and plant cells transformed with the sequences may be provided. The construction of vectors which may be employed in conjunction with plant transformation techniques using these or other sequences according to the disclosure will be known to those of skill of the art in light of the present disclosure (see, for example, Sambrook et al., 1989; Gelvin et al., 1990). The techniques of the current disclosure are thus not limited to any particular nucleic acid sequences.

The choice of any additional elements used in conjunction with a coding sequences or corresponding encoded product may depend on the purpose of the transformation. One of the major purposes of transformation of crop plants is to add commercially desirable, agronomically important traits to the plant, as described herein.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the disclosure, this could be used to introduce genes corresponding to, e.g., an entire biosynthetic pathway, into a plant.

Particularly useful for transformation are expression cassettes which have been isolated from such vectors. DNA segments used for transforming plant cells will generally comprise the cDNA, gene, or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. Preferred components likely to be included with vectors used in the current disclosure are as follows.

A. Regulatory Elements

Exemplary promoters for expression of a nucleic acid sequence include plant promoters such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those promoters associated with the R gene complex (Chandler et al., 1989). Tissue-specific promoters such as leaf specific promoters, or tissue selective promoters (e.g., promoters that direct greater expression in leaf primordia than in other tissues), and tissue-specific enhancers (Fromm et al., 1986) are also contemplated to be useful, as are inducible promoters such as ABA- and turgor-inducible promoters. Any suitable promoters known in the art may be used to express coding sequences in a plant.

The DNA sequence between the transcription initiation site and the start of the coding sequence, i.e., the untranslated leader sequence, can also influence gene expression. One may thus wish to employ a particular leader sequence with a transformation construct of the disclosure. In an embodiment, leader sequences are contemplated to include those which comprise sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure.

It is envisioned that a sequence useful for altering activity levels of ACCase as described herein may comprise any nucleotide or amino acid sequence set forth herein, for example SEQ ID NOs: 1-92. In certain embodiments, a gene useful for altering ACCase levels may comprise altering expression of a CTI gene, such as CTI1, CTI2, CTI3, set forth herein as SEQ ID NOs: 1, 3, 5, and 34-59, respectively, or orthologs or homologs thereof. Such an ortholog or homolog may be from any species useful in accordance with the disclosure. Such a sequence may be introduced into a plant under the control of novel promoters, enhancers, etc., or homologous or tissue-specific or tissue-selective promoters or control elements. Vectors for use in tissue-specific targeting of genes in transgenic plants will typically include tissue-specific or tissue-selective promoters and may also include other tissue-specific or tissue-selective control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters, which have higher activity in roots; or napin and glycinin promoters, which have higher activity in developing seed.

Plant promoters can be selected to control the expression of the transgene in different plant tissues or organelles for all of which methods are known to those skilled in the art (Gasser & Fraley, 1989, Science 244: 1293-1299). In one embodiment, promoters are selected from those of eukaryotic or synthetic origin that are known to yield high levels of expression in plants and algae. In a preferred embodiment, promoters are selected from those that are known to provide high levels of expression in monocots.

Constitutive promoters include, for example, the core promoter of the Rsyn7 promoter and other constitutive promoters disclosed in WO 99/43838 and U.S. Pat. No. 6,072,050, the core CaMV 35S promoter (Odell et al., 1985, *Nature* 313: 810-812), rice actin (McElroy et al., 1990, *Plant Cell* 2: 163-171), ubiquitin (Christensen et al., 1989, *Plant Mol. Biol.* 12: 619-632; Christensen et al., 1992, *Plant Mol. Biol.* 18: 675-689), pEMU (Last et al., 1991, *Theor. Appl. Genet.* 81: 581-588), MAS (Velten et al., 1984, *EMBO J.* 3: 2723-2730), and ALS promoter (U.S. Pat. No. 5,659,026). Other constitutive promoters are described in U.S. Pat. Nos. 5,608,149; 5,608,144; 5,604,121; 5,569,597; 5,466,785; 5,399,680; 5,268,463; and 5,608,142.

"Tissue-preferred" promoters can be used to target gene expression within a particular tissue. Tissue-preferred promoters include those described by Van Ex et al., 2009, *Plant Cell Rep.* 28: 1509-1520; Yamamoto et al., 1997, *Plant J.* 12: 255-265; Kawamata et al., 1997, *Plant Cell Physiol.* 38: 792-803; Hansen et al., 1997, *Mol. Gen. Genet.* 254: 337-343; Russell et al., 199), *Transgenic Res.* 6: 157-168; Rinehart et al., 1996, *Plant Physiol.* 112: 1331-1341; Van Camp et al., 1996, *Plant Physiol.* 112: 525-535; Canevascini et al., 1996, *Plant Physiol.* 112: 513-524; Yamamoto et al., 1994, *Plant Cell Physiol.* 35: 773-778; Lam, 1994, *Results Probl. Cell Difer.* 20: 181-196, Orozco et al., 1993, *Plant Mol. Biol.* 23: 1129-1138; Matsuoka et al., 1993, *Proc. Natl. Acad. Sci. USA* 90: 9586-9590, and Guevara-Garcia et al., 1993, *Plant J.* 4: 495-505. Such promoters can be modified, if necessary, for weak expression.

Seed-specific promoters can be used to target gene expression to seeds in particular. Seed-specific promoters include promoters that are expressed in various tissues within seeds and at various stages of development of seeds. Seed-specific promoters can be absolutely specific to seeds, such that the promoters are only expressed in seeds, or can be expressed preferentially in seeds, e.g. at rates that are higher by 2-fold, 5-fold, 10-fold, or more, in seeds relative to one or more other tissues of a plant, e.g. stems, leaves, and/or roots, among other tissues. Seed-specific promoters include, for example, seed-specific promoters of dicots and seed-specific promoters of monocots, among others. For dicots, seed-specific promoters include, but are not limited to, bean β-phaseolin, napin, β-conglycinin, soybean oleosin 1, *Arabidopsis thaliana* sucrose synthase, flax conlinin soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, and globulin 1.

Exemplary promoters useful for expression of CTI proteins for specific dicot crops are disclosed in Table 4. Examples of promoters useful for increasing the expression of CTI proteins in specific monocot plants are disclosed in Table 5. For example, one or more of the promoters from soybean (*Glycine max*) listed in Table 5 may be used to drive the expression of one or more CTI genes encoding the proteins listed or the gene sequences in Tables 1, 2, and 3. It may also be useful to increase or otherwise alter the expression of one or more mitochondrial transporters in a specific crop using genome editing approaches as described herein.

TABLE 4

Promoters useful for expression of genes in dicots.

| Gene/Promoter | Expression | Native organism of promoter | Gene ID* |
|---|---|---|---|
| CaMV 35S | Constitutive | Cauliflower mosaic virus | N/A |

TABLE 4-continued

Promoters useful for expression of genes in dicots.

| Gene/Promoter | Expression | Native organism of promoter | Gene ID* |
|---|---|---|---|
| Hsp70 | Constitutive | Glycine max | Glyma.02G093200 |
| Chlorophyll A/B Binding Protein (Cab5) | Constitutive | Glycine max | Glyma.08G082900 |
| Pyruvate phosphate dikinase (PPDK) | Constitutive | Glycine max | Glyma.06G252400 |
| Actin | Constitutive | Glycine max | Glyma.19G147900 |
| ADP-glucose pyrophos-phorylase (AGPase) | Seed-specific | Glycine max | Glyma.04G011900 |
| Glutelin C (GluC) | Seed-specific | Glycine max | Glyma.03G163500 |
| □-fructofuranosidase insoluble isoenzyme 1 (CIN1) | Seed-specific | Glycine max | Glyma.17G227800 |
| MADS-Box | Cob-specific | Glycine max | Glyma.04G257100 |
| Glycinin (subunit G1) | Seed-specific | Glycine max | Glyma.03G163500 |
| oleosin isoform A | Seed-specific | Glycine max | Glyma.16G071800 |
| Hsp70 | Constitutive | Brassica napus | BnaA09g05860D |
| Chlorophyll A/B Binding Protein (Cab5) | Constitutive | Brassica napus | BnaA04g20150D |
| Pyruvate phosphate dikinase (PPDK) | Constitutive | Brassica napus | BnaA01g18440D |
| Actin | Constitutive | Brassica napus | BnaA03g34950D |
| ADP-glucose pyrophos-phorylase (AGPase) | Seed-specific | Brassica napus | BnaA06g40730D |
| Glutelin C (GluC) | Seed-specific | Brassica napus | BnaA09g50780D |
| □-fructofuranosidase insoluble isoenzyme 1 (CIN1) | Seed-specific | Brassica napus | BnaA04g05320D |
| MADS-Box | Cob-specific | Brassica napus | BnaA05g02990D |
| Glycinin (subunit G1) | Seed-specific | Brassica napus | BnaA01g08350D |
| oleosin isoform A | Seed-specific | Brassica napus | BnaC06g12930D |
| 1.7S napin (napA) | Seed-specific | Brassica napus | BnaA01g17200D |

*Gene ID includes sequence information for coding regions as well as associated promoters. 5' UTRs, and 3' UTRs and are available at Phytozome (see JGI website phytozome.jgi.doe.gov/pz/portal.html).

TABLE 5

Promoters useful for expression of genes in monocots, including maize and rice.

| Gene/Promoter | Expression | Rice* | Maize* | Other |
|---|---|---|---|---|
| Hsp70 | Constitutive | LOC_Os05g38530* | GRMZM2G310431* | |
| Chlorophyll A/B Binding Protein (Cab5) | Constitutive | LOC_Os01g41710* | AC207722.2_FG009* GRMZM2G351977 | |
| maize ubiquitin promoter/maize ubiquitin intron (sequence listed in Genbank KT962835) | Constitutive | | | |
| maize ubiquitin promoter/maize ubiquitin intron (maize promoter and intron sequence with 99% identity to sequence in Genbank KT985051.1) | Constitutive | | | |
| CaMV 35S | Constitutive | | | Cauliflower mosaic virus |
| Pyruvate phosphate dikinase (PPDK) | Constitutive | LOC_Os05g33570* | GRMZM2G306345* | |
| Actin | Constitutive | LOC_Os03g50885* | GRMZM2G047055* | |
| Hybrid cab5/hsp70 intron promoter | Constitutive | N/A | | |
| ADP-glucose pyrophos-phorylase (AGPase) | Seed-specific | LOC_Os01g44220* | GRMZM2G429899* | |
| Glutelin C (GluC) | Seed-specific | LOC_Os02g25640* | N/A | |
| β-fructofuranosidase insoluble isoenzyme 1 (CIN1) | Seed-specific | LOC_Os02g33110* | GRMZM2G139300* | |
| MADS-Box | Cob-specific | LOC_Os12g10540* | GRMZM2G160687* | |
| Maize TrpA promoter | Seed-specific | | GRMZM5G841619 | |

*Gene ID includes sequence information for coding regions as well as associated promoters. 5' UTRs, and 3' UTRs and are available at Phytozome (see JGI website phytozome.jgi.doe.gov/pz/portal.html).

B. Terminators

Transformation constructs prepared in accordance with the disclosure may include a 3' end DNA sequence that acts as a signal to terminate transcription and allow for the polyadenylation of the mRNA produced by coding sequences operably linked to a promoter. In one embodiment of the disclosure, the native terminator of a CTI coding sequence may be used. Alternatively, a heterologous 3' end may enhance the expression of sense or antisense CTI coding sequences. Examples of terminators that may be used in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II gene from potato or tomato. Regulatory elements such as an Adh intron (Callis et al., 1987), sucrose synthase intron (Vasil et al., 1989) or TMV omega element (Gallie et al., 1989) may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, Golgi apparatus, and outside of the cellular membrane). By facilitating the transport of the protein into compartments inside and outside the cell, these sequences may increase the accumulation of gene products by protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed.

D. Marker Genes

By employing a selectable or screenable marker, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the disclosure.

Many selectable marker coding regions are known and could be used with the present disclosure including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromo* genes. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

One beneficial use of the sequences provided by the disclosure may be in the alteration of plant phenotypes such as fatty acid or triacylglycerol production, as well as protein production, in plants and/or algae by genetic transformation with a coding sequence set forth herein, such as a CTI coding sequence. A CTI coding sequence such as described herein may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

II. Genetic Transformation

Additionally provided herein are transgenic plants transformed with the above-identified recombinant vector encoding a CTI, or a sequence modulating expression thereof.

Suitable methods for transformation of plant or other cells for use with the current disclosure are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. Nos. 5,591,616 and 5,563,055; both specifically incorporated herein by reference) and by acceleration of DNA coated particles (U.S. Pat. Nos. 5,550,318; 5,538,877;

and 5,538,880; each specifically incorporated herein by reference in its entirety), etc. Through the application of techniques such as these, the cells of virtually any plant species may be stably transformed, and these cells developed into transgenic plants.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, including alfalfa (Thomas et al., 1990), it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. Gateway™ and other recombination-based cloning technology are also available in vectors useful for plant transformation. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Another method for delivering transforming DNA segments to plant cells in accordance with the disclosure is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

The transgenic plants of the present disclosure expressing heterologous CTI can be of any plant or algal species, such as *Amborella trichopoda, Arabidopsis lyrata, Arabidopsis alpine, Arabidopsis thaliana, Arachis hypogaea, Auxenochlorella prototheocoides, Brassica napus, Brassica rapa, Camelina sativa, Capsella rubella, Cathamus tinctorius, Chlamydomonas reinhardtii, Chlorella variabilis, Cicer arietinum, Citrus clementina, Citrus sinensis, Coccomyxa subellipsoideas* C-169, *Coffea canephora, Cucumis melo, Cucumis sativus, Cynara cardunculus, Elaeis guineensis, Erythranthe guttata, Eucalyptus grandis, Eutrema salsugineum, Fragaria vesca, Genlisea aurea, Glycine max, Helianthus annuus, Helicosporidium* ATCC50920, *Jatropha curcas, Lotus japonicas, Medicago truncatula, Moms notabilis, Musa acuminate, Nelumbo nucifera, Nicotiana sylvestris, Nicotiana tomentosiformis, Phaseolus vulgaris, Pheonix dactyhfera, Physcomitrella patens, Picea sitchensis, Polytomella parva, Populus trichocarpa, Prunus mume, Prunes persica, Pyrus×bretschneideri, Ricinus communis, Selaginella moellendorfli, Sesamum indicum, Solanum lycopersicum, Solanum tuberosum, Theobroma cacao, Thaspi arvense, Vitis vinifera,* and *Volvox carteri*. The plant can be an Ro transgenic plant (i.e., a plant derived from the original transformed tissue). The plant can also be a progeny plant of any generation of an Ro transgenic plant, wherein the transgenic plant has the nucleic acid sequence from the Ro transgenic plant.

Seeds of the any above-described transgenic plants may also be provided, particularly where the seed comprises the nucleic acid sequence. Additionally contemplated are host cells transformed with the above-identified recombinant vector. In some embodiments, the host cell is a plant cell. Also contemplated herein is a plant genetically engineered to increase expression of a CTI protein, where the CTI protein comprises a protein product of genes comprising the nucleotide sequences of SEQ ID NOs: 1, 3, 5, or 34-59 where the protein product (e.g. a polypeptide) alters plant morphology as described herein. Such a protein product may comprise the amino acid sequences of SEQ ID NOs: 2, 4, 6, 7-33, or 60-92 or any other sequence described herein that is appropriate for use with the present disclosure. In an embodiment, the altered plant morphology may be increased or decreased fatty acid content. Such altered morphology may be accomplished by increasing or decreasing ACCase activity levels by down- or up-regulating a CTI gene described herein. Such plants are described in the Examples, and may be useful, e.g., as commercial plants.

The plants of these embodiments having altered expression of ACCase or one or more CTI genes may be of any species. The species may be any monocotyledonous or dicotyledonous plant, such as those described herein. One of skill in the art will recognize that the present disclosure may be applied to plants of other species by employing methods described herein and others known in the art.

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. A medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. The rate of cell growth also will vary among cultures initiated with the array of media that permit growth of that cell type. Tissue that can be grown in a culture includes meristem cells, Type I, Type II, and Type III callus, immature embryos and gametic cells such as microspores, pollen, sperm, and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

A. Altering Gene Expression in a Plant

In accordance with the disclosure, alteration of expression of a gene as described herein may comprise increasing expression of a gene, or decreasing expression of a gene. As described herein, the present disclosure may comprise altering expression of a CTI gene. In some embodiments, methods are provided comprising completely silencing or down-regulating expression of a gene. In other embodiments, partial or incomplete silencing or down-regulation of a gene may be sufficient to achieve the desired effect.

Alteration of gene expression in a plant may be accomplished by a variety of methods known in the art. In accordance with the disclosure, any method useful for altering expression of a gene or gene product may be used, including, but not limited to, antisense, RNAi, CRISPR, TALON, nanobodies, EMS, T-DNA or transposon-mediated gene knockout, or conventional mutagenesis/targeted breeding. Such methods are known in the art. As used herein the words "gene suppression" are intended to refer to any of the well-known methods for reducing the levels of protein produced as a result of gene transcription to mRNA and subsequent translation of the mRNA.

Gene suppression is also intended to mean the reduction of protein expression from a gene or a coding sequence including post-transcriptional gene suppression and transcriptional suppression. Post-transcriptional gene suppression is mediated by the homology between of all or a part of an mRNA transcribed from a gene or coding sequence targeted for suppression and the corresponding double stranded RNA used for suppression, and refers to the substantial and measurable reduction of the amount of available mRNA available in the cell for binding by ribosomes. The transcribed RNA may be in the sense orientation to effect what is called co-suppression, in the anti-sense orientation to effect what is called anti-sense suppression, or in both orientations, in which case a dsRNA may be produced to achieve RNA interference (RNAi). Such methods may be useful in accordance with the disclosure for down-regulating or silencing a CTI gene as described herein. Transcriptional suppression is mediated by the presence in the cell of a dsRNA, a gene suppression agent, exhibiting substantial sequence identity to a DNA sequence or the complement thereof to result in promoter trans-suppression. Gene suppression may be effective against a native gene associated with a trait, e.g., to produce a plant with reduced levels of a protein encoded by the native gene or with enhanced or reduced levels of an affected gene product. A gene product may include an RNA molecule, including, but not limited to, mRNA, rRNA, tRNA, siRNA, shRNA, or the like. A gene product may also include a protein or polypeptide, or a fragment thereof.

Post-transcriptional gene suppression by anti-sense or sense-oriented RNA to regulate gene expression in plant cells is known in the art, as is the use of dsRNA to suppress genes in plants. Post-transcriptional gene suppression in plants may employ both sense-oriented and anti-sense-oriented, transcribed RNA that is stabilized, e.g., as a hairpin or stem-and-loop structure.

As used herein, the term "expression" refers to the transcription and stable accumulation of sense or anti-sense RNA derived from a nucleic acid. "Expression" may also refer to translation of mRNA into a polypeptide or protein. As used herein, the term "antisense RNA" refers to an RNA transcript that is complementary to all or a part of an mRNA that is normally produced in a cell. The complementarity of an antisense RNA may be with any part of the specific gene transcript, i.e., at the 5' non-coding sequence, 3' non-translated sequence, introns, or the coding sequence. As used herein, the term "RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from post-transcriptional processing of the primary transcript and is referred to as the mature RNA.

As used herein, the phrase "inhibition of gene expression" or "inhibiting expression of a target gene" refers to the absence (or observable decrease) in the level of protein and/or mRNA product from the target gene. Specificity refers to the ability to inhibit the target gene without manifest effects on other genes of the cell and without any effects on any gene within the cell that is producing the dsRNA molecule. The inhibition of gene expression of a target gene as described herein may result in novel phenotypic traits in the plant.

III. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the disclosure. In this case, one would then generally assay the potentially transformed cell population by exposing the cells to a selective agent or agents, or one would screen the cells for the desired marker gene trait.

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce, into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA. One herbicide which constitutes a desirable selection agent is the broad-spectrum herbicide bialaphos. Another example of a herbicide which is useful for selection of transformed cell lines in the practice of the disclosure is the broad-spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived therefrom. U.S. Pat. No. 4,535,060 describes the isolation of EPSPS mutations which confer glyphosate resistance on the EPSPS of *Salmonella typhimurium*, encoded by the gene aroA. The EPSPS gene from *Zea mays* was cloned and mutations similar to those found in a glyphosate resistant aroA gene were introduced in vitro. Mutant genes encoding glyphosate resistant EPSPS enzymes are described in, for example, International Patent WO 97/4103.

To use the aroA-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 weeks, then transferred to media conducive to maturation of embryoids. Cultures are transferred every 2 weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm CO2, and 25-250 microeinsteins m"2 s"1 of light. Plants may be matured in a growth chamber or greenhouse. Plants can be regenerated in from about 6 weeks to 10 months after a transformant is identified, depending on the initial tissue. During regeneration, cells are grown on solid media in tissue culture vessels. Illustrative embodiments of such vessels are Petri dishes and Plant Cons. Regenerating plants can be grown at about 19 to 28° C. After the regenerating plants have reached the stage of shoot and root development, they may be transferred to a greenhouse for further growth and testing.

To confirm the presence of the exogenous DNA or "transgene(s)" in the regenerating plants, a variety of assays may be performed. Such assays include, for example, "molecular biological" assays, such as Southern and northern blotting and PCR™; "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

The expression of a gene product is often determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes that change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IV. Breeding Plants of the Disclosure

In addition to direct transformation of a particular plant genotype with a construct prepared according to the current disclosure, transgenic plants may be made by crossing a plant having a selected DNA of the disclosure to a second plant lacking the construct. For example, a selected CTI coding sequence can be introduced into a particular plant variety by crossing, without the need for ever directly transforming a plant of that given variety. Therefore, the current disclosure not only encompasses a plant directly transformed or regenerated from cells which have been transformed in accordance with the current disclosure, but also the progeny of such plants. As used herein, the term "progeny" denotes the offspring of any generation of a parent plant prepared in accordance with the instant disclosure, wherein the progeny comprises a selected DNA construct prepared in accordance with the disclosure. "Crossing" a plant to provide a plant line having one or more added transgenes relative to a starting plant line, as disclosed herein, is defined as the techniques that result in a transgene of the disclosure being introduced into a plant line by crossing a plant of a starting line with a plant of a donor plant line that comprises a transgene of the disclosure. To achieve this one could, for example, perform the following steps:
(a) plant seeds of the first (starting line) and second (donor plant line that comprises a transgene of the disclosure) parent plants;
(b) grow the seeds of the first and second parent plants into plants that bear flowers;
(c) pollinate a flower from the first parent plant with pollen from the second parent plant; and
(d) harvest seeds produced on the parent plant bearing the fertilized flower.

Backcrossing is herein defined as the process including the steps of:
(a) crossing a plant of a first genotype containing a desired gene, DNA sequence or element to a plant of a second genotype lacking the desired gene, DNA sequence or element;
(b) selecting one or more progeny plant containing the desired gene, DNA sequence or element;
(c) crossing the progeny plant to a plant of the second genotype; and
(d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

V. Definitions

As used herein, accessions AT3G56130, AT1G52670, and AT3G15690 are intended to refer to CTI1, CTI2, and CTI3, respectively.

As used herein, α-CT refers to AT2G38040; β-CT refers to ATCG00500; BC refers to AT5G35360; BCCP1 refers to AT5G16390; BCCP2 refers to AT5G15530; BADC1 refers to AT3G56130; BADC2 refers to AT1G52670; and BADC3 refers to AT3G15690.

Endogenous: A sequence natively found in a host cell or a cell of the same species. In one embodiment, an endogenous sequence may be overexpressed or expressed at a higher level compared to wildtype and still be considered endogenous.

Expression: The combination of intracellular processes, including transcription and translation, undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found. In this respect, the sequence may be native to the host genome, but be rearranged with respect to other genetic sequences within the host sequence. For example, a regulatory sequence may be heterologous in that it is linked to a different coding sequence relative to the native regulatory sequence. In addition, a particular sequence can be "heterologous" with respect to a cell or organism into which it is introduced (for example, a sequence that does not naturally occur in that particular cell or organism).

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an Ro transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

Ro transgenic plant: A plant that has been genetically transformed or has been regenerated from a plant cell or cells that have been genetically transformed.

Regeneration: The process of growing a plant from a plant cell (e.g., plant protoplast, callus, or explant). Selected DNA: A DNA segment which one desires to introduce or has introduced into a plant genome by genetic transformation.

Transformation construct: A chimeric DNA molecule designed for introduction into a host genome by genetic transformation. Preferred transformation constructs will comprise all of the genetic elements necessary to direct the expression of one or more exogenous genes. In particular embodiments of the instant disclosure, it may be desirable to introduce a transformation construct into a host cell in the form of an expression cassette.

Transformed cell: A cell in which the DNA complement has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

The description herein is merely exemplary in nature and, thus, variations that do not depart from the gist of that which is described are intended to be within the scope of the teachings. Such variations are not to be regarded as a departure from the spirit and scope of the teachings.

EXAMPLES

The following examples are included to demonstrate preferred embodiments of the disclosure. It should be appreciated by those of skill in the art that the techniques disclosed in the examples, which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments, which are disclosed and still obtain a like or similar result without departing from the spirit and scope of the disclosure.

Example 1: Evaluation of α-CT Interacting Proteins

To evaluate the interaction of candidate proteins CTI1 (ATG42960, SEQ ID NO:2), CTI2 (AT3G02900, SEQ ID NO:4), and CTI3 (AT5G16660, SEQ ID NO:6) with α-CT, the following experiments were conducted.

The 30 kDa non-catalytic domain of α-CT was used as bait to screen an *Arabidopsis* cDNA library in a yeast two-hybrid (Y2H) screen. The cDNA library was prepared and built by introducing cDNA into pGATD7 vectors (Clontech) (Ye et al., 2016). The screening assays were conducted according to Clontech yeast handbook. α-CT Coiled-coil sequence was cloned into pGBKT7 vector. 100 ng pGBKT7-α-CT vector was transformed into AH109 yeast and plated on synthetic dropout (SD) medium lacking tryptophan. 100 μg cDNA library was transformed into 300 ml AH109 cells containing pGBKT7-α-CT, and plated on synthetic dropout (SD) medium lacking leucine, tryptophan, histidine, adenine. Plates were incubated at 30° C. for 4 d and then positive clones were identified by PCR and sequenced using T7 sequencing primer and 3'AD sequencing primer. For protein interaction assays, 100 ng of pGADT7 (CTI1-Coiled coil, CTI2-Coiled coil, CTI3-Coiled coil) and 100 ng pGBKT7-α-CT (full length) were transformed into AH109 and plated on SD/-leu-trp, after 3 days, and the positive clones were transferred to SD/-leu-trp-his plate with 50 mg/L X-α-Gal for another 4 day under 30° C.

Figure 7A:
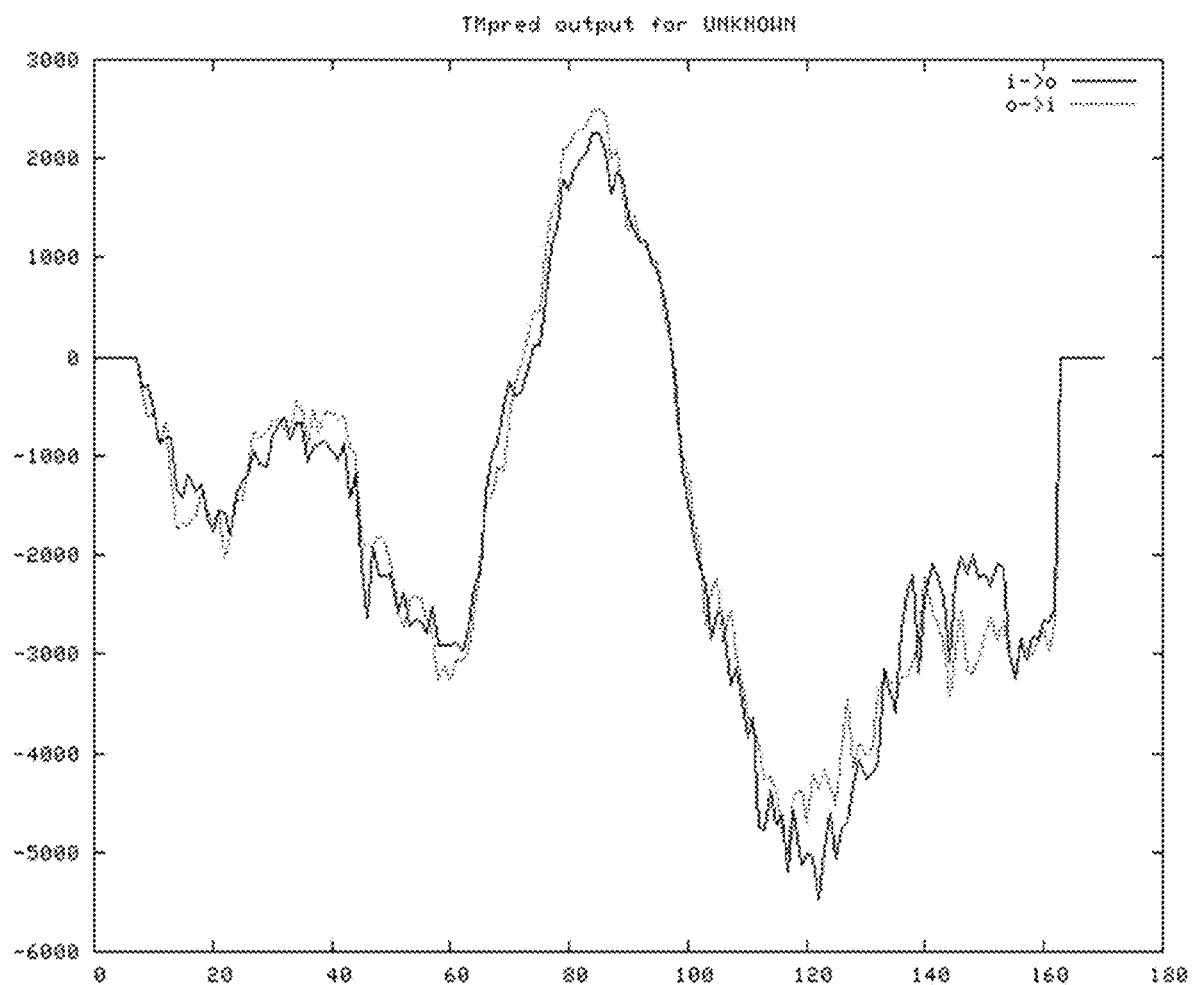
FIG. 7A is a graph summarizing the predicted transmembrane domain distribution of CTI1.
Figure 8A:
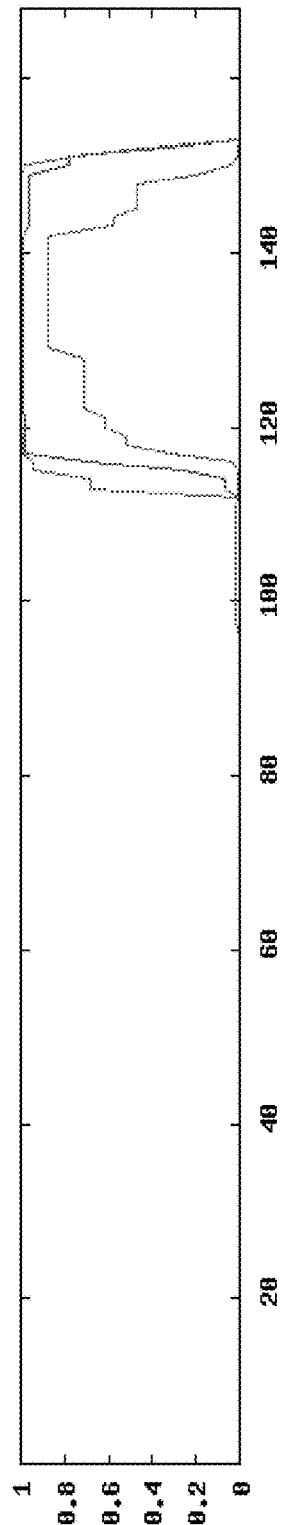
FIG. 8A is a graph summarizing the predicted coiled-coil domain distribution of CTI1.

After screening, CTI1, α-CT Interactor 1, was selected for further analysis as a potential interactor with α-CT. The CTI protein contains a putative transmembrane domain, a coiled-coil domain and predicted transit peptide residues, as illustrated in FIGS. 6, 7A, and 8A. Further, CTI was annotated as an inner envelope protein of the chloroplast by TAIR. In addition, because α-CT is localized in chloroplasts, the CT subcomplex is thought to be associated with the plastid envelope, as described below.

Figure 2A:
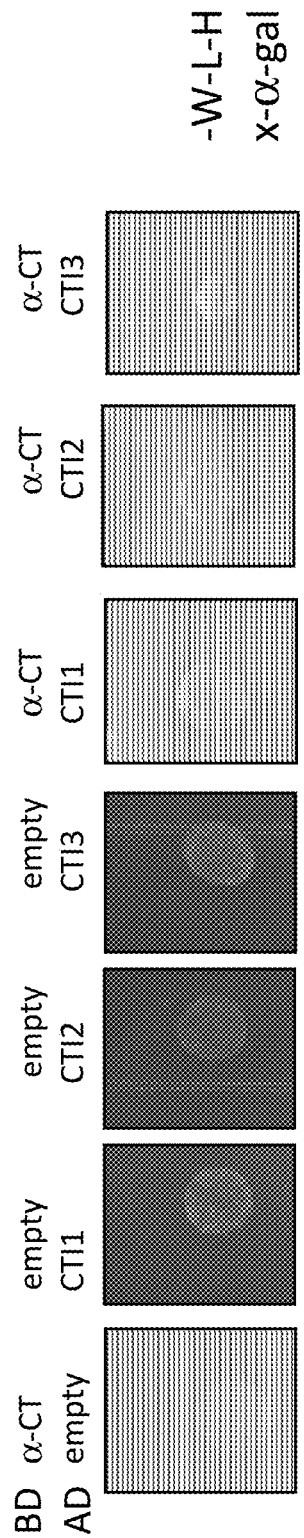
FIG. 2A contains a series of microscope images showing protein-protein interactions between α-CT and various candidate regulating proteins: ATG42960, AT3G02900, and AT5G42960.

To further confirm the interaction of CTI1 and α-CT, the coiled-coil domain of CTI and full-length α-CT was cloned and an additional Y2H assay was performed. α-CT was fused to a GAL4 DNA-binding domain (BD) and membrane proteins CT1, CT2, and CT3 were fused with GAL4 activation domain (AD). The protein interactions were examined using yeast cells with indicated constructs grown on synthetic droulet (-Leu-Trp-His) medium with x-a-gal (50 mg/L) for 3 days. FIG. 2A is a series of images of the yeast cells after 3 days of growth, indicating that CTI1, CTI2, and CTI3 all interacted with α-CT.

Figure 2B:
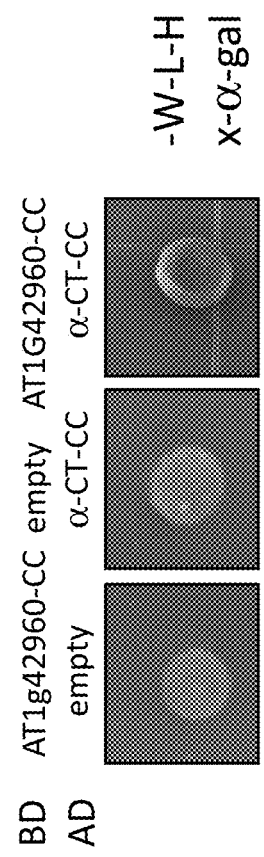
FIG. 2B contains a series of microscope images showing protein-protein interactions between the coiled coil domains of α-CT (α-CT-CC) and AT1G42960 (AT1G42960-CC).

In addition, the isolated coiled coil domain of α-CT was fused to a GAL4 DNA-binding domain (BD) and the isolated coiled coil domain of CT1 was fused with GAL4 activation domain (AD). The protein interactions were examined using yeast cells with the indicated constructs grown on synthetic drouplet (-Leu-Trp-His) medium with x-α-gal (50 mg/L) for 3 days. FIG. 2B is a series of images of the yeast cells after 3 days of growth, indicating that the coiled coil domain of CTI interacted with the coiled coil domain of α-CT.

The results of these experiments identified the interaction of three proteins (CTI1, CTI2, and CTI3) with α-CT. Further, the results of this experiment demonstrated that coiled-coil (CC) domains of the α-CT and CTI1 proteins were sufficient to enable the protein-protein interaction.

Example 2: Evaluation of Candidate Interacting Proteins Using BiFC Assay

To evaluate the interaction of candidate protein CTI1 (AT1G42960, SEQ ID NO:2) with α-CT, the following experiments were conducted.

Bimolecular fluorescence complementation (BiFC) assays using the split YFP system in protoplasts were performed to characterize the interaction between α-CT and CTI1. Arabidopsis protoplasts were transformed with different construct combinations harboring both the C- and N-terminal of the YFP to both α-CT and CTI1, CTI only (control), and α-CT only (control). Pictures were taken 16 hours after transformation using confocal microscope.

Figure 10:
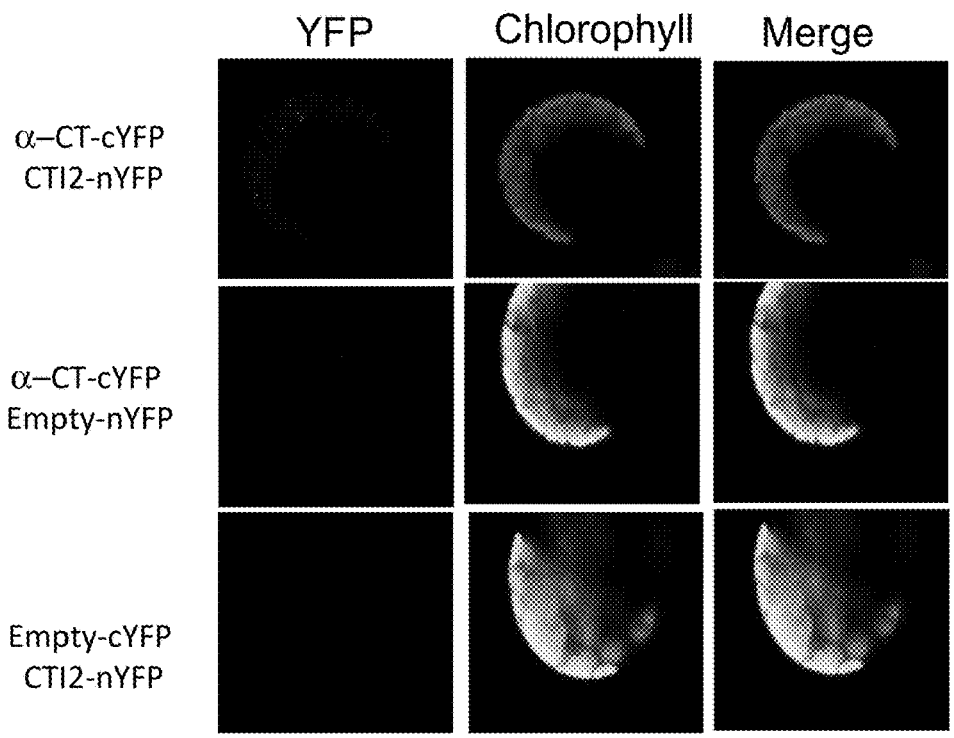
FIG. 10 contains a series of confocal microscope images of bimolecular fluorescence complementation (BiFC) assays of protein-protein interaction between α-CT and CTI2 using the split YFP system.
Figure 11:
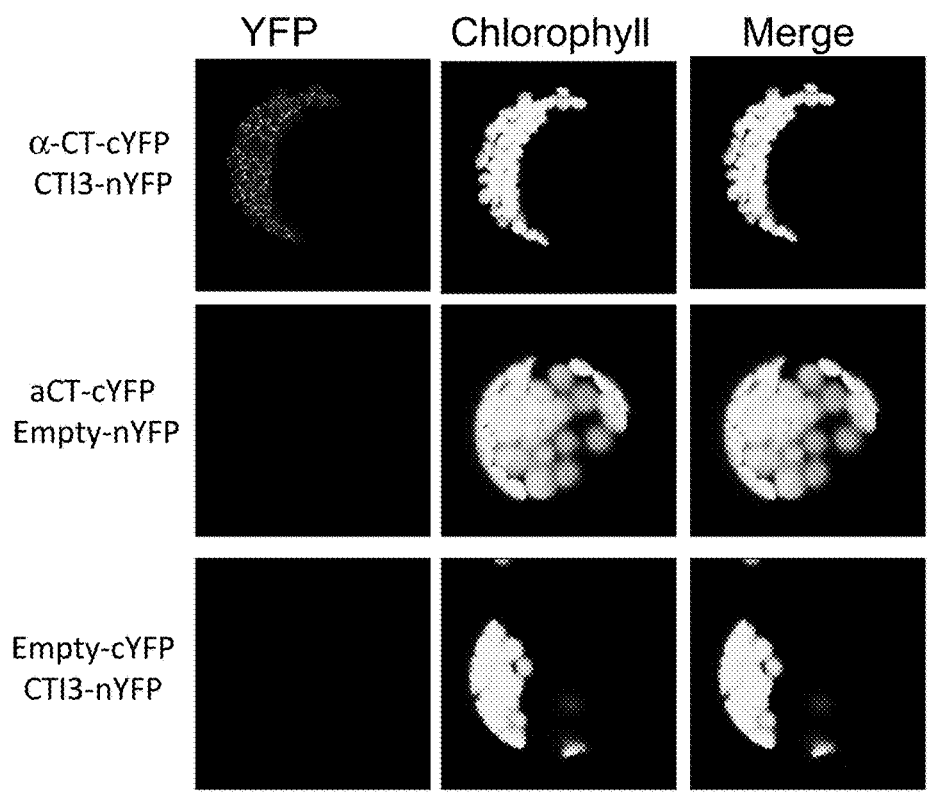
FIG. 11 contains a series of confocal microscope images of bimolecular fluorescence complementation (BiFC) assays of protein-protein interaction between α-CT and CTI3 using the split YFP system.

Similarly, BiFC assays using the split YFP system in protoplasts were performed to characterize the interaction between α-CT and CTI2 and CTI3, using methods similar to those described for CTI1 above. FIG. 10 and FIG. 11 illustrate that CTI2 and CTI3 interact with α-CT in a manner similar to the interaction previously observed for CTI1 (see FIG. 3).

Figure 3:
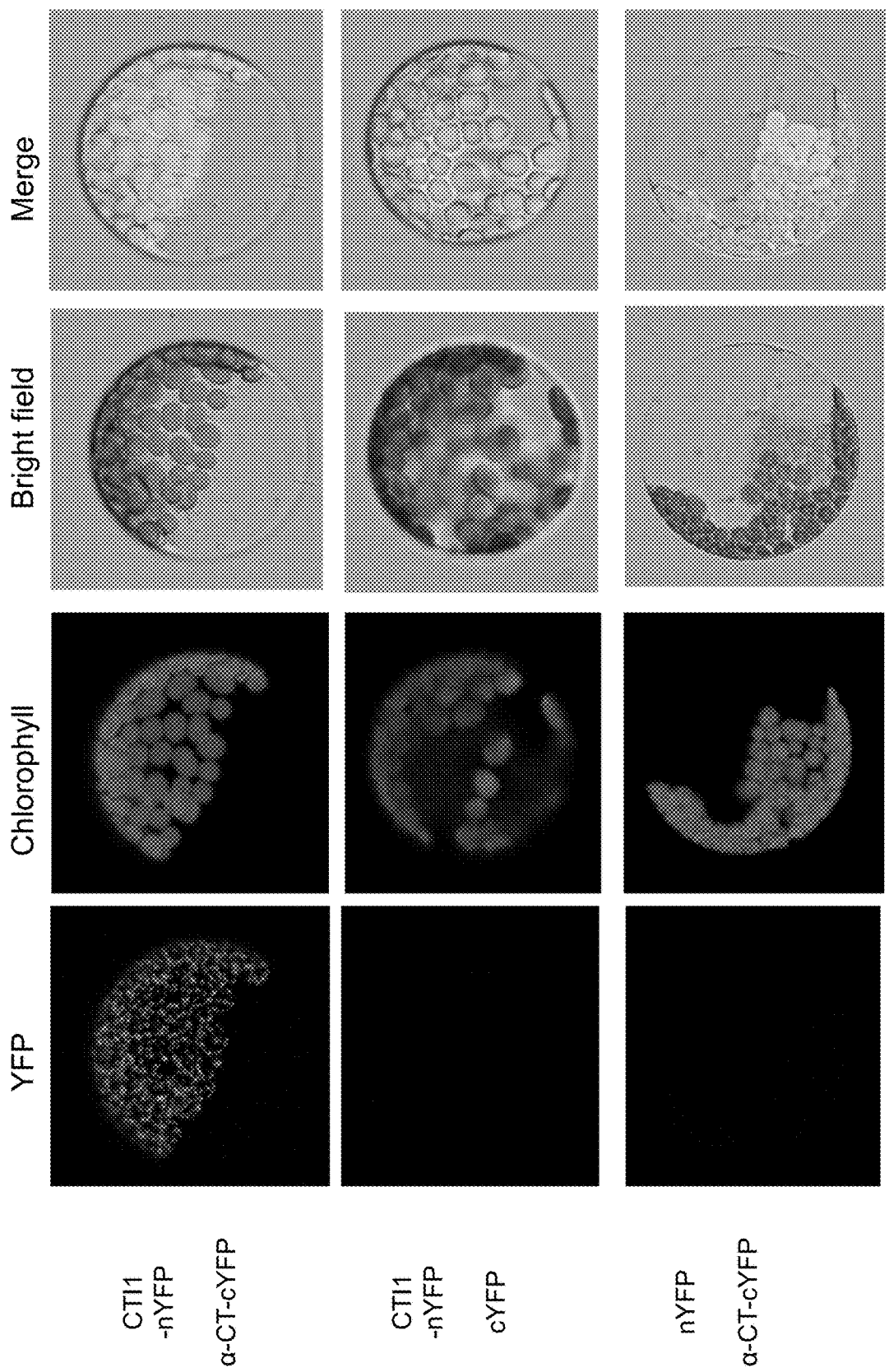
FIG. 3 contains a series of confocal microscope images of bimolecular fluorescence complementation (BiFC) assays of protein-protein interaction between α-CT and CTI1 using the split YFP system.

FIG. 3 is a series of confocal microscope images of the Arabidopsis protoplasts 16 hours after transformation of both the C- and N-terminal of the YFP to both α-CT and CTI1 (top row), CTI only (center row), and α-CT only (bottom row). CTI was observed to interact with α-CT, as illustrated in the top row of images in FIG. 3. When CTI1-nYFP and α-CT-cYFP were co-transformed into protoplast the YFP signal was detectable. In contrast, when CTI1-nYFP or α-CT-cYFP were co-transformed with the empty BiFC vector, a YFP signal was not detectable.

The results of these experiments confirmed the interaction of CTI with α-CT.

Example 3: Effect of CTI Knockdown on Seed Weight and Oil Content

To evaluate the effect of the modulation of CTI expression on seed weight and seed oil content in plants, the following experiments were conducted.

T-DNA mutants were developed to produce two genotypes: CTI2 knockout (Salk_057141) and CTI3 knockout (Salk_209093). Plants with CTI2 and CTI3 knockout genotypes, as well as a control (WT) with no CTI knockouts were grown and seeds from each plant were harvested and analyzed to determined seed weight of 100 seeds, as well as raw oil content per seed.

Figures 4A, 4B:
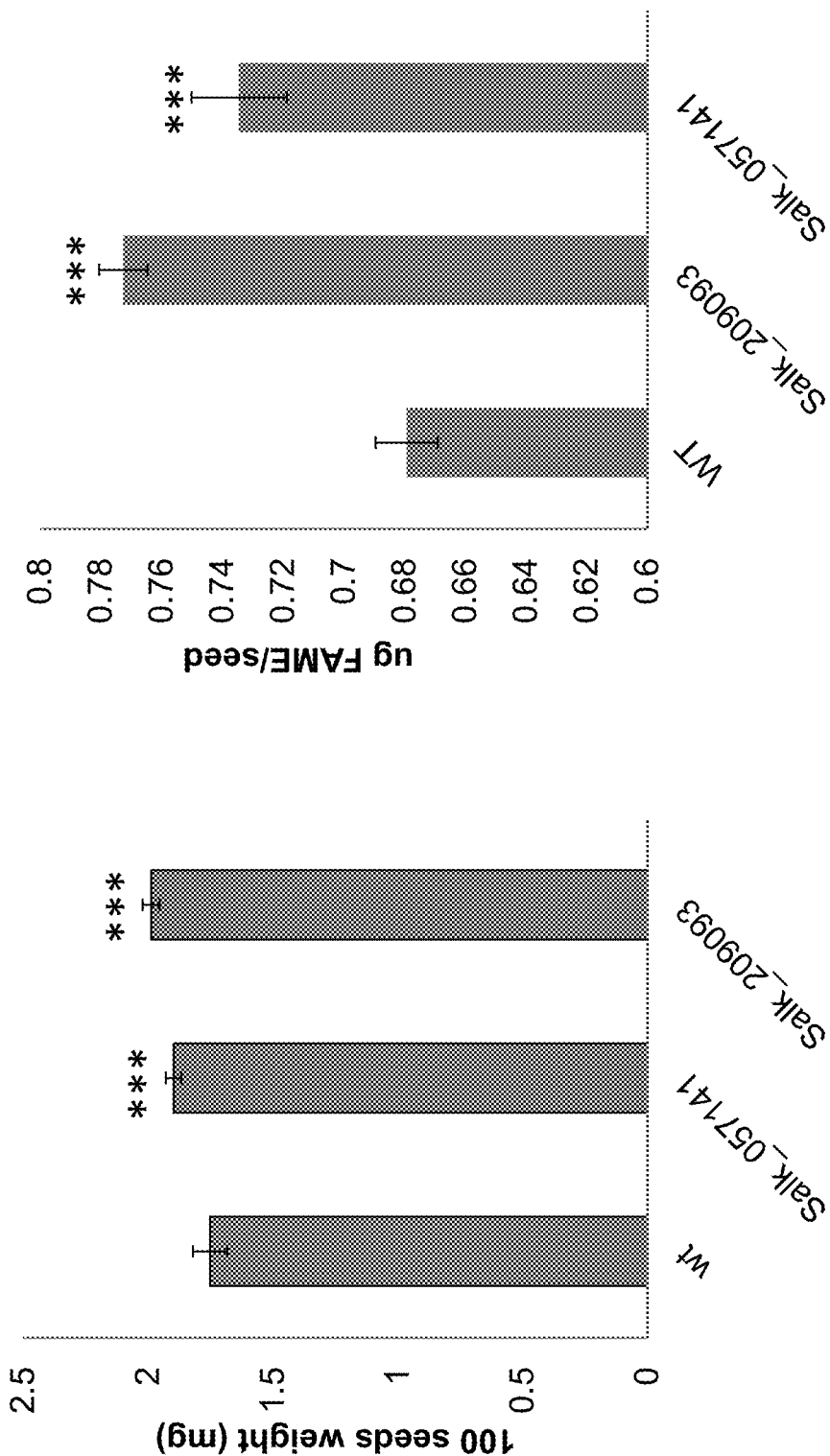
FIG. 4A contains a bar graph summarizing the effects of mutations in α-CT regulation protein variants on seed weight.
FIG. 4B contains a bar graph summarizing the effects of mutations in α-CT regulation protein variants on seed oil content.

FIG. 4A and FIG. 4B compare the seed weight and seed oil content, respectively, obtained from the seeds of the CTI knockouts and the wild type. As illustrated in FIG. 4A, seed weight of both CTI knockout seeds were significantly heavier (8.12%, 13.7% weight increase compared to wild type, respectively), as determined by Student's t test (P<0.001). FIG. 4B compares the average amount of fatty acid methyl esters in micrograms identified per seed of five replicates of the CT2 knockout, CT3 knockout, and wild type. The results summarized in FIG. 4B demonstrate a significant difference in seed oil content of the CTI knockouts (5.1%, 9.8% increase compared to wild type, respectively), as determined by Student's t test (P<0.001). All values shown in FIG. 4AZ and FIG. 4B are presented as means SD of five biological replicates.

CRISPR/Cas9 technology was also used to specifically knockout the CTIs. Single-guide RNAs (sgRNAs) that specifically targeted the CTI's DNA sequences were designed, which are ahead of the coiled-coil coding sequences (see FIG. 6). The 20-nt sgRNAs carefully chosen to avoid off-target effects using the web-based tool CRISPR-P (Liu et al., 2017). The Cas9 was placed under Yao promoter, which is highly expressed in tissues undergoing active cell division (Yan et al., 2015). Two CRISPR/Cas9-induced homozygous frameshift mutants were recovered for the CTI gene, two homozygous frameshift mutants for CTI2 gene, and one homozygous frameshift mutants for CTI3 gene (FIG. 25). To further confirm the knockout of CTI1 protein, we used anti-CTI antibody to detect the chloroplast protein extract.

FIG. 26 shows that the CTI band was absent in the cti1 mutant, indicating that the cti1 mutant is a null mutant. Western blot analysis confirmed knock-out of CTI protein expression in CRISPR/Cas9 mutants. Chloroplast proteins from wild-type or cti1/2 were detected by anti-CTI1 antibody. For each genetic background, two replicates were displayed. Asterisk indicates non-specific bands, which were regarded as protein loading control.

Figure 28A:
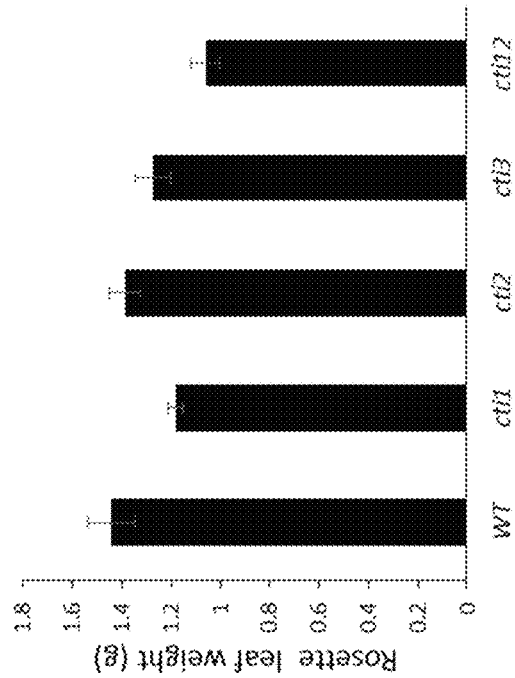
FIG. 28A is a graph summarizing rosette leaf fresh weight in wild-type and homozygous mutant plants grown on soil for 3-weeks (mean±SE, n=12, *P<0.05, **P<0.01).
Figure 28B:
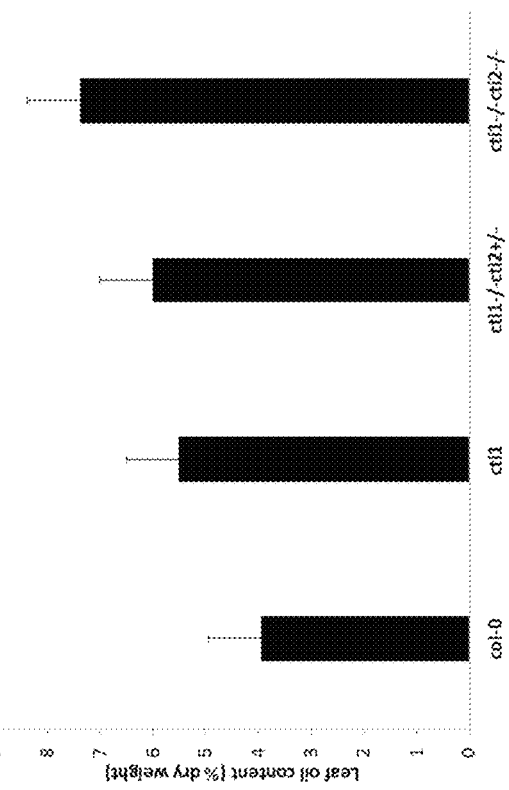
FIG. 28B is a graph summarizing leaf oil content in various different cti mutants.
Figure 27:
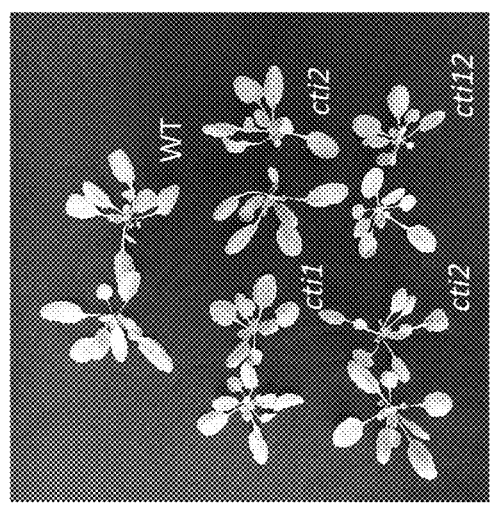
FIG. 27 is a photograph of the growth phenotypes of various cti homozygous mutants.

The growth and development phenotype of cti mutants are summarized in FIG. 27. Plants were 3-week old in different genetic backgrounds. Two plants for each genetic background are displayed. The three-week old cti1 and cti1/2 double mutant lines showed smaller rosette leaves than the wild-type, but not the cti2 nor the cti3 single mutant. As illustrated in FIG. 28, the rosette leaf fresh weights were also lighter in cti1 and cti1/2 mutants compared to wild-type. As illustrated in FIG. 28B, the various cti knockout phenotypes were characterized by higher leaf oil content as compared to the wild type.

Example 4: Bioinformatic Prediction of Functional Domains of CTI Proteins

To assess and predict functional domains within several plant CTI proteins, the following experiments were conducted. The three carboxyltransferase interactor (CTI) proteins from Arabidopsis thaliana described above were subjected to bioinformatic analysis: CTI1 (SEQ ID NO:2), CTI2 (SEQ ID NO:4), and CTI3 (SEQ ID NO:3). CTI1, CTI2, and CTI3 were aligned using commercially available sequence alignment software (ClustW, EMBL-EBI, Hinxton, Cambridgeshire, UK), and the percent amino acid identities were calculated from these alignments. The percent amino acid identities are summarized below in Table 6 below:

TABLE 6

| AMINO ACID SEQUENCE IDENTITIES OF CTI PROTEINS | | |
|---|---|---|
| PROTEIN | CTI1 | CTI2 |
| CTI2 | 41.1% | — |
| CTI3 | 41.2% | 64.1% |

Figure 7B:
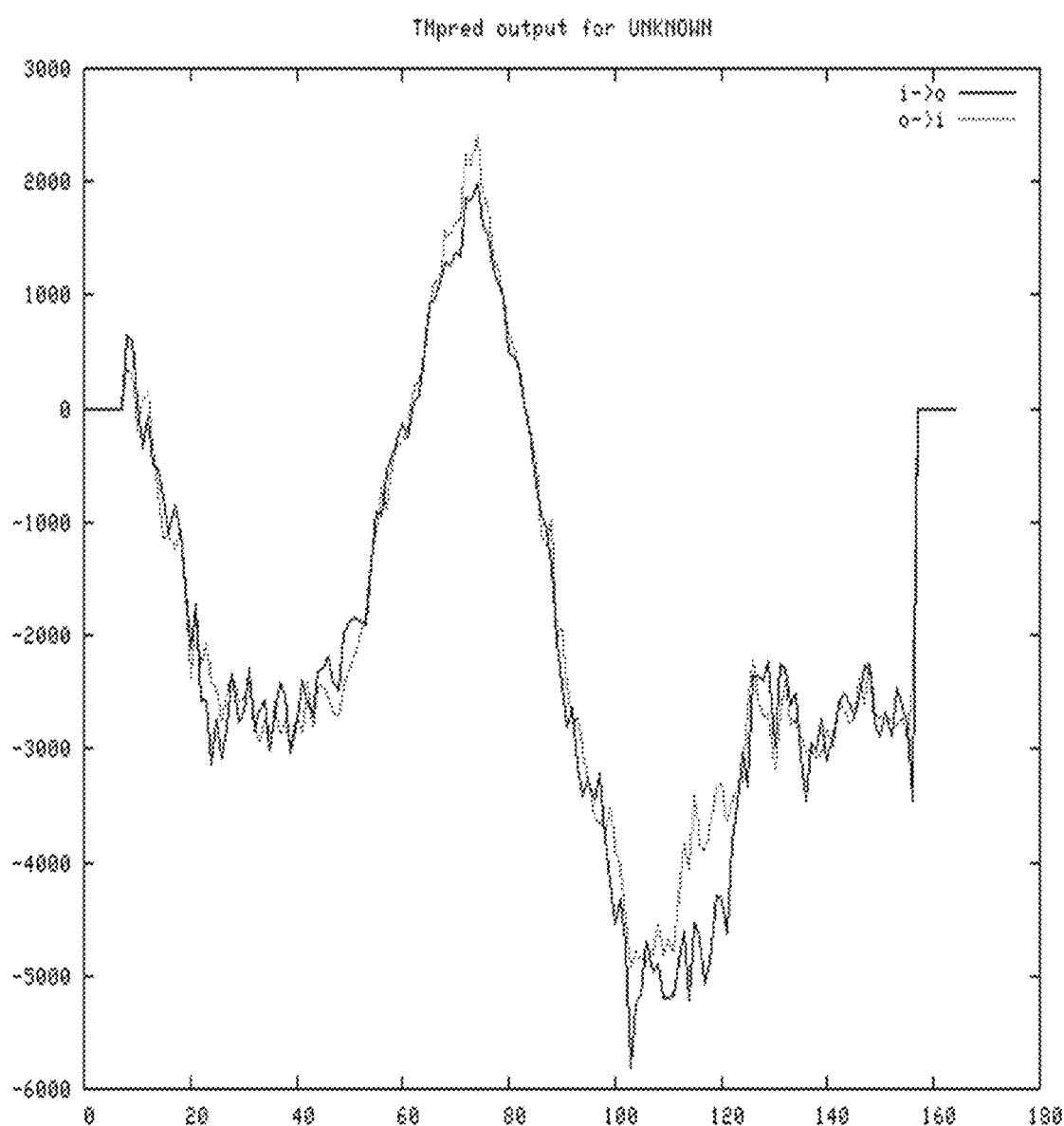
FIG. 7B is a graph summarizing the predicted transmembrane domain distribution of CTI2.
Figure 7C:
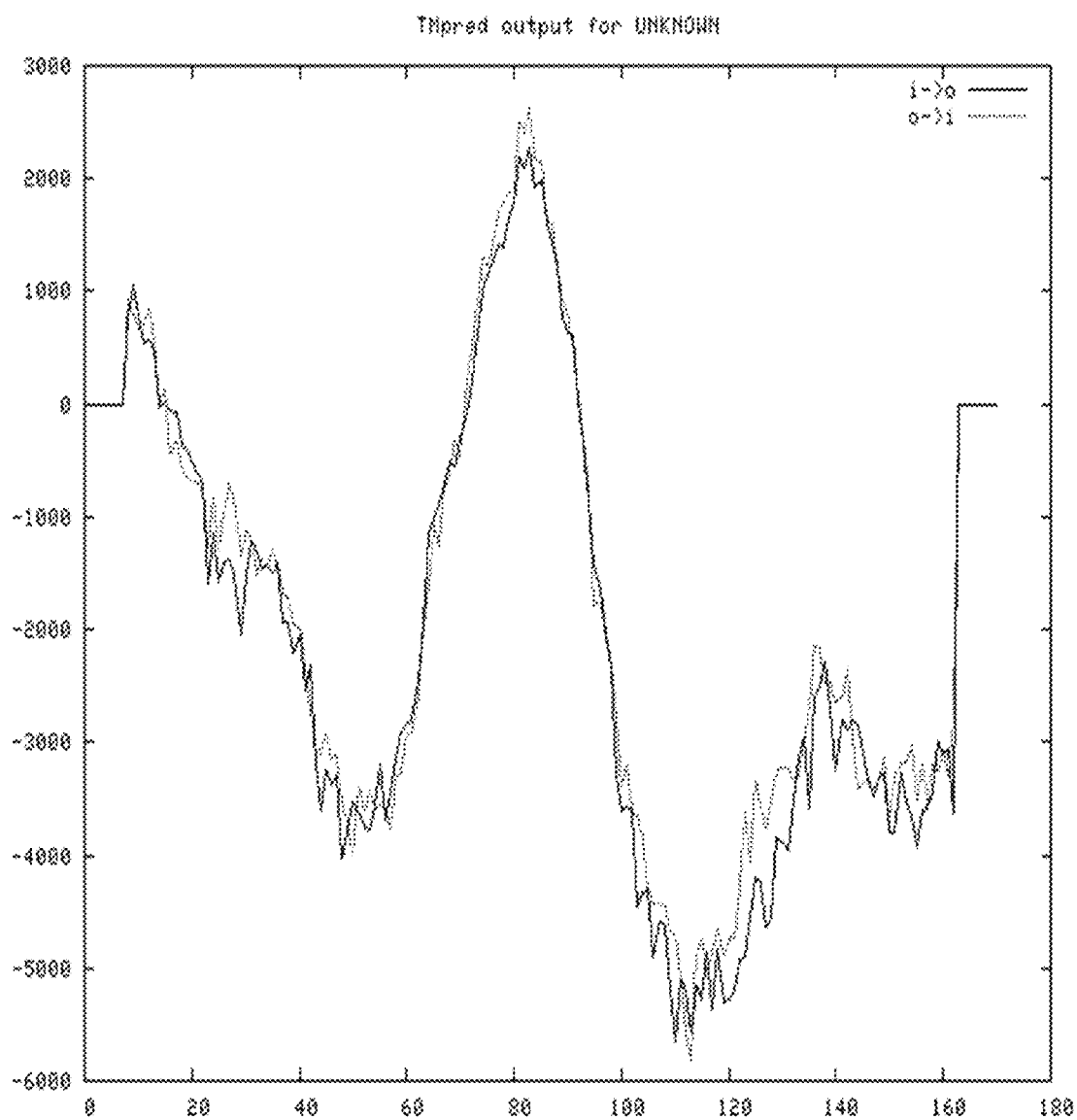
FIG. 7C is a graph summarizing the predicted transmembrane domain distribution of CTI3.
Figure 8B:
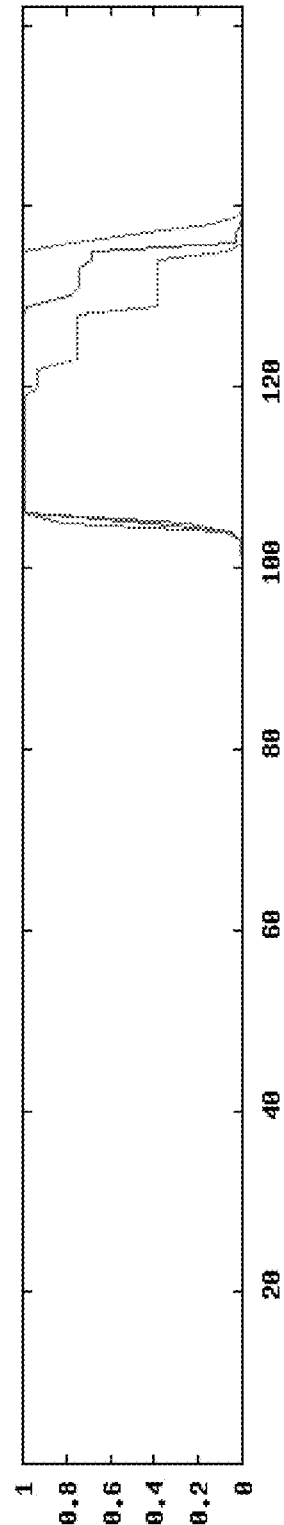
FIG. 8B is a graph summarizing the predicted coiled-coil domain distribution of CTI2.
Figure 8C:
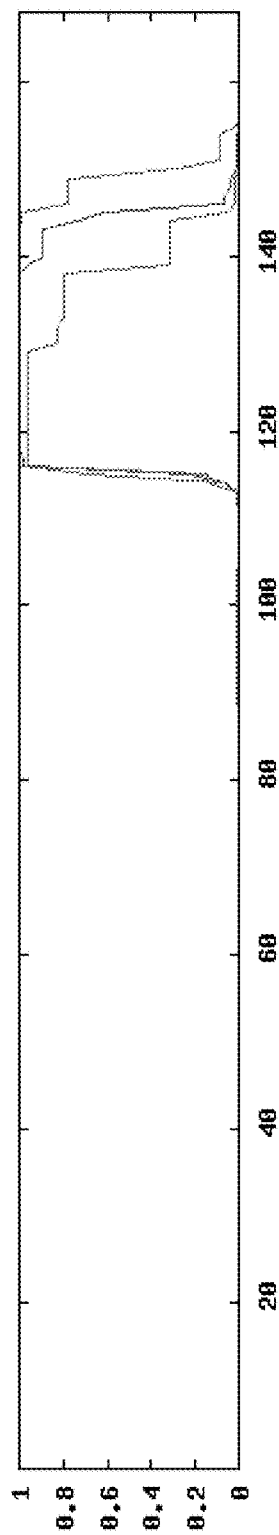
FIG. 8C is a graph summarizing the predicted coiled-coil domain distribution of CTI3.

FIG. 6 contains the amino acid sequence alignments of CTI1, CTI2, and CTI3 obtained as described above. In addition, transit peptides, transmembrane domains (TM))

and coiled-coil domains were predicted by the Target P, TMPred, and Coiled Coils prediction software accessed via the ExPASy bioinformatics resource portal (Swiss Institute of Bioinformatics, Lausanne, Switzerland). The amino acid sequences associated with each predicted domain are annotated in FIG. 6. FIGS. 7A, 7B, and 7C are graphs summarizing the predicted transmembrane domain distributions of CTI1, CTI2, and CTI3, respectively. FIGS. 8A, 8B, and 8C are graphs summarizing the predicted coiled-coil domain distributions of CTI1, CTI2, and CI3, respectively.

The results of these experiments indicated that the α-CT C-terminus encodes coiled-coil domains. In *Arabidopsis*, the α-CT C-terminus has a tandem of coiled-coil domains. Without being limited to any particular theory, the coiled-coil domain is a common structural motif conserved in both animal and plant proteins, which is thought to sometimes mediate various protein-protein interactions.

Example 5: Evaluation of Candidate Interacting Proteins Using Co-Immunoprecipitation Assay To evaluate the interaction of candidate protein CTI1 (AT1G42960, SEQ ID NO:2) with α-CT, the following experiments were conducted. Co-immunoprecipitation (co-IP) were conducted using purified chloroplast protein from wild-type or CTI1-MYC transgenic lines. Chloroplast proteins from wild-type (as control) or CTI1:MYC transgenic plants were immunoprecipitated with MYC antibody and detected by anti-MYC or anti-α-CT antibody.

Crude chloroplasts were isolated from 4-week-old Col-0 plants. Around 5 g of fresh leaves were homogenized by pestle and mortar in 30 mL ice-cold isolation buffer (50 mM pH 8.0 HEPES, 2 mM EDTA, 2.5 mM MgCl2, 5 mM NaHCO$_3$, 0.33 M sorbitol, 0.5% BSA). After filtration of the homogenate through a miracloth, the flow-through was centrifuged at 1000×g for 10 min at 4° C. The pellet was re-suspended in 1 mL protein extraction buffer containing 50 mM pH 7.5 Tris, 150 mM NaCl, 1% Triton-X 100 and 1× protease inhibitor cocktail (Sigma). After incubation for 30-min on ice, the solution was centrifuged at 20,000×g for 15 min at 4° C., the supernatant was decanted and 1 µg anti-Myc antibody (Millipore; Cat. No. 05-724) was added to the supernatant and incubated for 4 h with end-to-end shaking at 4° C. Afterwards, 25 µL protein A resin (Genescript; Cat. No. L00210) was added and incubated for another 2 h. The mixture was spun down and washed three times with washing buffer (50 mM Tris (pH 7.5), 150 mM NaCl). After washing, the resin was incubated with 50 µL 1×SDS-PAGE loading buffer, and then heated at 100° C. for 10 min. The protein was separated on 15% SDS-PAGE gels, and then transferred to PVDF membrane. After membrane transfer, the proteins were detected by immunoblotting with anti-Myc or anti-☐-CT antibody (Salie., et al., 2016). A horseradish peroxidase-conjugated secondary antibody was used and the horseradish peroxidase activity was detected by ECL western blotting substrate (ThermoFisher; Cat. No. 32106).

Figure 9:
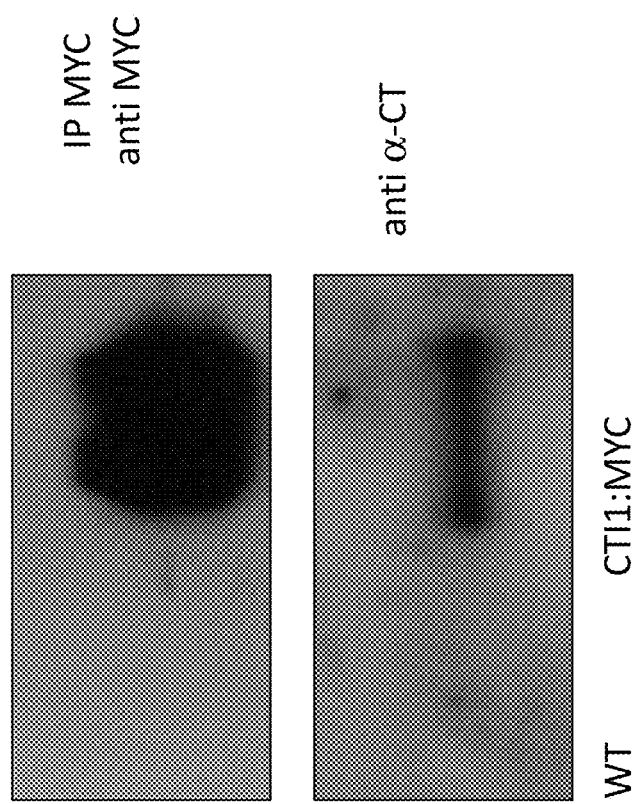
FIG. 9 contains images of BiFC assays assessing the interaction between CTI1 and α-CT.

As illustrated in FIG. 9, CTI1 co-immunoprecipitated with α-CT, indicating an association in vivo. CTI1 was identified as a novel member of the hetACCase complex through the observed interaction with α-CT.

Example 7: Evaluation of Binding Affinity of Interacting Proteins Using Microscale Thermophoresis To evaluate the binding affinity of candidate proteins CTI1, CTI2, and CTI3 with α-CT, the following experiments were conducted.

Figure 12:
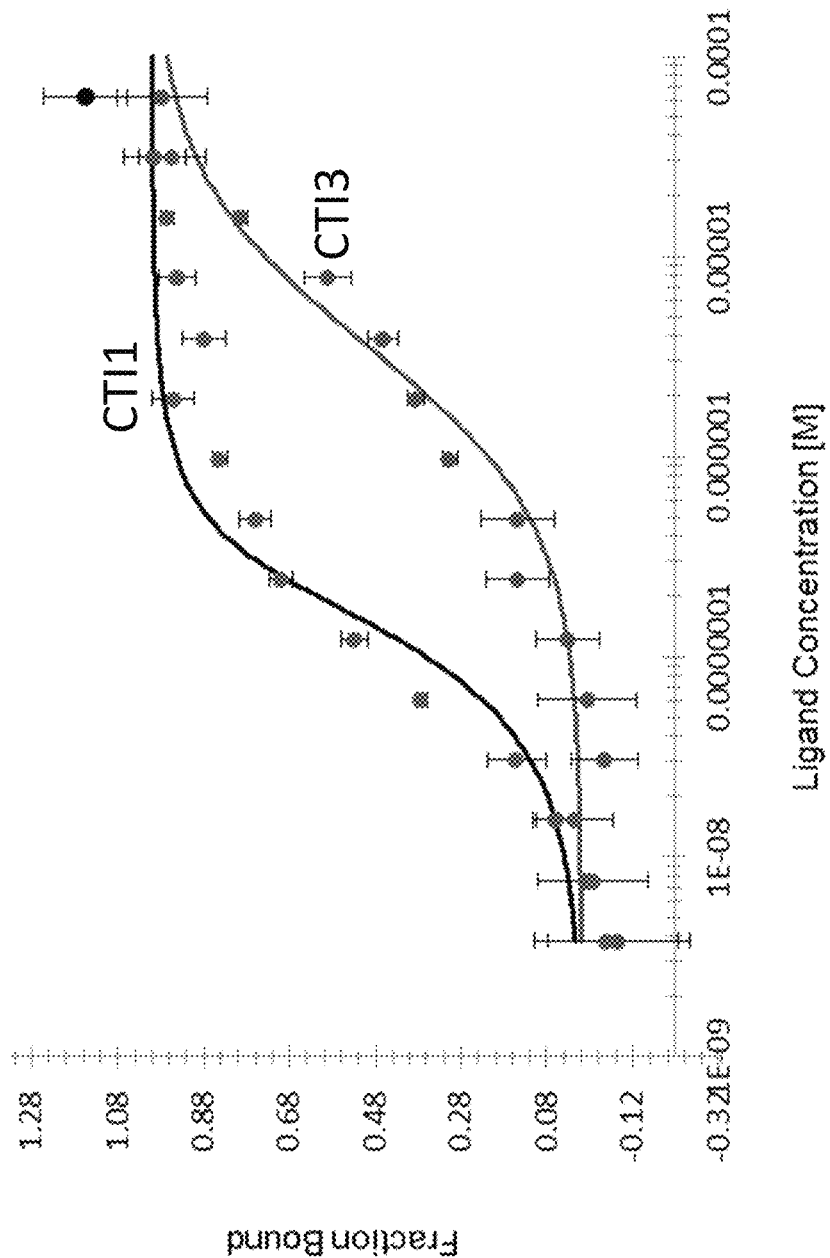
FIG. 12 is a graph summarizing the results of a microscale thermophoresis assay of the binding affinity of α-CT and CTI1/CTI3.

To determine the binding affinity between different CTIs to α-CT, His tagged α-CT coiled-coil, CTI, and CTI3 coiled-coil domains was purified and used to conduct Microscale thermophoresis (MST). The results showed that only the coiled-coil domains from both proteins are enough for the protein-protein interactions, more interestingly, CTI1 has a higher affinity towards α-CT then CTI3, which are indicated by the $K_d$ difference, as indicated in FIG. 12. The data points of FIG. 12 represent the fraction of labeled CTI1 and CTI3 coiled-coil domains bound to the coiled-coil domain of α-CT (mean SD, n=3).

The results of this experiment identified a family of novel proteins associated with hetACCase through direct interacting with coiled-coil domain of α-CT.

Example 8: Inner Envelope Localization of Candidate Proteins

To investigate the subcellular localization of CTI1, CTI2, and CTI3 described above, and α-CT, a construct encoding a full-length C-terminal fusion between CTIs or α-CT with YFP was transiently expressed in *Arabidopsis* protoplasts. Empty protoplasts were used as a control.

*Arabidopsis* protoplasts were made from 4-week old Col-0 plants and isolated according to previously reported methods (Yoo et al., 2007). About 40 leaves were cut into strips with sharp razor blade and then transferred into 20 mL of enzyme solution (20 mM pH 5.7 MES, 1.5% (wt/vol) cellulase R10, 0.4% (wt/vol) macerozyme R10, 0.4 M mannitol, 20 mM KCl and 0.1% BSA) for 3 h at room temperature. After 3 h, the enzyme solution was filtered through 75-µm nylon mesh and washed with around 20 mL W5 solution (2 mM pH 5.7 MES, 154 mM NaCl, 125 mM CaCl2), 5 mM KCl). The flow-through was centrifuged in a 50 ml falcon tube under 200 g's for 2 min. As much supernatant as possible was removed and the protoplast pellet was re-suspended with 1 mL W5 solution and the protoplasts were rested on ice for 30 min. The protoplasts were pelleted under 200 g's for 2 min, and re-suspended within 500 µL of MMG solution (4 mM pH 5.7 MES, 0.4 M mannitol and 15 mM MgCl2). In a 2 mL microfuge tube, 10 µL purified plasmid (10-20 µg) was added into 100 µL of protoplasts and then 110 µl PEG solution was added (40% (wt/vol) PEG4000 in ddH2O containing 0.2 M mannitol and 100 mM CaCl2).

The transfection reaction was mixed by gently tapping the tube, and the tube was incubated at room temperature for around 10 min. After 10 min, the transfection mixture with 500 µl W5 solution was diluted and mixed well by gently rocking the tube to stop the transfection process. The mixture was centrifuged for 2 min at 200 g's, and the pellet was re-suspended in 1 mL of W5 solution. The mixture was incubated overnight in 23° C. chamber under dark conditions.

Figure 15:
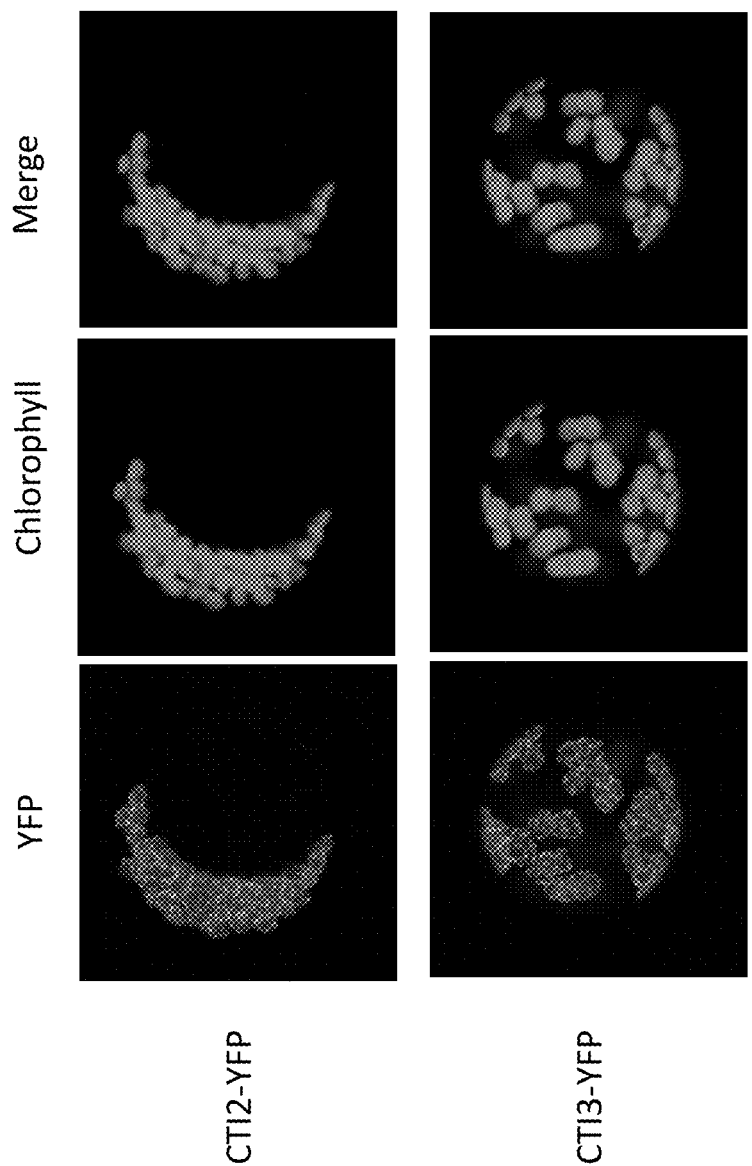
FIG. 15 contains a series of images were taken using 2-week old leaf tissues by confocal microscopy illustrating the subcellular localization of CTI2 (top row) and CTI3 (bottom row) in a 35S:CTI1:GFP transgenic plant.

CTI1/2/3 and α-CT were fused with YFP (C-terminus), and transformed into protoplasts using the above method. After transformation, the fluorescence was observed by confocal laser microscope (Leica TCS SP8), as illustrated in FIG. 15.

For co-localization, the CDS of CTI1 was cloned into pGWB605 vector and the CDS of α-CT and TIC40 were cloned into pGWB654 vector. The vectors were transformed into *Agrobacterium tumefaciens* strain GV3101. 2 ml GV3101 cells with different vectors were pelleted and re-suspended using 500 µL injection buffer (50 mM pH 5.7 MES, 10 mM MgCl2). Different cell combinations were infiltrated into the leaves of *Nicotiana benthamiana* with P19 (Papp et al., 2003). After a 2-day incubation in a growth chamber, the fluorescence was observed by confocal laser microscope (Leica TCS SP8). The CTI1-GFP and α-CT fusions were visible in discrete spots at the periphery of chloroplasts, as illustrated in FIG. 13. In addition, the GFP signal from the 35S:CTII:GFP transgenic plant showed similar fluorescence pattern as the transiently expressed CTI-YFP signal, as illustrated in FIG. 14. It should be noted that the CTI1-YFP and α-CT-YFP showed a similar punctate fluorescence pattern at the chloroplast surface like another chloroplast inner envelope protein TGD2 (Awai et al., 2006). Likewise, when CTI2-YFP and CTI3-YFP were transiently expressed in protoplasts, the fluorescence signals showed similar pattern as CTI1-YFP, as illustrated in FIG. 15.

Figure 16:
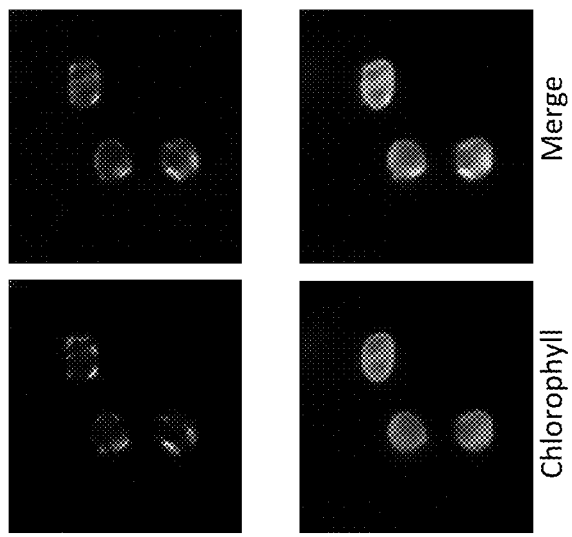
FIG. 16 contains a series of images taken 2-days after transformation and during transient expression of CI1-GFP and α-CT-RFP in tobacco cells illustrating the subcellular colocalization of CTI1 and α-CT in the chloroplasts.
Figure 19:
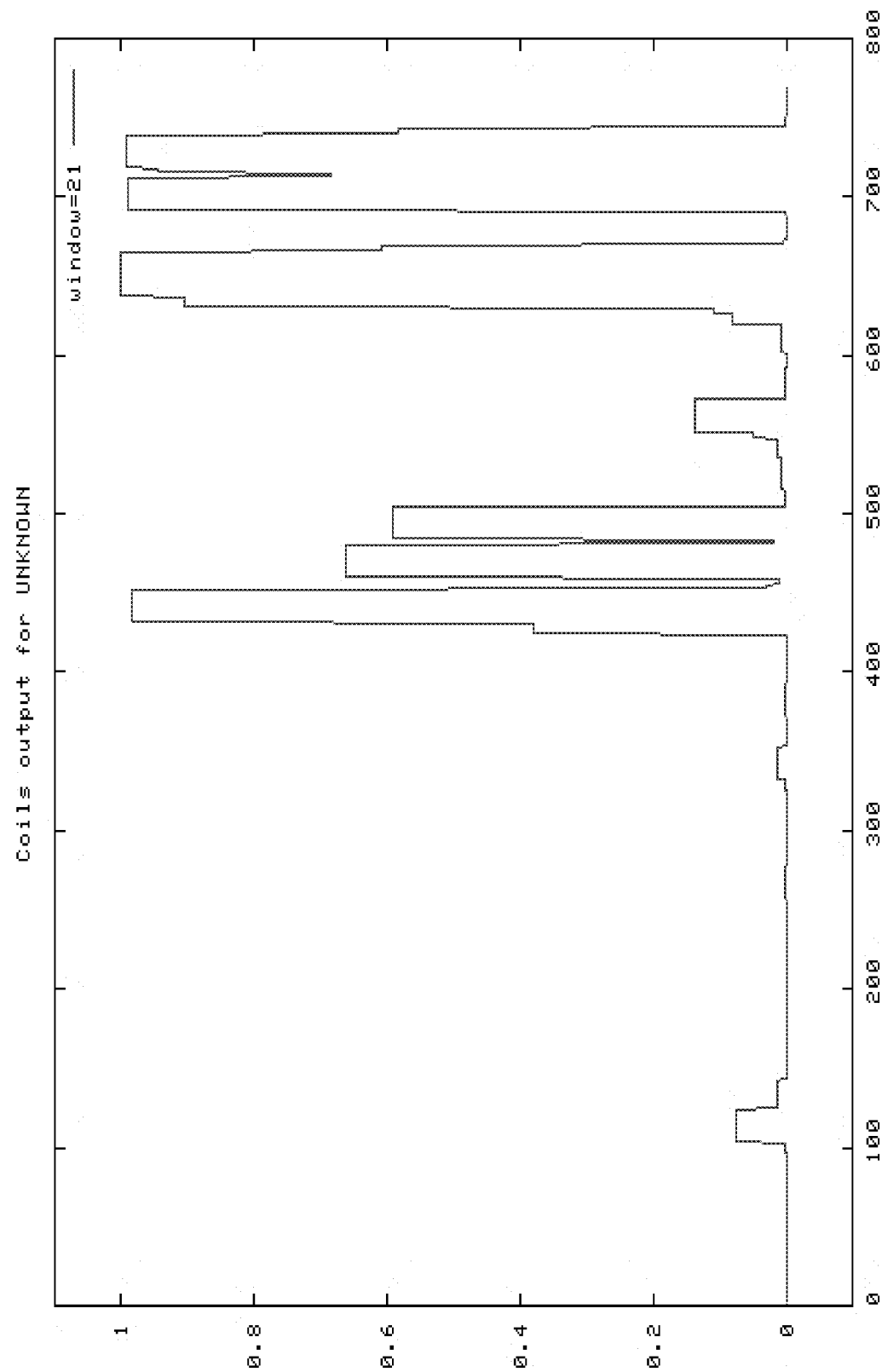
FIG. 19 is a graph summarizing the predicted coiled-coil domain distribution of a CTI protein.
Figure 20:
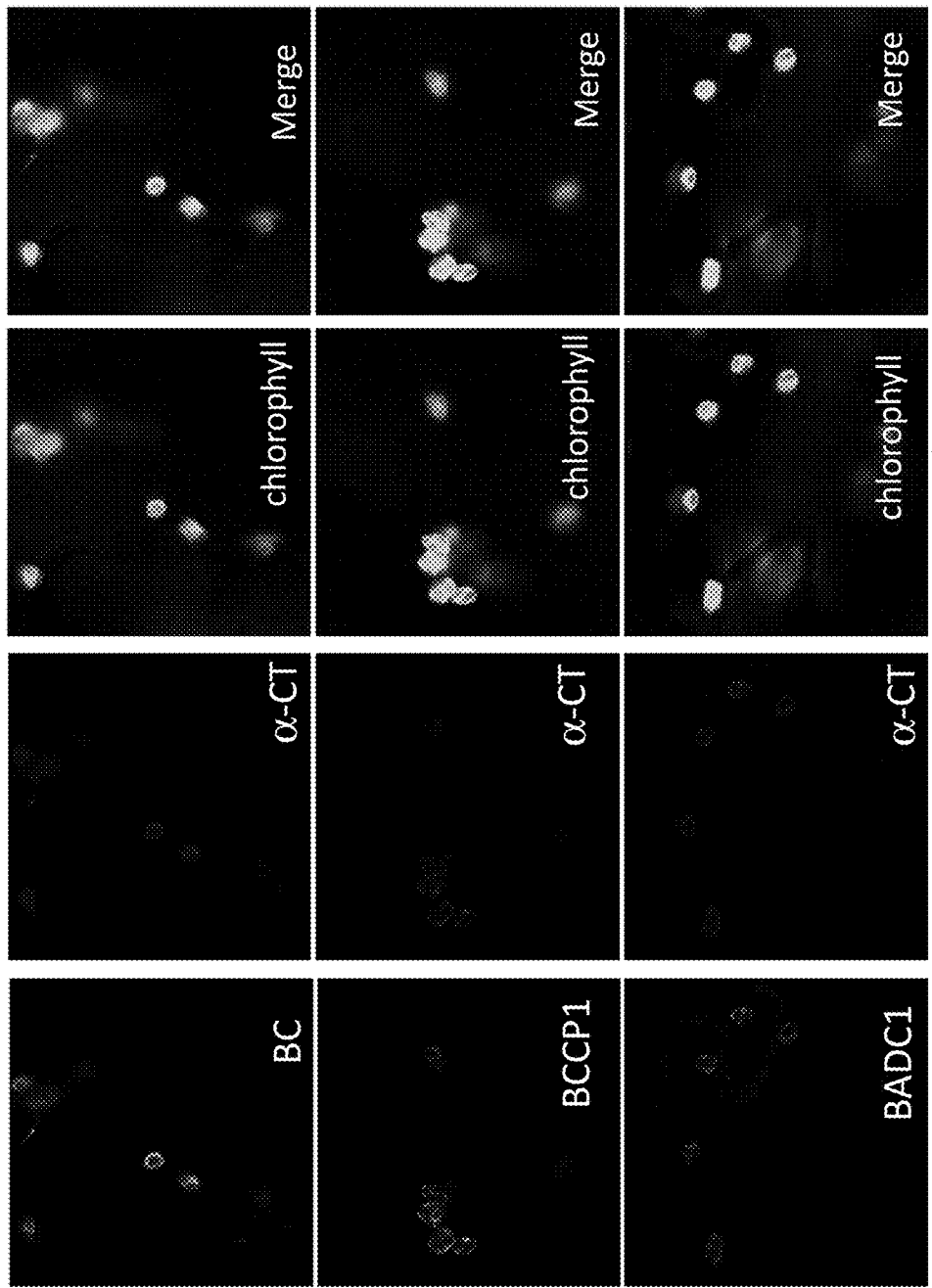
FIG. 20 contains a series of images illustrating the co-localization of hetACCase subunits (BC, BCCP1 and BADC1); GFP tagged small subunits and α-CT-RFP was transiently transformed into tobacco cells, and pictures were taken 2-d after transformation.

Since CTI could associate with α-CT, the proteins are likely to be colocalized with each other in the chloroplast. To test this hypothesis, CTI1-GFP and α-CT-RFP were co-transformed into tobacco leaf cells using methods similar to those described above. The confocal images (see FIG. 16) showed that CTI1-GFP and α-CT-RFP display exactly the same localization on the chloroplast surface, confirming their co-localization.

Figure 17:
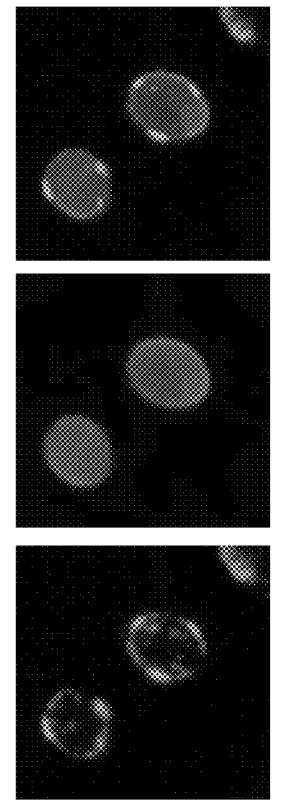
FIG. 17 contains a series of images taken 2-days after transformation and during transient expression of CTI1-GFP and TIC40-RFP in tobacco cells illustrating the subcellular colocalization of CTI and TIC40 in the chloroplasts.

As discussed above, CTI was annotated by TAIR as a chloroplast inner envelope protein and the fluorescence label assays described above further confirmed that CTI was localized at the chloroplast surface. To further confirm its chloroplast inner envelope localization, a co-localization analysis was performed between CTI and TIC40, an inner envelope anchored protein. CTI1-GFP and TIC40-RFP were co-transformed into tobacco leaf cells., and the results showed that most of the GFP signal could co-localize with the RFP signal (see FIG. 17), confirming the chloroplast inner membrane localization of CTI1.

To further explore the association of CTI1 protein with inner envelope membrane and to determine its topology, a dual-protease digestion assay was used. Intact chloroplasts were isolated from CTI1-MYC plants and treated with thermolysin (a protease unable to penetrate the outer envelope membrane) or trypsin (a protease able to penetrate the outer envelope but not the inner envelope membrane).

10 g of 4-week-old Col-0 leaves were harvested and the crude chloroplasts were isolated according to above method. Chloroplasts were re-suspended in 1 ml of isolation buffer, and the resuspension was loaded to the Percoll gradient. Percoll gradient was produced by mixing 15 mL of Percoll and 15 mL of 2× isolation buffer, and centrifuging at 38,700 g's for 30 min at 4° C. The Percoll was centrifuged with the chloroplasts using a prechilled swinging-bucket rotor at 7,700 g's for 10 min at 4° C. with no brake. After centrifuging, the upper green band was removed and discarded. The lower green band was retrieved into a new 50-mL centrifuge tube containing 10 mL isolation buffer. The mixture was spun down at 1,500 g's for 5 min at 4° C., and the pellet was re-suspended with 1 mL reaction buffer (50 mM pH 8.0 HEPES, 0.33 M sorbitol). To set up the protease digestion reaction for the mock treatment, 150 µL chloroplasts and 100 µL reaction buffer were used; for thermolysin, 150 µL chloroplasts, 5/10 µL of thermolysin stock solution (1 mg/mL, freshly prepared in 5 mM CaCl2)/reaction buffer) and 95/90 µL reaction buffer were used; for trypsin, 150 µL chloroplasts, 5/10 µL of trypsin stock solution (1 mg/mL, freshly made in reaction buffer) and 95/90 µL of reaction buffer were used. All reactions were incubated on ice for 30 min. Each protease reaction was quenched on ice for 5 min as following: for mock, 50 µL reaction buffer was added; for, added 50 µL quench solution (60 mM EDTA/reaction buffer) was added; for trypsin, 50 µL trypsin inhibitor solution (1 mg/mL in reaction buffer) (Sigma; Cat. No. T6522) was added. SDS PAGE loading buffer was added to each reaction, and western blot was conducted using anti-Myc or anti-α-CT antibody as described previously.

Figure 18:
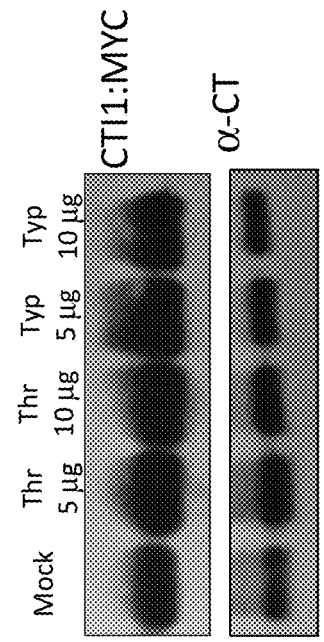
FIG. 18 contains images summarizing the results of a dual-protease digestion assay.

The CTI1 large C-terminus faces the chloroplast stroma. Intact chloroplasts were digested by thermolysin (Thr) or trypsin (Typ), after 30-minute digestion proteins were detected by anti-MYC or anti-α-CT antibody. Both CTI1 and α-CT were resistant to both proteases, suggesting that the α-CT protein was positioned inside the inner envelope membrane, and CTI1, the transmembrane domain containing protein, is an integral component of inner envelope membrane with C terminus facing the stroma (see FIG. 18).

Example 9: Expression Patterns of CTI Proteins

To compare the expression patterns of the *Arabidopsis* CTI proteins CTI1, CTI2, and CTI3, described above, during different stages of *Arabidopsis* growth and development, the following experiments were conducted.

*Arabidopsis thaliana* accession Col-0 was used as wild-type in this study. All plants were grown in growth chamber under a 16-hour light/8-hour dark cycle at 22° C. The light intensity is 82-115 (average 98) µmol m-2 s-1 and humidity is 50.7%.

Independent transgenic plants expressing GUS fusion protein using CTI promoter with its genomic DNA were generated. The coding sequence (CDS) of CTI1, CTI2, CTI3, and other subunits of hetACCase were amplified by PCR from cDNA of Col-0. The fragments were then cloned into entry vector pENTR/D-TOPO. The pGWB6** series vectors (Nakamura et al., 2010) were used as destination vectors. The plasmids for CRISPR/Cas9 were designed according to the protocol described in (Feng et al., 2013). Briefly, the single-guide RNAs (sgRNA) were designed for CRISPR/Cas9 using online software CRISPR-P 2.0 (Liu et al., 2017). The oligo pairs were annealed to generate double-strand DNA. The sgRNAs were cloned into the BbsI site of a gateway compatible entry vector U6-sgRNA, and the U6-sgRNA cassette introduced into a modified binary vector pCambia1300, in which hspCas9 is driven by YAO promoter (Yan et al., 2015). For the GUS transgenic plants, the genomic DNA with promoter was cloned into pGWB633 vector. The binary vectors were transformed into *Agrobacterium tumefaciens* strain GV3101. And the transformed agrobacteria were used to transform via the floral dip method (Clough and Bent, 1998).

Figure 23:
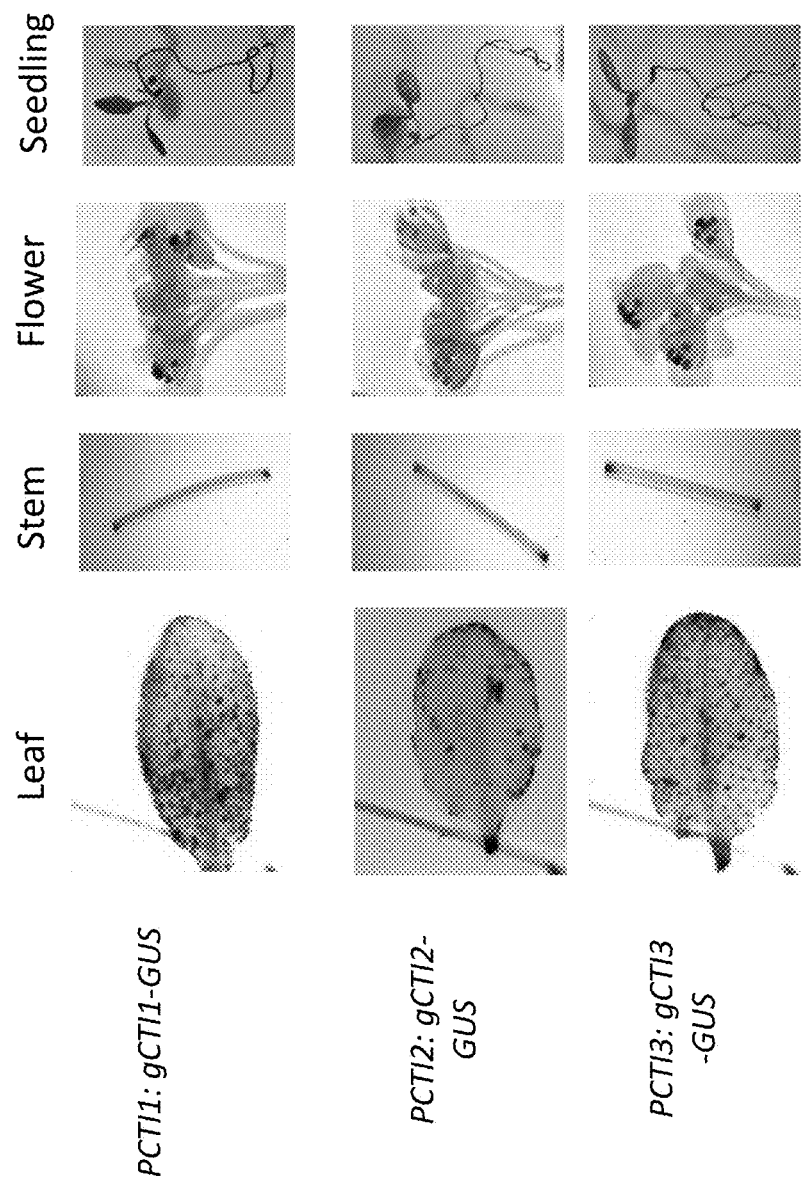
FIG. 23 contains a series of images of GUS histochemical staining of PCTI1/2/3:gCTI-GUS transgenic plants at different developmental stages.

FIG. 23 illustrates that all three CTIs are highly expressed in different *Arabidopsis* tissues, including leaf, stem, flower, cotyledon, root and silique. For flowers, the CTIs were only expressed in pistil and mature stamen. More importantly, all the three CTIs share highly similar expression pattern along the growth and development of *Arabidopsis*. The GUS staining signal indicated that CTI1 was the most abundantly expressed isoform and CTI2 was the least expressed isoform.

The expression pattern summarized in FIG. 23 was further confirmed by qRT-PCR using RNAs from different *Arabidopsis* tissues. Total RNA was isolated using TRIzol reagent (Invitrogen; Cat. No. 15596-018). Genomic DNA was removed by RapidOut DNA Removal Kit (Thermo Scientific; Cat. No. K2981). cDNA was synthesized from 2 µg total RNA using a reverse transcription kit (Thermo Scientific; Cat. No. 4368814). Quantitative real-time PCR was conducted using SYBR Green PCR Master Mix (Thermo Scientific; Cat. No. 4309155). Actin2 was used as an internal control in all experiments. Each sample reaction was replicated three times and each experiment was repeated in three biological replicates.

Figure 24:
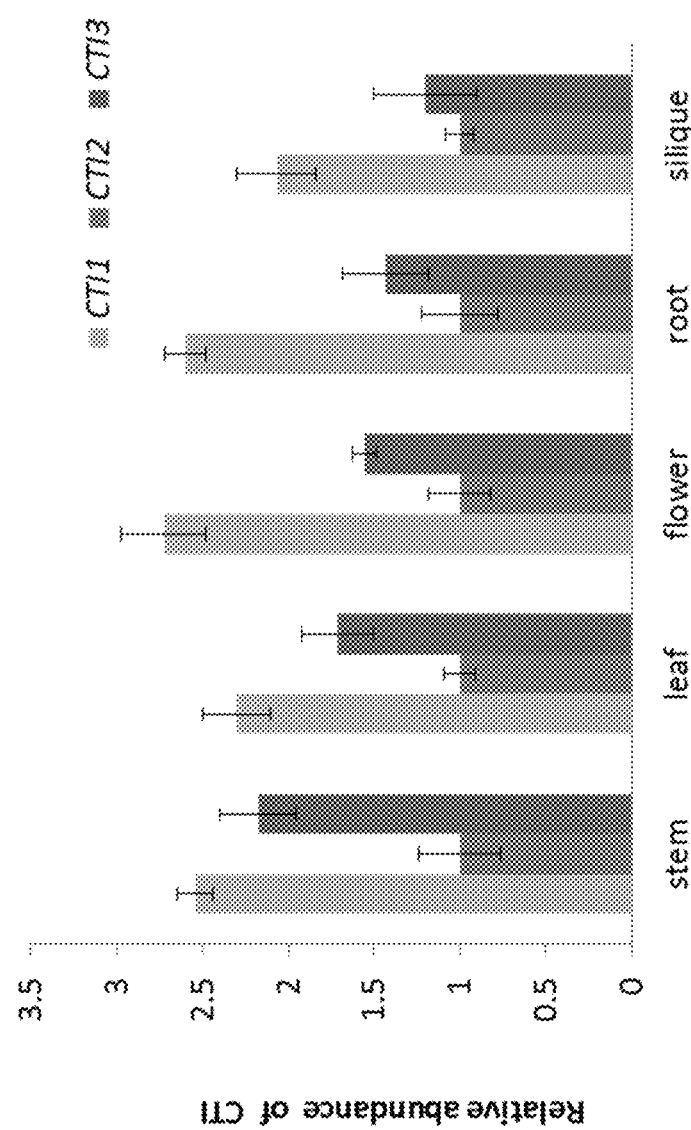
FIG. 24 is a graph summarizing a qRT-PCR analysis of the expression of CTI genes in different plant organs; Actin2 was used as reference gene for normalization (mean±SD, n=3).

The results, summarized in FIG. 24, are consistent with the GUS transgenic plants staining results. In addition, the qRT-PCR results also showed that CTI is the most abundant isoform in distinct tissues. These results suggest that CTIs function broadly during *Arabidopsis* growth and development and the three homologs may be functional redundant due to their similar expression pattern.

Example 10: Expression of Mutant CTI Proteins

To assess the fatty acid synthesis rate and leaf oil content of plants with mutated cti genes, the following experiments were conducted.

CTIs interact with α-CT, the subunit of hetACCase involved in de novo fatty acid synthesis. The fatty acid synthesis process is considered the top gene ontology enrichment of CTI1 and CTI2 co-expressed genes (see FIGS. 21A and 21B). To investigate the rate of fatty acid synthesis in cti mutants, 14C-acetate pulse-chase labeling experiments were performed using detached 4-week old leaves. In vivo labeling experiments with 14C-acetate were done according to previously published methods (Bates et al., 2014 and Fan et al., 2015). Three leaves from 4-week-old plants were cut into strips for a single biological replicate. The leaf strips were transferred to 2 mL reaction buffer (20 mM pH 5.5 MES, ½ MS salts, and 0.01% Tween 20) in a 6-well plate. The labeling assays were initiated by the addition of 1 µCi of [14C] acetate (PerkinElmer; Cat. No. NEC084H001MC). After labeling assay initiation, the 6-well plates were incubated on a shaker in the light (40 µmolm-2 s-1 at room temperature). The samples were collected at 5, 10, 20 and 40 min, respectively. At the end of labeling, the leaf strips were washed with water three times.

Total lipids were extracted according to previously reported methods (Dormann et al., 1995). The plant samples were incubated in 800 µL extraction buffer (methanol: chloroform: formic acid (20:10:1, v/v) and then vortexed for 10 seconds. The mixture was incubated for around 30-min, and then 500 µl IM KC-0.2 M H3PO4 was added. The mixture was vortexed and centrifuged at 12,000 g's for 30 seconds to obtain the lipid in the chloroform phase. 80 µL of the lipid was suspended in 1.5 mL liquid scintillation cocktail (Sigma; Cat. No. 03999-5L). The incorporated radioactivity was measured in cpm with a scintillation counter.

To quantify the total fatty acid content total lipids were transmethylated into fatty acid methyl esters (FAMEs) (Salie et al., 2016). FAMEs were analyzed by a Hewlett Packard 6890 gas chromatograph. For the leaf tissue, one mature leaf was collected and dried by centrivap SpeedVac overnight. For seed oil content, the seeds were dried over desiccant for 1 week prior to analysis.

Figures 29, 30, 31:
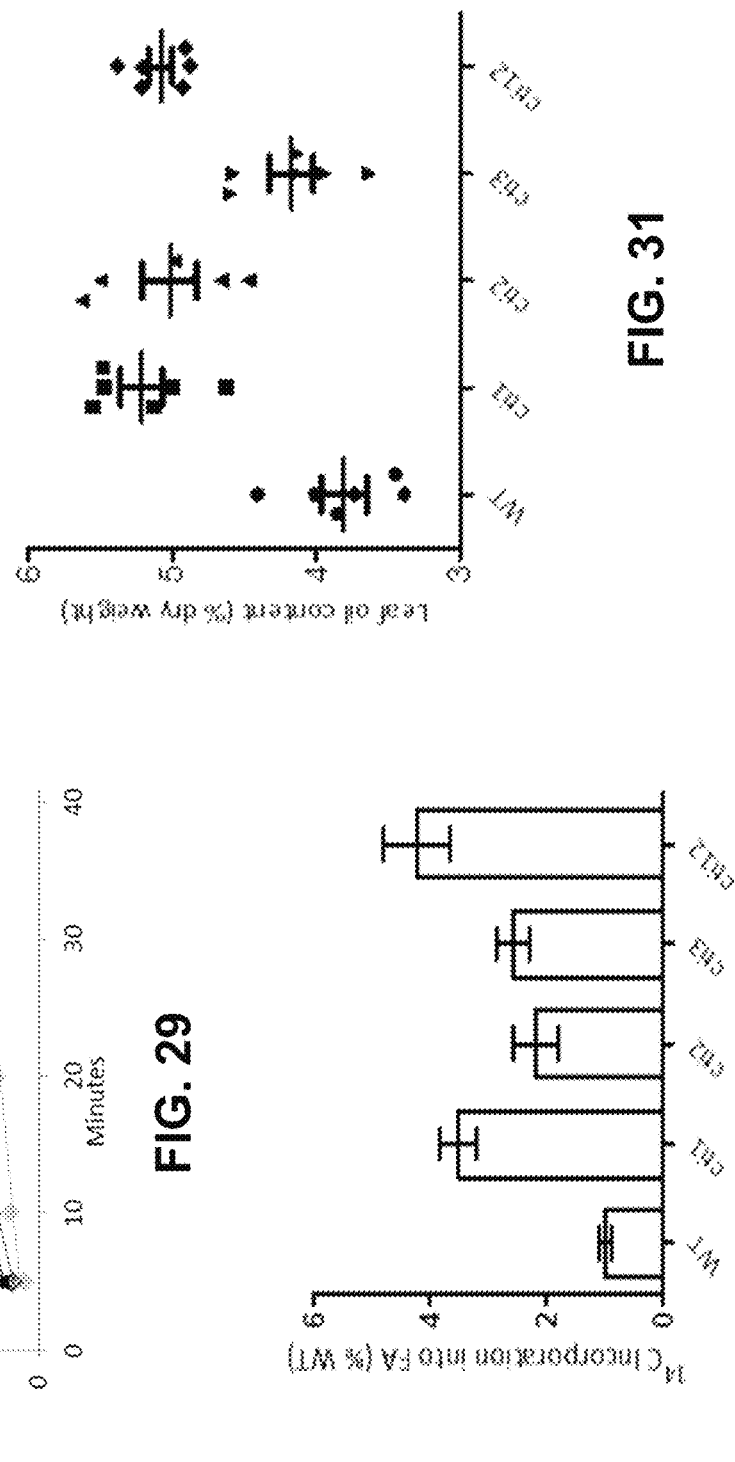
FIG. 29 is a graph summarizing [14C] acetate incorporation into total fatty acids (mean±SE n=3) over time within 4-week old leaf strips in different genetic backgrounds.
FIG. 30 is a graph summarizing relative [14C] acetate incorporation after a 40-minute pulse.
FIG. 31 is a graph summarizing total leaf oil content in wild-type and different cti mutants.
Figure 32:
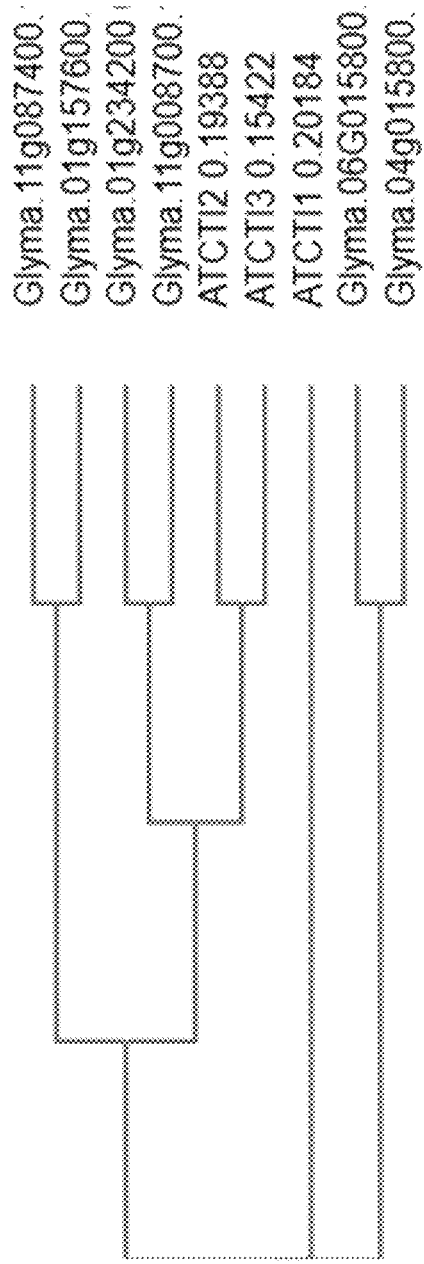
FIG. 32 is a cladogram of various CTI protein homologs from different plant species.
Figure 34A:
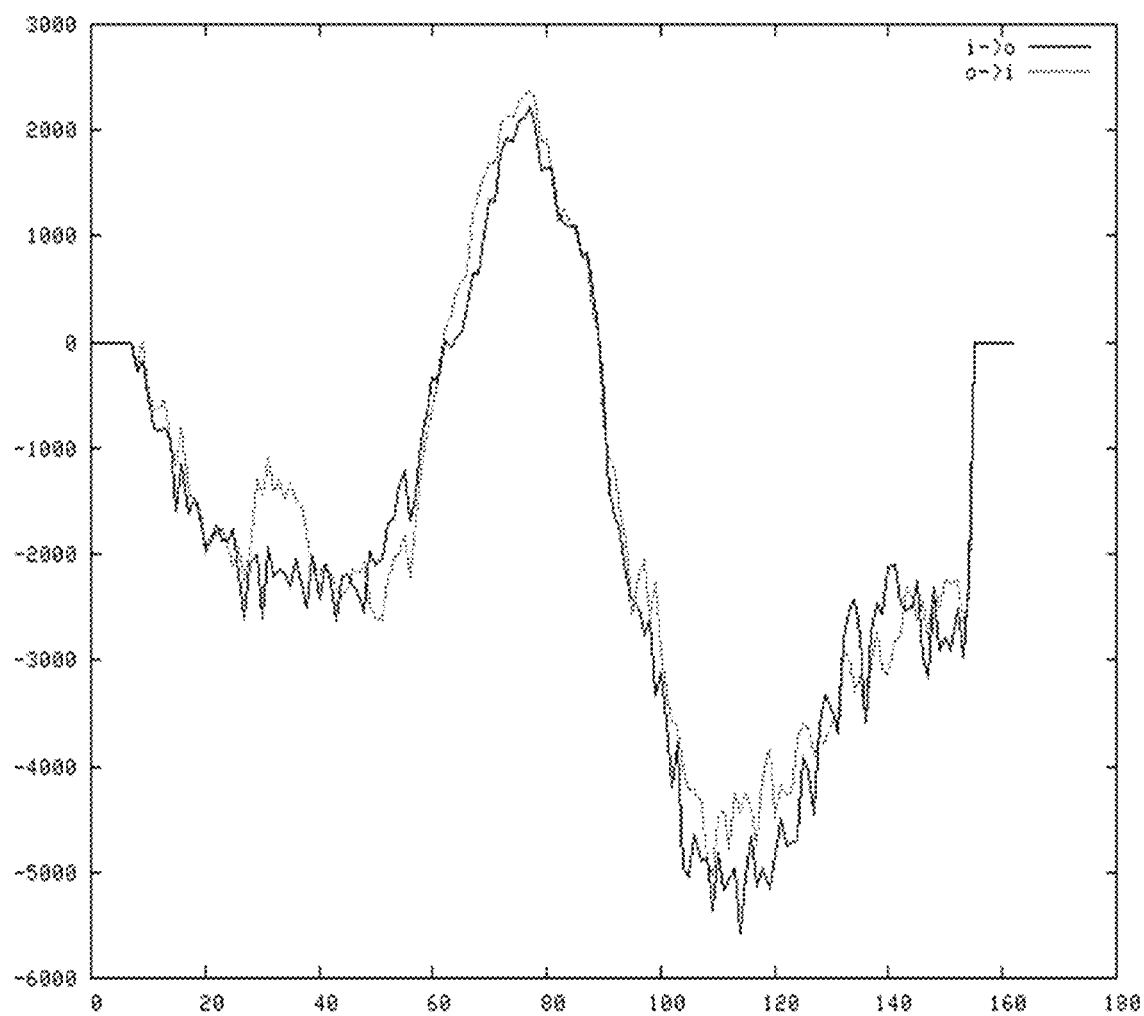
FIG. 34A is a graph summarizing the predicted transmembrane domain distribution of Glyma.06G015800.1.
Figure 34B:
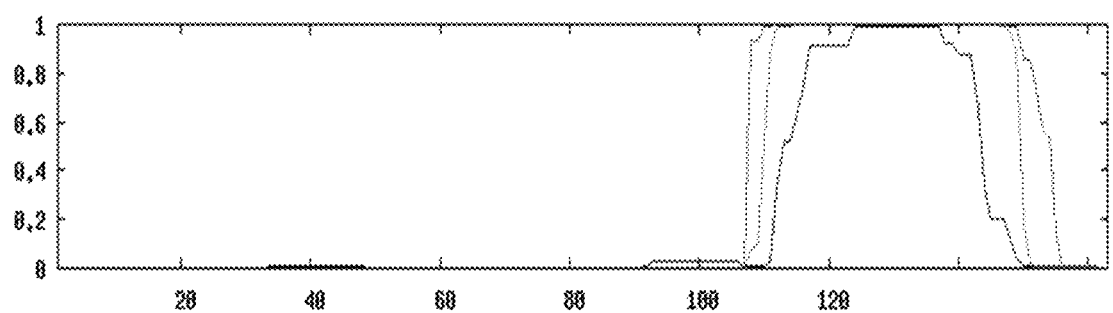
FIG. 34B is a graph summarizing the predicted coiled-coil domain distribution of Glyma.06G015800.1.
Figure 35A:
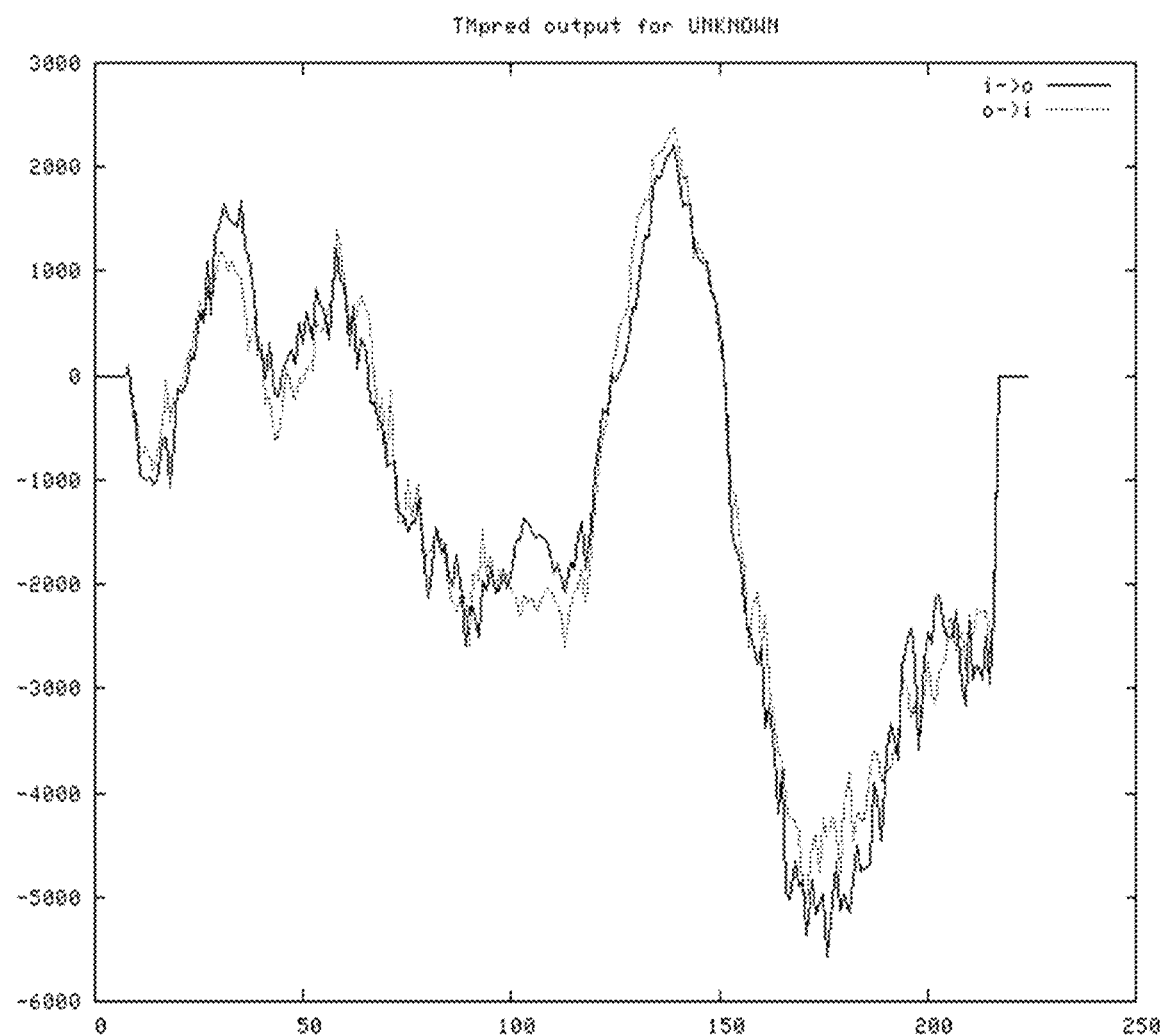
FIG. 35A is a graph summarizing the predicted transmembrane domain distribution of Glyma.04g015800.1.
Figure 35B:
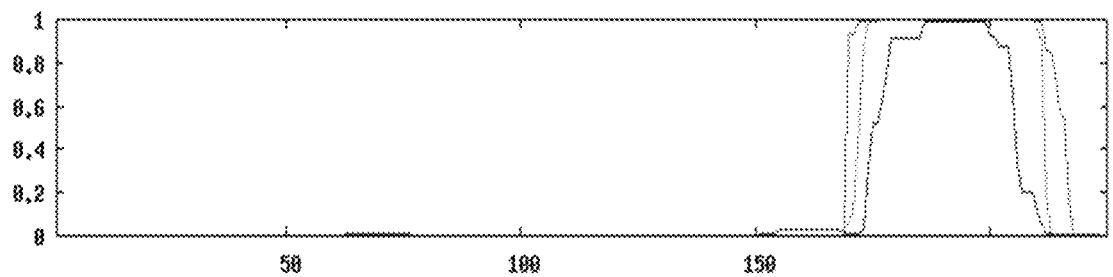
FIG. 35B is a graph summarizing the predicted coiled-coil domain distribution of Glyma.04g015800.1.
Figure 36A:
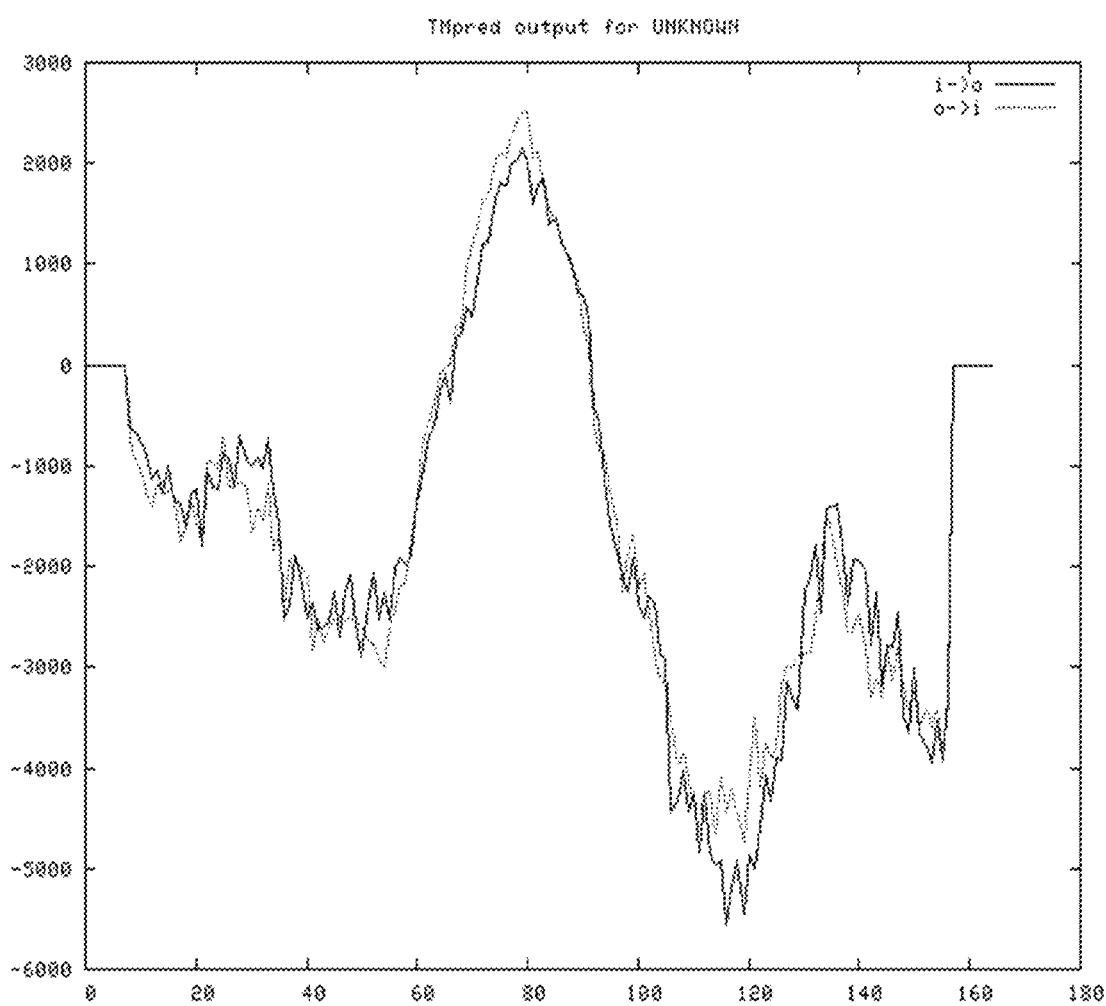
FIG. 36A is a graph summarizing the predicted transmembrane domain distribution of Glyma.11g087400.1.
Figure 36B:
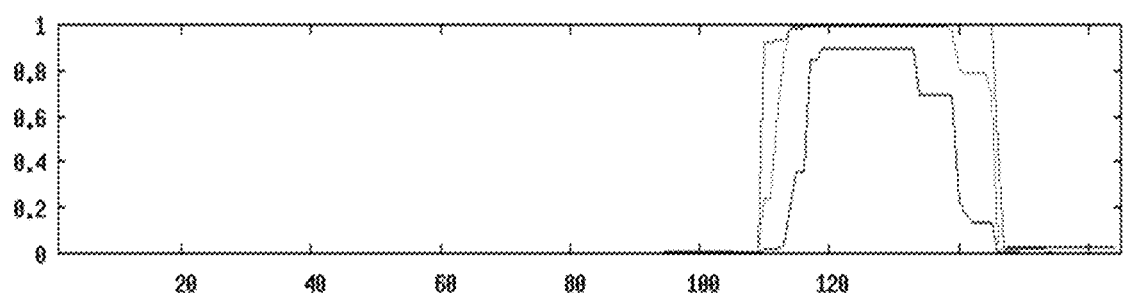
FIG. 36B is a graph summarizing the predicted coiled-coil domain distribution of Glyma.11g087400.1.
Figure 37A:
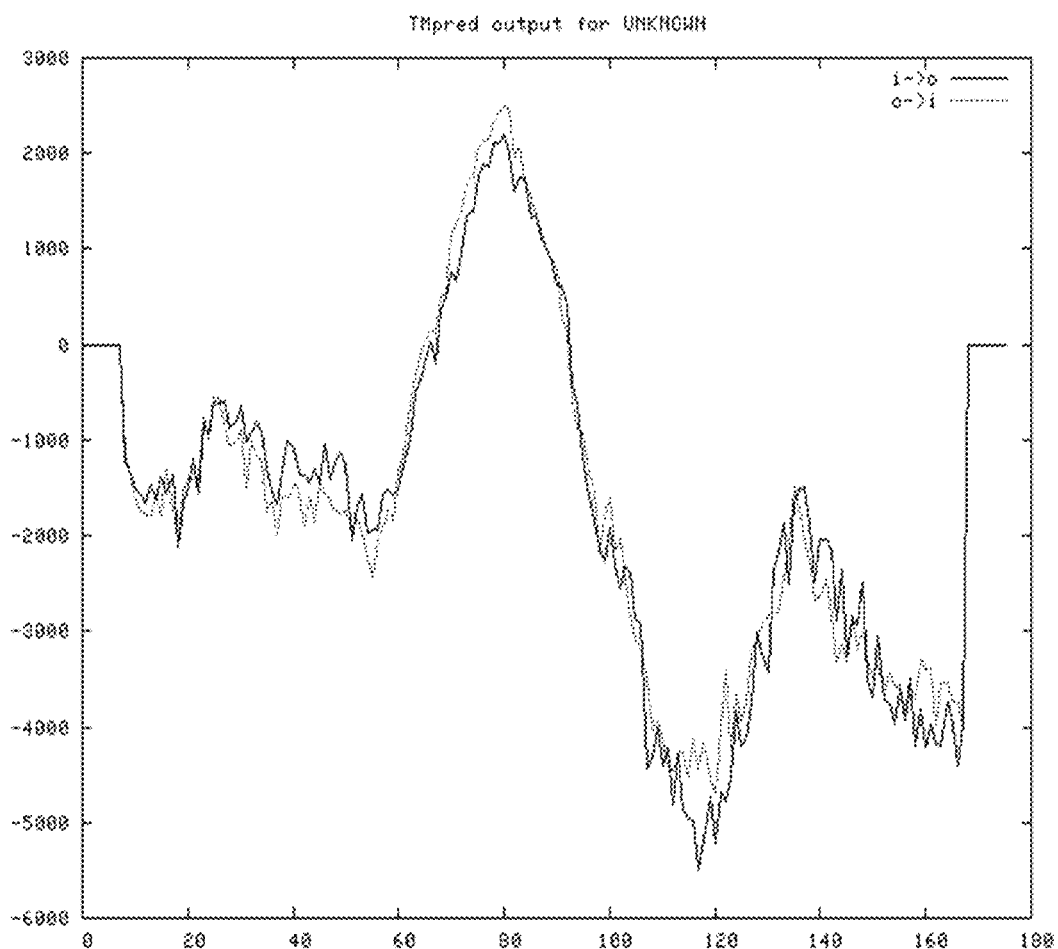
FIG. 37A is a graph summarizing the predicted transmembrane domain distribution of Gyma.01g157600.1.
Figure 37B:
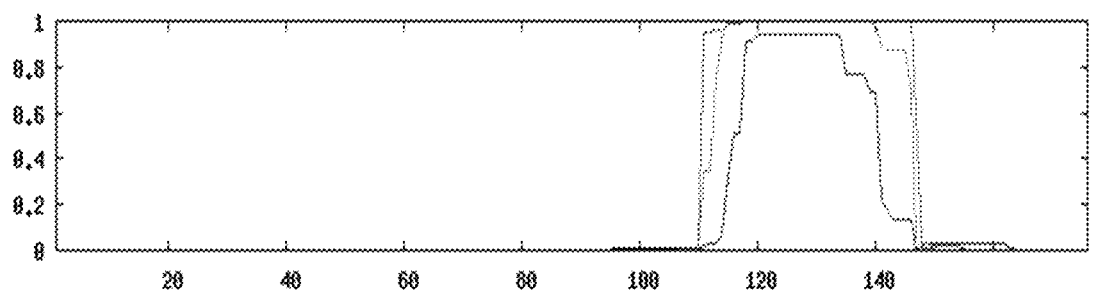
FIG. 37B is a graph summarizing the predicted coiled-coil domain distribution of Gyma.01g157600.1.
Figures 38A, 38B:
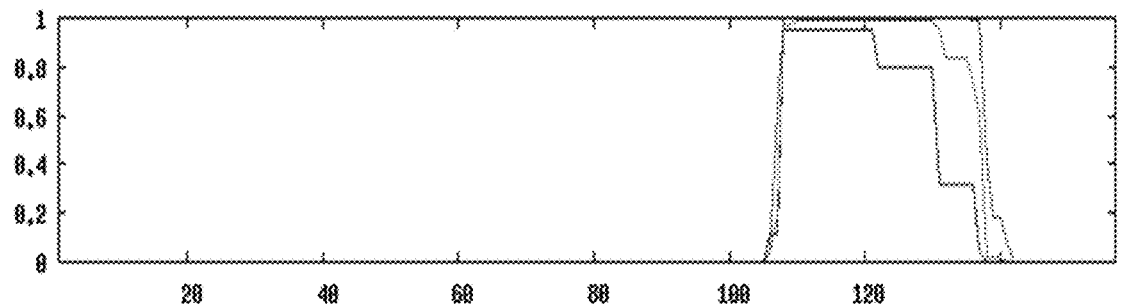
Figure 38B:
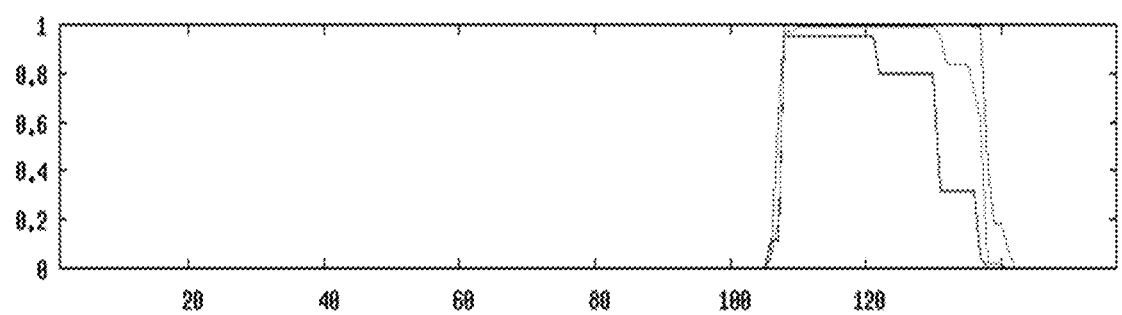
Figure 39A:
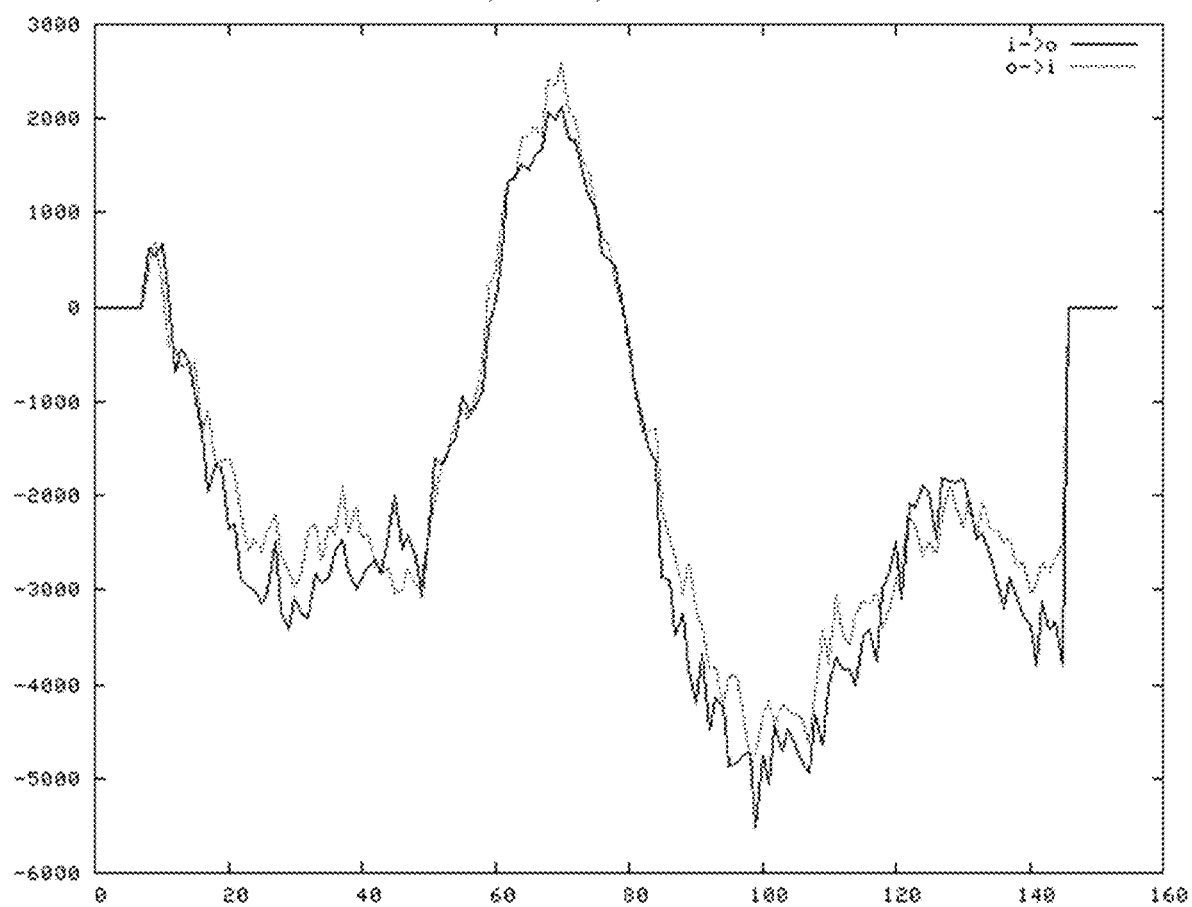
FIG. 39A is a graph summarizing the predicted transmembrane domain distribution of Glyma.11g008700.1.
Figure 39B:
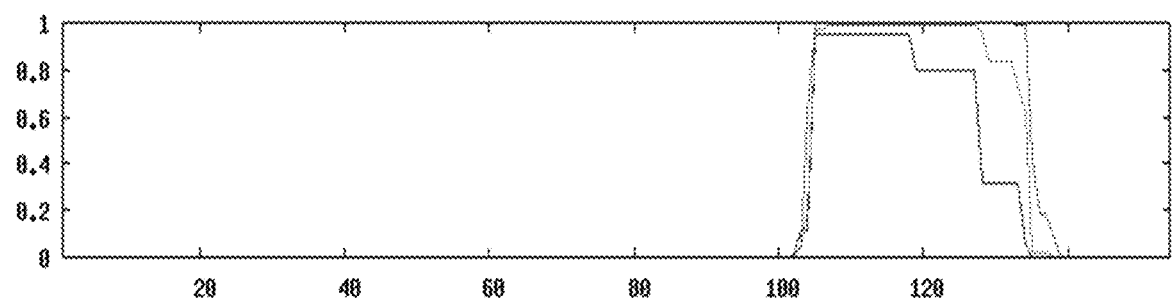
FIG. 39B is a graph summarizing the predicted coiled-coil domain distribution of Glyma.11g008700.1.

FIG. 29 demonstrates that the rates of 14C-acetate incorporation into fatty acids were linear from 5 to 40 minutes. Further, the rates of fatty acid labeling in cti mutants were much higher than wild-type at different time-points of 14C-acetate labeling, especially in cti1 and cti1/2 mutants. At the forty-minute pulse, compared to wild-type, the rates of 14C-acetate incorporation were 3.5 fold, 2.2 fold, 2.5 fold and 4.2 fold higher in cti1, cti2, cti3 and cti1/2 mutants, respectively, than in wild-type, as illustrated in FIG. 30. Increased fatty acid synthesis is a logical prerequisite for elevated oil content. The leaf oil content in the mutants and wild-type was also determined as described above. As illustrated in FIG. 31, the leaf oil content in the cit mutants demonstrated a significant elevation compared to the wild-type.

What is claimed is:

1. A method of increasing fatty acid and/or triacylglycerol production in plants and/or algae, comprising genetically modifying the plants and/or algae to increase activity levels of alpha-carboxyltransferase (α-CT) comprising the step of decreasing intracellular concentrations of one or more carboxyl transferase interactor (CTI) proteins with a polypeptide sequence having at least 95% sequence identity to a polypeptide sequence selected from the group consisting of SEQ ID NOs: 2, 4, and 6, and wherein the one or more CTI proteins inhibit activity levels of α-CT, wherein α-CT comprises a catalytic subunit of acetyl-CoA carboxylase (ACCase).

2. The method of claim 1, wherein decreasing intracellular concentrations of the one or more CTI proteins further comprises decreasing expression of one or more carboxyl transferase interactor (CTI) genes.

3. The method of claim 2, wherein the one or more CTI genes comprise a sequence having at least 95% sequence identity to a nucleotide sequence selected from the group consisting of SEQ ID NOs: 1, 3, 5, or a complement thereof.

4. The method of claim 2, wherein increasing fatty acid and/or triacylglycerol production in plants comprises increasing fatty acid and/or triacylglycerol production in plants by increasing activity levels of α-CT, and increasing activity levels of α-CT comprises decreasing intracellular concentrations of the one or more CTI proteins by decreasing expression of the one or more CTI genes.

5. The method of claim 4, wherein expression of the one or more CTI genes is decreased using a gene silencing method selected from the group consisting of antisense, RNAi, CRISPR, TALEN, nanobodies, EMS, T-DNA gene knockout, transposon-mediated gene knockout, conventional mutagenesis, and targeted breeding.

6. The method of claim 1, wherein the plant species is selected from the group consisting of *Amborella trichopoda, Arabidopsis lyrata, Arabidopsis alpine, Arabidopsis thaliana, Arachis hypogaea, Auxenochlorella prototheocoides, Brassica napus, Brassica rapa, Camelina sativa, Capsella rubella, Cathamus tinctorius, Chlamydomonas reinhardtii, Chlorella variabilis, Cicer arietinum, Citrus clementina, Citrus sinensis, Coccomyxa subellipsoideas* C-169, *Coffea canephora, Cucumis melo, Cucumis sativus, Cynara cardunculus, Elaeis guineensis, Erythranthe guttata, Eucalyptus grandis, Eutrema salsugineum, Fragaria vesca, Genlisea aurea, Glycine max, Helianthus annuus, Helicosporidium* ATCC50920, *Jatropha curcas, Lotus japonicas, Medicago truncatula, Moms notabilis, Musa acuminate, Nelumbo nucifera, Nicotiana sylvestris, Nicotiana tomentosiformis, Phaseolus vulgaris, Pheonix dactylifera, Physcomitrella patens, Picea sitchensis, Polytomella parva, Populus trichocarpa, Prunus mume, Prunes persica, Pyrus×bretschneideri, Ricinus communis, Selaginella moellendorffii, Sesamum indicum, Solanum lycopersicum, Solanum tuberosum, Theobroma cacao, Thlaspi arvense, Vitis vinifera,* and *Volvox carteri.*

7. A genetically modified plant or part thereof produced by the method of claim 2 and having a decreased level of expression of one or more carboxyl transferase interactor (CTI) genes in comparison to a wild type plant or part thereof, wherein the plant produces seed comprising increased seed oil content.

8. The genetically modified plant or part thereof of claim 7, wherein the plant is a species selected from the group consisting of *Amborella trichopoda, Arabidopsis lyrata, Arabidopsis alpine, Arabidopsis thaliana, Arachis hypogaea, Auxenochlorella prototheocoides, Brassica napus, Brassica rapa, Camelina sativa, Capsella rubella, Cathamus tinctorius, Chlamydomonas reinhardtii, Chlorella variabilis, Cicer arietinum, Citrus clementina, Citrus sinensis, Coccomyxa subellipsoideas* C-169, *Coffea canephora, Cucumis melo, Cucumis sativus, Cynara cardunculus, Elaeis guineensis, Erythranthe guttata, Eucalyptus grandis, Eutrema salsugineum, Fragaria vesca, Genlisea aurea, Glycine max, Helianthus annuus, Helicosporidium* ATCC50920, *Jatropha curcas, Lotus japonicas, Medicago truncatula, Moms notabilis, Musa acuminate, Nelumbo nucifera, Nicotiana sylvestris, Nicotiana tomentosiformis, Phaseolus vulgaris, Pheonix dactylifera, Physcomitrella patens, Picea sitchensis, Polytomella parva, Populus trichocarpa, Prunus mume, Prunes persica, Pyrus×bretschneideri, Ricinus communis, Selaginella moellendorffii, Sesamum indicum, Solanum lycopersicum, Solanum tuberosum, Theobroma cacao, Thlaspi arvense, Vitis vinifera,* and *Volvox carteri.*

9. The genetically plant or plant part of claim 7, wherein the plant part is selected from the group consisting of a leaf, pollen, an ovule, a fruit, rootstock, a scion, a flower, and a cell.

10. A genetically modified plant having an increased activity level of alpha-carboxyltransferase (α-CT) and a decreased expression of one or more CTI genes in comparison to a wild-type plant of the same species grown under the same conditions, wherein α-CT comprises a catalytic subunit of acetyl-CoA carboxylase (ACCase), wherein the one or more CTI genes comprise a sequence having at least 95% sequence identity to a nucleotide sequence selected from the group consisting of SEQ ID NOs: 1, 3, 5, or a complement thereof, or wherein the one or more CTI genes encode a CTI protein with a polypeptide sequence having at least 95% sequence identity to a polypeptide sequence selected from the group consisting of SEQ ID NOs: 2, 4, and 6.

11. The genetically modified plant of claim 10, wherein the modified plant is a species selected from the group consisting of *Amborella trichopoda, Arabidopsis lyrata, Arabidopsis alpine, Arabidopsis thaliana, Arachis hypogaea, Auxenochlorella prototheсoides, Brassica napus, Brassica rapa, Camelina sativa, Capsella rubella, Cathamus tinctorius, Chlamydomonas reinhardtii, Chlorella variabilis, Cicer arietinum, Citrus clementina, Citrus sinensis, Coccomyxa subellipsoideas* C-169, *Coffea canephora, Cucumis melo, Cucumis sativus, Cynara cardunculus, Elaeis guineensis, Erythranthe guttata, Eucalyptus grandis, Eutrema salsugineum, Fragaria vesca, Genlisea aurea, Glycine max, Helianthus annuus, Helicosporidium* ATCC50920, *Jatropha curcas, Lotus japonicas, Medicago truncatula, Moms notabilis, Musa acuminate, Nelumbo nucifera, Nicotiana sylvestris, Nicotiana tomentosiformis, Phaseolus vulgaris, Pheonix dactylifera, Physcomitrella patens, Picea sitchensis, Polytomella parva, Populus trichocarpa, Prunus mume, Prunes persica, Pyrus× bretschneideri, Ricinus communis, Selaginella moellendorffii, Sesamum indicum, Solanum lycopersicum, Solanum tuberosum, Theobroma cacao, Thlaspi arvense, Vitis vinifera,* and *Volvox carteri.*

12. The genetically modified plant of claim 10, wherein the activity level of alpha-carboxyltransferase (α-CT) is increased in comparison to a wild type plant of the same species and grown under the same conditions by decreasing intracellular concentrations of one or more carboxyl transferase interactor (CTI) proteins, wherein the one or more CTI proteins inhibit activity levels of α-CT.

13. The genetically modified plant of claim 10, wherein increasing intracellular concentrations of the one or more CTI proteins further comprises reducing expression of one or more carboxyl transferase interactor (CTI) genes.

14. The genetically modified plant of claim 13, wherein the one or more CTI genes comprise genes and gene orthologs of CTI1, CTI2, and CTI3, or artificial genes containing essential CTI motifs.

15. The genetically modified plant of claim 10, wherein the one or more CTI genes encode a CTI protein with a polypeptide sequence having at least 98% sequence identity to a polypeptide sequence selected from the group consisting of SEQ ID NOs: 2, 4, and 6.

16. The genetically modified plant of claim 12, wherein the modified plant has an increased content of fatty acid and/or triacylglycerol in comparison to a wild-type plant of the same species grown under the same conditions.

* * * * *

SEQUENCE LISTING

<160> NUMBER OF SEQ ID NOS: 92

<210> SEQ ID NO 1
<211> LENGTH: 1556
<212> TYPE: DNA
<213> ORGANISM: Arabidopsis thaliana

<400> SEQUENCE: 1

```
ttgtaataaa tatttaaata aataattacc actgaatcga agaagctttg cttagatatc      60
atcgaacttg ctccaactgc tctatctcag gatctctctc agacacagtt tcttccatcc     120
atggcgtctc tttcttctac ctctctctct ctccccaaga attctcacca actccatcct     180
tcatctggta ataacttctt caatctctcc aatcttcgtg ctttatagat tttcaatatc     240
ctccattttc gagctcatga gattcgtaca gtcatgttac gatttctaat ttagcatctc     300
acaaaaccca atttaattgt gtattggacg atcttgattc ctttatgttg ttgggtcctt     360 tcttttttact tgtgctgatt tgtcaaaaca atgcaaaatt agagcttgaa gctgttttgt     420
tagaaaactg ttcaacttgt tatgtataag tcactgattg ttgtttgttc ttgttacctt     480
ctaggttttt ctctgaatcc aaatgctcgt tgtgtcagtg tttcatttgg actgaatcac     540
tccaacaaac ttcatatttc tgctcctaga accaaaagga tcctaaccat tcaatctgca     600
tacaggtata taactttatc ttatacaaat tattgtttga gatgtcgaaa actgtggttc     660
ttgttactcc ttaatgtttt gtgagcatcg taacatttt tagtatactt tagttttcta     720
ttggcaactt atgtttacag agacagtttg caatgtctaa tagcatcaaa acttgcagag     780
```

```
atgatgatgg ttcaggcagc acaggcctat tcgtcggagg gtttattttg ggcggactta        840
tagtcggtgc cctcggatgt gtatatgcac cacaggtagt aatctgttac atggtttagt        900
ttgatcactc ttagagcttg tattcgtttc aatcaagaag ttcttgagtg gactcgagga        960
gctctgtaac cttctctgtt tcactttgac tcatcaatgt gtgatgttac ttttgtgaat       1020
tgtatcagat cagcaaggct atagctggag cagaccgaaa ggatctcatg aggaagttgc       1080
ctaaattcat atatgacgag gaaaaagctt tggaggtaag ttattgctaa gcctcttgat       1140
tcatatttta tctcactttt tgttgaattt acttatgaac aatgttgtct actgttaatg       1200
cagaaaacac gtaaggtact agctgagaaa attgctcagc ttaactctgc tatcgacgat       1260
gtctcctctc agctcaaatc agaagatact ccgaatggtg cagctctaag caccgatgaa       1320
atcgaggcta cagcctgaaa tcatctgttt taggatttg aaattgaatc atgggagatt       1380
acttactatg atcccaataa ttgttttcct ttctgtgtaa tgttgtacaa ctttcgtct        1440 actatcttca aatgactgct tcttccttc tcttttttt ctcgaaatcg cggtgttgaa        1500
ggatatatca cagttatatg cgaaaccaga cgttatgaag actatataat atcctg           1556
```

<210> SEQ ID NO 2
<211> LENGTH: 168
<212> TYPE: PRT
<213> ORGANISM: Arabidopsis thaliana

<400> SEQUENCE: 2

```
Met Ala Ser Leu Ser Ser Thr Ser Leu Ser Leu Pro Lys Asn Ser His
1               5                   10                  15

Gln Leu His Pro Ser Ser Gly Phe Ser Leu Asn Pro Asn Ala Arg Cys
            20                  25                  30

Val Ser Val Ser Phe Gly Leu Asn His Ser Asn Lys Leu His Ile Ser
        35                  40                  45

Ala Pro Arg Thr Lys Arg Ile Leu Thr Ile Gln Ser Ala Tyr Arg Asp
    50                  55                  60

Asp Asp Gly Ser Gly Ser Thr Gly Leu Phe Val Gly Gly Phe Ile Leu
65                  70                  75                  80

Gly Gly Leu Ile Val Gly Ala Leu Gly Cys Val Tyr Ala Pro Gln Ile
                85                  90                  95

Ser Lys Ala Ile Ala Gly Ala Asp Arg Lys Asp Leu Met Arg Lys Leu
            100                 105                 110

Pro Lys Phe Ile Tyr Asp Glu Glu Lys Ala Leu Glu Lys Thr Arg Lys
        115                 120                 125

Val Leu Ala Glu Lys Ile Ala Gln Leu Asn Ser Ala Ile Asp Asp Val
    130                 135                 140

Ser Ser Gln Leu Lys Ser Glu Asp Thr Pro Asn Gly Ala Ala Leu Ser
145                 150                 155                 160

Thr Asp Glu Ile Glu Ala Thr Ala
                165
```

<210> SEQ ID NO 3
<211> LENGTH: 1975
<212> TYPE: DNA
<213> ORGANISM: Arabidopsis thaliana

<400> SEQUENCE: 3

```
gagtgtattt tgggaaataa gtaactctta agggatatgt tttagaaaat agataactct         60
tctggtggac aaatggcgta tgtgttcgtc ttcctcttgt atgttactct tctcagatct        120
```

-continued

```
cttgttcgtt tgatgtaca atggcgtcct tggtagcagc tcctatctct ttctcaggta      180
gtcaatcgct ttttctctt ctccagtttt cagttcattg cttcctctat cttcttcgtt      240
ttgaactcaa atttctgagt aacccgagag agaaagattc gccgatttgc atttgcttac     300
tcattcaaat ttatcctcgt atcttcgatt agtattcaaa atttccgtta ggtatttaac     360
attttagcga gatcatagtt tgttcatagt ctgaaactag ttcaacatat agcaaatcga     420
cgtaaaggaa atacgaaaat ccactgatat aacggaccaa catatgatta gagacctgtg     480
tatttgaggg tttctccata tctcgttaga ttactttata tatgaaaact cacttgcatt     540
ttcagagttt actcaaactg aaccaaagca gcttcttgat tcacacctta tggctcaggt     600
gactctcatg tcaaagcaca ccgaaacttc aatgcgattc gcaagagctc tacattgact     660
gttcaaacaa aatcaaaccg cagtcacaaa ctctcggttt ctgcaggtta ccggtatatt     720
tctctctctg tatatatata taggccatta aacctcttct aggttacatt tgacagtttt     780
actgtgttga ttattgcagt gggggaagta agggtggtgg aagtagtgat tttgttaccg     840
gttttcttct aggaagtgct gtgttcggaa ctctggctta tatctttgct ccacaggtac     900
attcttaaaa aaccatttca ttgtttctat aacagaaaac tagacataga ttatgatttt     960
tggctttaga tctttaccaa ctcccttcac ccttgttatg atttagttga tttcgagctt    1020
tgtccttctt gaaatcaaca acattaacaa caaactacgg ttatctattc aattctaaca    1080
tatcttatgt tggcttaagg catacttaga gctgtttatt cttggtttta tttcttcctc    1140
taagatctct gagctttgtt cttcctaatg attaagtaat tctgagtttt gttcttggag    1200
ggattaaaag attttgagct ttgcttttcc aaatgattaa gtactaattc tgacctttgt    1260
tcttgaggtg attaaatgat tctgagcttt gttcttgcaa atgaaatcac caacattaac    1320
aatataaatt cttaagttga ctttgctttc cgagcttggg atgatattct catgtgatct    1380
cttacttcca catgctgtca tgctttttt attcagatcc gaagatcagt gctgagcgag    1440
aatgaatatg gtttcaagaa accggagcag ccgatgtact atgacgaagg cctagaggta    1500
taaaagaaaa acttagtacc gaaattgtta aaaatactaa aactaagaca caaatatggg    1560
tttgatgttt ataacaggag agaagagaga tattgaatga gaaaatcggc caactcaatt    1620
ccgccattga caaggtttcg tcgcgtctga aggaggtcg aagcggtagc agcaagaaca    1680
cttcttcgcc gtctgtccca gttgaaaccg acgcagaagc agaagctact gcatgattga    1740
atgtaatgct ctgctccatt ttaccaattc aaaactgcct tccattggtt ctgtggtttt    1800
tttgttggaa ctattcctag gggctttcct gactttaga tattgaaaga aaagacaat    1860 cgtcgtatta actcgtaccg aaccaaaaca aaactatcta tactaagaga acacgatacg    1920
aaatcttaat ctttcaatat tgataatgtc aataagataa atgcaaattc taaat         1975
```

<210> SEQ ID NO 4
<211> LENGTH: 168
<212> TYPE: PRT
<213> ORGANISM: Arabidopsis thaliana

<400> SEQUENCE: 4

Met Cys Ser Ser Ser Cys Met Leu Leu Phe Ser Asp Leu Leu Phe
1               5                   10                  15

Val Leu Met Tyr Asn Gly Val Leu Ala His Arg Asn Phe Asn Ala Ile
            20                  25                  30

Arg Lys Ser Ser Thr Leu Thr Val Gln Thr Lys Ser Asn Arg Ser His
        35                  40                  45

```
Lys Leu Ser Val Ser Ala Gly Tyr Arg Gly Gly Ser Lys Gly Gly Gly
 50                  55                  60

Ser Ser Asp Phe Val Thr Gly Phe Leu Leu Gly Ser Ala Val Phe Gly
 65                  70                  75                  80

Thr Leu Ala Tyr Ile Phe Ala Pro Gln Ile Arg Arg Ser Val Leu Ser
                 85                  90                  95

Glu Asn Glu Tyr Gly Phe Lys Lys Pro Glu Gln Pro Met Tyr Tyr Asp
                100                 105                 110

Glu Gly Leu Glu Glu Arg Arg Glu Ile Leu Asn Glu Lys Ile Gly Gln
            115                 120                 125

Leu Asn Ser Ala Ile Asp Lys Val Ser Ser Arg Leu Lys Gly Gly Arg
        130                 135                 140

Ser Gly Ser Ser Lys Asn Thr Ser Ser Pro Ser Val Pro Val Glu Thr
145                 150                 155                 160

Asp Ala Glu Ala Glu Ala Thr Ala
                165

<210> SEQ ID NO 5
<211> LENGTH: 1845
<212> TYPE: DNA
<213> ORGANISM: Arabidopsis thaliana

<400> SEQUENCE: 5
atttcatctg tctccacttc tctatagttg attacaatct ggttaacatg tgatattatt      60
tgaagaaatt tgttcatcca agtagtaatc aactatttgt agtcatttgg taaaagatca     120
attggagctg tgtcgtactc tgtcgtccgg tcggtaactg agcaaataat aagaacgagg     180
gtagaatagt aaatttatat atagttttcc caagcaagga gaagaagata tacatagtat     240
atccaaaaaa aaaaaacatg tctacatatt cttcttctag ctcagatctc tcttttgttc     300
gtcttcagtt ccaatggcgt cgtgtattgc tactgctcct ctttctctat ctggtaatcg     360
atcctccttt tagcttcacc tcgatcctta atttctctac ctactaagct cctttttgtt     420
tcctcctgaa ttttcaaatt gctccgtctt tactagaatt tcatcgtcga agtttcagat     480
tgattgaatt tcatttgatt ttgtacaatt cggtagcgtt ttaatcagta tggagacact     540
tgttaatttg atcgttgcat cgttcctcta taaattaggc ttattttcta gcttaggtaa     600
aataaaattg agatcaaaat caattcctta tttgcgaaga attatagata gctatagagt     660
aagcaactga acaaactcta gctgctattg agctctactt tgtgatttgt aagaaatttc     720
aagagagatt catattagca agcttcttga atctgtggtt ttacaggcgt gtctcaatct     780
cattatgtga aagctaatgg attgtctaca acaacaaaac tcagttctat ttgtaaaacc     840
tctgatttga ctattcacaa gaaatcaaac cggactcgca agttttctgt ttctgcaggg     900
tatcggtatg tatgtatgca tttcgttcgc tatagcgttc tctcttctat tgaattgact     960
taaaattgtt gaaacttaat tcagagatgg aagtagaagc ggaagcagtg gtgatttcat    1020
tgctggtttt cttctaggag gtgctgtctt tggcgctgtt gcttatatct tgctccaca    1080 ggtaatgatg atgtttactc tttagaaacc taaatgggaa ttagacatta tctcatgttt    1140
tcaatggttt tggtttatgt tactgactgt tttgatctag tcttttgaaa tgatgagtag    1200
actgtgcttt tgttccctac ttatgcacat tccactgcct aaaacagaca gtatctttgt    1260
tgttctcatt actgcttcgt tggttctatt ttgattggtt cttggagctt tggatgatat    1320
aactgtttat ctttctcatg caatctaaaa agctgatggt tatgattatt cttgtgttgt    1380
```

-continued

```
ggtgatttag atccgaagat cggttctaaa tgaagaagac gagtacggtt ttgagaagcc    1440
gaaacagcca acgtactacg atgaaggttt agagaaaaca agagagacac tgaatgagaa    1500
aataggacaa cttaattcag cgatagacaa tgtctcttcg cgtttacgag gtcgagaaaa    1560
gaacacttct tccctaaatg taccggtcga aactgaccca gaggttgaag ctacgacttg    1620
aaggaagaaa caaacagctt tcttcttctg tgtttcattt gtaaactaga gttaaaaaac    1680
cattacttat atgtttgatt tggttctttt ctttctggtt tgcctttgtg ctcagtcctt    1740
agtagaaaga actcttgcaa agtgaaatgt atacgtcttt tggttttagt gtgaatttgg    1800
ttcaatttaa ttcgaaaaaa tctttgttct cttagtaata tattg                   1845
```

<210> SEQ ID NO 6
<211> LENGTH: 168
<212> TYPE: PRT
<213> ORGANISM: Arabidopsis thaliana

<400> SEQUENCE: 6

```
Met Ala Ser Cys Ile Ala Thr Ala Pro Leu Ser Leu Ser Gly Val Ser
1               5                   10                  15

Gln Ser His Tyr Val Lys Ala Asn Gly Leu Ser Thr Thr Thr Lys Leu
            20                  25                  30

Ser Ser Ile Cys Lys Thr Ser Asp Leu Thr Ile His Lys Lys Ser Asn
        35                  40                  45

Arg Thr Arg Lys Phe Ser Val Ser Ala Gly Tyr Arg Asp Gly Ser Arg
    50                  55                  60

Ser Gly Ser Ser Gly Asp Phe Ile Ala Gly Phe Leu Leu Gly Gly Ala
65                  70                  75                  80

Val Phe Gly Ala Val Ala Tyr Ile Phe Ala Pro Gln Ile Arg Arg Ser
                85                  90                  95

Val Leu Asn Glu Glu Asp Glu Tyr Gly Phe Glu Lys Pro Lys Gln Pro
            100                 105                 110

Thr Tyr Tyr Asp Glu Gly Leu Glu Lys Thr Arg Glu Thr Leu Asn Glu
        115                 120                 125

Lys Ile Gly Gln Leu Asn Ser Ala Ile Asp Asn Val Ser Ser Arg Leu
    130                 135                 140

Arg Gly Arg Glu Lys Asn Thr Ser Ser Leu Asn Val Pro Val Glu Thr
145                 150                 155                 160

Asp Pro Glu Val Glu Ala Thr Thr
                165
```

<210> SEQ ID NO 7
<211> LENGTH: 164
<212> TYPE: PRT
<213> ORGANISM: Camelina sativa

<400> SEQUENCE: 7

```
Met Ala Ser Leu Ser Thr Ser Leu Ser Leu Pro Asn Asn Ala Gln Gln
1               5                   10                  15

Leu His Pro Ser Ser Gly Phe Ser Leu Lys Pro Cys Val Ser Val Ser
            20                  25                  30

Phe Gly Leu Asn Arg Ser Asn Asn Leu His Ile Ser Ala Pro Arg Ser
        35                  40                  45

Lys Arg Ile Leu Thr Val Gln Ser Ala Tyr Arg Asp Asp Asp Gly Ser
    50                  55                  60

Gly Ser Thr Gly Leu Phe Val Gly Gly Phe Ile Leu Gly Gly Leu Ile
65                  70                  75                  80
```

Val Gly Ala Leu Gly Cys Val Tyr Ala Pro Gln Ile Ser Lys Ala Ile
                85                  90                  95

Ala Gly Ala Asp Arg Lys Asp Leu Met Arg Lys Leu Pro Lys Phe Ile
            100                 105                 110

Tyr Asp Glu Glu Lys Ala Leu Glu Lys Thr Arg Lys Val Leu Ala Glu
        115                 120                 125

Lys Ile Ala Gln Leu Asn Ser Ala Ile Asp Asp Val Ser Ser Gln Leu
    130                 135                 140

Lys Ser Glu Asp Thr Pro Asn Gly Ala Ala Leu Ser Thr Asp Glu Val
145                 150                 155                 160

Glu Ala Thr Ala

<210> SEQ ID NO 8
<211> LENGTH: 164
<212> TYPE: PRT
<213> ORGANISM: Camelina sativa

<400> SEQUENCE: 8

Met Ala Ser Leu Ser Thr Ser Leu Ser Leu Pro Asn Asn Ala Gln Gln
1               5                   10                  15

Leu His Pro Ser Ser Gly Phe Ser Leu Lys Pro Cys Val Ser Val Ser
            20                  25                  30

Phe Gly Leu Asn Arg Ser Asn Asn Leu His Ile Ser Ala Pro Arg Ser
        35                  40                  45

Lys Arg Ile Leu Ile Val Gln Ser Ala Tyr Arg Asp Asp Asp Gly Ser
    50                  55                  60

Gly Ser Thr Gly Leu Phe Val Gly Gly Phe Ile Leu Gly Gly Leu Ile
65                  70                  75                  80

Val Gly Ala Leu Gly Cys Val Tyr Ala Pro Gln Ile Ser Lys Ala Ile
                85                  90                  95

Ala Gly Ala Asp Arg Lys Asp Leu Met Arg Lys Leu Pro Lys Phe Ile
            100                 105                 110

Tyr Asp Glu Glu Lys Ala Leu Glu Lys Thr Arg Lys Val Leu Ala Glu
        115                 120                 125

Lys Ile Ala Gln Leu Asn Ser Ala Ile Asp Asp Val Ser Ser Gln Leu
    130                 135                 140

Lys Ser Glu Asp Thr Pro Asn Gly Ala Ala Leu Ser Thr Asp Glu Val
145                 150                 155                 160

Glu Ala Thr Ala

<210> SEQ ID NO 9
<211> LENGTH: 164
<212> TYPE: PRT
<213> ORGANISM: Camelina sativa

<400> SEQUENCE: 9

Met Ala Ser Leu Ser Thr Ser Leu Ser Leu Pro Asn Asn Ala Gln Gln
1               5                   10                  15

Leu His Pro Ser Ser Gly Phe Ser Leu Lys Pro Cys Val Ser Val Ser
            20                  25                  30

Phe Gly Leu Asn Arg Ser Asn Asn Leu His Ile Ser Ala Pro Arg Ser
        35                  40                  45

Lys Arg Ile Val Thr Val Gln Ser Ala Tyr Arg Asp Asp Asp Gly Ser
    50                  55                  60

Gly Ser Thr Gly Leu Phe Val Gly Gly Phe Ile Leu Gly Gly Leu Ile

```
                65                  70                  75                  80

Val Gly Ala Leu Gly Cys Val Tyr Ala Pro Gln Ile Ser Lys Ala Ile
                85                  90                  95

Ala Gly Ala Asp Arg Lys Asp Leu Met Arg Lys Leu Pro Lys Phe Ile
            100                 105                 110

Tyr Asp Glu Glu Lys Ala Leu Glu Lys Thr Arg Lys Val Leu Ala Glu
            115                 120                 125

Lys Ile Ala Gln Leu Asn Ser Ala Ile Asp Asp Val Ser Ser Gln Leu
        130                 135                 140

Lys Ser Glu Asp Thr Pro Asn Gly Ala Ala Leu Ser Thr Asp Glu Val
145                 150                 155                 160

Glu Ala Thr Ala

<210> SEQ ID NO 10
<211> LENGTH: 161
<212> TYPE: PRT
<213> ORGANISM: Camelina sativa

<400> SEQUENCE: 10

Met Ala Ser Phe Val Ala Pro Asn Ser Leu Ser Gly Asp Ser His
1               5                   10                  15

Leu Lys Ala His Cys Leu Ser Ser Thr Asn Leu Asn Leu Ile Arg Lys
                20                  25                  30

Ser Ser Thr Leu Thr Val Ile Thr Lys Ser Asn Arg Ser His Lys Leu
            35                  40                  45

Ser Val Ser Ala Gly Tyr Arg Glu Gly Ser Arg Gly Gly Gly Ser Ser
        50                  55                  60

Asp Phe Val Thr Gly Phe Leu Leu Gly Ser Ala Val Phe Gly Thr Leu
65                  70                  75                  80

Ala Tyr Val Phe Ala Pro Gln Ile Arg Arg Ser Leu Leu Asn Glu Asn
                85                  90                  95

Glu His Gly Phe Lys Lys Pro Gly Gln Pro Met Tyr Tyr Asp Glu Gly
            100                 105                 110

Leu Glu Glu Arg Arg Glu Ile Leu Asn Glu Lys Ile Gly Gln Leu Asn
        115                 120                 125

Ser Ala Ile Asp Asn Val Ser Ser Arg Leu Arg Gly Ser Lys Asn Ser
    130                 135                 140

Ser Ser Gln Ser Val Thr Val Glu Thr Asp Ala Glu Ala Glu Ala Thr
145                 150                 155                 160

Ala

<210> SEQ ID NO 11
<211> LENGTH: 165
<212> TYPE: PRT
<213> ORGANISM: Camelina sativa

<400> SEQUENCE: 11

Met Ala Ser Phe Val Ala Ala Pro Ile Ser Leu Ser Gly Asp Ser His
1               5                   10                  15

Val Lys Ala His Cys Leu Leu Ser Thr Asn Leu Asn Pro Ile Arg Lys
                20                  25                  30

Ser Ser Thr Leu Thr Val Arg Thr Lys Ser Asn Arg Ser His Lys Leu
            35                  40                  45

Ser Val Ser Ala Gly Tyr Arg Glu Gly Ser Arg Gly Gly Gly Ser Ser
        50                  55                  60
```

```
Asp Phe Val Thr Gly Cys Leu Leu Gly Ser Ala Val Phe Gly Thr Leu
65                  70                  75                  80

Ala Tyr Val Phe Ala Pro Gln Ile Arg Arg Ser Leu Leu Asn Glu Asn
                85                  90                  95

Glu His Gly Phe Lys Lys Pro Glu Gln Pro Met Tyr Tyr Asp Glu Gly
            100                 105                 110

Leu Glu Glu Arg Arg Glu Ile Leu Asn Glu Lys Ile Gly Gln Leu Asn
            115                 120                 125

Ser Ala Ile Asp Asn Val Ser Ser Arg Leu Arg Gly Ser Gly Ser
            130                 135                 140

Gly Lys Asn Ser Ser Ser Gln Ser Val Thr Val Glu Thr Asp Ala Glu
145                 150                 155                 160

Ala Glu Ala Thr Ala
            165

<210> SEQ ID NO 12
<211> LENGTH: 206
<212> TYPE: PRT
<213> ORGANISM: Helianthus annuus

<400> SEQUENCE: 12

Met Val Ala Glu Ser Pro Ile Tyr Val Asn Tyr Gln Phe Tyr Pro Ser
1               5                   10                  15

Ser Pro Thr Leu Leu Cys Tyr Ile Leu His Cys Leu Ala Val Cys Phe
            20                  25                  30

Leu Thr His Phe Thr Leu Asp Leu Ser Leu Gln Ser Leu Leu Met Ala
            35                  40                  45

Thr Thr Thr Ile Ile Ser Pro Ala Ser Ile Ser Val Arg Thr Ser Leu
50                  55                  60

Lys Gly His Asp Ser Leu Ser Gly Asn Ser Ser Phe Tyr Gly Lys Thr
65                  70                  75                  80

Ala Leu Thr Leu Gln Lys Lys Ser Asn Gln Gln Arg Ala Leu Lys Lys
                85                  90                  95

Leu Ala Thr Cys Ala Gln Tyr Asn Asp Arg Ser Gly Gly Gly Gly
            100                 105                 110

Asp Phe Val Ala Gly Phe Leu Leu Gly Gly Ala Leu Cys Gly Thr Leu
            115                 120                 125

Ala Tyr Ile Phe Ala Pro Gln Ile Arg Arg Ser Leu Leu Asn Glu Asp
            130                 135                 140

Glu Tyr Gly Phe Arg Arg Ala Lys Arg Pro Ile Tyr Tyr Asp Glu Gly
145                 150                 155                 160

Leu Glu Lys Thr Arg Gln Thr Leu Asn Ala Lys Ile Ser Gln Leu Asn
                165                 170                 175

Ser Ala Ile Asp Asn Val Ser Ser Arg Leu Arg Gly Gly Asn Asn Met
            180                 185                 190

Pro Pro Val Pro Val Glu Thr Asp Pro Glu Glu Ala Thr Met
            195                 200                 205

<210> SEQ ID NO 13
<211> LENGTH: 166
<212> TYPE: PRT
<213> ORGANISM: Camelina sativa

<400> SEQUENCE: 13

Met Ala Ser Phe Val Ala Pro Ile Ser Leu Ser Gly Asp Ser His
1               5                   10                  15
```

```
Val Lys Ala His Arg Phe Ser Ser Thr Asn Leu Asn Pro Phe Arg Lys
            20                  25                  30

Ser Ser Thr Leu Thr Val Arg Thr Lys Ser Asn Arg Ser His Lys Leu
        35                  40                  45

Ser Val Ser Ala Gly Tyr Arg Glu Gly Ser Arg Gly Gly Gly Ser Ser
50                  55                  60

Asp Phe Val Thr Gly Phe Leu Leu Gly Ser Ala Val Phe Gly Thr Leu
65                  70                  75                  80

Ala Tyr Ile Phe Ala Pro Gln Ile Arg Arg Ser Leu Leu Asn Glu Asn
                85                  90                  95

Glu His Gly Phe Lys Lys Pro Glu Gln Pro Ile Tyr Tyr Asp Glu Gly
                100                 105                 110

Leu Glu Glu Arg Arg Glu Ile Leu Asn Glu Lys Ile Gly Gln Leu Asn
            115                 120                 125

Ser Ala Ile Asp Asn Val Ser Ser Arg Leu Arg Gly Gly Gly Ser Gly
        130                 135                 140

Ser Ser Lys Asn Ser Ser Ser Gln Ser Val Thr Val Glu Thr Asp Ala
145                 150                 155                 160

Glu Ala Glu Ala Thr Ala
                165

<210> SEQ ID NO 14
<211> LENGTH: 168
<212> TYPE: PRT
<213> ORGANISM: Camelina sativa

<400> SEQUENCE: 14

Met Ala Ser Cys Val Val Ala Pro Leu Ser Leu Ser Gly Gly Ser
1               5                   10                  15

Gln Ser His His Val Lys Ala Asn Gly Leu Ser Ser Thr Thr Lys Leu
                20                  25                  30

Ser Ser Ile Cys Lys Pro Ser Ala Leu Ser Ile Leu Asn Lys Ser Asn
            35                  40                  45

Arg Thr Arg Lys Phe Ser Val Ser Ala Gly Tyr Gln Asp Gly Ser Arg
50                  55                  60

Ser Gly Ser Ser Gly Asp Phe Ile Ala Gly Phe Leu Leu Gly Gly Ala
65                  70                  75                  80

Val Phe Gly Ala Val Ala Tyr Ile Phe Ala Pro Gln Ile Arg Arg Ser
                85                  90                  95

Leu Leu Asn Glu Glu Asp Glu Tyr Gly Phe Lys Lys Pro Gln Gln Pro
            100                 105                 110

Thr Tyr Tyr Asp Glu Gly Leu Glu Lys Thr Arg Glu Thr Leu Asn Glu
        115                 120                 125

Lys Ile Gly Gln Leu Asn Ser Ala Ile Asp Asn Val Ser Ser Arg Leu
    130                 135                 140

Arg Gly Arg Glu Lys Asn Ser Ser Ser Pro Asn Val Pro Val Glu Thr
145                 150                 155                 160

Asp Pro Glu Val Glu Ala Thr Thr
                165

<210> SEQ ID NO 15
<211> LENGTH: 167
<212> TYPE: PRT
<213> ORGANISM: Camelina sativa

<400> SEQUENCE: 15
```

```
Met Ala Ser Cys Val Val Ala Pro Leu Ser Leu Ser Gly Gly Ser Gln
1               5                   10                  15

Ser His His Leu Lys Ala Asn Gly Leu Ser Ser Thr Thr Lys Leu Ser
                20                  25                  30

Ser Ile Cys Lys Pro Cys Ala Leu Ser Ile Leu Asn Lys Ser Asn Arg
                35                  40                  45

Thr Arg Asn Phe Ser Val Ser Ala Gly Tyr Arg Asp Gly Ser Arg Ser
            50                  55                  60

Gly Ser Ser Gly Asp Phe Ile Ala Gly Phe Leu Gly Gly Ala Val
65                  70                  75                  80

Phe Gly Ala Val Ala Tyr Ile Phe Ala Pro Gln Ile Arg Arg Ser Val
                85                  90                  95

Leu Asn Glu Glu Asp Glu Tyr Gly Phe Lys Lys Pro Gln Gln Pro Thr
                100                 105                 110

Tyr Tyr Asp Glu Gly Leu Glu Lys Thr Arg Glu Thr Leu Asn Glu Lys
                115                 120                 125

Ile Gly Gln Leu Asn Ser Ala Ile Asp Asn Val Ser Ser Arg Leu Arg
                130                 135                 140

Gly Arg Glu Lys Asn Ser Ser Ser Pro Asn Val Pro Val Glu Thr Asp
145                 150                 155                 160

Pro Glu Val Glu Ala Thr Thr
                165
```

<210> SEQ ID NO 16
<211> LENGTH: 167
<212> TYPE: PRT
<213> ORGANISM: Camelina sativa

<400> SEQUENCE: 16

```
Met Ala Ser Cys Val Val Ala Pro Leu Ser Leu Ser Gly Gly Ser Gln
1               5                   10                  15

Ser His His Val Lys Ala Asn Gly Leu Ser Ser Thr Thr Lys Leu Asn
                20                  25                  30

Ser Ile Cys Lys Pro Ser Ala Leu Ser Ile Leu Asn Lys Ser Asn Arg
                35                  40                  45

Thr Leu Lys Phe Ser Val Ser Ala Glu Tyr Arg Asp Gly Ser Arg Ser
            50                  55                  60

Gly Ser Ser Gly Asp Phe Ile Gly Phe Leu Gly Gly Ala Val
65                  70                  75                  80

Phe Gly Ala Val Ala Tyr Ile Phe Ala Pro Gln Ile Arg Arg Ser Val
                85                  90                  95

Leu Asn Glu Glu Asp Glu Tyr Gly Phe Lys Lys Pro Gln Gln Pro Thr
                100                 105                 110

Tyr Tyr Asp Glu Gly Leu Glu Lys Thr Arg Glu Thr Leu Asn Glu Lys
                115                 120                 125

Ile Gly Gln Leu Asn Ser Ala Ile Asp Asn Val Ser Ser Arg Leu Arg
                130                 135                 140

Gly Arg Glu Lys Asn Thr Ser Ser Pro Asn Val Pro Val Glu Thr Asp
145                 150                 155                 160

Pro Glu Val Glu Ala Thr Thr
                165
```

<210> SEQ ID NO 17
<211> LENGTH: 167
<212> TYPE: PRT
<213> ORGANISM: Brassica napus

<400> SEQUENCE: 17

```
Met Ala Ala Leu Ser Thr Ser Leu Ser Leu Ser Arg Asn Thr Gln Gln
1               5                   10                  15

Leu His Pro Ser Ser Gly Phe Ser Leu Lys Pro Ile Gly Arg Arg Ala
            20                  25                  30

Asn Val Ser Phe Gly Leu Asn Pro Ser Lys Lys Ile Gln Leu Ser Ala
        35                  40                  45

Pro Ser Gly Lys Arg Ile Leu Thr Ile Gln Ser Ala Tyr Arg Asp Asp
    50                  55                  60

Asp Ser Ser Gly Ser Thr Gly Leu Phe Val Gly Gly Phe Ile Leu Gly
65                  70                  75                  80

Gly Leu Ile Val Gly Ala Leu Gly Cys Val Tyr Ala Pro Gln Ile Ser
                85                  90                  95

Lys Ala Ile Ala Gly Ala Asp Arg Lys Asp Phe Met Arg Lys Leu Pro
                100                 105                 110

Lys Phe Ile Tyr Asp Glu Glu Lys Ala Leu Glu Lys Thr Arg Lys Val
            115                 120                 125

Leu Ala Asp Lys Ile Ala Gln Leu Asn Ser Ala Ile Asp Asp Val Ser
        130                 135                 140

Ser Gln Leu Lys Ser Glu Asp Thr Pro Asn Gly Ala Ala Leu Ser Thr
145                 150                 155                 160

Asp Glu Val Glu Ala Thr Ala
                165
```

<210> SEQ ID NO 18
<211> LENGTH: 167
<212> TYPE: PRT
<213> ORGANISM: Brassica napus

<400> SEQUENCE: 18

```
Met Ala Ala Leu Ser Thr Ser Leu Ser Leu Ser Arg Asn Thr Gln Gln
1               5                   10                  15

Leu His Pro Ser Ser Gly Phe Ser Leu Lys Pro Ile Ala Arg Arg Ala
            20                  25                  30

Asn Val Ser Phe Gly Leu Asn Pro Ser Lys Lys Ile Gln Leu Ser Ala
        35                  40                  45

Pro Arg Gly Lys Arg Ile Leu Thr Ile Pro Ser Ala Tyr Arg Asp Asp
    50                  55                  60

Asp Ser Ser Gly Ser Thr Gly Leu Phe Val Gly Gly Phe Ile Leu Gly
65                  70                  75                  80

Gly Leu Ile Val Gly Ala Leu Gly Cys Val Tyr Ala Pro Gln Ile Ser
                85                  90                  95

Lys Ala Ile Ala Gly Ala Asp Arg Lys Asp Leu Met Arg Lys Leu Pro
                100                 105                 110

Lys Phe Ile Tyr Asp Glu Glu Lys Ala Leu Glu Lys Thr Arg Lys Val
            115                 120                 125

Leu Ala Asp Lys Ile Ala Gln Leu Asn Ser Ala Ile Asp Asp Val Ser
        130                 135                 140

Ser Gln Leu Lys Ser Glu Asp Thr Pro Asn Gly Ala Ala Leu Ser Thr
145                 150                 155                 160

Asp Glu Val Glu Ala Thr Ala
                165
```

<210> SEQ ID NO 19

```
<211> LENGTH: 162
<212> TYPE: PRT
<213> ORGANISM: Brassica napus

<400> SEQUENCE: 19

Met Ala Ser Ser Cys Val Ala Asn Leu Ser Leu Ser Gly Val Ser Gln
1               5                   10                  15

Ser His Tyr Val Lys Ala Asn Gly Leu Ser Thr Ala Lys Leu Asn Ser
                20                  25                  30

Ile Cys Lys Thr Ser Ala Leu Ser Ile Gln Lys Arg Ser Asn Arg Ser
            35                  40                  45

Arg Lys Phe Ser Val Ser Ala Glu Tyr Gly Ser Arg Arg Gly Ser Gly
    50                  55                  60

Gly Gly Asp Phe Val Ala Gly Phe Leu Leu Gly Ala Leu Phe Gly
65                  70                  75                  80

Ala Ala Ala Tyr Ile Phe Ala Pro Gln Ile Arg Arg Ser Ile Met Ser
                85                  90                  95

Glu Glu Asp Glu Tyr Gly Phe Lys Lys Pro Asp Gln Pro Ser Tyr Tyr
                100                 105                 110

Asp Glu Gly Leu Glu Lys Thr Arg Glu Thr Leu Asn Glu Lys Ile Gly
                115                 120                 125

Gln Leu Asn Ser Ala Ile Asp Asn Val Ser Ser Arg Leu Arg Gly Arg
                130                 135                 140

Ala Lys Lys Thr Ser Ser Pro Val Glu Thr Asp Pro Glu Val Glu Ala
145                 150                 155                 160

Thr Thr

<210> SEQ ID NO 20
<211> LENGTH: 167
<212> TYPE: PRT
<213> ORGANISM: Brassica napus

<400> SEQUENCE: 20

Met Ala Ser Cys Val Ala His Leu Pro Leu Ser Ser Gly Ser Gln Ser
1               5                   10                  15

His Leu Val Lys Ala Asn Gly Leu Ser Thr Thr Lys Leu Ser Ser Ile
                20                  25                  30

Cys Lys Thr Ser Ala Leu Thr Val Gln Lys Lys Ser Ser Gln Gly Arg
            35                  40                  45

Lys Phe Ser Val Ser Ala Arg Tyr Gly Asp Glu Gly Ser Arg Arg Ala
    50                  55                  60

Ser Gly Gly Gly Asp Phe Ile Ala Gly Phe Leu Leu Gly Gly Ala Val
65                  70                  75                  80

Phe Gly Ala Val Ala Tyr Ile Phe Ala Pro Gln Ile Arg Arg Ser Ile
                85                  90                  95

Met Ser Glu Glu Asp Glu Tyr Gly Phe Lys Lys Pro Gln Gln Pro Thr
                100                 105                 110

Tyr Tyr Asp Glu Gly Leu Glu Lys Thr Arg Glu Thr Leu Asn Lys Lys
                115                 120                 125

Ile Glu Gln Leu Asn Ser Ala Ile Asp Asn Val Ser Ser Arg Leu Arg
                130                 135                 140

Gly Arg Glu Lys Asn Thr Ser Ser Pro Asn Val Pro Val Glu Thr Asp
145                 150                 155                 160

Pro Glu Val Glu Ala Thr Thr
                165
```

```
<210> SEQ ID NO 21
<211> LENGTH: 161
<212> TYPE: PRT
<213> ORGANISM: Brassica napus

<400> SEQUENCE: 21

Met Ala Ser Ser Cys Val Ala His Leu Ser Leu Ser Gly Val Ser Gln
1               5                   10                  15

Ser His Tyr Val Lys Ala Asn Gly Leu Ser Thr Thr Ser Lys Leu Asn
                20                  25                  30

Ser Ile Cys Lys Thr Ser Ala Leu Ser Ile Gln Lys Arg Ser Asn Arg
            35                  40                  45

Ser Arg Lys Phe Ser Val Ser Ala Glu Tyr Gly Ser Arg Arg Gly Gly
        50                  55                  60

Gly Asp Phe Val Ala Gly Phe Leu Leu Gly Gly Ala Leu Phe Gly Ala
65                  70                  75                  80

Ala Ala Tyr Ile Phe Ala Pro Gln Ile Arg Arg Ser Ile Met Ser Glu
                85                  90                  95

Glu Asp Glu Tyr Gly Phe Lys Lys Pro Glu Gln Pro Ser Tyr Tyr Asp
                100                 105                 110

Glu Gly Leu Glu Lys Thr Arg Glu Thr Leu Asn Glu Lys Ile Gly Gln
            115                 120                 125

Leu Asn Ser Ala Ile Asp Asn Val Ser Ser Arg Leu Arg Gly Arg Glu
        130                 135                 140

Lys Lys Thr Ser Ser Pro Val Gln Thr Asp Pro Glu Val Glu Ala Thr
145                 150                 155                 160

Thr

<210> SEQ ID NO 22
<211> LENGTH: 173
<212> TYPE: PRT
<213> ORGANISM: Brassica napus

<400> SEQUENCE: 22

Met Ala Ser Cys Val Ala His Leu Ser Leu Ser Val Leu Val Ser Gly
1               5                   10                  15

Gly Lys Gly Gly Ser Gln Ser His His Val Lys Ala Asn Gly Leu Ser
                20                  25                  30

Ala Lys Lys Leu Ser Ser Ile Cys Lys Thr Ser Val Leu Thr Val Gln
            35                  40                  45

Lys Lys Ser Ser Arg Ser Gly Lys Phe Ser Val Ser Ala Arg Asp Glu
        50                  55                  60

Gly Ser Lys Arg Gly Gly Gly Gly Asp Phe Ile Ala Gly Phe
65                  70                  75                  80

Leu Leu Gly Gly Ala Val Phe Gly Ala Val Ala Tyr Ile Phe Ala Pro
                85                  90                  95

Gln Ile Arg Arg Ile Ile Met Ser Glu Glu Asp Glu Tyr Gly Phe Asn
                100                 105                 110

Lys Pro Gln Gln Pro Thr Tyr Tyr Asp Glu Gly Leu Glu Lys Thr Arg
            115                 120                 125

Glu Thr Leu Asn Lys Lys Ile Glu Gln Leu Asn Ser Ala Ile Asp Asn
        130                 135                 140

Val Ser Ser Arg Leu Arg Gly Arg Glu Lys Asn Thr Ser Ser Pro Asn
145                 150                 155                 160

Val Pro Val Glu Thr Asp Pro Glu Val Glu Ala Thr Thr
```

165            170

<210> SEQ ID NO 23
<211> LENGTH: 167
<212> TYPE: PRT
<213> ORGANISM: Brassica napus

<400> SEQUENCE: 23

Met Ala Ala Leu Ser Thr Ser Leu Ser Leu Ser Arg Asn Thr Gln Gln
1               5                   10                  15

Leu His Pro Ser Ser Gly Phe Ser Leu Lys Pro Ile Gly Arg Arg Ala
            20                  25                  30

Asn Val Ser Phe Gly Leu Asn Pro Ser Lys Gln Ile Gln Leu Ser Ala
        35                  40                  45

Pro Arg Gly Lys Arg Ile Leu Thr Ile Gln Ser Ala Tyr Arg Asp Asp
    50                  55                  60

Asp Ser Ser Gly Ser Thr Gly Leu Phe Val Gly Phe Ile Leu Gly
65                  70                  75                  80

Gly Leu Ile Val Gly Ala Leu Gly Cys Val Tyr Ala Pro Gln Ile Ser
                85                  90                  95

Lys Ala Ile Ala Gly Ala Asp Arg Lys Asp Leu Met Arg Lys Leu Pro
            100                 105                 110

Lys Phe Ile Tyr Asp Glu Glu Lys Ala Leu Glu Lys Thr Arg Lys Val
        115                 120                 125

Leu Ala Asp Lys Ile Ala Gln Leu Asn Ser Ala Ile Asp Asp Val Ser
    130                 135                 140

Ser Gln Leu Lys Ser Glu Asp Thr Pro Asn Gly Ala Ala Leu Ser Thr
145                 150                 155                 160

Asp Glu Val Glu Ala Thr Ala
                165

<210> SEQ ID NO 24
<211> LENGTH: 167
<212> TYPE: PRT
<213> ORGANISM: Brassica napus

<400> SEQUENCE: 24

Met Ala Ala Leu Ser Thr Ser Leu Ser Leu Ser Arg Asn Thr Gln Gln
1               5                   10                  15

Leu His Pro Ser Ser Gly Phe Ser Leu Lys Pro Ile Ala Arg Arg Ala
            20                  25                  30

Asn Val Ser Phe Gly Leu Asn Pro Ser Lys Lys Ile Gln Leu Ser Ala
        35                  40                  45

Pro Arg Gly Lys Arg Ile Leu Thr Ile Gln Ser Ala Tyr Arg Asp Asp
    50                  55                  60

Asp Ser Ser Gly Ser Thr Gly Leu Phe Val Gly Phe Ile Leu Gly
65                  70                  75                  80

Gly Leu Ile Val Gly Ala Leu Gly Cys Val Tyr Ala Pro Gln Ile Ser
                85                  90                  95

Lys Ala Ile Ala Gly Ala Asp Arg Lys Asp Leu Met Arg Lys Leu Pro
            100                 105                 110

Lys Phe Ile Tyr Asp Glu Glu Lys Ala Leu Glu Lys Thr Arg Lys Val
        115                 120                 125

Leu Ala Asp Lys Ile Ala Gln Leu Asn Ser Ala Ile Asp Asp Val Ser
    130                 135                 140

Ser Gln Leu Lys Ser Glu Asp Thr Pro Asn Gly Ala Ala Leu Ser Thr

```
                145                 150                 155                 160

Asp Glu Val Glu Ala Thr Ala
                165

<210> SEQ ID NO 25
<211> LENGTH: 162
<212> TYPE: PRT
<213> ORGANISM: Brassica napus

<400> SEQUENCE: 25

Met Ala Ser Ser Cys Val Ala Asn Leu Ser Leu Ser Gly Val Ser Gln
1               5                   10                  15

Ser His Tyr Val Lys Ala Asn Gly Leu Ser Thr Ala Lys Leu Asn Ser
                20                  25                  30

Ile Cys Lys Thr Ser Ala Leu Ser Ile Gln Lys Arg Ser Asn Arg Ser
            35                  40                  45

Arg Lys Phe Ser Val Ser Ala Glu Tyr Gly Ser Arg Arg Gly Ser Gly
        50                  55                  60

Gly Gly Asp Phe Val Ala Gly Phe Leu Leu Gly Ala Leu Phe Gly
65                  70                  75                  80

Ala Ala Ala Tyr Ile Phe Ala Pro Gln Ile Arg Arg Ser Ile Met Ser
                85                  90                  95

Glu Glu Asp Glu Tyr Gly Phe Lys Lys Pro Asp Gln Pro Ser Tyr Tyr
                100                 105                 110

Asp Glu Gly Leu Glu Lys Thr Arg Glu Thr Leu Asn Glu Lys Ile Gly
            115                 120                 125

Gln Leu Asn Ser Ala Ile Asp Asn Val Ser Ser Arg Leu Arg Gly Arg
        130                 135                 140

Ala Lys Lys Thr Ser Ser Pro Val Glu Thr Asp Pro Glu Val Glu Ala
145                 150                 155                 160

Thr Thr

<210> SEQ ID NO 26
<211> LENGTH: 169
<212> TYPE: PRT
<213> ORGANISM: Brassica napus

<400> SEQUENCE: 26

Met Ala Ser Cys Val Ala His Leu Pro Leu Ser Ser Gly Ser Gln Ser
1               5                   10                  15

Arg His Val Lys Ala Asn Gly Leu Ser Thr Thr Lys Leu Ser Ser Ile
                20                  25                  30

Cys Lys Thr Ser Ala Leu Thr Val Gln Lys Lys Ser Ser Arg Ser Arg
            35                  40                  45

Lys Phe Ser Val Ser Ala Arg Tyr Gly Asp Glu Gly Ser Arg Arg Ala
        50                  55                  60

Ser Gly Gly Gly Gly Asp Phe Ile Ala Gly Phe Leu Leu Gly Gly
65                  70                  75                  80

Ala Val Phe Gly Ala Val Ala Tyr Ile Phe Ala Pro Gln Ile Arg Arg
                85                  90                  95

Ser Ile Met Ser Glu Glu Asp Glu Tyr Gly Phe Lys Lys Pro Gln Gln
                100                 105                 110

Pro Thr Tyr Tyr Asp Glu Gly Leu Glu Lys Thr Arg Glu Thr Leu Asn
            115                 120                 125

Lys Lys Ile Glu Gln Leu Asn Ser Ala Ile Asp Asn Val Ser Ser Arg
        130                 135                 140
```

```
Leu Arg Gly Arg Glu Asn Asn Thr Ser Ser Pro Asn Val Pro Val Glu
145                 150                 155                 160

Thr Gly Pro Glu Val Glu Ala Thr Thr
                165
```

<210> SEQ ID NO 27
<211> LENGTH: 161
<212> TYPE: PRT
<213> ORGANISM: Brassica napus

<400> SEQUENCE: 27

```
Met Ala Ser Ser Cys Val Ala His Leu Ser Leu Ser Gly Val Ser Gln
1               5                   10                  15

Ser His Tyr Val Lys Ala Asn Gly Leu Ser Thr Thr Ser Lys Leu Asn
                20                  25                  30

Ser Ile Cys Lys Thr Ser Ala Leu Ser Ile Gln Lys Arg Ser Asn Arg
            35                  40                  45

Ser Arg Lys Phe Ser Val Ser Ala Glu Tyr Gly Ser Arg Arg Gly Gly
        50                  55                  60

Gly Asp Phe Val Ala Gly Phe Leu Leu Gly Gly Ala Leu Phe Gly Ala
65                  70                  75                  80

Ala Ala Tyr Ile Phe Ala Pro Gln Ile Arg Arg Ser Ile Met Ser Glu
                85                  90                  95

Glu Asp Glu Tyr Gly Phe Lys Lys Pro Glu Gln Pro Ser Tyr Tyr Asp
            100                 105                 110

Glu Gly Leu Glu Lys Thr Arg Glu Thr Leu Asn Glu Lys Ile Gly Gln
        115                 120                 125

Leu Asn Ser Ala Ile Asp Asn Val Ser Ser Arg Leu Arg Gly Arg Glu
130                 135                 140

Lys Lys Thr Ser Ser Pro Val Gln Thr Asp Pro Glu Val Glu Ala Thr
145                 150                 155                 160

Thr
```

<210> SEQ ID NO 28
<211> LENGTH: 175
<212> TYPE: PRT
<213> ORGANISM: Brassica napus

<400> SEQUENCE: 28

```
Met Ala Ser Cys Val Ala His Leu Ser Leu Ser Val Leu Val Ser Gly
1               5                   10                  15

Gly Lys Gly Gly Ser Gln Ser His His Val Lys Ala Asn Gly Leu Ser
                20                  25                  30

Ala Lys Lys Leu Ser Ser Ile Cys Lys Thr Ser Val Leu Thr Val Gln
            35                  40                  45

Lys Lys Ser Ser Arg Ser Gly Lys Phe Ser Val Ser Ala Arg Tyr Gly
        50                  55                  60

Asp Glu Gly Ser Lys Arg Gly Ser Gly Gly Gly Asp Phe Ile Ala
65                  70                  75                  80

Gly Phe Leu Leu Gly Gly Ala Val Phe Gly Ala Val Ala Tyr Ile Phe
                85                  90                  95

Ala Pro Gln Ile Arg Arg Ile Ile Met Ser Glu Glu Asp Glu Tyr Gly
            100                 105                 110

Phe Asn Lys Pro Gln Gln Pro Thr Tyr Tyr Asp Glu Gly Leu Glu Lys
        115                 120                 125
```

```
Thr Arg Glu Thr Leu Asn Lys Lys Ile Glu Gln Leu Asn Ser Ala Ile
            130                 135                 140

Asp Asn Val Ser Ser Arg Leu Arg Gly Arg Glu Lys Asn Thr Ser Ser
145                 150                 155                 160

Pro Asn Val Pro Val Glu Thr Asp Pro Glu Val Glu Ala Thr Thr
                165                 170                 175

<210> SEQ ID NO 29
<211> LENGTH: 167
<212> TYPE: PRT
<213> ORGANISM: Brassica napus

<400> SEQUENCE: 29

Met Ala Ala Leu Ser Thr Ser Leu Ser Leu Ser Arg Asn Thr Gln Gln
1               5                   10                  15

Leu His Pro Ser Ser Gly Phe Ser Leu Lys Pro Ile Gly Arg Arg Ala
            20                  25                  30

Asn Val Ser Phe Gly Leu Asn Pro Ser Lys Lys Ile Gln Leu Ser Ala
        35                  40                  45

Pro Ser Gly Lys Arg Ile Leu Thr Ile Gln Ser Ala Tyr Arg Asp Asp
50                  55                  60

Asp Ser Ser Gly Ser Thr Gly Leu Phe Val Gly Phe Ile Leu Gly
65                  70                  75                  80

Gly Leu Ile Val Gly Ala Leu Gly Cys Val Tyr Ala Pro Gln Ile Ser
                85                  90                  95

Lys Ala Ile Ala Gly Ala Asp Arg Lys Asp Phe Met Arg Lys Leu Pro
            100                 105                 110

Lys Phe Ile Tyr Asp Glu Glu Lys Ala Leu Glu Lys Thr Arg Lys Val
        115                 120                 125

Leu Ala Asp Lys Ile Ala Gln Leu Asn Ser Ala Ile Asp Val Ser
            130                 135                 140

Ser Gln Leu Lys Ser Glu Asp Thr Pro Asn Gly Ala Ala Leu Ser Thr
145                 150                 155                 160

Asp Glu Val Glu Ala Thr Ala
                165

<210> SEQ ID NO 30
<211> LENGTH: 167
<212> TYPE: PRT
<213> ORGANISM: Brassica napus

<400> SEQUENCE: 30

Met Ala Ala Leu Ser Thr Ser Leu Ser Leu Ser Arg Asn Thr Gln Gln
1               5                   10                  15

Leu His Pro Ser Ser Gly Phe Ser Leu Lys Pro Ile Ala Arg Arg Ala
            20                  25                  30

Asn Val Ser Phe Gly Leu Asn Pro Ser Lys Lys Ile Gln Leu Ser Ala
        35                  40                  45

Pro Arg Gly Lys Arg Ile Leu Thr Ile Gln Ser Ala Tyr Arg Asp Asp
50                  55                  60

Asp Ser Ser Gly Ser Thr Gly Leu Phe Val Gly Phe Ile Leu Gly
65                  70                  75                  80

Gly Leu Ile Val Gly Ala Leu Gly Cys Val Tyr Ala Pro Gln Ile Ser
                85                  90                  95

Lys Ala Ile Ala Gly Ala Asp Arg Lys Asp Leu Met Arg Lys Leu Pro
            100                 105                 110
```

```
Lys Phe Ile Tyr Asp Glu Glu Lys Ala Leu Glu Lys Thr Arg Lys Val
            115                 120                 125
Leu Ala Asp Lys Ile Ala Gln Leu Asn Ser Ala Ile Asp Asp Val Ser
        130                 135                 140
Ser Gln Leu Lys Ser Glu Asp Thr Pro Asn Gly Ala Ala Leu Ser Thr
145                 150                 155                 160
Asp Glu Val Glu Ala Thr Ala
                165

<210> SEQ ID NO 31
<211> LENGTH: 162
<212> TYPE: PRT
<213> ORGANISM: Brassica napus

<400> SEQUENCE: 31

Met Ala Ser Ser Cys Val Ala Asn Leu Ser Leu Ser Gly Val Ser Gln
1               5                   10                  15
Ser His Tyr Val Lys Ala Asn Gly Leu Ser Thr Ala Lys Leu Asn Ser
            20                  25                  30
Ile Cys Lys Thr Ser Ala Leu Ser Ile Gln Lys Arg Ser Asn Arg Ser
        35                  40                  45
Arg Lys Phe Ser Val Ser Ala Glu Tyr Gly Ser Arg Gly Ser Gly
    50                  55                  60
Gly Gly Asp Phe Val Ala Gly Phe Leu Leu Gly Ala Leu Phe Gly
65                  70                  75                  80
Ala Ala Ala Tyr Ile Phe Ala Pro Gln Ile Arg Arg Ser Ile Met Ser
                85                  90                  95
Glu Glu Asp Glu Tyr Gly Phe Lys Lys Pro Asp Gln Pro Ser Tyr Tyr
            100                 105                 110
Asp Glu Gly Leu Glu Lys Thr Arg Glu Thr Leu Asn Glu Lys Ile Gly
        115                 120                 125
Gln Leu Asn Ser Ala Ile Asp Asn Val Ser Ser Arg Leu Arg Gly Arg
    130                 135                 140
Ala Lys Lys Thr Ser Ser Pro Val Glu Thr Asp Pro Glu Val Glu Ala
145                 150                 155                 160
Thr Thr

<210> SEQ ID NO 32
<211> LENGTH: 167
<212> TYPE: PRT
<213> ORGANISM: Brassica napus

<400> SEQUENCE: 32

Met Ala Ser Cys Val Ala His Leu Pro Leu Ser Ser Gly Ser Gln Ser
1               5                   10                  15
Arg His Val Lys Ala Asn Gly Leu Ser Thr Thr Lys Leu Ser Ser Ile
            20                  25                  30
Cys Lys Thr Ser Ala Leu Thr Val Gln Lys Ser Ser Gln Gly Arg
        35                  40                  45
Lys Phe Ser Val Ser Ala Arg Tyr Gly Asp Glu Gly Ser Arg Arg Gly
    50                  55                  60
Ser Gly Gly Gly Asp Phe Ile Ala Gly Phe Leu Leu Gly Gly Ala Val
65                  70                  75                  80
Phe Gly Ala Val Ala Tyr Ile Phe Ala Pro Gln Ile Arg Arg Ser Ile
                85                  90                  95
Met Ser Glu Glu Asp Glu Tyr Gly Phe Lys Lys Pro Gln Gln Pro Thr
```

```
                      100                 105                 110

Tyr Tyr Asp Glu Gly Leu Glu Lys Thr Arg Glu Thr Leu Asn Lys Lys
        115                 120                 125

Ile Glu Gln Leu Asn Ser Ala Ile Asp Asn Val Ser Ser Arg Leu Arg
    130                 135                 140

Gly Arg Glu Lys Asn Thr Ser Ser Pro Asn Val Pro Val Glu Thr Asp
145                 150                 155                 160

Pro Glu Val Glu Ala Thr Thr
                165

<210> SEQ ID NO 33
<211> LENGTH: 161
<212> TYPE: PRT
<213> ORGANISM: Brassica napus

<400> SEQUENCE: 33

Met Ala Ser Ser Cys Val Ala His Leu Ser Leu Ser Gly Val Ser Gln
1               5                   10                  15

Ser His Tyr Val Lys Ala Asn Gly Leu Ser Thr Thr Ser Lys Leu Asn
            20                  25                  30

Ser Ile Cys Lys Thr Ser Ala Leu Ser Ile Gln Lys Arg Ser Asn Arg
        35                  40                  45

Ser Arg Lys Phe Ser Val Ser Ala Glu Tyr Gly Cys Gly Gly Gly Gly
    50                  55                  60

Gly Asp Phe Val Ala Gly Phe Leu Leu Gly Gly Ala Leu Phe Gly Ala
65                  70                  75                  80

Ala Ala Tyr Ile Phe Ala Pro Gln Ile Arg Arg Ser Ile Met Ser Glu
                85                  90                  95

Glu Asp Glu Tyr Gly Phe Lys Lys Pro Glu Gln Pro Ser Tyr Tyr Asp
            100                 105                 110

Glu Gly Leu Glu Lys Thr Arg Glu Thr Leu Asn Glu Lys Ile Gly Gln
        115                 120                 125

Leu Asn Ser Ala Ile Asp Asn Val Ser Ser Arg Leu Arg Gly Arg Glu
    130                 135                 140

Lys Lys Thr Ser Ser Pro Val Gln Thr Asp Pro Glu Val Glu Ala Thr
145                 150                 155                 160

Thr

<210> SEQ ID NO 34
<211> LENGTH: 495
<212> TYPE: DNA
<213> ORGANISM: Camelina sativa

<400> SEQUENCE: 34
atggcgtctc tttctacctc tctctctctc cccaataacg ctcaacaact ccatccttca      60
tccggctttt ccctgaagcc atgtgtcagt gtttcttttg gactgaatcg ctccaacaac     120
cttcatattt ctgctcctag aagcaaaagg atcctcaccg ttcaatcagc atacagagat     180
gatgacggtt caggcagcac aggcttattt gtcggagggt ttattctggg cggactcata     240
gttggtgctc tcggatgtgt atacgcacca cagatcagca aggcaattgc tggagcagac     300
cgaaaggatc tcatgaggaa attgccgaaa ttcatatatg atgaggaaaa agctttggag     360
aaaactcgga aggtactggc tgaaaaaatt gctcagctta actctgctat cgacgatgtg     420
tcctctcagc tcaaatcaga agatacaccg aatggtgcag ctctaagcac cgatgaagtc     480
gaggctacag cctaa                                                      495
```

<210> SEQ ID NO 35
<211> LENGTH: 495
<212> TYPE: DNA
<213> ORGANISM: Camelina sativa

<400> SEQUENCE: 35

| | | | | | |
|---|---|---|---|---|---|
| atggcgtctc | tttctacctc | gctctctctc | cccaataacg | ctcaacaact | ccatccttca | 60 |
| tctggctttt | ccctgaagcc | atgtgtcagt | gtttcttttg | gactgaatcg | ctccaacaac | 120 |
| cttcatattt | ctgctcctag | aagcaaaagg | atcctcatcg | ttcaatcagc | atacagagat | 180 |
| gatgacggtt | caggcagcac | aggcttattt | gtcggagggt | ttattttggg | cggactcata | 240 |
| gttggtgctc | tcggatgtgt | atacgcacca | cagatcagca | aggctatagc | tggagcagac | 300 |
| cgaaaggatc | tcatgaggaa | attgccgaaa | ttcatatatg | acgaggaaaa | agctttggag | 360 |
| aaaacacgga | aggtgctggc | tgaaaaaatt | gctcagctca | actctgctat | cgacgatgtg | 420 |
| tcctctcagc | tcaaatcaga | agatacccccg | aatggtgcag | ctctaagcac | cgatgaagtc | 480 |
| gaggctacag | cctga | | | | | 495 |

<210> SEQ ID NO 36
<211> LENGTH: 495
<212> TYPE: DNA
<213> ORGANISM: Camelina sativa

<400> SEQUENCE: 36

| | | | | | |
|---|---|---|---|---|---|
| atggcgtctc | tttctacctc | tctctctctc | cccaataacg | ctcaacaact | ccatccttca | 60 |
| tccggctttt | ccctgaagcc | atgtgtcagt | gtttcttttg | gactgaatcg | atccaacaac | 120 |
| cttcatattt | ctgctcctag | aagcaaaagg | atcgtcaccg | ttcaatcagc | atacagagat | 180 |
| gatgacggtt | caggcagcac | aggcttattt | gtcggagggt | ttattctggg | cggactcata | 240 |
| gttggtgccc | tcggatgtgt | atacgcacca | cagatcagca | aggctatagc | tggagcagac | 300 |
| cgaaaggatc | tcatgaggaa | attgccgaaa | ttcatatatg | acgaggaaaa | agctttggag | 360 |
| aaaacacgga | aggtgctggc | tgaaaaaatt | gctcagctca | actctgctat | cgacgacgtg | 420 |
| tcctctcagc | tcaaatcaga | agatacccccg | aatggtgcag | ctctaagcac | cgatgaagtc | 480 |
| gaggctacag | cctga | | | | | 495 |

<210> SEQ ID NO 37
<211> LENGTH: 486
<212> TYPE: DNA
<213> ORGANISM: Camelina sativa

<400> SEQUENCE: 37

| | | | | | |
|---|---|---|---|---|---|
| atggcgtcct | tcgtagcagc | tcctaactct | ctctcaggtg | actctcatct | caaagcacac | 60 |
| tgtttgtcgt | ctacaaacct | caatctgatt | cgcaagagct | ctacattaac | tgttataaca | 120 |
| aaatcgaatc | gcagtcacaa | actctcggtt | tctgcaggtt | accgtgaagg | aagcaggggc | 180 |
| ggtggaagta | gtgattttgt | tacgggtttt | cttctaggaa | gtgctgtgtt | tggtactttg | 240 |
| gcttatgtct | ttgctccaca | gatccgaaga | tcgttgctga | acgaaaatga | acatggtttc | 300 |
| aagaaaccag | agcagccaat | gtactacgat | gaaggcctag | aggagagaag | agagatattg | 360 |
| aatgagaaaa | taggccaact | gaattcagcc | atagacaatg | tttcgtcgcg | tctgagagga | 420 |
| agcaagaaca | gttcttcgca | gtctgtcaca | gttgaaaccg | acgcagaagc | agaagctact | 480 |
| gcatga | | | | | | 486 |

<210> SEQ ID NO 38
<211> LENGTH: 498
<212> TYPE: DNA
<213> ORGANISM: Camelina sativa

<400> SEQUENCE: 38

| | | | | | |
|---|---|---|---|---|---|
| atggcgtcct | tcgtagcagc | tcctatctct | ctctcaggtg | actctcatgt | caaagcacac | 60 |
| tgtttgttgt | ctacaaacct | taatccgatt | cgcaagagct | ctacattgac | tgttagaaca | 120 |
| aaatcgaacc | gcagtcacaa | actctcggtt | tctgcaggct | accgtgaagg | aagcaggggc | 180 |
| ggtggaagta | gtgattttgt | tacgggttgt | cttctaggaa | gtgctgtgtt | tggtactttg | 240 |
| gcttatgtct | ttgctccaca | gatccgaaga | tcgttgctga | acgaaaatga | acatggtttc | 300 |
| aagaaaccag | agcagccgat | gtactacgat | gaaggcctag | aggagagaag | agaaatattg | 360 |
| aatgagaaaa | tcgccaact | gaattcagcc | atagacaatg | tttcatcgcg | tctgagaggt | 420 |
| ggaagcggaa | gcggcaagaa | cagttcttcg | cagtctgtca | ccgttgaaac | cgacgcagaa | 480 |
| gcagaagcta | ctgcatga | | | | | 498 |

<210> SEQ ID NO 39
<211> LENGTH: 501
<212> TYPE: DNA
<213> ORGANISM: Camelina sativa

<400> SEQUENCE: 39

| | | | | | |
|---|---|---|---|---|---|
| atggcgtcct | tcgtagcagc | tcctatctct | ctctcaggtg | actctcatgt | caaagcacac | 60 |
| cgtttctcgt | ctacaaacct | caatccgttt | cgcaagagct | ctacattgac | tgttagaaca | 120 |
| aaatcgaatc | gcagtcacaa | actctcggtt | tctgcaggtt | accgtgaagg | aagcaggggc | 180 |
| ggtggaagta | gtgattttgt | tacgggtttt | cttctaggaa | gtgctgtgtt | tggtactttg | 240 |
| gcctatatct | ttgctccgca | gatccgaaga | tcgttgctga | acgaaaatga | acatggtttc | 300 |
| aagaaaccag | agcagccgat | atactacgat | gaaggcctag | aggagagaag | agagatattg | 360 |
| aatgagaaaa | tcggccaatt | gaattcagcc | atagacaatg | tttcatcgcg | tctgagagga | 420 |
| ggtggaagcg | gtagcagcaa | gaacagttct | tcgcagtctg | tcaccgttga | aaccgacgca | 480 |
| gaagcagaag | ctactgcatg | a | | | | 501 |

<210> SEQ ID NO 40
<211> LENGTH: 507
<212> TYPE: DNA
<213> ORGANISM: Camelina sativa

<400> SEQUENCE: 40

| | | | | | |
|---|---|---|---|---|---|
| atggcgtcat | gtgttgttgt | tgctcctcta | tctctctctg | gtggctctca | atctcatcat | 60 |
| gtgaaagcta | atggattgtc | gtctaccaca | aagctcagtt | ctatttgtaa | accttctgca | 120 |
| ttgtcaatcc | tgaataaatc | aaaccggact | cgcaagtttt | ctgtttctgc | tgggtaccaa | 180 |
| gatgggagta | ggagtggaag | cagtggtgac | ttcatagctg | gttttcttct | aggaggtgct | 240 |
| gtgtttggcg | ctgttgcata | tatctttgct | ccacagatcc | ggagatcgct | actgaatgaa | 300 |
| gaagatgagt | atggtttcaa | gaagccgcaa | cagccaacgt | actacgatga | aggtttagag | 360 |
| aaaacaagag | agacattgaa | tgagaaaatc | ggacagctta | attccgcgat | tgacaatgtt | 420 |
| tcttcgcgtt | taagaggtcg | agaaaagaac | agttcttccc | ccaatgtacc | ggtcgaaact | 480 |
| gacccccgaag | ttgaagctac | aacttga | | | | 507 |

<210> SEQ ID NO 41
<211> LENGTH: 504
<212> TYPE: DNA
<213> ORGANISM: Camelina sativa

<400> SEQUENCE: 41

```
atggcgtcat gtgttgttgc tcctctttct ctctctggtg ggtctcaatc tcatcatttg     60
aaagctaatg gattgtcgtc taccacgaag ctcagttcta tttgtaaacc ttgtgcattg    120
tcaatcctga ataaatcaaa ccggactcgc aattttctg tttctgctgg gtaccgagat    180
gggagtagga gtggaagcag tggtgacttc atagctggtt ttcttctagg aggtgctgtg    240
tttggcgctg ttgcttatat ctttgctcca cagatccgga gatcggtact gaatgaagaa    300
gatgagtatg gtttcaagaa gccgcaacag ccaacgtact acgatgaagg tttagagaaa    360
acaagagaga cattgaatga gaaaatcgga cagcttaatt ccgcgattga caatgttcct    420
tcgcgtttaa gaggtcgaga aaagaacagt tcttccccca atgtaccggt cgaaactgac    480
cctgaagttg aagctacaac ttga                                           504
```

<210> SEQ ID NO 42
<211> LENGTH: 504
<212> TYPE: DNA
<213> ORGANISM: Camelina sativa

<400> SEQUENCE: 42

```
atggcgtcgt gtgttgttgc tcctctttct ctctctggtg ggtctcaatc tcatcatgtg     60
aaggctaatg gattgtcttc taccacaaag ctcaattcta tctgtaaacc ttctgcattg    120
tcaatcctga ataaatcaaa ccggactctc aagttttctg tttctgctga gtaccgagat    180
gggagtagga gtggaagcag tggtgatttc atagctggtt ttcttctagg aggtgctgtg    240
tttggcgctg ttgcttatat ctttgctcca cagatccgga gatcggtact gaatgaagaa    300
gatgagtatg gtttcaagaa gccgcaacag ccaacgtatt acgatgaagg tttagagaaa    360
acaagagaga cattgaatga gaaaatagga cagcttaatt cggcgattga caatgttcct    420
tcgcgtttaa gaggtcgaga aaagaacact tcttccccca atgtaccggt cgaaactgac    480
cccgaagttg aagctacaac ttga                                           504
```

<210> SEQ ID NO 43
<211> LENGTH: 504
<212> TYPE: DNA
<213> ORGANISM: Brassica napus

<400> SEQUENCE: 43

```
atggcggctc tttcgacatc tctctctctt tccaggaata tcagcaact ccatccttca      60
tctggctttt ctctgaagcc aattggtcgt cgtgccaacg tttctttcgg gctgaatccc    120
tctaaaaaga tccagctttc tgctcctagt ggcaaaagga tcctaaccat ccaatcagca    180
tacagagatg atgacagttc aggcagcact ggcctgtttg tgggagggtt cattttgggc    240
gggctcatag tcggtgctct tggatgtgtg tatgcaccac agatcagcaa ggctatagct    300
ggagcagacc gaaaggattt catgaggaaa ttgcctaagt tcatatatga tgaggaaaaa    360
gctttggaga aaactcgcaa ggtattggct gacaaaattg ctcagctcaa ctctgctatc    420
gacgatgtgt cctctcagct aaaatcagaa gacaccccta atggtgcagc tctaagcacc    480
gatgaagtcg aggctacagc ctga                                           504
```

<210> SEQ ID NO 44

<211> LENGTH: 504
<212> TYPE: DNA
<213> ORGANISM: Brassica napus

<400> SEQUENCE: 44

```
atggcggctc tttcgacatc tctctctctt tccaggaata ctcagcaact ccatccttca      60
tctggctttt ctctgaagcc aattgctcgt cgtgccaacg tttctttcgg gctgaatccc     120
tctaaaaaga tccagctttc tgctcctaga ggcaaaagga tcctaaccat cccatcagca     180
tacagagatg atgacagttc aggcagcact ggcctgtttg tgggagggtt cattttgggc     240
gggctcatag tcggtgctct tggatgtgtg tatgcaccac agatcagcaa ggctatagct     300
ggagcagacc gaaaggatct catgaggaaa ttgcctaagt tcatatatga tgaggaaaaa     360
gctttggaga aaactcgcaa ggtattggct gacaaaattg ctcagctcaa ctctgctatc     420
gacgatgtgt cctctcagct aaaatcagaa gacacccctg atggtgcagc tctaagcacc     480
gatgaagttg aggctacagc ctga                                            504
```

<210> SEQ ID NO 45
<211> LENGTH: 489
<212> TYPE: DNA
<213> ORGANISM: Brassica napus

<400> SEQUENCE: 45

```
atggcgtcct cctgtgttgc taatctttct ctgtcaggtg tgtctcaatc tcattatgtc      60
aaggcaaatg ggttgtctac cgcaaagctc aattcgattt gtaaaacctc tgcattgagt     120
atccagaaga gatcaaaccg gagtcgcaag ttttcagttt ctgcagagta tgggagtagg     180
agaggaagtg gtggtggtga tttcgttgct ggttttcttc ttggtggtgc tttgttcggc     240
gctgccgctt acatctttgc tccacagata cgaagatcga taatgagtga agaagatgag     300
tatggtttca agaagccaga tcaaccaagt tactacgatg aaggtttaga gaaaacaagg     360
gagaccttga cgagaaaaat cggacagctt aactcagcta ttgacaatgt ctcttcgcgt     420
ttaagaggtc gagcaaagaa gacttcttcc ccggtcgaaa ctgatccaga agttgaagct     480
actacttga                                                             489
```

<210> SEQ ID NO 46
<211> LENGTH: 504
<212> TYPE: DNA
<213> ORGANISM: Brassica napus

<400> SEQUENCE: 46

```
atggcgtcct gtgttgctca tcttccactc tcaagtgggt ctcagtctca tcttgtgaaa      60
gcaaatggat tgtccaccac aaagctcagt tccatttgta aaacttctgc attgactgtt     120
cagaagaaat caagccaggg tcgcaagttt tcggtttctg cacggtatgg agacgaaggg     180
agtaggagag caagtggtgg tggtgatttc atagctggtt tcttctctagg aggtgctgtc     240
tttggcgctg ttgcctatat ctttgctcca cagatcagaa gatcgataat gagtgaagaa     300
gatgagtatg gtttcaagaa gccacagcaa ccaacgtact acgatgaagg tttggagaaa     360
acaagagaga cactgaacaa gaaaatcgaa caacttaact cagcaatcga caatgtttct     420
tcccggttaa gaggtcgaga aagaacacct tcttctccca atgtaccggt ggaaactgac     480
ccagaagttg aagctacgac ttga                                            504
```

<210> SEQ ID NO 47
<211> LENGTH: 486

<212> TYPE: DNA
<213> ORGANISM: Brassica napus

<400> SEQUENCE: 47

```
atggcgtcct cctgtgttgc tcatctttct ctctcaggtg tgtctcaatc tcattatgtc    60
aaggcaaatg ggttgtctac cacctcaaag ctcaattcga tttgtaaaac ctctgcattg   120
agtatccaga agagatcaaa ccggagtcgc aagttttcag tttctgcaga gtatgggagt   180
aggagaggtg gtggtgattt cgtagctggt tttcttcttg gtggtgcttt gtttggcgct   240
gctgcctaca tctttgctcc acagatcaga agatctataa tgagtgaaga agatgagtat   300
ggattcaaga agccagaaca accaagttac tacgatgaag gtttagagaa aacaagggag   360
accttgaacg agaaaatcgg acagcttaac tcagctattg acaatgtctc ttcgcgttta   420
agaggtcgag agaagaagac ttcttcccct gtccaaactg acccggaagt tgaagctact   480
acttga                                                              486
```

<210> SEQ ID NO 48
<211> LENGTH: 522
<212> TYPE: DNA
<213> ORGANISM: Brassica napus

<400> SEQUENCE: 48

```
atggcgtcct gtgttgctca tctttctctc tcagttcttg tatctggtgg caaaggtggg    60
tctcaatctc atcatgtgaa agcaaatgga ttgtctgcca aaaagctcag ttccatttgt   120
aaaacttctg tattgactgt tcagaagaaa tcaagccgga gtggcaagtt ttcggttttct   180
gcacgagacg aagggagtaa gagaggaagt ggtggtggtg gtgatttcat agctggtttt   240
cttctaggag gtgctgtctt tggcgctgtt gcctatatct ttgctccaca gatcagaaga   300
attattatga gtgaagaaga tgagtatggt ttcaataagc cacaacaacc aacgtactac   360
gatgaaggtt tggagaaaac aagagagacg ctgaacaaga aaatcgaaca acttaactca   420
gcaatcgaca atgtttcttc ccggttaaga ggtcgagaaa gaacacatc ttctcccaat   480
gtaccggtgg aaactgaccc agaagttgaa gctacgactt aa                      522
```

<210> SEQ ID NO 49
<211> LENGTH: 504
<212> TYPE: DNA
<213> ORGANISM: Brassica napus

<400> SEQUENCE: 49

```
atggcggctc tttcgacatc tctctctctt tccaggaata tcagcaact ccatccttca     60
tctggctttt ctctgaagcc aattggtcgt cgtgccaacg tttctttcgg gctgaatccc   120
tctaaacaga tccagctttc tgctcctaga ggcaaaagga tcctaaccat ccaatcagca   180
tacagagatg atgacagttc aggcagcact ggcctgtttg tgggagggtt cattttgggc   240
gggctcatag tcggtgctct tggatgtgtg tatgcaccac agatcagcaa ggctatagct   300
ggagcagacc gaaaggatct catgaggaaa ttgcctaagt tcatatatga tgaggaaaaa   360
gctttggaga aaactcgcaa ggtattggct gacaaaattg ctcagctcaa ctctgctatc   420
gacgatgtgt cctctcagct aaaatcagaa gacacccta atggtgcagc tctaagcacc   480
gatgaagtcg aggctacagc ctga                                          504
```

<210> SEQ ID NO 50
<211> LENGTH: 504
<212> TYPE: DNA

<213> ORGANISM: Brassica napus

<400> SEQUENCE: 50

```
atggcggctc tttcgacatc tctctctctt tccaggaata ctcagcaact ccatccttca    60
tctggctttt ctctgaagcc aattgctcgt cgtgccaacg tttctttcgg gctgaatccc   120
tctaaaaaga tccagctttc tgctcctaga ggcaaaagga tcctaaccat ccaatcagca   180
tacagagatg atgacagttc aggcagcact ggcctgtttg tggggggggtt cattttgggc   240
gggctcatag tcggtgctct tggatgtgtg tatgcaccac agatcagcaa ggctatagct   300
ggagcagacc gaaaggatct catgaggaaa ttgcctaagt tcatatatga tgaggaaaaa   360
gctttggaga aaactcgcaa ggtattggct gacaaaattg ctcagctcaa ctctgctatc   420
gacgatgtgt cctctcagct aaaatcagaa gacacccta atggtgcagc tctaagcacc    480
gatgaagttg aggctacagc ctga                                           504
```

<210> SEQ ID NO 51
<211> LENGTH: 489
<212> TYPE: DNA
<213> ORGANISM: Brassica napus

<400> SEQUENCE: 51

```
atggcgtcct cctgtgttgc taatctttct ctgtcaggtg tgtctcaatc tcattatgtc    60
aaggcaaatg ggttgtctac cgcaaagctc aattcgattt gtaaaacctc tgcattgagt   120
atccagaaga gatcaaaccg gagtcgcaag ttttcagttt ctgcagagta tgggagtagg   180
agaggaagtg tggtggtgga tttcgttgct ggttttcttc ttggtggtgc tttgttcggc   240
gctgccgctt acatctttgc tccacagata cgaagatcga taatgagtga agaagatgag   300
tatggtttca gaagccaga tcaaccaagt tactacgatg aaggtttaga gaaacaagg    360
gagaccttga acgagaaaat cggacagctt aactcagcta ttgacaatgt ctcttcgcgt   420
ttaagaggtc gagcaaagaa gacttcttcc ccggtcgaaa ctgatccaga agttgaagct   480
actacttga                                                            489
```

<210> SEQ ID NO 52
<211> LENGTH: 510
<212> TYPE: DNA
<213> ORGANISM: Brassica napus

<400> SEQUENCE: 52

```
atggcgtcct gtgttgctca tcttccactc tcaagtgggt ctcagtctcg tcatgtaaaa    60
gcaaatggat tgtccaccac aaagctcagt tccatttgta aaacttctgc attgactgtt   120
cagaagaaat caagccggag tcgtaagttt cggttttctg cacggtatgg agacgaaggg   180
agtaggagag caagtggtgg tggtggtggt gatttcatag ctggttttct tctaggaggt   240
gctgtgtttg cgctgtcgc ctatatcttt gctccacaga tcagaagatc gataatgagt    300
gaagaagatg agtatggttt caagaagcca cagcaaccaa cgtactacga tgaaggtttg   360
gagaagacaa gagagacgct gaataagaaa atcgaacaac ttaactcagc aatcgacaat   420
gtttcatcgc ggttaagagg tcgagaaaat aacacttctt ctcccaatgt accagtggaa   480
actggcccag aagttgaagc tacgacttaa                                     510
```

<210> SEQ ID NO 53
<211> LENGTH: 486
<212> TYPE: DNA
<213> ORGANISM: Brassica napus

```
<400> SEQUENCE: 53
atggcgtcct cctgtgttgc tcatctttct ctctcaggtg tgtctcaatc tcattatgtc    60
aaggcaaatg ggttgtctac cacctcaaag ctcaattcga tttgtaaaac ctctgcattg   120
agtatccaga agagatcaaa ccggagtcgc aagttttcag tttctgcaga gtatgggagt   180
aggagaggtg gtggtgattt cgtagctggt tttcttcttg gtggtgcttt gtttggcgct   240
gctgcctaca tctttgctcc acagatcaga agatctataa tgagtgaaga agatgagtat   300
ggattcaaga agccagaaca accaagttac tacgatgaag gtttagagaa acaagggag    360 accttgaacg agaaaatcgg acagcttaac tcagctattg acaatgtctc ttcgcgttta   420
agaggtcgag agaagaagac ttcttcccct gtccaaactg acccggaagt tgaagctact   480
acttga                                                              486

<210> SEQ ID NO 54
<211> LENGTH: 528
<212> TYPE: DNA
<213> ORGANISM: Brassica napus

<400> SEQUENCE: 54
atggcgtcct gtgttgctca tctttctctc tcagttcttg tatctggtgg caaaggtggg    60
tctcaatctc atcatgtgaa agcaaatgga ttgtctgcca aaaagctcag ttccatttgt   120
aaaacttctg tattgactgt tcagaagaaa tcaagccgga gtggcaagtt ttcggtttct   180
gcacggtatg gagacgaagg gagtaagaga ggaagtggtg gtggtggtga tttcatagct   240
ggttttcttc taggaggtgc tgtctttggc gctgttgcct atatctttgc tccacagatc   300
agaagaatta ttatgagtga agaagatgag tatggtttca ataagccaca acaaccaacg   360
tactacgatg aaggtttgga gaaaacaaga gagacgctga acaagaaaat cgaacaactt   420
aactcagcaa tcgacaatgt tcttcccgg ttaagaggtc gagaaaagaa cacatcttct    480
cccaatgtac cggtggaaac tgacccagaa gttgaagcta cgacttaa                528

<210> SEQ ID NO 55
<211> LENGTH: 504
<212> TYPE: DNA
<213> ORGANISM: Brassica napus

<400> SEQUENCE: 55
atggcggctc tttcgacatc tctctctctt tccaggaata ctcagcaact ccatccttca    60
tctggctttt ctctgaagcc aattggtcgt cgtgccaacg tttctttcgg gctgaatccc   120
tctaaaaaga tccagctttc tgctcctagt ggcaaaagga tcctaaccat ccaatcagca   180
tacagagatg atgacagttc aggcagcact ggcctgtttg tgggagggtt cattttgggc   240
gggctcatag tcggtgctct tggatgtgtg tatgcaccac agatcagcaa ggctatagct   300
ggagcagacc gaaaggattt catgaggaaa ttgcctaagt tcatatatga tgaggaaaaa   360
gctttggaga aaactcgcaa ggtattggct gacaaaattg ctcagctcaa ctctgctatc   420
gacgatgtgt cctctcagct aaaatcagaa gacaccccta atggtgcagc tctaagcacc   480
gatgaagtcg aggctacagc ctga                                          504

<210> SEQ ID NO 56
<211> LENGTH: 504
<212> TYPE: DNA
<213> ORGANISM: Brassica napus
```

<400> SEQUENCE: 56

| | | | | |
|---|---|---|---|---|
| atggcggctc | tttcgacatc | tctctctctt | tccaggaata | ctcagcaact ccatccttca | 60 |
| tctggctttt | ctctgaagcc | aattgctcgt | cgtgccaacg | tttctttcgg gctgaatccc | 120 |
| tctaaaaaga | tccagctttc | tgctcctaga | ggcaaaagga | tcctaaccat ccaatcagca | 180 |
| tacagagatg | atgacagttc | aggcagcact | ggcctgtttg | tgggggggtt cattttgggc | 240 |
| gggctcatag | tcggtgctct | tggatgtgtg | tatgcaccac | agatcagcaa ggctatagct | 300 |
| ggagcagacc | gaaaggatct | catgaggaaa | ttgcctaagt | tcatatatga tgaggaaaaa | 360 |
| gctttggaga | aaactcgcaa | ggtattggct | gacaaaattg | ctcagctcaa ctctgctatc | 420 |
| gacgatgtgt | cctctcagct | aaaatcagaa | gacacccta | atggtgcagc tctaagcacc | 480 |
| gatgaagttg | aggctacagc | ctga | | | 504 |

<210> SEQ ID NO 57
<211> LENGTH: 489
<212> TYPE: DNA
<213> ORGANISM: Brassica napus

<400> SEQUENCE: 57

| | | | | |
|---|---|---|---|---|
| atggcgtcct | cctgtgttgc | taatctttct | ctgtcaggtg | tgtctcaatc tcattatgtc | 60 |
| aaggcaaatg | ggttgtctac | cgcaaagctc | aattcgattt | gtaaaacctc tgcattgagt | 120 |
| atccagaaga | gatcaaaccg | gagtcgcaag | ttttcagttt | ctgcagagta tgggagtagg | 180 |
| agaggaagtg | gtggtggtga | tttcgttgct | ggttttcttc | ttggtggtgc tttgttcggc | 240 |
| gctgccgctt | acatctttgc | tccacagata | cgaagatcga | taatgagtga agaagatgag | 300 |
| tatggtttca | agaagccaga | tcaaccaagt | tactacgatg | aaggtttaga gaaaacaagg | 360 |
| gagaccttga | cgagaaaaat | cggacagctt | aactcagcta | ttgacaatgt ctcttcgcgt | 420 |
| ttaagaggtc | gagcaaagaa | gacttcttcc | ccggtcgaaa | ctgatccaga agttgaagct | 480 |
| actacttga | | | | | 489 |

<210> SEQ ID NO 58
<211> LENGTH: 504
<212> TYPE: DNA
<213> ORGANISM: Brassica napus

<400> SEQUENCE: 58

| | | | | |
|---|---|---|---|---|
| atggcgtcct | gtgttgctca | tcttccactc | tcaagtgggt | ctcagtctcg tcatgtaaaa | 60 |
| gcaaatggat | tgtccaccac | aaagctcagt | tccatttgta | aaacttctgc attgactgtt | 120 |
| cagaagaaat | caagccaggg | tcgcaagttt | tcggtttctg | cacggtatgg agacgaaggg | 180 |
| agtaggagag | gaagtggtgg | tggtgatttc | atagctggtt | ttcttctagg aggtgctgtc | 240 |
| tttggcgctg | ttgcctatat | ctttgctcca | cagatcagaa | gatcgataat gagtgaagaa | 300 |
| gatgagtatg | gtttcaagaa | gccacagcaa | ccaacgtact | acgatgaagg tttggagaaa | 360 |
| acaagagaga | cactgaacaa | gaaaatcgaa | caacttaact | cagcaatcga caatgtttct | 420 |
| tcccggttaa | gaggtcgaga | aaagaacact | tcttctccca | atgtaccggt ggaaactgac | 480 |
| ccagaagttg | aagctacgac | ttga | | | 504 |

<210> SEQ ID NO 59
<211> LENGTH: 486
<212> TYPE: DNA
<213> ORGANISM: Brassica napus

<400> SEQUENCE: 59

```
atggcgtcct cctgtgttgc tcatctttct ctctcaggtg tgtctcaatc tcattatgtc      60
aaggcaaatg ggttgtctac cacctcaaag ctcaattcga tttgtaaaac ctctgcattg     120
agtatccaga agagatcaaa ccggagtcgc aagttttcag tttctgcaga gtatgggtgt     180
ggtggtggtg gtggtgattt cgtagctggt tttcttcttg gtggtgcttt gtttggcgct     240
gctgcctaca tctttgctcc acagatcaga agatctataa tgagtgaaga agatgagtat     300
ggattcaaga agccagaaca accaagttac tacgatgaag gtttagagaa acaagggag     360 accttgaacg agaaaatcgg acagcttaac tcagctattg acaatgtctc ttcgcgttta     420
agaggtcgag agaagaagac ttcttcccct gtccaaactg acccggaagt tgaagctact     480
acttga                                                                486
```

<210> SEQ ID NO 60
<211> LENGTH: 168
<212> TYPE: PRT
<213> ORGANISM: Arabidopsis thaliana

<400> SEQUENCE: 60

```
Met Ala Ser Leu Ser Ser Thr Ser Leu Ser Leu Pro Lys Asn Ser His
1               5                   10                  15

Gln Leu His Pro Ser Ser Gly Phe Ser Leu Asn Pro Asn Ala Arg Cys
            20                  25                  30

Val Ser Val Ser Phe Gly Leu Asn His Ser Asn Lys Leu His Ile Ser
        35                  40                  45

Ala Pro Arg Thr Lys Arg Ile Leu Thr Ile Gln Ser Ala Tyr Arg Asp
    50                  55                  60

Asp Asp Gly Ser Gly Ser Thr Gly Leu Phe Val Gly Phe Ile Leu
65                  70                  75                  80

Gly Gly Leu Ile Val Gly Ala Leu Gly Cys Val Tyr Ala Pro Gln Ile
                85                  90                  95

Ser Lys Ala Ile Ala Gly Ala Asp Arg Lys Asp Leu Met Arg Lys Leu
            100                 105                 110

Pro Lys Phe Ile Tyr Asp Glu Glu Lys Ala Leu Glu Lys Thr Arg Lys
        115                 120                 125

Val Leu Ala Glu Lys Ile Ala Gln Leu Asn Ser Ala Ile Asp Asp Val
    130                 135                 140

Ser Ser Gln Leu Lys Ser Glu Asp Thr Pro Asn Gly Ala Ala Leu Ser
145                 150                 155                 160

Thr Asp Glu Ile Glu Ala Thr Ala
                165
```

<210> SEQ ID NO 61
<211> LENGTH: 162
<212> TYPE: PRT
<213> ORGANISM: Arabidopsis thaliana

<400> SEQUENCE: 61

```
Met Ala Ser Leu Val Ala Ala Pro Ile Ser Phe Ser Gly Asp Ser His
1               5                   10                  15

Val Lys Ala His Arg Asn Phe Asn Ala Ile Arg Lys Ser Ser Thr Leu
            20                  25                  30

Thr Val Gln Thr Lys Ser Asn Arg Ser His Lys Leu Ser Val Ser Ala
        35                  40                  45

Gly Tyr Arg Gly Gly Ser Lys Gly Gly Gly Ser Ser Asp Phe Val Thr
    50                  55                  60
```

```
Gly Phe Leu Leu Gly Ser Ala Val Phe Gly Thr Leu Ala Tyr Ile Phe
 65                  70                  75                  80

Ala Pro Gln Ile Arg Arg Ser Val Leu Ser Glu Asn Glu Tyr Gly Phe
                 85                  90                  95

Lys Lys Pro Glu Gln Pro Met Tyr Tyr Asp Glu Gly Leu Glu Glu Arg
            100                 105                 110

Arg Glu Ile Leu Asn Glu Lys Ile Gly Gln Leu Asn Ser Ala Ile Asp
        115                 120                 125

Lys Val Ser Ser Arg Leu Lys Gly Gly Arg Ser Gly Ser Ser Lys Asn
130                 135                 140

Thr Ser Ser Pro Ser Val Pro Val Glu Thr Asp Ala Glu Ala Glu Ala
145                 150                 155                 160

Thr Ala

<210> SEQ ID NO 62
<211> LENGTH: 168
<212> TYPE: PRT
<213> ORGANISM: Arabidopsis thaliana

<400> SEQUENCE: 62

Met Ala Ser Cys Ile Ala Thr Ala Pro Leu Ser Leu Ser Gly Val Ser
 1               5                  10                  15

Gln Ser His Tyr Val Lys Ala Asn Gly Leu Ser Thr Thr Thr Lys Leu
                 20                  25                  30

Ser Ser Ile Cys Lys Thr Ser Asp Leu Thr Ile His Lys Lys Ser Asn
            35                  40                  45

Arg Thr Arg Lys Phe Ser Val Ser Ala Gly Tyr Arg Asp Gly Ser Arg
 50                 55                  60

Ser Gly Ser Ser Gly Asp Phe Ile Ala Gly Phe Leu Leu Gly Gly Ala
 65                 70                  75                  80

Val Phe Gly Ala Val Ala Tyr Ile Phe Ala Pro Gln Ile Arg Arg Ser
                 85                  90                  95

Val Leu Asn Glu Glu Asp Glu Tyr Gly Phe Glu Lys Pro Lys Gln Pro
            100                 105                 110

Thr Tyr Tyr Asp Glu Gly Leu Glu Lys Thr Arg Glu Thr Leu Asn Glu
        115                 120                 125

Lys Ile Gly Gln Leu Asn Ser Ala Ile Asp Asn Val Ser Ser Arg Leu
130                 135                 140

Arg Gly Arg Glu Lys Asn Thr Ser Ser Leu Asn Val Pro Val Glu Thr
145                 150                 155                 160

Asp Pro Glu Val Glu Ala Thr Thr
                165

<210> SEQ ID NO 63
<211> LENGTH: 167
<212> TYPE: PRT
<213> ORGANISM: Brassica napus

<400> SEQUENCE: 63

Met Ala Ala Leu Ser Thr Ser Leu Ser Leu Ser Arg Asn Thr Gln Gln
 1               5                  10                  15

Leu His Pro Ser Ser Gly Phe Ser Leu Lys Pro Ile Ala Arg Arg Ala
                 20                  25                  30

Asn Val Ser Phe Gly Leu Asn Pro Ser Lys Lys Ile Gln Leu Ser Ala
            35                  40                  45
```

```
Pro Arg Gly Lys Arg Ile Leu Thr Ile Gln Ser Ala Tyr Arg Asp Asp
         50                  55                  60

Asp Ser Ser Gly Ser Thr Gly Leu Phe Val Gly Gly Phe Ile Leu Gly
 65                  70                  75                  80

Gly Leu Ile Val Gly Ala Leu Gly Cys Val Tyr Ala Pro Gln Ile Ser
                     85                  90                  95

Lys Ala Ile Ala Gly Ala Asp Arg Lys Asp Leu Met Arg Lys Leu Pro
                100                 105                 110

Lys Phe Ile Tyr Asp Glu Glu Lys Ala Leu Glu Lys Thr Arg Lys Val
                115                 120                 125

Leu Ala Asp Lys Ile Ala Gln Leu Asn Ser Ala Ile Asp Asp Val Ser
        130                 135                 140

Ser Gln Leu Lys Ser Glu Asp Thr Pro Asn Gly Ala Ala Leu Ser Thr
145                 150                 155                 160

Asp Glu Val Glu Ala Thr Ala
                165

<210> SEQ ID NO 64
<211> LENGTH: 167
<212> TYPE: PRT
<213> ORGANISM: Brassica napus

<400> SEQUENCE: 64

Met Ala Ala Leu Ser Thr Ser Leu Ser Leu Ser Arg Asn Thr Gln Gln
 1               5                  10                  15

Leu His Pro Ser Ser Gly Phe Ser Leu Lys Pro Ile Gly Arg Arg Ala
                 20                  25                  30

Asn Val Ser Phe Gly Leu Asn Pro Ser Lys Gln Ile Gln Leu Ser Ala
             35                  40                  45

Pro Arg Gly Lys Arg Ile Leu Thr Ile Gln Ser Ala Tyr Arg Asp Asp
         50                  55                  60

Asp Ser Ser Gly Ser Thr Gly Leu Phe Val Gly Gly Phe Ile Leu Gly
 65                  70                  75                  80

Gly Leu Ile Val Gly Ala Leu Gly Cys Val Tyr Ala Pro Gln Ile Ser
                     85                  90                  95

Lys Ala Ile Ala Gly Ala Asp Arg Lys Asp Leu Met Arg Lys Leu Pro
                100                 105                 110

Lys Phe Ile Tyr Asp Glu Glu Lys Ala Leu Glu Lys Thr Arg Lys Val
                115                 120                 125

Leu Ala Asp Lys Ile Ala Gln Leu Asn Ser Ala Ile Asp Asp Val Ser
        130                 135                 140

Ser Gln Leu Lys Ser Glu Asp Thr Pro Asn Gly Ala Ala Leu Ser Thr
145                 150                 155                 160

Asp Glu Val Glu Ala Thr Ala
                165

<210> SEQ ID NO 65
<211> LENGTH: 161
<212> TYPE: PRT
<213> ORGANISM: Brassica napus

<400> SEQUENCE: 65

Met Ala Ser Ser Cys Val Ala His Leu Ser Leu Ser Gly Val Ser Gln
 1               5                  10                  15

Ser His Tyr Val Lys Ala Asn Gly Leu Ser Thr Thr Lys Leu Asn
                 20                  25                  30
```

```
Ser Ile Cys Lys Thr Ser Ala Leu Ser Ile Gln Lys Arg Ser Asn Arg
        35                  40                  45

Ser Arg Lys Phe Ser Val Ser Ala Glu Tyr Gly Ser Arg Arg Gly Gly
 50                  55                  60

Gly Asp Phe Val Ala Gly Phe Leu Gly Gly Ala Leu Phe Gly Ala
 65                  70                  75                  80

Ala Ala Tyr Ile Phe Ala Pro Gln Ile Arg Arg Ser Ile Met Ser Glu
                 85                  90                  95

Glu Asp Glu Tyr Gly Phe Lys Lys Pro Gln Pro Ser Tyr Tyr Asp
             100                 105                 110

Glu Gly Leu Glu Lys Thr Arg Glu Thr Leu Asn Glu Lys Ile Gly Gln
             115                 120                 125

Leu Asn Ser Ala Ile Asp Asn Val Ser Ser Arg Leu Arg Gly Arg Glu
130                 135                 140

Lys Lys Thr Ser Ser Pro Val Gln Thr Asp Pro Glu Val Glu Ala Thr
145                 150                 155                 160

Thr

<210> SEQ ID NO 66
<211> LENGTH: 169
<212> TYPE: PRT
<213> ORGANISM: Brassica napus

<400> SEQUENCE: 66

Met Ala Ser Cys Val Ala His Leu Pro Leu Ser Ser Gly Ser Gln Ser
1               5                   10                  15

Arg His Val Lys Ala Asn Gly Leu Ser Thr Thr Lys Leu Ser Ser Ile
             20                  25                  30

Cys Lys Thr Ser Ala Leu Thr Val Gln Lys Lys Ser Ser Arg Ser Arg
         35                  40                  45

Lys Phe Ser Val Ser Ala Arg Tyr Gly Asp Glu Gly Ser Arg Arg Ala
 50                  55                  60

Ser Gly Gly Gly Gly Gly Asp Phe Ile Ala Gly Phe Leu Leu Gly Gly
 65                  70                  75                  80

Ala Val Phe Gly Ala Val Ala Tyr Ile Phe Ala Pro Gln Ile Arg Arg
                 85                  90                  95

Ser Ile Met Ser Glu Glu Asp Glu Tyr Gly Phe Lys Lys Pro Gln Gln
            100                 105                 110

Pro Thr Tyr Tyr Asp Glu Gly Leu Glu Lys Thr Arg Glu Thr Leu Asn
            115                 120                 125

Lys Lys Ile Glu Gln Leu Asn Ser Ala Ile Asp Asn Val Ser Ser Arg
130                 135                 140

Leu Arg Gly Arg Glu Asn Asn Thr Ser Ser Pro Asn Val Pro Val Glu
145                 150                 155                 160

Thr Gly Pro Glu Val Glu Ala Thr Thr
                165

<210> SEQ ID NO 67
<211> LENGTH: 168
<212> TYPE: PRT
<213> ORGANISM: Brassica napus

<400> SEQUENCE: 67

Met Ala Ser Cys Val Ala His Leu Ser Leu Ser Gly Gly Ser Gln Ser
1               5                   10                  15

His His Val Lys Ala Asn Gly Leu Ser Ala Lys Lys Leu Ser Ser Ile
```

```
                20                  25                  30
Cys Lys Thr Ser Val Leu Thr Val Gln Lys Ser Ser Arg Ser Gly
                35                  40                  45

Lys Phe Ser Val Ser Ala Arg Tyr Gly Asp Glu Gly Ser Lys Arg Gly
            50                  55                  60

Ser Gly Gly Gly Gly Asp Phe Ile Ala Gly Phe Leu Leu Gly Gly Ala
65                  70                  75                  80

Val Phe Gly Ala Val Ala Tyr Ile Phe Ala Pro Gln Ile Arg Arg Ile
                85                  90                  95

Ile Met Ser Glu Glu Asp Glu Tyr Gly Phe Asn Lys Pro Gln Gln Pro
                100                 105                 110

Thr Tyr Tyr Asp Glu Gly Leu Glu Lys Thr Arg Glu Thr Leu Asn Lys
                115                 120                 125

Lys Ile Glu Gln Leu Asn Ser Ala Ile Asp Asn Val Ser Ser Arg Leu
            130                 135                 140

Arg Gly Arg Glu Lys Asn Thr Ser Ser Pro Asn Val Pro Val Glu Thr
145                 150                 155                 160

Asp Pro Glu Val Glu Ala Thr Thr
                165
```

<210> SEQ ID NO 68
<211> LENGTH: 164
<212> TYPE: PRT
<213> ORGANISM: Camelina sativa

<400> SEQUENCE: 68

```
Met Ala Ser Leu Ser Thr Ser Leu Ser Leu Pro Asn Asn Ala Gln Gln
1               5                   10                  15

Leu His Pro Ser Ser Gly Phe Ser Leu Lys Pro Cys Val Ser Val Ser
                20                  25                  30

Phe Gly Leu Asn Arg Ser Asn Asn Leu His Ile Ser Ala Pro Arg Ser
            35                  40                  45

Lys Arg Ile Leu Thr Val Gln Ser Ala Tyr Arg Asp Asp Asp Gly Ser
        50                  55                  60

Gly Ser Thr Gly Leu Phe Val Gly Gly Phe Ile Leu Gly Gly Leu Ile
65                  70                  75                  80

Val Gly Ala Leu Gly Cys Val Tyr Ala Pro Gln Ile Ser Lys Ala Ile
                85                  90                  95

Ala Gly Ala Asp Arg Lys Asp Leu Met Arg Lys Leu Pro Lys Phe Ile
            100                 105                 110

Tyr Asp Glu Glu Lys Ala Leu Glu Lys Thr Arg Lys Val Leu Ala Glu
        115                 120                 125

Lys Ile Ala Gln Leu Asn Ser Ala Ile Asp Asp Val Ser Ser Gln Leu
    130                 135                 140

Lys Ser Glu Asp Thr Pro Asn Gly Ala Ala Leu Ser Thr Asp Glu Val
145                 150                 155                 160

Glu Ala Thr Ala
```

<210> SEQ ID NO 69
<211> LENGTH: 164
<212> TYPE: PRT
<213> ORGANISM: Camelina sativa

<400> SEQUENCE: 69

```
Met Ala Ser Leu Ser Thr Ser Leu Ser Leu Pro Asn Asn Ala Gln Gln
1               5                   10                  15
```

-continued

```
Leu His Pro Ser Ser Gly Phe Ser Leu Lys Pro Cys Val Ser Val Ser
        20                  25                  30

Phe Gly Leu Asn Arg Ser Asn Asn Leu His Ile Ser Ala Pro Arg Ser
        35                  40                  45

Lys Arg Ile Val Thr Val Gln Ser Ala Tyr Arg Asp Asp Asp Gly Ser
 50                  55                  60

Gly Ser Thr Gly Leu Phe Val Gly Gly Phe Ile Leu Gly Gly Leu Ile
 65                  70                  75                  80

Val Gly Ala Leu Gly Cys Val Tyr Ala Pro Gln Ile Ser Lys Ala Ile
                 85                  90                  95

Ala Gly Ala Asp Arg Lys Asp Leu Met Arg Lys Leu Pro Lys Phe Ile
                100                 105                 110

Tyr Asp Glu Glu Lys Ala Leu Glu Lys Thr Arg Lys Val Leu Ala Glu
                115                 120                 125

Lys Ile Ala Gln Leu Asn Ser Ala Ile Asp Asp Val Ser Ser Gln Leu
    130                 135                 140

Lys Ser Glu Asp Thr Pro Asn Gly Ala Ala Leu Ser Thr Asp Glu Val
145                 150                 155                 160

Glu Ala Thr Ala

<210> SEQ ID NO 70
<211> LENGTH: 164
<212> TYPE: PRT
<213> ORGANISM: Camelina sativa

<400> SEQUENCE: 70

Met Ala Ser Leu Ser Thr Ser Leu Ser Leu Pro Asn Asn Ala Gln Gln
 1               5                  10                  15

Leu His Pro Ser Ser Gly Phe Ser Leu Lys Pro Cys Val Ser Val Ser
        20                  25                  30

Phe Gly Leu Asn Arg Ser Asn Asn Leu His Ile Ser Ala Pro Arg Ser
        35                  40                  45

Lys Arg Ile Leu Ile Val Gln Ser Ala Tyr Arg Asp Asp Asp Gly Ser
 50                  55                  60

Gly Ser Thr Gly Leu Phe Val Gly Gly Phe Ile Leu Gly Gly Leu Ile
 65                  70                  75                  80

Val Gly Ala Leu Gly Cys Val Tyr Ala Pro Gln Ile Ser Lys Ala Ile
                 85                  90                  95

Ala Gly Ala Asp Arg Lys Asp Leu Met Arg Lys Leu Pro Lys Phe Ile
                100                 105                 110

Tyr Asp Glu Glu Lys Ala Leu Glu Lys Thr Arg Lys Val Leu Ala Glu
                115                 120                 125

Lys Ile Ala Gln Leu Asn Ser Ala Ile Asp Asp Val Ser Ser Gln Leu
    130                 135                 140

Lys Ser Glu Asp Thr Pro Asn Gly Ala Ala Leu Ser Thr Asp Glu Val
145                 150                 155                 160

Glu Ala Thr Ala

<210> SEQ ID NO 71
<211> LENGTH: 167
<212> TYPE: PRT
<213> ORGANISM: Camelina sativa

<400> SEQUENCE: 71

Met Ala Ser Cys Val Val Ala Pro Leu Ser Leu Ser Gly Gly Ser Gln
```

```
                1               5                   10                  15
            Ser His His Leu Lys Ala Asn Gly Leu Ser Ser Thr Thr Lys Leu Ser
                            20                  25                  30

Ser Ile Cys Lys Pro Cys Ala Leu Ser Ile Leu Asn Lys Ser Asn Arg
                            35                  40                  45

Thr Arg Asn Phe Ser Val Ser Ala Gly Tyr Arg Asp Gly Ser Arg Ser
                        50                  55                  60

Gly Ser Ser Gly Asp Phe Ile Ala Gly Phe Leu Leu Gly Gly Ala Val
            65                      70                  75                  80

Phe Gly Ala Val Ala Tyr Ile Phe Ala Pro Gln Ile Arg Arg Ser Val
                                85                  90                  95

Leu Asn Glu Glu Asp Glu Tyr Gly Phe Lys Lys Pro Gln Gln Pro Thr
                            100                 105                 110

Tyr Tyr Asp Glu Gly Leu Glu Lys Thr Arg Glu Thr Leu Asn Glu Lys
                        115                 120                 125

Ile Gly Gln Leu Asn Ser Ala Ile Asp Asn Val Ser Ser Arg Leu Arg
                    130                 135                 140

Gly Arg Glu Lys Asn Ser Ser Pro Asn Val Pro Val Glu Thr Asp
            145                 150                 155                 160

Pro Glu Val Glu Ala Thr Thr
                            165

<210> SEQ ID NO 72
<211> LENGTH: 167
<212> TYPE: PRT
<213> ORGANISM: Camelina sativa

<400> SEQUENCE: 72

Met Ala Ser Cys Val Val Ala Pro Leu Ser Leu Ser Gly Gly Ser Gln
            1               5                   10                  15

Ser His His Val Lys Ala Asn Gly Leu Ser Ser Thr Thr Lys Leu Asn
                            20                  25                  30

Ser Ile Cys Lys Pro Ser Ala Leu Ser Ile Leu Asn Lys Ser Asn Arg
                            35                  40                  45

Thr Leu Lys Phe Ser Val Ser Ala Glu Tyr Arg Asp Gly Ser Arg Ser
                        50                  55                  60

Gly Ser Ser Gly Asp Phe Ile Ala Gly Phe Leu Leu Gly Gly Ala Val
            65                      70                  75                  80

Phe Gly Ala Val Ala Tyr Ile Phe Ala Pro Gln Ile Arg Arg Ser Val
                                85                  90                  95

Leu Asn Glu Glu Asp Glu Tyr Gly Phe Lys Lys Pro Gln Gln Pro Thr
                            100                 105                 110

Tyr Tyr Asp Glu Gly Leu Glu Lys Thr Arg Glu Thr Leu Asn Glu Lys
                        115                 120                 125

Ile Gly Gln Leu Asn Ser Ala Ile Asp Asn Val Ser Ser Arg Leu Arg
                    130                 135                 140

Gly Arg Glu Lys Asn Thr Ser Pro Asn Val Pro Val Glu Thr Asp
            145                 150                 155                 160

Pro Glu Val Glu Ala Thr Thr
                            165

<210> SEQ ID NO 73
<211> LENGTH: 168
<212> TYPE: PRT
<213> ORGANISM: Camelina sativa
```

<400> SEQUENCE: 73

```
Met Ala Ser Cys Val Val Ala Pro Leu Ser Leu Ser Gly Gly Ser
1               5                   10                  15

Gln Ser His His Val Lys Ala Asn Gly Leu Ser Ser Thr Thr Lys Leu
                20                  25                  30

Ser Ser Ile Cys Lys Pro Ser Ala Leu Ser Ile Leu Asn Lys Ser Asn
            35                  40                  45

Arg Thr Arg Lys Phe Ser Val Ser Ala Gly Tyr Gln Asp Gly Ser Arg
50                      55                  60

Ser Gly Ser Ser Gly Asp Phe Ile Ala Gly Phe Leu Leu Gly Gly Ala
65                  70                  75                  80

Val Phe Gly Ala Val Ala Tyr Ile Phe Ala Pro Gln Ile Arg Arg Ser
                85                  90                  95

Leu Leu Asn Glu Glu Asp Glu Tyr Gly Phe Lys Lys Pro Gln Gln Pro
                100                 105                 110

Thr Tyr Tyr Asp Glu Gly Leu Glu Lys Thr Arg Glu Thr Leu Asn Glu
            115                 120                 125

Lys Ile Gly Gln Leu Asn Ser Ala Ile Asp Asn Val Ser Ser Arg Leu
130                 135                 140

Arg Gly Arg Glu Lys Asn Ser Ser Pro Asn Val Pro Val Glu Thr
145                 150                 155                 160

Asp Pro Glu Val Glu Ala Thr Thr
                165
```

<210> SEQ ID NO 74
<211> LENGTH: 161
<212> TYPE: PRT
<213> ORGANISM: Camelina sativa

<400> SEQUENCE: 74

```
Met Ala Ser Phe Val Ala Ala Pro Asn Ser Leu Ser Gly Asp Ser His
1               5                   10                  15

Leu Lys Ala His Cys Leu Ser Ser Thr Asn Leu Asn Leu Ile Arg Lys
                20                  25                  30

Ser Ser Thr Leu Thr Val Ile Thr Lys Ser Asn Arg Ser His Lys Leu
            35                  40                  45

Ser Val Ser Ala Gly Tyr Arg Glu Gly Ser Arg Gly Gly Gly Ser Ser
50                      55                  60

Asp Phe Val Thr Gly Phe Leu Leu Gly Ser Ala Val Phe Gly Thr Leu
65                  70                  75                  80

Ala Tyr Val Phe Ala Pro Gln Ile Arg Arg Ser Leu Leu Asn Glu Asn
                85                  90                  95

Glu His Gly Phe Lys Lys Pro Glu Gln Pro Met Tyr Tyr Asp Glu Gly
                100                 105                 110

Leu Glu Glu Arg Arg Glu Ile Leu Asn Glu Lys Ile Gly Gln Leu Asn
            115                 120                 125

Ser Ala Ile Asp Asn Val Ser Ser Arg Leu Arg Gly Ser Lys Asn Ser
130                 135                 140

Ser Ser Gln Ser Val Thr Val Glu Thr Asp Ala Glu Ala Glu Ala Thr
145                 150                 155                 160

Ala
```

<210> SEQ ID NO 75
<211> LENGTH: 166
<212> TYPE: PRT

<213> ORGANISM: Camelina sativa

<400> SEQUENCE: 75

```
Met Ala Ser Phe Val Ala Ala Pro Ile Ser Leu Ser Gly Asp Ser His
1               5                   10                  15

Val Lys Ala His Arg Phe Ser Ser Thr Asn Leu Asn Pro Phe Arg Lys
            20                  25                  30

Ser Ser Thr Leu Thr Val Arg Thr Lys Ser Asn Arg Ser His Lys Leu
        35                  40                  45

Ser Val Ser Ala Gly Tyr Arg Glu Gly Ser Arg Gly Gly Gly Ser Ser
    50                  55                  60

Asp Phe Val Thr Gly Phe Leu Leu Gly Ser Ala Val Phe Gly Thr Leu
65                  70                  75                  80

Ala Tyr Ile Phe Ala Pro Gln Ile Arg Arg Ser Leu Leu Asn Glu Asn
                85                  90                  95

Glu His Gly Phe Lys Lys Pro Glu Gln Pro Ile Tyr Tyr Asp Glu Gly
            100                 105                 110

Leu Glu Glu Arg Arg Glu Ile Leu Asn Glu Lys Ile Gly Gln Leu Asn
        115                 120                 125

Ser Ala Ile Asp Asn Val Ser Ser Arg Leu Arg Gly Gly Gly Ser Gly
    130                 135                 140

Ser Ser Lys Asn Ser Ser Ser Gln Ser Val Thr Val Glu Thr Asp Ala
145                 150                 155                 160

Glu Ala Glu Ala Thr Ala
                165
```

<210> SEQ ID NO 76
<211> LENGTH: 165
<212> TYPE: PRT
<213> ORGANISM: Camelina sativa

<400> SEQUENCE: 76

```
Met Ala Ser Phe Val Ala Ala Pro Ile Ser Leu Ser Gly Asp Ser His
1               5                   10                  15

Val Lys Ala His Cys Leu Leu Ser Thr Asn Leu Asn Pro Ile Arg Lys
            20                  25                  30

Ser Ser Thr Leu Thr Val Arg Thr Lys Ser Asn Arg Ser His Lys Leu
        35                  40                  45

Ser Val Ser Ala Gly Tyr Arg Glu Gly Ser Arg Gly Gly Gly Ser Ser
    50                  55                  60

Asp Phe Val Thr Gly Cys Leu Leu Gly Ser Ala Val Phe Gly Thr Leu
65                  70                  75                  80

Ala Tyr Val Phe Ala Pro Gln Ile Arg Arg Ser Leu Leu Asn Glu Asn
                85                  90                  95

Glu His Gly Phe Lys Lys Pro Glu Gln Pro Met Tyr Tyr Asp Glu Gly
            100                 105                 110

Leu Glu Glu Arg Arg Glu Ile Leu Asn Glu Lys Ile Gly Gln Leu Asn
        115                 120                 125

Ser Ala Ile Asp Asn Val Ser Ser Arg Leu Arg Gly Gly Ser Gly Ser
    130                 135                 140

Gly Lys Asn Ser Ser Ser Gln Ser Val Thr Val Glu Thr Asp Ala Glu
145                 150                 155                 160

Ala Glu Ala Thr Ala
                165
```

```
<210> SEQ ID NO 77
<211> LENGTH: 164
<212> TYPE: PRT
<213> ORGANISM: Cynara cardunculus

<400> SEQUENCE: 77

Met Thr Thr Leu Ala Asn Ser Phe Val Ser Val Pro Asn Gln Arg Asn
1               5                  10                  15

Gln Leu Phe Ser Gly Ser Leu Met Gln Ala Asp Gln Cys Leu Gly Ser
            20                  25                  30

Thr Asn Leu Cys Ile Gly His Ser Gly Thr Thr Lys Leu Lys Lys His
        35                  40                  45

Arg Lys Ser Leu Ile Val Arg Ala Gly Thr Asn Asp Asp Arg Leu Gly
    50                  55                  60

Gly Ala Ser Leu Phe Val Gly Gly Phe Val Leu Gly Gly Ile Val Val
65                  70                  75                  80

Gly Thr Leu Gly Ala Ile Tyr Ala Pro Gln Ile Ser Lys Ala Leu Ala
                85                  90                  95

Gly Ala Asp Arg Lys Asp Leu Met Arg Lys Leu Pro Lys Phe Ile Tyr
            100                 105                 110

Asp Glu Glu Lys Ala Leu Glu Lys Thr Arg Lys Ile Leu Thr Asp Lys
        115                 120                 125

Ile Ala Gln Leu Asn Ser Ala Ile Asp Asp Val Ser Ala Gln Leu Arg
    130                 135                 140

Ala Asp Asp Pro Pro Asn Gly Ser Ser Val Thr Thr Asn Gly Val Glu
145                 150                 155                 160

Ala Ser Ser Tyr

<210> SEQ ID NO 78
<211> LENGTH: 166
<212> TYPE: PRT
<213> ORGANISM: Cynara cardunculus

<400> SEQUENCE: 78

Met Ile Ala Leu Ser Asn Pro Leu Val Leu Pro Thr Asn Asn Pro Asn
1               5                  10                  15

Gln Ser Ser Ser Gly Ser Ser Met Lys Ser Leu Asp Gln Ser Thr Lys
            20                  25                  30

Leu Leu Phe Gly Gln Gly His Val Gly Asn Val Arg Leu Arg Thr Ser
        35                  40                  45

Lys Arg Met Leu Ser Val Gln Ala Arg Tyr Ser Asp Asn Gly Arg Ser
    50                  55                  60

Thr Asn Gly Ser Ala Phe Gly Phe Gly Phe Val Leu Gly Gly Leu Ile
65                  70                  75                  80

Val Gly Thr Leu Gly Cys Val Tyr Ala Pro Gln Ile Ser Lys Ala Leu
                85                  90                  95

Ala Glu Ala Asp Lys Lys Glu Leu Leu Arg Lys Leu Pro Thr Phe Ile
            100                 105                 110

Tyr Asp Glu Glu Lys Ala Leu Glu Lys Thr Arg Lys Lys Leu Thr Glu
        115                 120                 125

Lys Ile Ala Gln Leu Asn Asp Ala Ile Asp Val Ser Ser Gln Leu
    130                 135                 140

Lys Ser Glu Asp Glu Glu Ser Asn Lys Asn Gly Ala Val Val Phe Glu
145                 150                 155                 160

Lys Ser Gln Ser Val Ala
                165
```

```
<210> SEQ ID NO 79
<211> LENGTH: 168
<212> TYPE: PRT
<213> ORGANISM: Cynara cardunculus

<400> SEQUENCE: 79

Met Ser Ala Ile Ser Asn Ser Ser Leu Leu Pro Lys Asn Arg Ser
1               5                   10                  15

Asp Gln Leu Ser Ser Gly Ser Ser Val Lys Lys Leu Asp Gln Gly Phe
                20                  25                  30

Thr Lys Leu Ser Phe Gly Gln Ser Arg Val Gly Asn Leu Gln Leu Leu
                35                  40                  45

Thr Ser Lys Arg Thr Phe Ser Ile Gln Ala Gly Tyr Ser Asp Asp Gly
        50                  55                  60

Arg Ser Asn Ser Gly Ser Ala Phe Val Gly Phe Val Leu Gly Gly
65                  70                  75                  80

Leu Leu Val Gly Thr Leu Gly Cys Ile Tyr Ala Pro Gln Ile Ser Lys
                85                  90                  95

Ala Leu Ala Gly Ala Asp Lys Lys Glu Leu Leu Arg Lys Leu Pro Asp
                100                 105                 110

Phe Ile Tyr Asp Glu Glu Lys Ala Leu Glu Lys Thr Arg Gln Lys Leu
                115                 120                 125

Ala Lys Lys Ile Ala Glu Leu Asn Ser Ala Ile Asp Asp Val Ser Ser
        130                 135                 140

Gln Leu Lys Ser Asp Asp Asp Glu Pro Val Thr Asn Asn Gly Val Val
145                 150                 155                 160

Pro Asp Glu Ser Glu Ala Leu Ala
                165

<210> SEQ ID NO 80
<211> LENGTH: 161
<212> TYPE: PRT
<213> ORGANISM: Cynara cardunculus

<400> SEQUENCE: 80

Met Ala Thr Thr Gly Ile Val Ala Pro Ala Ser Ile Ser Val Arg Thr
1               5                   10                  15

Ser Leu Lys Gly His Asp Gly Trp Ser Gly Asn Ser Cys Leu Tyr Gly
                20                  25                  30

Lys Thr Pro Thr Leu Thr His Gln Arg Lys Ser Asn Gln Gln Arg Thr
        35                  40                  45

Gln Arg Lys Leu Ala Ile Ser Ala Gln Tyr Asn Asp Arg Ser Gly Gly
        50                  55                  60

Gly Ser Gly Asp Phe Val Ala Gly Phe Phe Leu Gly Gly Ala Leu Cys
65                  70                  75                  80

Gly Thr Leu Ala Tyr Ile Phe Ala Pro Gln Ile Arg Arg Ser Leu Leu
                85                  90                  95

Asn Glu Asp Glu Tyr Gly Phe Arg Arg Ala Lys Arg Pro Ile Tyr Tyr
                100                 105                 110

Asp Glu Gly Leu Glu Lys Thr Arg Gln Thr Leu Asn Ala Lys Ile Ser
                115                 120                 125

Gln Leu Asn Ser Ala Ile Asp Asn Val Ser Ser Arg Leu Arg Gly Gly
        130                 135                 140

Asn Asn Met Pro Gln Val Pro Val Glu Thr Asp Pro Glu Glu Ala Thr
145                 150                 155                 160
```

Met

<210> SEQ ID NO 81
<211> LENGTH: 166
<212> TYPE: PRT
<213> ORGANISM: Rizinus communis

<400> SEQUENCE: 81

```
Met Thr Ala Ile Ser Asn Ser Leu Ala Leu Thr Arg Asn Pro Val Gly
1               5                   10                  15

Thr Val Gln Leu Ser Ala Gly Ser Leu Gly Lys Ser Leu Gln Asn Val
            20                  25                  30

Gly Pro Thr Lys Leu Ser Phe Ser Leu Asn Ser Pro Gly Lys Val Gln
        35                  40                  45

Leu Thr Thr Ser Arg Arg Ser Leu Thr Val Arg Ala Ala Ser Asp Asp
    50                  55                  60

Gly Arg Pro Ser Gly Ser Ile Phe Val Gly Phe Val Leu Gly
65                  70                  75                  80

Gly Leu Ile Val Gly Ala Leu Gly Cys Val Tyr Ala Pro Gln Ile Ser
                85                  90                  95

Lys Ala Leu Ala Gly Thr Asp Arg Lys Asp Leu Met Arg Lys Leu Pro
            100                 105                 110

Lys Phe Ile Tyr Asp Glu Glu Lys Ala Leu Glu Lys Thr Arg Lys Val
        115                 120                 125

Leu Thr Glu Lys Ile Ala Gln Leu Asn Ser Ala Ile Asp Asp Val Ser
    130                 135                 140

Ala Gln Leu Arg Ser Asp Asp Ser Pro Asn Gly Val Ala Val Asn Asp
145                 150                 155                 160

Glu Ile Glu Ala Ala Ile
                165
```

<210> SEQ ID NO 82
<211> LENGTH: 163
<212> TYPE: PRT
<213> ORGANISM: Rizinus communis

<400> SEQUENCE: 82

```
Met Thr Ser Leu Ser Ser Pro Phe Leu Pro Phe Thr Thr Pro Gln Thr
1               5                   10                  15

Ser Gly Ser Ser Leu Lys Pro Ser Asn Pro Ser Ile Ser Ser Ile Ser
            20                  25                  30

Pro Cys Asn Leu Ser Ser Lys Ser Lys Arg Leu Pro Ser Ile Gln Ala
        35                  40                  45

Arg Tyr Asn Val Ser Val Ser Val Ser Gly Glu Arg Asp Leu Ser Ser
    50                  55                  60

Ser Ala Gly Ile Phe Ile Gly Gly Phe Val Leu Gly Gly Ile Ala Val
65                  70                  75                  80

Gly Ala Leu Gly Cys Ile Tyr Ala Pro Gln Ile Ser Lys Ala Leu Ala
                85                  90                  95

Gly Ala Asp Arg Lys Asp Leu Met Arg Lys Leu Pro Lys Phe Ile Tyr
            100                 105                 110

Asp Glu Glu Lys Ala Leu Glu Lys Thr Arg Lys Ile Leu Thr Glu Lys
        115                 120                 125

Ile Ala Gln Leu Asn Ser Ala Ile Asp Glu Val Ser Thr Gln Leu His
    130                 135                 140
```

```
Pro Asp Asp Thr Pro Asn Gly Ser Thr Val Asn Ser Asp Glu Ile Glu
145                 150                 155                 160

Ala Ser Thr
```

<210> SEQ ID NO 83
<211> LENGTH: 161
<212> TYPE: PRT
<213> ORGANISM: Rizinus communis

<400> SEQUENCE: 83

```
Met Ala Ala Ser Leu Ala Pro Val Ser Ile Ser Gly Gly Ser Asn Leu
1               5                   10                  15

Lys Ala Arg Glu Leu Cys Ser Ser Lys Ser Leu Ser Phe Gly Lys Thr
            20                  25                  30

Ser Arg Leu Ala Val Gln Arg Lys Leu Asn Leu Val Gly Thr Asn Cys
        35                  40                  45

Asn Leu Ser Val Arg Ala Asn Tyr Gln Asp Gly Asn Arg Gly Gly Gly
    50                  55                  60

Ser Asp Phe Val Ala Gly Phe Leu Leu Gly Gly Ala Ile Phe Gly Thr
65                  70                  75                  80

Leu Ala Tyr Val Phe Ala Pro Gln Ile Arg Arg Ser Leu Leu Asn Glu
                85                  90                  95

Asp Glu Tyr Gly Phe Arg Lys Ala Lys Arg Pro Ile Tyr Tyr Asp Glu
            100                 105                 110

Gly Leu Glu Lys Thr Arg Gln Thr Leu Asn Ala Lys Ile Ser Gln Leu
        115                 120                 125

Asn Ser Ala Ile Asp Asn Val Ser Ser Arg Leu Arg Gly Gly Asn Asn
    130                 135                 140

Asn Pro Pro Thr Val Pro Val Glu Thr Asp Pro Glu Val Glu Ala Thr
145                 150                 155                 160

Met
```

<210> SEQ ID NO 84
<211> LENGTH: 163
<212> TYPE: PRT
<213> ORGANISM: Glycine max

<400> SEQUENCE: 84

```
Met Ala Ala Val Pro Ser Thr Phe Ala Leu Thr Lys Ser Ala Leu Ser
1               5                   10                  15

Ile Asn Lys Leu Asp His Ser Leu Val Lys Ile Lys Pro Tyr Ser Phe
            20                  25                  30

Ser Leu Asn Leu Asn Arg Leu Gly Arg Met Glu Thr Ser Leu Thr Arg
        35                  40                  45

Arg Pro Leu Thr Ile Gln Ala Thr Tyr Ser Asp Gly Gly Arg Pro Ser
    50                  55                  60

Ser Ala Ser Val Phe Val Gly Gly Phe Leu Leu Gly Gly Leu Ile Val
65                  70                  75                  80

Gly Thr Leu Gly Cys Val Tyr Ala Pro Gln Ile Ser Lys Ala Ile Ala
                85                  90                  95

Gly Ala Asp Arg Lys Glu Leu Met Arg Lys Leu Pro Lys Phe Ile Tyr
            100                 105                 110

Asp Glu Glu Lys Ala Leu Glu Lys Thr Arg Lys Val Leu Ala Glu Lys
        115                 120                 125

Ile Glu Gln Leu Asn Ala Ala Ile Asp Asp Val Ser Ala Gln Leu Arg
    130                 135                 140
```

```
Ser Glu Glu Ala Ser Asn Gly Val Ala Val Asn Ser Asp Glu Ile Glu
145                 150                 155                 160

Ala Ala Thr
```

<210> SEQ ID NO 85
<211> LENGTH: 225
<212> TYPE: PRT
<213> ORGANISM: Glycine max

<400> SEQUENCE: 85

```
Met Leu Tyr Leu Tyr Gln Phe Phe Ser Pro Cys Leu Val Gly Arg Gly
1               5                   10                  15

Arg Leu Tyr Lys Asp Leu Cys Ile Leu Val Ser Cys Asn Val Ala Met
                20                  25                  30

Leu Leu Phe Asn Ile Thr Arg Leu Leu Ala Ser Ala Leu Trp Gln Lys
            35                  40                  45

Leu Trp Leu Gln Leu Asp Ser Ser Ile Ile Cys Val Cys Phe Phe Leu
    50                  55                  60

Thr Glu Arg Leu Leu Leu Gln Lys Leu Leu Leu Ala Ser Ser Ile Asn
65                  70                  75                  80

Lys Val Asp His Ser Leu Val Lys Ile Lys Pro Tyr Asn Phe Ser Leu
                85                  90                  95

Asn Leu Asn Arg Gln Gly Thr Met Gln Thr Ser Leu Thr Arg Arg Pro
            100                 105                 110

Leu Thr Ile Gln Ala Thr Tyr Ser Asp Gly Gly Arg Pro Ser Ser Ala
        115                 120                 125

Ser Val Phe Val Gly Gly Phe Leu Gly Gly Leu Ile Val Gly Thr
    130                 135                 140

Leu Gly Cys Val Tyr Ala Pro Gln Ile Ser Lys Ala Leu Ala Gly Ala
145                 150                 155                 160

Asp Arg Lys Glu Leu Met Arg Lys Leu Pro Lys Phe Ile Tyr Asp Glu
                165                 170                 175

Glu Lys Ala Leu Glu Lys Thr Arg Lys Val Leu Ala Glu Lys Ile Glu
            180                 185                 190

Gln Leu Asn Ala Ala Ile Asp Asp Val Ser Ala Gln Leu Arg Ser Glu
        195                 200                 205

Glu Ala Ser Asn Gly Val Ala Val Asn Ser Asp Glu Ile Glu Ala Ala
    210                 215                 220

Thr
225
```

<210> SEQ ID NO 86
<211> LENGTH: 165
<212> TYPE: PRT
<213> ORGANISM: Glycine max

<400> SEQUENCE: 86

```
Met Ala Thr Leu Ser Ser Phe Ile Ala Thr Pro Lys Asn Pro Asn Thr
1               5                   10                  15

His Phe Leu Ser Gly Ser Ser Leu Thr Met Asp Lys Cys Phe Leu Lys
                20                  25                  30

Ile Ser Ser Ser Glu His Phe Pro Gly Ser Leu Lys Thr Lys Ala
            35                  40                  45

Thr Arg Asn Gln Pro Leu Val Ile Arg Ala Gly Gly Asp Gly Gly Arg
        50                  55                  60
```

```
Pro Ser Ser Gly Ser Gly Phe Val Gly Phe Val Leu Gly Gly Leu
 65                  70                  75                  80

Ile Val Gly Ala Leu Gly Cys Leu Tyr Ala Pro Gln Ile Ser Arg Ala
                 85                  90                  95

Leu Ala Gly Ala Asp Ser Lys Asp Leu Met Arg Lys Leu Pro Lys Phe
            100                 105                 110

Met Tyr Asp Glu Glu Lys Ala Leu Glu Arg Thr Arg Lys Val Leu Thr
        115                 120                 125

Glu Lys Ile Ala Gln Leu Asn Ser Ala Ile Asp Gly Val Ser Ala Gln
    130                 135                 140

Leu Arg Pro Asp Glu Asp Ser Asn Glu Ile Ala Leu Asn Ser Glu Glu
145                 150                 155                 160

Ile Glu Ala Ser Ile
                165

<210> SEQ ID NO 87
<211> LENGTH: 176
<212> TYPE: PRT
<213> ORGANISM: Glycine max

<400> SEQUENCE: 87

Met Ala Thr Leu Ser Ser Phe Ile Thr Thr Pro Lys Asn Pro Lys Thr
 1               5                  10                  15

His Phe Leu Ser Gly Ser Ser Phe Met Ser Met Asp Lys Cys Phe Leu
                 20                  25                  30

Lys Ile Ser Thr Ser Gly His Phe Thr Asp Phe Ser Leu Arg Ala Lys
             35                  40                  45

Ala Thr Ser Asn Gln Pro Leu Val Ile Arg Ala Gly Gly Asp Gly Gly
 50                  55                  60

Arg Pro Ser Ser Gly Ser Ile Phe Val Gly Phe Val Leu Gly Gly
 65                  70                  75                  80

Leu Ile Ala Gly Ala Leu Gly Cys Leu Tyr Ala Pro Gln Ile Ser Arg
                 85                  90                  95

Ala Leu Ala Gly Ala Asp Ser Lys Asp Leu Met Arg Lys Leu Pro Lys
            100                 105                 110

Phe Met Tyr Asp Glu Glu Lys Ala Leu Glu Arg Thr Arg Glu Val Leu
        115                 120                 125

Thr Glu Lys Ile Ala Gln Leu Asn Ser Ala Ile Asp Gly Val Ser Ala
    130                 135                 140

Gln Leu Arg Pro Asp Glu Asp Ser Asn Glu Ile Ala Val Asn Ser Glu
145                 150                 155                 160

Glu Ile Glu Ile Pro Ile Ser Asp Glu Ser Glu Ile Glu Val Asn Lys
                165                 170                 175

<210> SEQ ID NO 88
<211> LENGTH: 157
<212> TYPE: PRT
<213> ORGANISM: Glycine max

<400> SEQUENCE: 88

Met Ala Thr Cys Phe Ala Pro Phe Ser Val Ser Gly Gly Ser His Glu
 1               5                  10                  15

Leu Trp Leu Thr Lys Arg Val Gly Pro Lys Leu Thr Val Gln Arg Arg
                 20                  25                  30

Ser Asn Leu Val Ile Lys Arg Asn His Thr Ser Ser Ile Ser Ala Glu
             35                  40                  45
```

```
Tyr Arg Asp Asn Arg Gly Gly Gly Gly Asp Phe Val Ala Gly Phe
        50                  55                  60

Leu Leu Gly Gly Ala Val Phe Gly Thr Leu Ala Tyr Ile Phe Ala Pro
 65                  70                  75                  80

Gln Phe Val Met Gln Ile Arg Arg Ser Leu Leu Asn Glu Asp Glu Tyr
                85                  90                  95

Gly Phe Arg Lys Ala Lys Arg Pro Ile Tyr Tyr Asp Glu Gly Leu Glu
            100                 105                 110

Arg Thr Arg Gln Thr Leu Asn Glu Lys Ile Gly Gln Leu Asn Ser Ala
        115                 120                 125

Ile Asp Asn Val Ser Ser Arg Leu Arg Gly Gly Asn Asn Val Pro Ala
130                 135                 140

Ala Lys Ile Glu Ser Asp Pro Glu Val Glu Ala Thr Met
145                 150                 155

<210> SEQ ID NO 89
<211> LENGTH: 154
<212> TYPE: PRT
<213> ORGANISM: Glycine max

<400> SEQUENCE: 89

Met Ala Thr Cys Phe Ala Pro Phe Ser Val Ser Val Gly Gly Ser His
  1               5                  10                  15

Glu Leu Trp Ser Thr Lys Arg Val Gly Pro Lys Leu Ser Val Gln Arg
             20                  25                  30

Arg Ser Ser Leu Val Ile Lys Arg Asn His Thr Ser Ser Ile Cys Ala
         35                  40                  45

Glu Tyr Arg Asp Asn Arg Gly Gly Gly Gly Asp Phe Val Ala Gly
     50                  55                  60

Phe Leu Leu Gly Gly Ala Val Phe Gly Thr Leu Ala Tyr Ile Phe Ala
 65                  70                  75                  80

Pro Gln Phe Val Met Gln Ile Arg Arg Ser Leu Leu Asn Glu Asp Glu
                 85                  90                  95

Tyr Gly Phe Arg Lys Ala Lys Arg Pro Ile Tyr Tyr Asp Glu Gly Leu
            100                 105                 110

Glu Arg Thr Arg Gln Thr Leu Asn Glu Lys Ile Gly Gln Leu Asn Ser
        115                 120                 125

Ala Ile Asp Asn Val Ser Ser Arg Leu Arg Gly Gly Asn Asn Val Pro
    130                 135                 140

Ala Ala Lys Ile Glu Ser Asp Pro Glu Val Glu Ala Thr Met
145                 150

<210> SEQ ID NO 90
<211> LENGTH: 157
<212> TYPE: PRT
<213> ORGANISM: Helianthus annuus

<400> SEQUENCE: 90

Met Thr Thr Leu Ser Asn Ser Phe Leu Ser Leu Gln Thr His Arg Asn
  1               5                  10                  15

His Phe Phe Ser Asp Gln Gly Ile Gly Ser Ser Asn Leu Leu Ile Gly
             20                  25                  30

His Ser Gly Thr Leu Lys Leu Thr Lys Gln Lys Lys Ser Leu Thr Val
         35                  40                  45

Arg Ala Gly Ala Asn Asp Asp Arg Leu Gly Gly Ala Ser Leu Phe Val
     50                  55                  60
```

```
Gly Gly Phe Val Leu Gly Gly Ile Val Val Gly Ala Leu Gly Ala Ile
65                  70                  75                  80

Tyr Ala Pro Gln Ile Ser Lys Ala Leu Ala Gly Ala Asp Arg Lys Asp
                85                  90                  95

Leu Met Arg Arg Leu Pro Lys Phe Ile Tyr Asp Glu Glu Lys Ala Leu
            100                 105                 110

Glu Lys Thr Arg Lys Ile Leu Thr Glu Lys Ile Ala Gln Leu Asn Ser
            115                 120                 125

Ala Ile Asp Asp Val Ser Ala Gln Leu Arg Ala Asp Pro Pro Asn
        130                 135                 140

Gly Ser Ser Val Pro Thr Asp Glu Val Glu Ala Ser Tyr
145                 150                 155
```

<210> SEQ ID NO 91
<211> LENGTH: 158
<212> TYPE: PRT
<213> ORGANISM: Helianthus annuus

<400> SEQUENCE: 91

```
Met Ala Ala Leu Ser Asn Ser Leu Ile Leu Ser Pro Pro Gly Ser
1               5                   10                  15

Ser Met Lys Ser Phe Asp Gln Ser Thr Lys Leu Leu Phe Gly Gln Ser
            20                  25                  30

Leu Ala Gly Asn Val Gln Leu His Thr Ala Lys Arg Thr Leu Ser Val
        35                  40                  45

Gln Ala Val Tyr Ser Glu Arg Ser Ser Ser Gly Ser Ala Phe Val Gly
    50                  55                  60

Gly Phe Val Leu Gly Gly Leu Ile Val Gly Thr Leu Gly Cys Val Tyr
65                  70                  75                  80

Ala Pro Gln Ile Ser Lys Thr Leu Ala Gly Ala Asp Lys Lys Glu Leu
                85                  90                  95

Leu Arg Lys Leu Pro Ala Phe Ile Tyr Asp Glu Glu Lys Ala Leu Glu
            100                 105                 110

Arg Thr Arg Lys Lys Leu Thr Glu Lys Ile Ala Gln Leu Asn Asp Ala
            115                 120                 125

Ile Asp Asp Val Ser Ser Gln Leu Lys Ser Asp Glu Asn Ser Asn
        130                 135                 140

Glu Asn Gly Ala Val Val Pro Glu Thr Ser Gln Ser Val Ala
145                 150                 155
```

<210> SEQ ID NO 92
<211> LENGTH: 156
<212> TYPE: PRT
<213> ORGANISM: Helianthus annuus

<400> SEQUENCE: 92

```
Met Ser Met Leu Leu Pro Asn His Pro Leu Ser Ser Ser Gly Ser Ser
1               5                   10                  15

Ile Lys Lys His Asp Gln Ala Phe Thr Lys Leu Ser Phe Gly Gln Ser
            20                  25                  30

His Ile Gly Asn Val Lys Leu Val Thr Ser Lys Gln Thr Leu Ser Val
        35                  40                  45

Lys Ala Gly Tyr Ser Asp Asp Gly Arg Ser Asn Asn Gly Gly Ala Phe
    50                  55                  60

Ile Gly Gly Phe Val Leu Gly Gly Leu Leu Ile Gly Thr Leu Gly Cys
65                  70                  75                  80
```

```
                        -continued
Ile Tyr Ala Pro Gln Ile Ser Lys Ala Leu Ala Gly Thr Asp Lys Lys
                85                  90                  95

Glu Leu Leu Lys Lys Leu Pro Asn Phe Ile Tyr Asp Glu Glu Lys Ala
            100                 105                 110

Leu Glu Lys Thr Arg Gln Lys Leu Ala Gln Lys Ile Ala Glu Leu Asn
        115                 120                 125

Ser Ala Ile Asp Asp Val Ser Ser Gln Leu Lys Thr Asp Asp Ala
    130                 135                 140

Asn Gly Val Val Pro Asp Glu Thr Glu Ala Leu Ala
145                 150                 155
```